US006610698B2

(12) United States Patent
Spohr et al.

(10) Patent No.: US 6,610,698 B2
(45) Date of Patent: Aug. 26, 2003

(54) SUBSTITUTED PYRIMIDINE COMPOUNDS AND METHODS OF USE

(75) Inventors: Ulrike D. Spohr, Boulder, CO (US); Michael J. Malone, Boulder, CO (US); Nathan B. Mantlo, Lafayette, CO (US)

(73) Assignee: Amgen, Inc., Thousand Oaks, CA (US)

( * ) Notice: Subject to any disclaimer, the term of this patent is extended or adjusted under 35 U.S.C. 154(b) by 0 days.

(21) Appl. No.: 10/117,552

(22) Filed: Apr. 3, 2002

(65) Prior Publication Data

US 2003/0069425 A1 Apr. 10, 2003

Related U.S. Application Data

(60) Division of application No. 09/598,740, filed on Jun. 21, 2000, now Pat. No. 6,410,729, which is a continuation of application No. 08/984,774, filed on Dec. 4, 1997, now abandoned, which is a continuation-in-part of application No. 08/976,054, filed on Nov. 21, 1997, now abandoned.
(60) Provisional application No. 60/032,128, filed on Dec. 5, 1996, and provisional application No. 60/050,950, filed on Jun. 13, 1997.

(51) Int. Cl.$^7$ .................. A61K 31/505; C07D 239/02; C07D 401/00
(52) U.S. Cl. .................. 514/269; 514/272; 514/275; 544/320; 544/321; 544/330; 544/331; 544/332; 544/333
(58) Field of Search .................. 514/269, 272, 514/275; 544/320, 321, 330, 331, 332, 333

(56) References Cited

U.S. PATENT DOCUMENTS

| 3,929,807 A | 12/1975 | Fitzi .................. 260/294.8 |
| 4,438,117 A | 3/1984 | Cherkofsky .................. 424/251 |
| 4,578,459 A | 3/1986 | Durant et al. .................. 544/8 |
| 4,973,690 A | 11/1990 | Rempfler et al. .................. 544/279 |
| 4,990,512 A | 2/1991 | Perrior et al. .................. 514/264 |
| 5,077,142 A | 12/1991 | Sakon et al. .................. 428/690 |
| 5,250,530 A | 10/1993 | Giencke et al. .................. 514/256 |
| 5,298,481 A | 3/1994 | Tice .................. 504/242 |
| 5,300,477 A | 4/1994 | Tice .................. 504/242 |
| 5,366,982 A | 11/1994 | Dereu et al. .................. 514/340 |
| 5,434,157 A | 7/1995 | Wierenga et al. .................. 514/272 |
| 5,492,915 A | 2/1996 | Dereu et al. .................. 514/311 |
| 5,518,994 A | 5/1996 | Kawamura et al. .................. 504/242 |
| 9,504,509 | 2/2000 | Spohr et al. .................. 514/310 |
| 6,096,753 A | 8/2000 | Spohr et al. .................. 504/242 |

FOREIGN PATENT DOCUMENTS

| DE | 1271116 | 6/1968 |
| DE | 2056407 | 5/1971 |
| DE | 3319843 | 12/1984 |
| EP | 039051 | 11/1981 |
| EP | 0130046 | 1/1985 |
| WO | 9202513 | * 2/1992 |
| WO | WO 92/10190 | 6/1992 |
| WO | WO 92/10498 | 6/1992 |
| WO | WO 92/12154 | 7/1992 |
| WO | WO 93/14081 | 7/1993 |
| WO | WO 92/02513 | 5/1994 |
| WO | WO 95/35304 | 12/1995 |
| WO | WO 96/03387 | 2/1996 |
| WO | WO 96/21452 | 7/1996 |
| WO | WO 96/21654 | 7/1996 |
| WO | WO 96/24584 | 8/1996 |
| WO | WO 97/12876 | 4/1997 |
| WO | WO 97/16442 | 5/1997 |
| WO | WO 97/33883 | 9/1997 |
| WO | WO 97/38992 | 10/1997 |

OTHER PUBLICATIONS

Ife et al;"4–(2–pyridyl(–5–phenyl—as Novel . . . reverible inhibitors of K+–ATPase";Biorg.Med.Chem.lett 5/6,543–6(1995).*
Bennett et al,"Synth. and anti–inflamm. activity . . . ";J. Med. Chem.21/7,623–8(1978).*
Knoferl et al,"PubMed ,Abstr.:11770048,COX–2 mediated reguln . . . and subsequent sepsis"; Shock Dec 2001;16/6:479–83.*
Ribardo et al,"PubMed.Abstr.:11821123,"Toxicon, May 2002;40/5:519–26.*
Hoozemans et al,"PubMed Abst.:11250126",Exp Herontol, Mar. 2001;36/3:559–70.*
Joussen et al,"PubMed Abst.:11821258",FASEB J. Mar. 2002;16/3:438–40.*
Ife et al; "4–(2–pyridyl(5–phenyl—as Novel—ireversible inhib. of H + /K + ATpase", Biorg. Med.Chem. Lett. 5/6,543–6(1995).*
Baracos et al.,. "Stimulation of Muscle Protein Dedgradation and Prostaglandin $E_2$ Release by Leukocytic Pyrogen (Interleukin–1)", *New Eng. J. Med.,* 308, 553 (1983).
Benneche et al., "(tert–Butyldimethylsilyloxy)methyl Chloride: Synthesis and Use as N–protecting Group in Pyrimidinones", *Acta Chem Scand.* B 42, 384–389 (1988).
Bennett et al., "Synthesis and Anti–inflammatory Activity of Trisubstituted Pyrimidines and Triazines", *J. Med. Chem.* 21, 623 (1978).

(List continued on next page.)

*Primary Examiner*—Richard L. Raymond
*Assistant Examiner*—Sudhaker B. Patel
(74) *Attorney, Agent, or Firm*—Richard V. Person; Ron K. Levy; Stuart L. Wattt

(57) ABSTRACT

Selected novel substituted pyrimidine compounds are effective for prophylaxis and treatment of diseases, such as TNF-α, IL-1β, IL-6 and/or IL-8 mediated diseases, and other maladies, such as pain and diabetes. The invention encompasses novel compounds, analogs, prodrugs and pharmaceutically acceptable salts thereof, pharmaceutical compositions and methods for prophylaxis and treatment of diseases and other maladies or conditions involving inflammation, pain, diabetes and the like. The subject invention also relates to processes for making such compounds as well as to intermediates useful in such processes.

13 Claims, No Drawings

OTHER PUBLICATIONS

Bennett et al., Reversals in Regiospecificity. "The Reactivity of Vinylogous Amides toward Bis Electrophiles" *J. Org Chem.* 42, 221–225 (1977).

Berge et al., "Pharmaceutical Salts", *J. Pharm. Sci.* 66, 1 (1977).

Beutler et. al., "Recombinant Interleukin 1 Suppresses Lipoprotein Lipase Activity in 3T3–L1 Cells", *J. Immunol.* 135, 3969 (1985).

Beyaert et al., "The p38/RK Mitogen–activated Protein Kinase Pathway Regulates Interleukin–6 synthesis Response to Tumor Necrosis Factor", *EMBO Journal 1996*, vol. 15, p 1914–23.

Brahn et al., "Effects of Tumor Necrosis Factor Alpha (TNF–α) on Collagen Arthritis", *Lymphokine Cytokine Res.* 11, 253 (1992).

Bredereck et al., "Darstellung und Eigenschaften der Amidacatale und Aminalester", *Chem Ber.* 101, 41–50 (1968).

Bredereck et. al., "Synthesen Heterocyclischer Aldehyde. Pyrimidinaldehyd–(4)", *Chem. Ber.* 97, 3407–3417 (1964).

Brown, D. J., Heterocyclic Compounds: *"The Pyrimidines"*, Chapter 3, 1994, John Wiley & Sons.

Chandrasekhar et al., "Arthritis Induced by Interleukin–1 is Dependent on the Site and Frequency of Intraarticular Injection", *Clinical Immunol. Immunopathol.* 55, 382 (1990), Academic Press, Inc..

Clouse et al., "Monokine Regulation of Human Immunodeficiency Virus–1 Expression in a Chronically Infected Human T Cell Clone", *J. Immunol.* 142, 431 (1989).

Cooper, *Clin. Exp. Immunol.* 89, 244 (1992).

Courtenay, "Immunization Against Heterologous Type II Collagen Induces Arthritis in Mice", *J. S., Nature* (1980), vol. 283, p 666.

Davies et al., "Asymmetric Syntheses of •–Phenylalanine, •–Methyl–•–phenylalanines and Derivatives", *J.Chem.Soc., Chem. Commun.*, 1153 (1993).

Dey et al., "Synthesis and Regioselective [4+2] Cycloaddition/Nucleophilic Reactions of N–Arylamino–1,3–Diaza–1, 3–Butadienes with Ketenes and Accompanying Rearrangements", *Tetrahedron*, vol. 51, No. 27, pp. 7459–7468 (1995).

Dinarello, "The Biological Properties of Interleukin–1", *Eur. Cytokine Netw.* 5, 517–531 (1994).

Efimovsky and Rumpf, "No. 128—Recherches sur l'Acide Methyl–2 Pyridine–Carboxylique–4", *Bull. Soc. Chim. FR.* 648–649 (1954).

Firestein, "Stromelysin and Tissue Inhibitor of Metalloproteinases Gene Expression in Rheumatoid Arthritis Synovium", *Am. J. Pathol.* 140, 1309 (1992).

Folks et al., "Susceptibility of Normal Human Lymphocytes to Infection with HTLV–III/LAV", *J. Immunol.* 136, 40 (1986).

Gallagher et al, "2,4,5– Triarylimidazole Inhibitors of IL–1 Biosynthesis" *Biorg. Med. Chem. Lett.* 1995, 1171–1176.

Ife et al., "4–(2–Pyridyl) –5–Phenylthiazoles as Novel Non–Bicyclic Reversible Inhibitors of the Gastric H+/K+–ATPase", *Bioorg. Med. Chem. Lett.* 5, 543 (1995).

Joosten et al, "Anticytokine Treatment of Established Type II Collagen–Induced Arthritis in DBA/1 Mice", *Arthritis & Rheumatism* 39:797–809 (1996).

Kabbe, "Substituierte 4–Hydorxy– und 4–Amino–pyrimidine", *Lieb. Ann. Chem.* 704, 144 (1967).

Lahdevirta et al., "Elevated Levels of Circulating Cachectin/Tumor Necrosis Factor in Patients with Acquired Immunodeficiency Syndrome", *Am. J. Med.* 85, 289 (1988).

Lee et al, "Low–Molecular–Weight TNF Biosynthesis Inhibitors: Strategies and Prospectives", *Circulatory Shock* 44:97–103 (1995).

Lee et al., "A Protein Kinase Involved in the Regulation of Inflammatory Cytokine Biosynthesis", *Nature* 372:739 (1994).

Legrand and Lozac'h, "No. 9.—Sulfuration des composes organiques (VII)",*Bull. Soc. Chim. Fr.,* 79–81 (1955).

Liu et al., "Cytokine–induced Neutrophil Chemoattractant mRNA Expressed in Cerebral Ischemia", *Neurosci. Lett.* 164, 125 (1993).

Liu et al., "Tumor Necrosis Factor–α Expression in Ischemic Neurons", *Stroke* 25, 1481 (1994).

Maini et al., "Monoclonal anti–TNFα Antibody as a Probe of Pathogenesis and Thereby of Rheumatoid Disease", *Immunological Reviews,* pp. 195–223 (1995).

Mathes and Sauermilch, "Uber einige Abkommlinge des 2.4.6–Kollidins und des 2.4–Lutidins", *Chem. Ber.* 88, 1276–1283 (1955).

Peters et al., "Synthesis of Various 5–Substituted Uracils",*J. Heterocyclic Chem.* 27, 2165–2173 (1990).

Sakasi et al., "Studies on Pyrimidine Derivatives. XVII[1]Synthesis of Pyrimidine–4–Carboxylic Esters", *Heterocycles* 13, 235 (1978).

Sandosham and Undheim, "Stannylation Reactions and Palladium Catalysis in the Syntheses of Unsymmetrical Biheteroaryls", *Acta Chem. Scand.* 43, 684–689 (1989).

Sheldrake, "The Anion of 4–Dimethoxymethylpyridine", *Synthetic Communications* 23, 1967 (1993).

Shohami et al., "Closed Head Injury Triggers Early Production of TNFα and IL–6 by Brain Tissue", *J. Cereb. Blood Flow Metab.* 14. 615 (1994).

Stanonis, *J. Org. Chem.* 22, 475 1957.

Swingle, K. F., in R. A. Scherrer and M. W. Whitehouse, Eds., Antiinflammatory Agents, Chemistry and Pharmacology, vol. 13–II, Academic, New York, 1974, p. 33–122, Chapter 2.

Takahashi et al., "Synthesis of 3–Substituted 5, 6–Diphenylpyrimidin–4–Ones From Diphenylcyclopropenone and N–Substituted Amide Oximes", *Heterocycles,* vol. 22, No. 3, pp. 581–584 (1984).

Trentham et al, "Autoimmunity to Type II Collagen: An Experimental Model of Arthritis", *J. Exp. Med.* (1977) vol. 146, p 857.

Venemalm et al., *Tet. Lett.* 34, 5495–5496 (1993).

Wheeler, "A Chiral Synthesis of Dapoxetine Hydrochloride, A Serotonin Re–Uptake Inhibitor, and its [14]C Isotopomer[1]", *Journal of Labelled Compounds and Radiopharmaceuticals,* vol. XXXI, No. 4, pp. 305–312 (1992).

Winter et al, *Proc. Soc. Exp. Biol. Med.* (1962) vol. 111, p 544.

Yoshida et al., "the Cycloaddition Reaction of N–Imidoyl Sulfoximides with Diphenycyclopropenone to Yield Pyrimidinone or Pyrrolinone Derivatives", *Bulletin of the Chemical Society of Japan,* vol. 56, No. 8, pp. 2438–2441 (1983).

Brunner et al., "Synthesis and Antitumor Activity of Platinum(II) Complexes Containing Substituted Ethylenediamine Ligands", *Eur. J. Med. Chem.* 25, 35–44, 1990.

Bundgaard , "A Novel Solution–Stable, Water–Soluble Prodrug Type for Drugs containing a Hydroxyl or an NH–Acidic Group", *J. Med. Chem.,* vol. 32, 2503 (1989).

Cohen and S. Y. Weinstein, "Hydrolysis of D(−)–Ethyl •–Phenyl– •–hydroxypropionate and D(−)–Ethyl •–Phenyl– •–acetamidopropionate by •–Chymotrypsin", *J. Am. Chem. Soc.* 86, 725–728, 1964.

Davies and I.A.S. Walters, "Asymmetric Synthesis of Anti– •– Alkyl— •–amino Acids", *J. Chem. Soc. Perkin Trans.I,* 1129–1139 (1994).

Dornow and Fust, "•ber die Reduktion substituierter Cyanessigsäure–äthylester", *Chem. Ber.* 87, 985, 1954.

Freifelder and R. B. Hasbrouck, "Synthesis of Primary 1,2–Diamines by Hydrogenation of •–Aminonitriles[1]", *J. Am. Chem. Soc.* 82, 696–698, 1960.

Kojima and J. Fujita, "Preparation and Spectroscopic Studies of Steroisomers of the Tris[(S)–1–phenyl–1, 3–propanediamine] Cobalt (III) Complex", *Bull. Chem. Soc. Jpn.* 55, 1454–1459, 1982.

Lang, et al., "Tumor Necrosis Factor Impairs Insulin Action on Peripheral Glucose Disposal and Hepatic Glucose Output", *Endocrinol.* 130, 43–52, 1992.

Svensson and Tunek, "The Design and Bioactivation of Presystemically Stable Prodrugs", *Drug Metabolism Reviews,* vol. 19(2), 165 (1988).

Szalkowski et al., "Antidiabetic Thiazolidinediones lock the Inhibitory Effect of Tumor Necrosis Factor– • on Differentiation, Insulin–Stimulated Glucose Uptake, and Gene Expression in 3T3–L1 Cells", *Endocrinol.* 136, 1474–1481, 1995.

Lantos et al., "Synthetic and Mechanistic Studies on the Preparation of Pyridyl–Substituted Imidazothiazoles", *J. Org. Chem.,* vol. 53, 4223–4227 (1988).

Giammanco et al., "Reattivita dell' 1–2–4–trifenil–1–cian–4–cloro–3–azabuta–1–3–diene. Derivati 3–sostituiti del 2–5–6–trifenil–4(3H)–pirimidone.", *Annali di Chimica,* vol. 60(3), 188–97 (1970).

Giammanco, "Trasformazione Di Ossazinoni In Derivati Della Pirimidina", *Atti Della Accademia di Scienze Lettere E Arti Di Palermo,* vol. 27, 469–83 (1968).

\* cited by examiner

SUBSTITUTED PYRIMIDINE COMPOUNDS AND METHODS OF USE

This application is a division of application Ser. No. 09/598,740, filed Jun. 21, 2000 now U.S. Pat. No. 6,410,729 which is a continuation of application Ser. No. 08/984,774 filed Dec. 4, 1997 now abandoned which is a CIP of Ser. No. 08/976,054 filed Nov. 21, 1997 (abandoned) which claims the benefit of U.S. Provisional Application Nos. 60/032,128 filed Dec. 5, 1996 and 60/050,950 filed Jun. 13, 1997, which are hereby incorporated by reference.

BACKGROUND OF THE INVENTION

The present invention comprises a new class of compounds useful in treating diseases, such as TNF-α, IL-1β, IL-6 and/or IL-8 mediated diseases and other maladies, such as pain and diabetes. In particular, the compounds of the invention are useful for the prophylaxis and treatment of diseases or conditions involving inflammation. This invention also relates to intermediates and processes useful in the preparation of such compounds.

Interleukin-1 (IL-1) and Tumor Necrosis Factor α (TNF-α) are pro-inflammatory cytokines secreted by a variety of cells, including monocytes and macrophages, in response to many inflammatory stimuli (e.g., lipopolysaccharide—LPS) or external cellular stress (e.g., osmotic shock and peroxide).

Elevated levels of TNF-α and/or IL-1 over basal levels have been implicated in mediating or exacerbating a number of disease states including rheumatoid arthritis; Pagets disease; osteophorosis; multiple myeloma; uveititis; acute and chronic myelogenous leukemia; pancreatic β cell destruction; osteoarthritis; rheumatoid spondylitis; gouty arthritis; inflammatory bowel disease; adult respiratory distress syndrome (ARDS); psoriasis; Crohn's disease; allergic rhinitis; ulcerative colitis; anaphylaxis; contact dermatitis; asthma; muscle degeneration; cachexia; Reiter's syndrome; type I and type II diabetes; bone resorption diseases; graft vs. host reaction; ischemia reperfusion injury; atherosclerosis; brain trauma; multiple sclerosis; cerebral malaria; sepsis; septic shock; toxic shock syndrome; fever, and myalgias due to infection. HIV-1, HIV-2, HIV-3, cytomegalovirus (CMV), influenza, adenovirus, the herpes viruses (including HSV-1, HSV-2), and herpes zoster are also exacerbated by TNF-α.

It has been reported that TNF-α plays a role in head trauma, stroke, and ischemia. For instance, in animal models of head trauma (rat), TNF-α levels increased in the contused hemisphere (Shohami et al., *J. Cereb. Blood Flow Metab.* 14, 615 (1994)). In a rat model of ischemia wherein the middle cerebral artery was occluded, the levels of TNF-α mRNA of TNF-α increased (Feurstein et al., *Neurosci. Lett.* 164, 125 (1993)). Administration of TNF-α into the rat cortex has been reported to result in significant neutrophil accumulation in capillaries and adherence in small blood vessels. TNF-α promotes the infiltration of other cytokines (IL-1β, IL-6) and also chemokines, which promote neutrophil infiltration into the infarct area (Feurstein, *Stroke* 25, 1481 (1994)). TNF-α has also been implicated to play a role in type II diabetes (Endocrinol. 130, 43–52, 1994; and Endocrinol. 136, 1474–1481, 1995).

TNF-α appears to play a role in promoting certain viral life cycles and disease states associated with them. For instance, TNF-α secreted by monocytes induced elevated levels of HIV expression in a chronically infected T cell clone (Clouse et al., *J. Immunol.* 142, 431 (1989)). Lahdevirta et al., (*Am. J. Med.* 85, 289 (1988)) discussed the role of TNF-α in the HIV associated states of cachexia and muscle degradation.

TNF-α is upstream in the cytokine cascade of inflammation. As a result, elevated levels of TNF-α may lead to elevated levels of other inflammatory and proinflammatory cytokines, such as IL-1, IL-6, and IL-8.

Elevated levels of IL-1 over basal levels have been implicated in mediating or exacerbating a number of disease states including rheumatoid arthritis; osteoarthritis; rheumatoid spondylitis; gouty arthritis; inflammatory bowel disease; adult respiratory distress syndrome (ARDS); psoriasis; Crohn's disease; ulcerative colitis; anaphylaxis; muscle degeneration; cachexia; Reiter's syndrome; type I and type II diabetes; bone resorption diseases; ischemia reperfusion injury; atherosclerosis; brain trauma; multiple sclerosis; sepsis; septic shock; and toxic shock syndrome. Viruses sensitive to TNF-α inhibition, e.g., HIV-1, HIV-2, HIV-3, are also affected by IL-1.

TNF-α and IL-1 appear to play a role in pancreatic β cell destruction and diabetes. Pancreatic β cells produce insulin which helps mediate blood glucose homeostasis. Deterioration of pancreatic β cells often accompanies type I diabetes. Pancreatic β cell functional abnormalities may occur in patients with type II diabetes. Type II diabetes is characterized by a functional resistance to insulin. Further, type II diabetes is also often accompanied by elevated levels of plasma glucagon and increased rates of hepatic glucose production. Glucagon is a regulatory hormone that attenuates liver gluconeogenesis inhibition by insulin. Glucagon receptors have been found in the liver, kidney and adipose tissue. Thus glucagon antagonists are useful for attenuating plasma glucose levels (WO 97/16442, incorporated herein by reference in its entirety). By antagonizing the glucagon receptors, it is thought that insulin responsiveness in the liver will improve, thereby decreasing gluconeogenesis and lowering the rate of hepatic glucose production.

In rheumatoid arthritis models in animals, multiple intra-articular injections of IL-1 have led to an acute and destructive form of arthritis (Chandrasekhar et al., *Clinical Immunol Immunopathol.* 55, 382 (1990)). In studies using cultured rheumatoid synovial cells, IL-1 is a more potent inducer of stromelysin than is TNF-α (Firestein, *Am. J. Pathol.* 140, 1309 (1992)). At sites of local injection, neutrophil, lymphocyte, and monocyte emigration has been observed. The emigration is attributed to the induction of chemokines (e.g., IL-8), and the up-regulation of adhesion molecules (Dinarello, *Eur. Cytokine Netw.* 5, 517–531 (1994)).

IL-1 also appears to play a role in promoting certain viral life cycles. For example, cytokine-induced increase of HIV expression in a chronically infected macrophage line has been associated with a concomitant and selective increase in IL-1 production (Folks et al., *J. Immunol.* 136, 40 (1986)). Beutler et al. (*J. Immunol.* 135, 3969 (1985)) discussed the role of IL-1 in cachexia. Baracos et al. (*New Eng. J. Med.* 308, 553 (1983)) discussed the role of IL-1 in muscle degeneration.

In rheumatoid arthritis, both IL-1 and TNF-α induce synoviocytes and chondrocytes to produce collagenase and neutral proteases, which leads to tissue destruction within the arthritic joints. In a model of arthritis (collagen-induced arthritis (CIA) in rats and mice), intra-articular administration of TNF-α either prior to or after the induction of CIA led to an accelerated onset of arthritis and a more severe course of the disease (Brahn et al., *Lymphokine Cytokine Res.* 11, 253 (1992); and Cooper, *Clin. Exp. Immunol.* 898, 244 (1992)).

IL-8 has been implicated in exacerbating and/or causing many disease states in which massive neutrophil infiltration into sites of inflammation or injury (e.g., ischemia) is mediated by the chemotactic nature of IL-8, including, but not limited to, the following: asthma, inflammatory bowel disease, psoriasis, adult respiratory distress syndrome, cardiac and renal reperfusion injury, thrombosis and glomerulonephritis. In addition to the chemotaxis effect on neutrophils, IL-8 also has the ability to activate neutrophils. Thus, reduction in IL-8 levels may lead to diminished neutrophil infiltration.

Several approaches have been taken to block the effect of TNF-α. One approach involves using soluble receptors for TNF-α (e.g., TNFR-55 or TNFR-75), which have demonstrated efficacy in animal models of TNF-α-mediated disease states. A second approach to neutralizing TNF-α using a monoclonal antibody specific to TNF-α, cA2, has demonstrated improvement in swollen joint count in a Phase II human trial of rheumatoid arthritis (Feldmann et al., *Immunological Reviews*, pp. 195–223 (1995)). These approaches block the effects of TNF-α and IL-1 by either protein sequestration or receptor antagonism.

Bennett et al. (*J. Med. Chem.* 21, 623 (1978)) synthesized a number of pyrimidines of the form:

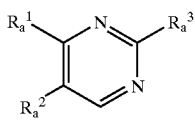

i where, inter alia, $R_a^1$ is 2-, 3-, or 4-pyridyl, $R_a^2$ is H, methyl, or phenyl, and $R_a^3$ is H, amino. They reported that none of these compounds tested against rat adjuvant-induced edema displayed a level of activity sufficient to warrant further investigation and that additional testing confirmed that the compounds represented a series of false positives in the carrageenan-induced edema model.

Ife et al. (Bioorg. Med. Chem. Lett. 5, 543 (1995)) reported that another pyrimidine ($R_a^1$=2-methylphenyl, $R_a^2$=2-pyridyl, and $R_a^3$=n-propyl, wherein $R_a^1$, $R_a^2$, and $R_a^3$ are as in structure i, supra) had several times lower $H^+/K^+$-ATPase inhibitory activity than related 4-(2-pyridyl)-5-phenylthiazole compounds.

WO 97/33883 describes substituted pyrimidine compounds useful in treating cytokine mediated diseases.

BRIEF DESCRIPTION OF THE INVENTION

The present invention comprises a new class of compounds useful in the prophylaxis and treatment of diseases, such as TNF-α, IL-1β, IL-6 and/or IL-8 mediated diseases and other maladies, such as pain and diabetes. In particular, the compounds of the invention are useful for the prophylaxis and treatment of diseases or conditions involving inflammation. Accordingly, the invention also comprises pharmaceutical compositions comprising the compounds, methods for the prophylaxis and treatment of TNF-α, IL-1β, IL-6 and/or IL-8 mediated diseases, such as inflammatory, pain and diabetes diseases, using the compounds and compositions of the invention, and intermediates and processes useful for the preparation of the compounds of the invention.

The compounds of the invention are represented by the following general structure:

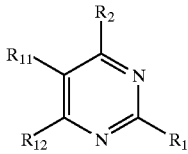

wherein $R^1$, $R^2$, $R^{11}$ and $R^{12}$ are defined below.

The foregoing merely summarizes certain aspects of the invention and is not intended, nor should it be construed, as limiting the invention in any way. All patents and other publications recited herein are hereby incorporated by reference in their entirety.

DETAILED DESCRIPTION OF THE INVENTION

In accordance with the present invention, there is provided compounds of the formula:

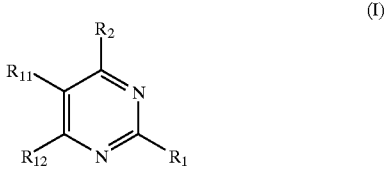

(I)

or a pharmaceutically acceptable salt thereof, wherein $R_1$ and $R_2$ are each independently -Z-Y, provided that (1) the total number of aryl, heteroaryl, cycloalkyl and heterocyclyl radicals in each -Z-Y is 0–3; preferably, 0–2; more preferably, 0–1; and (2) the combined total number of aryl, heteroaryl, cycloalkyl and heterocyclyl radicals in $R_1$ and $R_2$ is 0–4; preferably, 0–3; more preferably, 0–2; most preferably, 0–1;

preferably, $R_2$ is a radical of hydrogen, $C_1$–$C_4$ alkyl, halo, hydroxy, $C_1$–$C_4$ alkoxy, $C_1$–$C_2$ haloalkoxy of 1–3 halo radicals, thiol, $C_1$–$C_4$ alkylthio, aminosulfonyl, $C_1$–$C_4$ alkylaminosulfonyl, di-($C_1$–$C_4$ alkyl)aminosulfonyl, amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino or $C_1$–$C_2$ haloalkyl of 1–3 halo radicals;

more preferably, $R_2$ is a radical of hydrogen, $C_1$–$C_4$ alkyl, halo, hydroxy, $C_1$–$C_4$ alkoxy, trifluoromethoxy, thiol, $C_1$–$C_4$ alkylthio, amino, $C_1$–$C_4$ alkylamino, di-($C_1$–$C_4$ alkyl) amino, $C_1$–$C_5$ alkanoylamino, ($C_1$–$C_4$ alkoxy)carbonylamino, $C_1$–$C_4$ alkylsulfonylamino or trifluoromethyl;

more preferably, $R_2$ is a radical of hydrogen, methyl, ethyl, fluoro, chloro, hydroxy, methoxy, trifluoromethoxy, amino, methylamino, dimethylamino, acetylamino or trifluoromethyl; and most preferably, $R_2$ is a radical of hydrogen or hydroxy;

wherein each Z is independently a (1) bond;

(2) alkyl, alkenyl or alkynyl radical optionally substituted by (a) 1–3 radicals of amino, alkylamino, dialkylamino, alkanoylamino, alkoxycarbonylamino, alkylsulfonylamino, hydroxy, alkoxy, alkylthio or halo, and (b) 1–2 radicals of heterocyclyl, aryl or heteroaryl optionally substituted by 1–3 radicals of amino, alkylamino, dialkylamino, alkanoylamino, alkoxycarbonylamino, alkylsulfonylamino, hydroxy, alkoxy, alkylthio, halo, alkyl or haloalkyl;

(3) heterocyclyl radical optionally substituted by 1–3 radicals of amino, alkylamino, dialkylamino, alkanoylamino, alkoxycarbonylamino, alkylsulfonylamino, hydroxy, alkoxy, alkylthio, alkyl or haloalkyl; or (4) aryl or heteroaryl radical optionally substituted by 1–3 radicals of amino, alkylamino, dialkylamino, alkanoylamino, alkoxycarbonylamino, alkylsulfonylamino, hydroxy, alkoxy, alkylthio, cyano, halo, alkyl or haloalkyl;

preferably, each z is independently a (1) bond;

(2) $C_1$–$C_8$ alkyl, $C_2$–$C_8$ alkenyl or $C_2$–$C_8$ alkynyl radical optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio or halo, and (b) 1–2 radicals of heterocyclyl, aryl or heteroaryl optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, halo, $C_1$–$C_4$ alkyl or $C_1$–$C_4$ haloalkyl of 1–3 halo radicals;

(3) heterocyclyl radical optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, $C_1$–$C_4$ alkyl or $C_1$–$C_4$ haloalkyl of 1–3 halo radicals; or (4) aryl or heteroaryl radical optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, cyano, halo, $C_1$–$C_4$ alkyl or $C_1$–$C_4$ haloalkyl of 1–3 halo radicals;

more preferably, each Z is independently a (1) bond;

(2) $C_1$–$C_8$ alkyl, $C_2$–$C_8$ alkenyl or $C_2$–$C_8$ alkynyl radical optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio or halo, and (b) 1–2 radicals of heterocyclyl, aryl or heteroaryl optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, halo, $C_1$–$C_4$ alkyl or $C_1$–$C_4$ haloalkyl of 1–3 halo radicals;

(3) heterocyclyl radical optionally substituted by 1–2 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, cyano, halo, $C_1$–$C_4$ alkyl or $C_1$–$C_4$ haloalkyl of 1–3 halo radicals;

more preferably, each Z is independently a (1) bond;

(2) $C_1$–$C_8$ alkyl or $C_2$–$C_8$ alkenyl radical optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, hydroxy, $C_1$–$C_4$ alkoxy, $C_1$–$C_4$ alkylthio or halo, and (b) 1–2 radicals of heterocyclyl, aryl or heteroaryl optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, hydroxy, $C_1$–$C_4$ alkoxy, $C_1$–$C_4$ alkylthio, halo, $C_1$–$C_4$ alkyl or $C_1$–$C_2$ haloalkyl of 1–3 halo radicals;

(3) heterocyclyl radical optionally substituted by 1–2 radicals of amino, di-($C_1$–$C_4$ alkyl)amino, ($C_1$–$C_4$ alkoxy)carbonylamino, hydroxy, $C_1$–$C_4$ alkoxy, $C_1$–$C_4$ alkylthio or $C_1$–$C_4$ alkyl radicals; or (4) aryl or heteroaryl radical optionally substituted by 1–3 radicals of amino, $C_1$–$C_4$ alkylamino, di-($C_1$–$C_4$ alkyl) amino, $C_1$–$C_5$ alkanoylamino, ($C_1$–$C_4$ alkoxy) carbonylamino, $C_1$–$C_4$ alkylsulfonylamino, hydroxy, $C_1$–$C_4$ alkoxy, $C_1$–$C_4$ alkylthio, cyano, halo, $C_1$–$C_4$ alkyl or $C_1$–$C_2$ haloalkyl of 1–3 halo radicals;

more preferably, each Z is independently a (1) bond;

(2) $C_1$–$C_4$ alkyl or $C_2$–$C_5$ alkenyl radical optionally substituted by 1–3 radicals of amino, di-($C_1$–$C_2$ alkyl) amino, $C_1$–$C_5$ alkanoylamino, ($C_1$–$C_4$ alkoxy) carbonylamino, hydroxy, $C_1$–$C_2$ alkoxy, $C_1$–$C_2$ alkylthio or halo, and (b) 1–2 radicals of heterocyclyl, aryl or heteroaryl optionally substituted by 1–3 radicals of amino, $C_1$–$C_4$ alkylamino, di-($C_1$–$C_2$ alkyl)amino, $C_1$–$C_5$ alkanoylamino, ($C_1$–$C_4$ alkoxy)carbonylamino, hydroxy, $C_1$–$C_4$ alkoxy, $C_1$–$C_4$ alkylthio, halo, $C_1$–$C_4$ alkyl or trifluoromethyl radicals;

(3) heterocyclyl radical optionally substituted by 1–2 radicals of amino, di-($C_1$–$C_2$ alkyl)amino, ($C_1$–$C_4$ alkoxy)carbonylamino, hydroxy, $C_1$–$C_2$ alkoxy, $C_1$–$C_2$ alkylthio or $C_1$–$C_4$ alkyl radicals; or (4) aryl or heteroaryl radical optionally substituted by 1–3 radicals of amino, di-($C_1$–$C_2$ alkyl)amino, $C_1$–$C_5$ alkanoylamino, ($C_1$–$C_4$ alkoxy)carbonylamino, hydroxy, $C_1$–$C_2$ alkoxy, $C_1$–$C_2$ alkylthio, cyano, halo, $C_1$–$C_4$ alkyl or trifluoromethyl radicals;

more preferably, each Z is independently a (1) bond;

(2) $C_1$–$C_4$ alkyl or $C_2$–$C_5$ alkenyl radical optionally substituted by 1–3 radicals of amino, di-($C_1$–$C_2$ alkyl) amino, ($C_1$–$C_4$ alkoxy)carbonylamino, hydroxy, $C_1$–$C_2$ alkoxy, $C_1$–$C_2$ alkylthio or halo, and (b) 1–2 radicals of aryl or heteroaryl optionally substituted by 1–2 radicals of amino, di-($C_1$–$C_2$ alkyl)amino, acetamido, ($C_1$–$C_4$ alkoxy)carbonylamino, hydroxy, $C_1$–$C_2$ alkoxy, $C_1$–$C_2$ alkylthio, halo, $C_1$–$C_4$ alkyl or trifluoromethyl radicals; or (3) aryl or heteroaryl radical optionally substituted by 1–3 radicals of amino, di-($C_1$–$C_2$ alkyl)amino, acetamido, ($C_1$–$C_4$ alkoxy)carbonylamino, hydroxy, $C_1$–$C_2$ alkoxy, $C_1$–$C_2$ alkylthio, cyano, halo, $C_1$–$C_4$ alkyl or trifluoromethyl radicals;

more preferably, each Z is independently a (1) bond; or (2) $C_1$–$C_4$ alkyl radical optionally substituted by 1–2 radicals of amino, di-($C_1$–$C_2$ alkyl)amino, ($C_1$–$C_4$ alkoxy)carbonylamino, hydroxy, $C_1$–$C_2$ alkoxy, $C_1$–$C_2$ alkylthio, halo or aryl or heteroaryl optionally substituted by 1–2 radicals of hydroxy, $C_1$–$C_2$ alkoxy, $C_1$–$C_2$ alkylthio, halo, $C_1$–$C_4$ alkyl or trifluoromethyl radicals; and most preferably, each Z is independently a (1) bond; or
(2) $C_1$–$C_4$ alkyl radical optionally substituted by 1–2 radicals of amino, t-butoxycarbonylamino, dimethylamino, hydroxy, methoxy, methylthio or halo radicals;

each Y is independently a
(1) hydrogen radical;
(2) halo or nitro radical;
(3) —C(O)—$R_{20}$ or —C($NR_5$)—$NR_5R_{21}$ radical;
(4) —$OR_{21}$, —O—C(O)—$R_{21}$, —O—C(O)—$NR_5R_{21}$ or —O—C(O)—$NR_{22}$—S(O)$_2$—$R_{20}$ radical;
(5) —$SR_{21}$, —S(O)—$R_{20}$, —S(O)$_2$—$R_{20}$, —S(O)$_2$—$NR_5R_{21}$, —S(O)$_2$—$NR_{22}$C(O)—$R_{21}$, —S(O)$_2$—$NR_{22}$—C(O)—$OR_{20}$ or —S(O)$_2$—$NR_{22}$—C(O)—$NR_5R_{21}$ radical; or
(6) —$NR_5R_{21}$, —$NR_{22}$—C(O)—$R_{21}$, —$NR_{22}$—C(O)—$OR_{20}$, —$NR_{22}$—C(O)—$NR_5R_{21}$, —$NR_{22}$—C($NR_5$)—$NR_5R_{21}$, —$NR_{22}$—S(O)$_2$—$R_{20}$ or —$NR_{22}$—S(O)$_2$—$NR_5R_{21}$ radical;

preferably, each Y is independently a
(1) hydrogen radical;
(2) halo radical;
(3) —C(O)—$R_{20}$ or —C($NR_5$)—$NR_5R_{21}$ radical;
(4) —$OR_{21}$, —O—C(O)—$R_{21}$ or —O—C(O)—$NR_5R_{21}$ radical;
(5) —$SR_{21}$, —S(O)—$R_{20}$, —S(O)$_2$—$R_{20}$ or —S(O)$_2$—$NR_5R_{21}$ radical; or
(6) —$NR_5R_{21}$, —$NR_{22}$—C(O)—$R_{21}$, —$NR_{22}$—C(O)—$OR_{20}$, —$NR_{22}$—C(O)—$NR_5R_{21}$, —$NR_{22}$—C($NR_5$)—$NR_5R_{21}$, —$NR_{22}$—S(O)$_2$—$R_{20}$ or —$NR_{22}$—S(O)$_2$—$NR_5R_{21}$ radical;

more preferably, each Y is independently a
(1) hydrogen radical;
(2) —C(O)—$R_{20}$ radical;
(3) —$OR_{21}$, —$SR_{21}$, —S(O)—$R_{20}$, —S(O)$_2$—$R_{20}$ or —S(O)$_2$—$NR_5R_{21}$ radical; or
(4) —$NR_5R_{21}$, —$NR_{22}$—C(O)—$R_{21}$, —$NR_{22}$—C(O)—$OR_{20}$, —$NR_{22}$—C(O)—$NR_5R_{21}$, —$NR_{22}$—S(O)$_2$—$R_{20}$ or —$NR_{22}$—S(O)$_2$—$NR_5R_{21}$ radical;

more preferably, each Y is independently a
(1) hydrogen radical;
(2) —C(O)—$R_{20}$ radical;
(3) —$OR_{21}$, —$SR_{21}$, —S(O)—$R_{20}$, —S(O)$_2$—$R_{20}$ or —S(O)$_2$—$NR_5R_{21}$ radical; or
(4) —$NR_5R_{21}$, —$NR_{22}$—C(O)—$R_{21}$ or —$NR_{22}$—S(O)$_2$—$R_{20}$ radical;

more preferably, each Y is independently a
(1) —C(O)—$R_{20}$ radical;
(2) —$OR_{21}$, —$SR_{21}$, —S(O)—$R_{20}$, —S(O)$_2$—$R_{20}$ or —S(O)$_2$—$NR_5R_{21}$ radical; or
(3) —$NR_5R_{21}$, —$NR_{22}$—C(O)—$R_{21}$ or —$NR_{22}$—S(O)$_2$—$R_{20}$ radical.

most preferably, each Y is independently a —$OR_{21}$, —$SR_{21}$ or —$NR_5R_{21}$ radical;

wherein each $R_5$ is independently
(1) hydrogen radicals;
(2) alkyl, alkenyl or alkynyl radicals optionally substituted by 1–3 radicals of amino, alkylamino, dialkylamino, hydroxy, alkoxy, alkylthio, —$SO_3H$ or halo; or
(3) aryl, heteroaryl, aralkyl, heteroaralkyl, heterocyclyl, heterocyclylalkyl, cycloalkyl or cycloalkylalkyl radicals optionally substituted by 1–3 radicals of amino, alkylamino, dialkylamino, hydroxy, alkoxy, alkylthio, alkyl or haloalkyl;

preferably, each $R_5$ is independently
(1) hydrogen radicals;
(2) $C_1$–$C_8$ alkyl, $C_2$–$C_8$ alkenyl or $C_2$–$C_8$ alkynyl radicals optionally substituted by 1–3 radicals of amino, $C_1$–$C_4$ alkylamino, di-($C_1$–$C_4$-alkyl)amino, hydroxy, $C_1$–$C_4$ alkoxy, $C_1$–$C_4$ alkylthio, —$SO_3H$ or halo; or
(3) aryl, heteroaryl, aryl-$C_1$–$C_4$-alkyl, heteroaryl-$C_1$–$C_4$-alkyl, heterocyclyl, heterocyclyl-$C_1$–$C_4$-alkyl, $C_3$–$C_8$ cycloalkyl or $C_3$–$C_8$-cycloalkyl-$C_1$–$C_4$-alkyl radicals optionally substituted by 1–3 radicals of amino, $C_1$–$C_4$ alkylamino, di-($C_1$–$C_4$-alkyl)amino, hydroxy, $C_1$–$C_4$ alkoxy, $C_1$–$C_4$ alkylthio, $C_1$–$C_4$ alkyl or $C_1$–$C_4$ haloalkyl of 1–3 halo radicals;

more preferably, each $R_5$ is independently
(1) hydrogen radicals;
(2) $C_1$–$C_4$ alkyl, $C_2$–$C_5$ alkenyl or $C_2$–$C_5$ alkynyl radicals optionally substituted by 1–3 radicals of amino, $C_1$–$C_4$ alkylamino, di-($C_1$–$C_4$-alkyl)amino, hydroxy, $C_1$–$C_4$ alkoxy, $C_1$–$C_4$ alkylthio, —$SO_3H$ or halo; or
(3) aryl, heteroaryl, aryl-$C_1$–$C_4$-alkyl, heteroaryl-$C_1$–$C_4$-alkyl, heterocyclyl, heterocyclyl-$C_1$–$C_4$-alkyl, $C_3$–$C_8$ cycloalkyl or $C_3$–$C_8$-cycloalkyl-$C_1$–$C_4$-alkyl radicals optionally substituted by 1–3 radicals of amino, $C_1$–$C_4$ alkylamino, di-($C_1$–$C_4$-alkyl)amino, hydroxy, $C_1$–$C_4$ alkoxy, $C_1$–$C_4$ alkylthio, $C_1$–$C_4$ alkyl or $C_1$–$C_4$ haloalkyl of 1–3 halo radicals;

more preferably, each $R_5$ is independently
(1) hydrogen radicals;
(2) $C_1$–$C_4$ alkyl or $C_2$–$C_5$ alkenyl radicals optionally substituted by 1–3 radicals of amino, di-($C_1$–$C_4$-alkyl)amino, hydroxy, $C_1$–$C_4$ alkoxy, $C_1$–$C_4$ alkylthio, —$SO_3H$ or halo; or
(3) phenyl-$C_1$–$C_2$-alkyl, heteroaryl-$C_1$–$C_2$-alkyl, heterocyclyl-$C_1$–$C_2$-alkyl or $C_3$–$C_6$-cycloalkyl-$C_1$–$C_2$-alkyl radicals optionally substituted by 1–3 radicals of amino, di-($C_1$–$C_4$-alkyl)amino, hydroxy, $C_1$–$C_4$ alkoxy, $C_1$–$C_4$ alkylthio, $C_1$–$C_4$ alkyl or $C_1$–$C_2$ haloalkyl of 1–3 halo radicals;

more preferably, each $R_5$ is independently
(1) hydrogen radical;
(2) $C_1$–$C_4$ alkyl radical optionally substituted by 1–3 radicals of amino, di-($C_1$–$C_2$-alkyl)amino, hydroxy, $C_1$–$C_2$ alkoxy, $C_1$–$C_2$ alkylthio or halo; or
(3) phenyl-$C_1$–$C_2$-alkyl, heteroaryl-$C_1$–$C_2$-alkyl, heterocyclyl-$C_1$–$C_2$-alkyl or $C_3$–$C_6$-cycloalkyl-$C_1$–$C_2$-alkyl radicals optionally substituted by 1–3 radicals of amino, di-($C_1$–$C_2$-alkyl)amino, hydroxy, $C_1$–$C_2$ alkoxy, $C_1$–$C_2$ alkylthio, methoxy, methylthio, $C_1$–$C_4$ alkyl or trifluoromethyl radicals;

more preferably, each $R_5$ is independently
(1) hydrogen radical;
(2) $C_1$–$C_4$ alkyl radical optionally substituted by 1–3 halo radicals; or
(3) phenyl-$C_1$–$C_2$-alkyl or heteroaryl-$C_1$–$C_2$-alkyl, radicals optionally substituted by 1–3 radicals of amino, dimethylamino, hydroxy, methoxy, methylthio, methyl or trifluoromethyl radicals;

more preferably, each $R_5$ is independently hydrogen or $C_1$–$C_4$ alkyl radical; and most preferably, each $R_5$ is a hydrogen radical;

wherein each $R_{20}$ is independently
(1) alkyl, alkenyl or alkynyl radicals optionally substituted by 1–3 radicals of amino, alkylamino, dialkylamino, alkanoylamino, alkoxycarbonylamino, N-(alkoxycarbonyl)-N-(alkyl)amino, aminocarbonylamino, alkylsulfonylamino, hydroxy, alkoxy, alkylthio, alkylsulfinyl, alkylsulfonyl, halo or aralkoxy, aralkylthio, aralkylsulfonyl, cycloalkyl, heterocyclyl, aryl or heteroaryl radicals optionally substituted by 1–3 radicals of amino, alkylamino, dialkylamino, alkanoylamino, alkoxycarbonylamino, alkylsulfonylamino, alkanoyl, hydroxy, alkoxy, alkylthio, alkylsulfinyl, alkylsulfonyl, halo, alkyl or haloalkyl;
(2) heterocyclyl radical optionally substituted by 1–3 radicals of amino, alkylamino, dialkylamino, alkanoylamino, alkoxycarbonylamino, alkylsulfonylamino, hydroxy, alkoxy, alkylthio, alkyl or haloalkyl; or
(3) aryl or heteroaryl radicals optionally substituted by 1–3 radicals of amino, alkylamino, dialkylamino, alkanoylamino, alkoxycarbonylamino, alkylsulfonylamino, alkoxycarbonyl, hydroxy, alkoxy, alkylthio, cyano, halo, azido, alkyl or haloalkyl;
preferably, each $R_{20}$ is independently
(1) $C_1$–$C_8$ alkyl, $C_2$–$C_8$ alkenyl or $C_2$–$C_8$ alkynyl radicals optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, N—(($C_1$–$C_4$ alkoxy)carbonyl)-N—($C_1$–$C_4$ alkyl) amino, aminocarbonylamino, $C_1$–$C_4$ alkylsulfonylamino, hydroxy, $C_1$–$C_4$ alkoxy, $C_1$–$C_4$ alkylthio, $C_1$–$C_4$ alkylsulfinyl, $C_1$–$C_4$ alkylsulfonyl, halo or aryl-$C_1$–$C_4$-alkoxy, aryl-$C_1$–$C_4$-alkylthio, aryl-$C_1$–$C_4$-alkylsulfonyl, $C_3$–$C_8$ cycloalkyl, heterocyclyl, aryl or heteroaryl radicals optionally substituted by 1–3 radicals of amino, $C_1$–$C_4$ alkylamino, di-($C_1$–$C_4$ alkyl) amino, $C_1$–$C_5$ alkanoylamino, ($C_1$–$C_4$ alkoxy) carbonylamino, $C_1$–$C_4$ alkylsulfonylamino, $C_1$–$C_5$ alkanoyl, hydroxy, $C_1$–$C_4$ alkoxy, $C_1$–$C_4$ alkylthio, $C_1$–$C_4$ alkylsulfinyl, $C_1$–$C_4$ alkylsulfonyl, halo, $C_1$–$C_4$ alkyl or $C_1$–$C_4$ haloalkyl of 1–3 halo radicals;
(2) heterocyclyl radical optionally substituted by 1–3 radicals of amino, $C_1$–$C_4$ alkylamino, di-($C_1$–$C_4$ alkyl) amino, $C_1$–$C_5$ alkanoylamino, ($C_1$–$C_4$ alkoxy) carbonylamino, $C_1$–$C_4$ alkylsulfonylamino, hydroxy, $C_1$–$C_4$ alkoxy, $C_1$–$C_4$ alkylthio, $C_1$–$C_4$ alkyl or $C_1$–$C_4$ haloalkyl of 1–3 halo radicals; or
(3) aryl or heteroaryl radicals optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy) carbonylamino, $C_1$–$C_4$ alkylsulfonylamino, ($C_1$–$C_4$ alkoxy)carbonyl, hydroxy, $C_1$–$C_4$ alkoxy, $C_1$–$C_4$ alkylthio, cyano, halo, azido, $C_1$–$C_4$ alkyl or $C_1$–$C_4$ haloalkyl of 1–3 halo radicals;
more preferably, each $R_{20}$ is independently
(1) $C_1$–$C_8$ alkyl, $C_2$–$C_5$ alkenyl or $C_2$–$C_5$ alkynyl radicals optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, N—(($C_1$–$C_4$ alkoxy)carbonyl)-N—($C_1$–$C_4$ alkyl) amino, aminocarbonylamino, $C_1$–$C_4$ alkylsulfonylamino, hydroxy, $C_1$–$C_4$ alkoxy, $C_1$–$C_4$ alkylthio, $C_1$–$C_4$ alkylsulfinyl, $C_1$–$C_4$ alkylsulfonyl, halo or aryl-$C_1$–$C_4$-alkoxy, aryl-$C_1$–$C_4$-alkylthio, aryl-$C_1$–$C_4$-alkylsulfonyl, $C_3$–$C_8$ cycloalkyl, heterocyclyl, aryl or heteroaryl radicals optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, $C_1$–$C_5$ alkanoyl, hydroxy, $C_1$–$C_4$ alkoxy, $C_1$–$C_4$ alkylthio, halo, $C_1$–$C_4$ alkyl or $C_1$–$C_4$ haloalkyl of 1–3 halo radicals;
(2) heterocyclyl radical optionally substituted by 1–3 radicals of amino, $C_1$–$C_4$ alkylamino, di-($C_1$–$C_4$ alkyl) amino, $C_1$–$C_5$ alkanoylamino, ($C_1$–$C_4$ alkoxy) carbonylamino, $C_1$–$C_4$ alkylsulfonylamino, hydroxy, $C_1$–$C_4$ alkoxy, $C_1$–$C_4$ alkylthio, $C_1$–$C_4$ alkyl or $C_1$–$C_4$ haloalkyl of 1–3 halo radicals; or
(3) aryl or heteroaryl radicals optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy) carbonylamino, $C_1$–$C_4$ alkylsulfonylamino, ($C_1$–$C_4$ alkoxy)carbonyl, hydroxy, $C_1$–$C_4$ alkoxy, $C_1$–$C_4$ alkylthio, cyano, halo, azido, $C_1$–$C_4$ alkyl or $C_1$–$C_4$ haloalkyl of 1–3 halo radicals;

aryl or heteroaryl radicals optionally substituted by 1–3 radicals of amino, $C_1$–$C_4$ alkylamino, di-($C_1$–$C_4$ alkyl) amino, $C_1$–$C_5$ alkanoylamino, ($C_1$–$C_4$ alkoxy) carbonylamino, $C_1$–$C_4$ alkylsulfonylamino, $C_1$–$C_5$ alkanoyl, hydroxy, $C_1$–$C_4$ alkoxy, $C_1$–$C_4$ alkylthio, $C_1$–$C_4$ alkylsulfinyl, $C_1$–$C_4$ alkylsulfonyl, halo, $C_1$–$C_4$ alkyl or $C_1$–$C_4$ haloalkyl of 1–3 halo radicals;
(2) heterocyclyl radical optionally substituted by 1–3 radicals of amino, $C_1$–$C_4$ alkylamino, di-($C_1$–$C_4$ alkyl) amino, $C_1$–$C_5$ alkanoylamino, ($C_1$–$C_4$ alkoxy) carbonylamino, $C_1$–$C_4$ alkylsulfonylamino, hydroxy, $C_1$–$C_4$ alkoxy, $C_1$–$C_4$ alkylthio, $C_1$–$C_4$ alkyl or $C_1$–$C_4$ haloalkyl of 1–3 halo radicals; or
(3) aryl or heteroaryl radicals optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy) carbonylamino, $C_1$–$C_4$ alkylsulfonylamino, ($C_1$–$C_4$ alkoxy)carbonyl, hydroxy, $C_1$–$C_4$ alkoxy, $C_1$–$C_4$ alkylthio, cyano, halo, azido, $C_1$–$C_4$ alkyl or $C_1$–$C_4$ haloalkyl of 1–3 halo radicals;
more preferably, each $R_{20}$ is independently
(1) $C_1$–$C_8$ alkyl or $C_2$–$C_5$ alkenyl radicals optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, N—(($C_1$–$C_4$ alkoxy)carbonyl)-N—($C_1$–$C_4$ alkyl) amino, aminocarbonylamino, hydroxy, $C_1$–$C_4$ alkoxy, $C_1$–$C_4$ alkylthio, $C_1$–$C_4$ alkylsulfinyl, $C_1$–$C_4$ alkylsulfonyl, halo or aryl-$C_1$–$C_4$-alkoxy, aryl-$C_1$–$C_4$-alkylthio, aryl-$C_1$–$C_4$-alkylsulfonyl, $C_3$–$C_6$ cycloalkyl, heterocyclyl, aryl or heteroaryl radicals optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, $C_1$–$C_5$ alkanoyl, hydroxy, $C_1$–$C_4$ alkoxy, $C_1$–$C_4$ alkylthio, halo, $C_1$–$C_4$ alkyl or $C_1$–$C_2$ haloalkyl of 1–3 halo radicals;
(2) heterocyclyl radical optionally substituted by 1–2 radicals of amino, $C_1$–$C_4$ alkylamino, di-($C_1$–$C_4$ alkyl) amino, $C_1$–$C_5$ alkanoylamino, ($C_1$–$C_4$ alkoxy) carbonylamino, hydroxy, $C_1$–$C_4$ alkoxy, $C_1$–$C_4$ alkylthio or $C_1$–$C_4$ alkyl; or
(3) aryl or heteroaryl radicals optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy) carbonylamino, $C_1$–$C_4$ alkylsulfonylamino, ($C_1$–$C_4$ alkoxy)carbonyl, hydroxy, $C_1$–$C_4$ alkoxy, $C_1$–$C_4$ alkylthio, cyano, halo, azido, $C_1$–$C_4$ alkyl or $C_1$–$C_2$ haloalkyl of 1–3 halo radicals;
more preferably, each $R_{20}$ is independently
(1) $C_1$–$C_8$ alkyl or $C_2$–$C_5$ alkenyl radicals optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, N—(($C_1$–$C_4$ alkoxy)carbonyl)-N—($C_1$–$C_4$ alkyl) amino, aminocarbonylamino, hydroxy, $C_1$–$C_4$ alkoxy, $C_1$–$C_4$ alkylthio, $C_1$–$C_4$ alkylsulfinyl, $C_1$–$C_4$ alkylsulfonyl, halo or aryl-$C_1$–$C_4$-alkoxy, aryl-$C_1$–$C_4$-alkylthio, aryl-$C_1$–$C_4$-alkylsulfonyl, $C_3$–$C_6$ cycloalkyl, heterocyclyl, aryl or heteroaryl radicals optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, $C_1$–$C_5$ alkanoyl, hydroxy, $C_1$–$C_4$ alkoxy, $C_1$–$C_4$ alkylthio, halo, $C_1$–$C_4$ alkyl or $C_1$–$C_2$ haloalkyl of 1–3 halo radicals;

(2) heterocyclyl radical optionally substituted by 1–2 radicals of amino, di-($C_1$–$C_4$ alkyl)amino, ($C_1$–$C_4$ alkoxy)carbonylamino, hydroxy, $C_1$–$C_4$ alkoxy, $C_1$–$C_4$ alkylthio or $C_1$–$C_4$ alkyl; or (3) aryl or heteroaryl radicals optionally substituted by 1–2 radicals of amino, $C_1$–$C_4$ alkylamino, di-($C_1$–$C_4$ alkyl)amino, acetamido, ($C_1$–$C_4$ alkoxy)carbonylamino, $C_1$–$C_4$ alkylsulfonylamino, ($C_1$–$C_4$ alkoxy)carbonyl, hydroxy, $C_1$–$C_4$ alkoxy, $C_1$–$C_4$ alkylthio, cyano, halo, azido, $C_1$–$C_4$ alkyl or trifluoromethyl radicals;

more preferably, each $R_{20}$ is independently (1) $C_1$–$C_8$ alkyl radicals optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, N—(($C_1$–$C_4$ alkoxy)carbonyl)-N—($C_1$–$C_4$ alkyl)amino, aminocarbonylamino, hydroxy, $C_1$–$C_4$ alkoxy, $C_1$–$C_4$ alkylthio, $C_1$–$C_4$ alkylsulfinyl, $C_1$–$C_4$ alkylsulfonyl, halo or $C_3$–$C_6$ cycloalkyl, heterocyclyl, aryl or heteroaryl radicals optionally substituted by 1–2 radicals of amino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, halo, $C_1$–$C_4$ alkyl or trifluoromethyl radicals;

(2) heterocyclyl radical optionally substituted by 1–2 radicals of hydroxy, $C_1$–$C_4$ alkoxy, $C_1$–$C_4$ alkylthio or $C_1$–$C_4$ alkyl; or (3) aryl or heteroaryl radicals optionally substituted by 1–2 radicals of ($C_1$–$C_4$ alkoxy)carbonyl, amino, $C_1$–$C_4$ alkylamino, di-($C_1$–$C_4$ alkyl)amino, hydroxy, $C_1$–$C_4$ alkoxy, $C_1$–$C_4$ alkylthio, cyano, halo, azido, $C_1$–$C_4$ alkyl or trifluoromethyl radicals;

more preferably, each $R_{20}$ is independently (1) $C_1$–$C_6$ alkyl radicals optionally substituted by 1–3 radicals of amino, methylamino, dimethylamino, t-butoxycarbonylamino, N-((t-butoxy)carbonyl)-N-(methyl)amino, aminocarbonylamino, hydroxy, butoxy, methoxy, butylthio, methylthio, methylsulfinyl, methylsulfonyl, halo or $C_5$–$C_6$ cycloalkyl, heterocyclyl, phenyl or heteroaryl radicals optionally substituted by 1–2 radicals of amino, dimethylamino, acetamino, hydroxy, methoxy, methylthio, halo, methyl or trifluoromethyl radicals;

(2) heterocyclyl radical optionally substituted by 1–2 radicals of hydroxy or $C_1$–$C_4$ alkyl; or (3) aryl or heteroaryl radicals optionally substituted by 1–2 radicals of amino, dimethylamino, hydroxy, methoxy, methylthio, halo, methyl or trifluoromethyl radicals;

more preferably, each $R_{20}$ is independently (1) $C_1$–$C_6$ alkyl radicals optionally substituted by 1–3 radicals of amino, methylamino, dimethylamino, t-butoxycarbonylamino, N-((t-butoxy)carbonyl)-N-(methyl)amino, aminocarbonylamino, hydroxy, butoxy, methoxy, butylthio, methylthio, methylsulfinyl, methylsulfonyl, halo or $C_5$–$C_6$ cycloalkyl, heterocyclyl, phenyl or heteroaryl radicals optionally substituted by 1–2 radicals of amino, dimethylamino, acetamino, hydroxy, methoxy, methylthio, halo, methyl or trifluoromethyl radicals;

(2) heterocyclyl radical; or (3) aryl or heteroaryl radicals optionally substituted by 1–2 radicals of amino, dimethylamino, hydroxy, methoxy, methylthio, halo, methyl or trifluoromethyl radicals;

most preferably, each $R_{20}$ is independently (1) $C_1$–$C_6$ alkyl radicals optionally substituted by 1–3 radicals of amino, methylamino, dimethylamino, hydroxy or phenyl or heteroaryl radicals optionally substituted by 1–2 radicals of amino, dimethylamino, hydroxy, methoxy, methylthio, halo, methyl or trifluoromethyl radicals;

(2) heterocyclyl radical; or (3) aryl or heteroaryl radicals optionally substituted by 1–2 radicals of amino, dimethylamino, hydroxy, methoxy, methylthio, halo, methyl or trifluoromethyl radicals;

each $R_{21}$ is independently hydrogen radical or $R_{20}$;

each $R_{22}$ is independently (1) hydrogen radical;

(2) alkyl radical optionally substituted by a radical of heterocyclyl, aryl or heteroaryl optionally substituted by 1–3 radicals of amino, alkylamino, dialkylamino, alkanoylamino, alkoxycarbonylamino, alkylsulfonylamino, hydroxy, alkoxy, alkylthio, alkylsulfinyl, alkylsulfonyl, cyano, halo, alkyl or haloalkyl; or (3) heterocyclyl, aryl or heteroaryl radicals optionally substituted by 1–3 radicals of amino, alkylamino, dialkylamino, alkanoylamino, alkoxycarbonylamino, alkylsulfonylamino, hydroxy, alkoxy, alkylthio, alkylsulfinyl, alkylsulfonyl, cyano, halo, alkyl or haloalkyl; provided when Z is a bond and Y is —$NR_{22}$—C(O)—$NH_2$, then $R_{22}$ is other then an optionally substituted aryl radical;

preferably, each $R_{22}$ is independently (1) hydrogen radical;

(2) $C_1$–$C_4$ alkyl radical optionally substituted by a radical of heterocyclyl, aryl or heteroaryl optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, $C_1$–$C_4$ alkylsulfinyl, $C_1$–$C_4$ alkylsulfonyl, cyano, halo, $C_1$–$C_4$ alkyl or $C_1$–$C_4$ haloalkyl of 1–3 halo radicals; or (3) heterocyclyl, aryl or heteroaryl radicals optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, $C_1$–$C_4$ alkylsulfinyl, $C_1$–$C_4$ alkylsulfonyl, cyano, halo, $C_1$–$C_4$ alkyl or $C_1$–$C_4$ haloalkyl of 1–3 halo radicals; provided when Z is a bond and Y is —$NR_{22}$—C(O)—$NH_2$, then $R_{22}$ is other then an optionally substituted aryl radical;

more preferably, each $R_{22}$ is independently (1) hydrogen radical; or (2) $C_1$–$C_4$ alkyl radical optionally substituted by a radical of phenyl or heteroaryl optionally substituted by 1–3 radicals of amino, di-($C_1$–$C_2$ alkyl)amino, $C_1$–$C_5$ alkanoylamino, ($C_1$–$C_4$ alkoxy)carbonylamino, hydroxy, $C_1$–$C_4$ alkoxy, $C_1$–$C_4$ alkylthio, cyano, halo, $C_1$–$C_4$ alkyl or $C_1$–$C_2$ haloalkyl of 1–3 halo radicals;

more preferably, each $R_{22}$ is independently hydrogen or $C_1$–$C_4$ alkyl radical; and most preferably, each $R_{22}$ is independently hydrogen or methyl radical;

$R_{11}$ and $R_{12}$ are each independently an aryl or heteroaryl radical optionally substituted by 1–3 radicals of
(1) $R_{30}$;
(2) halo or cyano radicals;
(3) —C(O)—$R_{30}$, —C(O)—O$R_{29}$, —C(O)—N$R_{31}R_{32}$ or —C(N$R_{31}$)—N$R_{31}R_{32}$ or —C(N$R_{31}$)—N$R_{31}R_{32}$ radicals;
(4) —O$R_{29}$, —O—C(O)—$R_{29}$, —O—C(O)—N$R_{31}R_{32}$ or —O—C(O)—N$R_{33}$—S(O)$_2$—$R_{30}$ radicals;
(5) —S$R_{29}$, —S(O)—$R_{30}$, —S(O)$_2$—$R_{30}$, —S(O)$_2$—N$R_{31}R_{32}$, —S(O)$_2$—N$R_{33}$—C(O)—$R_{30}$, —S(O)$_2$—N$R_{33}$—C(O)—O$R_{30}$ or —S(O)$_2$—N$R_{33}$—C(O)—N$R_{31}R_{32}$ radicals; or
(6) —N$R_{31}R_{32}$, —N$R_{33}$—C(O)—$R_{29}$, —N$R_{33}$—C(O)—O$R_{30}$, —N$R_{33}$—C(O)—N$R_{31}R_{32}$, —N$R_{33}$—C(N$R_{31}$)—N$R_{31}R_{32}$, —N$R_{33}$—S(O)$_2$—$R_{30}$ or —N$R_{33}$—S(O)$_2$—N$R_{31}R_{32}$ radicals;

provided that (1) $R_{11}$ is other than a 4-pyridyl, 4-pyrimidinyl, 4-quinolyl or 6-isoquinolinyl radical optionally substituted by 1–2 substituents; and (2) the total number of aryl, heteroaryl, cycloalkyl and heterocyclyl radicals substituted on each of $R_{11}$ and $R_{12}$ is 0–1;

preferably, $R_{11}$ and $R_{12}$ are each independently an aryl or heteroaryl radical optionally substituted by 1–2 radicals of
(1) $R_{30}$;
(2) halo or cyano radicals;
(3) —C(O)—$R_{30}$, —C(O)—O$R_{29}$, —C(O)—N$R_{31}R_{32}$ or —C(N$R_{31}$)—N$R_{31}R_{32}$ radicals;
(4) —O$R_{29}$, —O—C(O)—$R_{29}$, —O—C(O)—N$R_{31}R_{32}$ or —O—C(O)—N$R_{33}$—S(O)$_2$—$R_{30}$ radicals;
(5) —S$R_{29}$, —S(O)—$R_{30}$, —S(O)$_2$—$R_{30}$, —S(O)$_2$—N$R_{31}R_{32}$, —S(O)$_2$—N$R_{33}$—C(O)—$R_{30}$, —S(O)$_2$—N$R_{33}$—C(O)—O$R_{30}$ or —S(O)$_2$—N$R_{33}$—C(O)—N$R_{31}R_{32}$ radicals; or
(6) —N$R_{31}R_{32}$, —N$R_{33}$—C(O)—$R_{29}$, —N$R_{33}$—C(O)—O$R_{30}$, —N$R_{33}$—C(O)—N$R_{31}R_{32}$, —N$R_{33}$—C(N$R_{31}$)—N$R_{31}R_{32}$, —N$R_{33}$—S(O)$_2$—$R_{30}$ or —N$R_{33}$—S(O)$_2$—N$R_{31}R_{32}$ radicals;

provided that (1) $R_{11}$ is other than a 4-pyridyl, 4-pyrimidinyl, 4-quinolyl or 6-isoquinolinyl radical optionally substituted by 1–2 substituents; and (2) the total number of aryl, heteroaryl, cycloalkyl and heterocyclyl radicals substituted on each of $R_{11}$ and $R_{12}$ is 0–1;

more preferably, $R_{11}$ and $R_{12}$ are each independently an aryl or heteroaryl radical optionally substituted by 1–2 radicals of
(1) $R_{30}$;
(2) halo or cyano radicals;
(3) —C(O)—$R_{30}$, —C(O)—O$R_{29}$, —C(O)—N$R_{31}R_{32}$ or —C(N$R_{31}$)—N$R_{31}R_{32}$ radicals; or
(4) —O$R_{29}$, —S$R_{29}$, —S(O)—$R_{30}$, —S(O)$_2$—$R_{30}$, —S(O)$_2$—N$R_{31}R_{32}$, —N$R_{31}R_{32}$, —N$R_{33}$—C(O)—$R_{29}$ or —N$R_{33}$—C(O)—O$R_{30}$ radicals;

more preferably, $R_{11}$ is an aryl radical and $R_{12}$ is a heteroaryl radical, wherein the aryl and heteroaryl radicals are optionally substituted by 1–2 radicals of
(1) $R_{30}$;
(2) halo or cyano radicals;
(3) —C(O)—$R_{30}$, —C(O)—O$R_{29}$, —C(O)—N$R_{31}R_{32}$ or —C(N$R_{31}$)—N$R_{31}R_{32}$ radicals; or
(4) —O$R_{29}$, —S$R_{29}$, —S(O)—$R_{30}$, —S(O)$_2$—$R_{30}$, —S(O)$_2$—N$R_{31}R_{32}$, —N$R_{31}R_{32}$ or —N$R_{33}$—C(O)—$R_{29}$ radicals;

more preferably, $R_{11}$ is an aryl radical and $R_{12}$ is a heteroaryl radical, wherein the aryl and heteroaryl radicals are optionally substituted by 1–2 radicals of
(1) $R_{30}$;
(2) halo or cyano radicals; or
(3) —C(O)—N$R_{31}R_{32}$, —O$R_{29}$, —S$R_{29}$, —S(O)—$R_{30}$, —S(O)$_2$—$R_{30}$, —S(O)$_2$—N$R_{31}R_{32}$, —N$R_{31}R_{32}$ or —N$R_{33}$—C(O)—$R_{29}$ radicals;

more preferably, $R_{11}$ is an aryl radical optionally substituted by 1–2 radicals of (1) $R_{30}$; (2) halo or cyano radicals; or (3) —C(O)—N$R_{31}R_{32}$, —O$R_{29}$, —S$R_{29}$, —S(O)—$R_{30}$, —S(O)$_2$—$R_{30}$, —S(O)$_2$—N$R_{31}R_{32}$, —N$R_{31}R_{32}$ or —N$R_{33}$—C(O)—$R_{29}$ radicals; more preferably, $R_{11}$ is an aryl radical optionally substituted by 1–2 radicals of amino, dimethylamino, acetamido, hydroxy, halo, cyano, methoxy, methylthio, methylsulfinyl, methylsulfonyl, aminocarbonyl, methyl or trifluoromethyl radicals; more preferably, $R_{11}$ is an unsubstituted phenyl or naphthyl radical or a phenyl radical substituted by 1–2 radicals of amino, dimethylamino, acetamido, hydroxy, halo, cyano, methoxy, methylthio, methylsulfinyl, methylsulfonyl, aminocarbonyl, methyl or trifluoromethyl radicals; and most preferably, $R_{11}$ is an unsubstituted phenyl radical or a phenyl radical substituted by 1–2 radicals of amino, dimethylamino, acetamido, hydroxy, halo, cyano, methoxy, methylthio, methylsulfonyl, methyl or trifluoromethyl radicals;

more preferably, $R_{12}$ is a heteroaryl radical optionally substituted by 1–2 radicals of (1) $R_{30}$; (2) halo or cyano radicals; or (3) —C(O)—N$R_{31}R_{32}$, —O$R_{29}$, —S$R_{29}$, —N$R_{31}R_{32}$ or —N$R_{33}$—C(O)—$R_{29}$ radicals; more preferably, $R_{12}$ is a heteroaryl radical optionally substituted by 1–2 radicals of amino, dimethylamino, acetamido, hydroxy, halo, cyano, methoxy, methyl or trifluoromethyl radicals; more preferably, $R_{12}$ is a 4-pyridyl, 4-quinolinyl, 4-imidazolyl or 4-pyrimidinyl radical optionally substituted by a radical of amino, dimethylamino, acetamido, hydroxy, halo, cyano, methoxy, methyl or trifluoromethyl radicals; and most preferably, $R_{12}$ is a 4-pyridyl radical optionally substituted by a radical of amino, dimethylamino, acetamido, hydroxy, halo, cyano, methoxy, methyl or trifluoromethyl radicals;

wherein each $R_{30}$ is independently
(1) alkyl, alkenyl or alkynyl radicals optionally substituted by 1–3 radicals of —N$R_{31}R_{31}$, —CO$_2R_{23}$, hydroxy, alkoxy, alkylthio, alkylsulfinyl, alkylsulfonyl, cyano, halo or aralkoxy, aralkylthio, aralkylsulfonyl, heterocyclyl, aryl or heteroaryl radicals optionally substituted by 1–3 radicals of amino, alkylamino, dialkylamino, alkanoylamino, alkoxycarbonylamino, alkylsulfonylamino, hydroxy, alkoxy, alkylthio, alkylsulfinyl, alkylsulfonyl, cyano, halo, alkyl or haloalkyl;
(2) heterocyclyl radical optionally substituted by 1–3 radicals of amino, alkylamino, dialkylamino, alkanoylamino, alkoxycarbonylamino, alkylsulfonylamino, hydroxy, alkoxy, alkylthio, cyano, alkyl or haloalkyl; or
(3) aryl or heteroaryl radicals optionally substituted by 1–3 radicals of amino, alkylamino, dialkylamino, alkanoylamino, alkoxycarbonylamino, alkylsulfonylamino, hydroxy, alkoxy, alkylthio, cyano, halo, alkyl or haloalkyl;

preferably, each $R_{30}$ is independently
(1) $C_1$–$C_4$ alkyl, $C_2$–$C_4$ alkenyl or $C_2$–$C_4$ alkynyl radicals optionally substituted by 1–3 radicals of —N$R_{31}R_{31}$, —CO$_2R_{23}$, hydroxy, $C_1$–$C_4$ alkoxy, $C_1$–$C_4$ alkylthio, $C_1$–$C_4$ alkylsulfinyl, $C_1$–$C_4$ alkylsulfonyl, cyano, halo or aryl-$C_1$–$C_4$-alkoxy, aryl-$C_1$–$C_4$-alkylthio, aryl-$C_1$–$C_4$-alkylsulfonyl, heterocyclyl, aryl or heteroaryl radicals optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, $C_1$–$C_4$ alkylsulfinyl, $C_1$–$C_4$ alkylsulfonyl, cyano, halo, $C_1$–$C_4$ alkyl or $C_1$–$C_4$ haloalkyl of 1–3 halo radicals;

(2) heterocyclyl radical optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, cyano, $C_1$–$C_4$ alkyl or $C_1$–$C_4$ haloalkyl of 1–3 halo radicals; or (3) aryl or heteroaryl radicals optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, cyano, halo, $C_1$–$C_4$ alkyl or $C_1$–$C_4$ haloalkyl of 1–3 halo radicals;

more preferably, each $R_{30}$ is independently (1) $C_1$–$C_4$ alkyl radical optionally substituted by 1–3 radicals of
  (a) —$NR_{31}R_{31}$;
  (b) $C_1$–$C_4$ alkoxy-carbonyl or phenoxycarbonyl or phenylmethoxycarbonyl optionally substituted by 1–3 radicals of amino, alkylamino, di-($C_1$–$C_4$-alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, cyano, halo, $C_1$–$C_4$ alkyl or trifluoromethyl; or
  (c) hydroxy, $C_1$–$C_4$ alkoxy, $C_1$–$C_4$ alkylthio, or phenyl-$C_1$–$C_4$-alkoxy, phenyl-$C_1$–$C_4$-alkylthio, heterocyclyl, phenyl or heteroaryl radicals optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, hydroxy, $C_1$–$C_4$ alkoxy, $C_1$–$C_4$ alkylthio, cyano, halo, $C_1$–$C_4$ alkyl or $C_1$–$C_4$ haloalkyl of 1–3 halo radicals;

(2) $C_1$–$C_4$ haloalkyl of 1–3 halo radical; or (3) aryl or heteroaryl radicals optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, hydroxy, $C_1$–$C_4$ alkoxy, $C_1$–$C_4$ alkylthio, cyano, halo, $C_1$–$C_4$ alkyl or trifluoromethyl radicals;

more preferably, each $R_{30}$ is independently (1) $C_1$–$C_4$ alkyl radical optionally substituted by
  (a) amino, $C_1$–$C_4$ alkylamino or di-($C_1$–$C_4$-alkyl) amino radicals; or
  (b) hydroxy, $C_1$–$C_4$ alkoxy, heterocyclyl, phenyl or heteroaryl radicals optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy) carbonylamino, hydroxy, $C_1$–$C_4$ alkoxy, $C_1$–$C_4$ alkylthio, cyano, halo, $C_1$–$C_4$ alkyl or trifluoromethyl radicals;

(2) $C_1$–$C_2$ haloalkyl of 1–3 halo radical; or (3) aryl or heteroaryl radicals optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy) carbonylamino, hydroxy, $C_1$–$C_4$ alkoxy, $C_1$–$C_4$ alkylthio, cyano, halo, $C_1$–$C_4$ alkyl or trifluoromethyl radicals;

more preferably, each $R_{30}$ is independently (1) $C_1$–$C_4$ alkyl radical optionally substituted by a phenyl or heteroaryl radical optionally substituted by 1–3 radicals of amino, di-($C_1$–$C_2$ alkyl)amino, acetamido, hydroxy, $C_1$–$C_2$ alkoxy, halo, $C_1$–$C_4$ alkyl or trifluoromethyl radicals;

(2) trifluoromethyl radical; or (3) aryl or heteroaryl radicals optionally substituted by 1–3 radicals of amino, di-($C_1$–$C_2$ alkyl)amino, acetamido, hydroxy, $C_1$–$C_2$ alkoxy, halo, $C_1$–$C_4$ alkyl or trifluoromethyl radicals;

more preferably, each $R_{30}$ is independently (1) $C_1$–$C_4$ alkyl radical optionally substituted by a phenyl or heteroaryl radical optionally substituted by 1–3 radicals of amino, dimethylamino, acetamido, hydroxy, halo, methoxy, methyl or trifluoromethyl radicals;

(2) trifluoromethyl radical; or (3) aryl or heteroaryl radicals optionally substituted by 1–3 radicals of amino, dimethylamino, acetamido, hydroxy, halo, methoxy, methyl or trifluoromethyl radicals;

most preferably, $R_{30}$ is independently (1) $C_1$–$C_4$ alkyl radical optionally substituted by a phenyl or heteroaryl radical optionally substituted by 1–2 radicals of amino, dimethylamino, acetamido, hydroxy, halo, methoxy, methyl or trifluoromethyl radicals;

(2) trifluoromethyl radical; or (3) aryl or heteroaryl radicals optionally substituted by 1–3 radicals of amino, dimethylamino, acetamido, hydroxy, halo, methoxy, methyl or trifluoromethyl radicals;

each $R_{29}$ is independently hydrogen radical or $R_{30}$; and most preferably, $R_{29}$ is an aryl or heteroaryl radicals optionally substituted by 1–2 radicals of amino, dimethylamino, acetamido, hydroxy, halo, methoxy, methyl or trifluoromethyl radicals;

each $R_{31}$ is independently (1) hydrogen radicals;

(2) alkyl radical optionally substituted by an cycloalkyl, aryl, heterocyclyl or heteroaryl radical optionally substituted by 1–3 radicals of amino, alkylamino, dialkylamino, alkanoylamino, alkoxycarbonylamino, alkylsulfonylamino, hydroxy, alkoxy, alkylthio, cyano, alkyl or haloalkyl; or (3) aryl, heteroaryl, heterocyclyl or cycloalkyl radical optionally substituted by 1–3 radicals of amino, alkylamino, dialkylamino, alkanoylamino, alkoxycarbonylamino, alkylsulfonylamino, hydroxy, alkoxy, alkylthio, cyano, alkyl or haloalkyl;

preferably, each $R_{31}$ is independently (1) hydrogen radicals;

(2) $C_1$–$C_4$ alkyl radical optionally substituted by an $C_3$–$C_8$ cycloalkyl, aryl, heterocyclyl or heteroaryl radical optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, cyano, $C_1$–$C_4$ alkyl or $C_1$–$C_4$ haloalkyl of 1–3 halo radicals; or (3) aryl, heteroaryl, heterocyclyl or $C_3$–$C_8$ cycloalkyl radical optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, cyano, $C_1$–$C_4$ alkyl or $C_1$–$C_4$ haloalkyl of 1–3 halo radicals;

more preferably, each $R_{31}$ is independently (1) hydrogen radicals; or (2) $C_1$–$C_4$ alkyl radical optionally substituted by an phenyl or heteroaryl radical optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, hydroxy, $C_1$–$C_4$ alkoxy, $C_1$–$C_4$ alkylthio, cyano, $C_1$–$C_4$ alkyl or trifluoromethyl radicals;

more preferably, each $R_{31}$ is independently hydrogen or $C_1$–$C_4$ alkyl radicals; and most preferably, each $R_{31}$ is independently hydrogen, methyl or ethyl radicals;

each $R_{32}$ is independently (1) hydrogen radicals;

(2) alkyl radical optionally substituted by an cycloalkyl, aryl, heterocyclyl or heteroaryl radical optionally substituted by 1–3 radicals of amino, alkylamino, dialkylamino, alkanoylamino, alkoxycarbonylamino, alkylsulfonylamino, hydroxy, alkoxy, alkylthio, cyano, alkyl or haloalkyl; or (3) aryl, heteroaryl, heterocyclyl or cycloalkyl radical optionally substituted by 1–3 radicals of amino, alkylamino, dialkylamino, alkanoylamino, alkoxycarbonylamino, alkylsulfonylamino, hydroxy, alkoxy, alkylthio, cyano, alkyl or haloalkyl;

preferably, each $R_{32}$ is independently (1) hydrogen radicals;

(2) $C_1$–$C_4$ alkyl radical optionally substituted by an $C_3$–$C_8$ cycloalkyl, aryl, heterocyclyl or heteroaryl radical optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, cyano, $C_1$–$C_4$ alkyl or $C_1$–$C_4$ haloalkyl of 1–3 halo radicals; or (3) aryl, heteroaryl, heterocyclyl or $C_3$–$C_8$ cycloalkyl radical optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, cyano, $C_1$–$C_4$ alkyl or $C_1$–$C_4$ haloalkyl of 1–3 halo radicals;

more preferably, each $R_{32}$ is independently (1) hydrogen radicals;

(2) $C_1$–$C_4$ alkyl radical optionally substituted by an $C_3$–$C_6$ cycloalkyl, aryl, heterocyclyl or heteroaryl radical optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, cyano, $C_1$–$C_4$ alkyl or $C_1$–$C_4$ haloalkyl of 1–3 halo radicals; or (3) aryl, heteroaryl, heterocyclyl or $C_3$–$C_6$ cycloalkyl radical optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, cyano, $C_1$–$C_4$ alkyl or $C_1$–$C_4$ haloalkyl of 1–3 halo radicals;

more preferably, each $R_{32}$ is independently (1) hydrogen radicals;

(2) $C_1$–$C_4$ alkyl radical optionally substituted by phenyl or heteroaryl radical optionally substituted by 1–3 radicals of amino, $C_1$–$C_4$ alkylamino, di-($C_1$–$C_4$ alkyl) amino, $C_1$–$C_5$ alkanoylamino, ($C_1$–$C_4$ alkoxy) carbonylamino, hydroxy, $C_1$–$C_4$ alkoxy, $C_1$–$C_4$ alkyl or trifluoromethyl radicals; or (3) phenyl or heteroaryl radical optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy) carbonylamino, hydroxy, $C_1$–$C_4$ alkoxy, $C_1$–$C_4$ alkyl or trifluoromethyl radicals;

more preferably, each $R_{32}$ is independently (1) hydrogen radicals;

(2) $C_1$–$C_4$ alkyl radical or $C_1$–$C_2$ alkyl radical substituted by phenyl or heteroaryl radical optionally substituted by 1–3 radicals of amino, dimethylamino, acetamido, hydroxy, methoxy, methyl or trifluoromethyl radicals; or (3) phenyl or heteroaryl radical optionally substituted by 1–3 radicals of amino, dimethylamino, acetamido, hydroxy, methoxy, methyl or trifluoromethyl radicals;

most preferably, $R_{32}$ is independently (1) hydrogen or $C_1$–$C_4$ alkyl radical; or (2) phenyl or heteroaryl radical optionally substituted by 1–2 radicals of amino, dimethylamino, acetamido, hydroxy, methoxy, methyl or trifluoromethyl radicals; and wherein each $R_{33}$ is independently (1) hydrogen radical; or (2) alkyl radical optionally substituted by a radical of heterocyclyl, aryl or heteroaryl optionally substituted by 1–3 radicals of amino, alkylamino, dialkylamino, alkanoylamino, alkoxycarbonylamino, alkylsulfonylamino, hydroxy, alkoxy, alkylthio, cyano, alkyl or haloalkyl;

preferably, each $R_{33}$ is independently (1) hydrogen radical; or (2) $C_1$–$C_4$ alkyl radical optionally substituted by a radical of heterocyclyl, aryl or heteroaryl optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, cyano, $C_1$–$C_4$ alkyl or $C_1$–$C_4$ haloalkyl of 1–3 halo radicals;

more preferably, each $R_{33}$ is independently hydrogen or $C_1$–$C_4$ alkyl radical; and most preferably, each $R_{33}$ is independently hydrogen or methyl radical.

The following provisos relate to compounds of the invention, only, and not to the pharmaceutical compositions or methods of use, which encompass the full breadth of compounds recited above (unless expressly stated otherwise):

1. when $R^1$ and $R^{12}$ are the same and are a 5- or 6-member ring having from 1–3 heteroatoms independently selected from N, S, and O, to which ring a benzene ring is optionally fused, $R^{11}$ is phenyl or naphthyl optionally substituted with halo, $C_1$–$C_6$ alkyl, $C_1$–$C_4$ alkoxy, $C_1$–$C_4$ alkylthiol, hydroxy, amino, $C_1$–$C_4$ alkylamino, or dialkylamino, or $R^{11}$ is a 5- or 6-membered ring having from 1–3 heteroatoms independently selected from N, S, and O, to which ring a benzene ring is optionally fused and optionally substituted with $C_1$–$C_6$ alkyl, then $R^2$ is other than OH or $NH_2$;

2. when $R^2$ is H, $R^{11}$ is phenyl and $R^{12}$ is phenyl or 4-pyridyl, then $R^1$ is other than H, methyl, or amino;

3. when $R^2$ is H, $R^{11}$ is 2-methylphenyl and $R^{12}$ is 2-pyridyl, then $R^1$ is other than n-propyl; and
4. when $R^{11}$ and $R^{12}$ are each an optionally substituted phenyl radical, then $R^1$ is other than an optionally substituted 2-pyridyl radical.

The compounds of this invention may have in general several asymmetric centers and are typically depicted in the form of racemic mixtures. This invention is intended to encompass racemic mixtures, partially racemic mixtures and separate enantiomers and diastereomers.

Compounds of interest include the following:

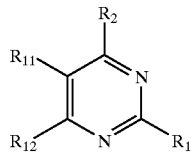

wherein $R^2$ is H and $R^{11}$, $R^{12}$, and $R^1$ are one of the combinations given in the following table:

| $R^{11}$ | $R^{12}$ | $R^1$ |
|---|---|---|
| Phenyl | 4-pyridyl | 1-piperazinyl |
| 4-fluorophenyl | 4-pyridyl | 1-piperazinyl |
| 3-fluorophenyl | 4-pyridyl | 1-piperazinyl |
| 2-fluorophenyl | 4-pyridyl | 1-piperazinyl |
| 4-chlorophenyl | 4-pyridyl | 1-piperazinyl |
| 3-chlorophenyl | 4-pyridyl | 1-piperazinyl |
| 2-chlorophenyl | 4-pyridyl | 1-piperazinyl |
| 4-tolyl | 4-pyridyl | 1-piperazinyl |
| 3-tolyl | 4-pyridyl | 1-piperazinyl |
| 2-tolyl | 4-pyridyl | 1-piperazinyl |
| 4-trifluoromethylphenyl | 4-pyridyl | 1-piperazinyl |
| 3-trifluoromethylphenyl | 4-pyridyl | 1-piperazinyl |
| 2,6-dichlorophenyl | 4-pyridyl | 1-piperazinyl |
| 2,6-dimethylphenyl | 4-pyridyl | 1-piperazinyl |
| 3,4-dichlorophenyl | 4-pyridyl | 1-piperazinyl |
| 3,4-dimethylphenyl | 4-pyridyl | 1-piperazinyl |
| 2,4-dichlorophenyl | 4-pyridyl | 1-piperazinyl |
| 2,4-dimethylphenyl | 4-pyridyl | 1-piperazinyl |
| Phenyl | 2-amino-4-pyridyl | 1-piperazinyl |
| 4-fluorophenyl | 2-amino-4-pyridyl | 1-piperazinyl |
| 3-fluorophenyl | 2-amino-4-pyridyl | 1-piperazinyl |
| 2-fluorophenyl | 2-amino-4-pyridyl | 1-piperazinyl |
| 4-chlorophenyl | 2-amino-4-pyridyl | 1-piperazinyl |
| 3-chlorophenyl | 2-amino-4-pyridyl | 1-piperazinyl |
| 2-chlorophenyl | 2-amino-4-pyridyl | 1-piperazinyl |
| 4-tolyl | 2-amino-4-pyridyl | 1-piperazinyl |
| 3-tolyl | 2-amino-4-pyridyl | 1-piperazinyl |
| 2-tolyl | 2-amino-4-pyridyl | 1-piperazinyl |
| 4-trifluoromethylphenyl | 2-amino-4-pyridyl | 1-piperazinyl |
| 3-trifluoromethylphenyl | 2-amino-4-pyridyl | 1-piperazinyl |
| 2,6-dichlorophenyl | 2-amino-4-pyridyl | 1-piperazinyl |
| 2,6-dimethylphenyl | 2-amino-4-pyridyl | 1-piperazinyl |
| 3,4-dichlorophenyl | 2-amino-4-pyridyl | 1-piperazinyl |
| 3,4-dimethylphenyl | 2-amino-4-pyridyl | 1-piperazinyl |
| 2,4-dichlorophenyl | 2-amino-4-pyridyl | 1-piperazinyl |
| 2,4-dimethylphenyl | 2-amino-4-pyridyl | 1-piperazinyl |
| Phenyl | 2-acetamido-4-pyridyl | 1-piperazinyl |
| 4-fluorophenyl | 2-acetamido-4-pyridyl | 1-piperazinyl |
| 3-fluorophenyl | 2-acetamido-4-pyridyl | 1-piperazinyl |
| 2-fluorophenyl | 2-acetamido-4-pyridyl | 1-piperazinyl |
| 4-chlorophenyl | 2-acetamido-4-pyridyl | 1-piperazinyl |
| 3-chlorophenyl | 2-acetamido-4-pyridyl | 1-piperazinyl |
| 2-chlorophenyl | 2-acetamido-4-pyridyl | 1-piperazinyl |
| 4-tolyl | 2-acetamido-4-pyridyl | 1-piperazinyl |
| 3-tolyl | 2-acetamido-4-pyridyl | 1-piperazinyl |
| 2-tolyl | 2-acetamido-4-pyridyl | 1-piperazinyl |
| 4-trifluoromethylphenyl | 2-acetamido-4-pyridyl | 1-piperazinyl |
| 3-trifluoromethylphenyl | 2-acetamido-4-pyridyl | 1-piperazinyl |
| 2,6-dichlorophenyl | 2-acetamido-4-pyridyl | 1-piperazinyl |
| 2,6-dimethylphenyl | 2-acetamido-4-pyridyl | 1-piperazinyl |
| 3,4-dichlorophenyl | 2-acetamido-4-pyridyl | 1-piperazinyl |
| 3,4-dimethylphenyl | 2-acetamido-4-pyridyl | 1-piperazinyl |
| 2,4-dichlorophenyl | 2-acetamido-4-pyridyl | 1-piperazinyl |
| 2,4-dimethylphenyl | 2-acetamido-4-pyridyl | 1-piperazinyl |
| Phenyl | 2-amino-4-pyrimidinyl | 1-piperazinyl |
| 4-fluorophenyl | 2-amino-4-pyrimidinyl | 1-piperazinyl |
| 3-fluorophenyl | 2-amino-4-pyrimidinyl | 1-piperazinyl |
| 2-fluorophenyl | 2-amino-4-pyrimidinyl | 1-piperazinyl |
| 4-chlorophenyl | 2-amino-4-pyrimidinyl | 1-piperazinyl |
| 3-chlorophenyl | 2-amino-4-pyrimidinyl | 1-piperazinyl |
| 2-chlorophenyl | 2-amino-4-pyrimidinyl | 1-piperazinyl |
| 4-tolyl | 2-amino-4-pyrimidinyl | 1-piperazinyl |
| 3-tolyl | 2-amino-4-pyrimidinyl | 1-piperazinyl |

-continued

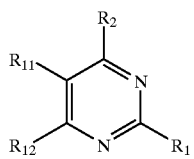

wherein R² is H and R¹¹, R¹², and R¹ are one of the combinations given in the following table:

| R¹¹ | R¹² | R¹ |
|---|---|---|
| 2-tolyl | 2-amino-4-pyrimidinyl | 1-piperazinyl |
| 4-trifluoromethylphenyl | 2-amino-4-pyrimidinyl | 1-piperazinyl |
| 3-trifluoromethylphenyl | 2-amino-4-pyrimidinyl | 1-piperazinyl |
| 2,6-dichlorophenyl | 2-amino-4-pyrimidinyl | 1-piperazinyl |
| 2,6-dimethylphenyl | 2-amino-4-pyrimidinyl | 1-piperazinyl |
| 3,4-dichlorophenyl | 2-amino-4-pyrimidinyl | 1-piperazinyl |
| 3,4-dimethylphenyl | 2-amino-4-pyrimidinyl | 1-piperazinyl |
| 2,4-dichlorophenyl | 2-amino-4-pyrimidinyl | 1-piperazinyl |
| 2,4-dimethylphenyl | 2-amino-4-pyrimidinyl | 1-piperazinyl |
| Phenyl | 4-pyridyl | 2,6-dichlorobenzyl |
| 4-fluorophenyl | 4-pyridyl | 2,6-dichlorobenzyl |
| 3-fluorophenyl | 4-pyridyl | 2,6-dichlorobenzyl |
| 2-fluorophenyl | 4-pyridyl | 2,6-dichlorobenzyl |
| 4-chlorophenyl | 4-pyridyl | 2,6-dichlorobenzyl |
| 3-chlorophenyl | 4-pyridyl | 2,6-dichlorobenzyl |
| 2-chlorophenyl | 4-pyridyl | 2,6-dichlorobenzyl |
| 4-tolyl | 4-pyridyl | 2,6-dichlorobenzyl |
| 3-tolyl | 4-pyridyl | 2,6-dichlorobenzyl |
| 2-tolyl | 4-pyridyl | 2,6-dichlorobenzyl |
| 4-trifluoromethylphenyl | 4-pyridyl | 2,6-dichlorobenzyl |
| 3-trifluoromethylphenyl | 4-pyridyl | 2,6-dichlorobenzyl |
| 2,6-dichlorophenyl | 4-pyridyl | 2,6-dichlorobenzyl |
| 2,6-dimethylphenyl | 4-pyridyl | 2,6-dichlorobenzyl |
| 3,4-dichlorophenyl | 4-pyridyl | 2,6-dichlorobenzyl |
| 3,4-dimethylphenyl | 4-pyridyl | 2,6-dichlorobenzyl |
| 2,4-dichlorophenyl | 4-pyridyl | 2,6-dichlorobenzyl |
| 2,4-dimethylphenyl | 4-pyridyl | 2,6-dichlorobenzyl |
| Phenyl | 2-amino-4-pyridyl | 2,6-dichlorobenzyl |
| 4-fluorophenyl | 2-amino-4-pyridyl | 2,6-dichlorobenzyl |
| 3-fluorophenyl | 2-amino-4-pyridyl | 2,6-dichlorobenzyl |
| 2-fluorophenyl | 2-amino-4-pyridyl | 2,6-dichlorobenzyl |
| 4-chlorophenyl | 2-amino-4-pyridyl | 2,6-dichlorobenzyl |
| 3-chlorophenyl | 2-amino-4-pyridyl | 2,6-dichlorobenzyl |
| 2-chlorophenyl | 2-amino-4-pyridyl | 2,6-dichlorobenzyl |
| 4-tolyl | 2-amino-4-pyridyl | 2,6-dichlorobenzyl |
| 3-tolyl | 2-amino-4-pyridyl | 2,6-dichlorobenzyl |
| 2-tolyl | 2-amino-4-pyridyl | 2,6-dichlorobenzyl |
| 4-trifluoromethylphenyl | 2-amino-4-pyridyl | 2,6-dichlorobenzyl |
| 3-trifluoromethylphenyl | 2-amino-4-pyridyl | 2,6-dichlorobenzyl |
| 2,6-dichlorophenyl | 2-amino-4-pyridyl | 2,6-dichlorobenzyl |
| 2,6-dimethylphenyl | 2-amino-4-pyridyl | 2,6-dichlorobenzyl |
| 3,4-dichlorophenyl | 2-amino-4-pyridyl | 2,6-dichlorobenzyl |
| 3,4-dimethylphenyl | 2-amino-4-pyridyl | 2,6-dichlorobenzyl |
| 2,4-dichlorophenyl | 2-amino-4-pyridyl | 2,6-dichlorobenzyl |
| 2,4-dimethylphenyl | 2-amino-4-pyridyl | 2,6-dichlorobenzyl |
| Phenyl | 2-acetamido-4-pyridyl | 2,6-dichlorobenzyl |
| 4-fluorophenyl | 2-acetamido-4-pyridyl | 2,6-dichlorobenzyl |
| 3-fluorophenyl | 2-acetamido-4-pyridyl | 2,6-dichlorobenzyl |
| 2-fluorophenyl | 2-acetamido-4-pyridyl | 2,6-dichlorobenzyl |
| 4-chlorophenyl | 2-acetamido-4-pyridyl | 2,6-dichlorobenzyl |
| 3-chlorophenyl | 2-acetamido-4-pyridyl | 2,6-dichlorobenzyl |
| 2-chlorophenyl | 2-acetamido-4-pyridyl | 2,6-dichlorobenzyl |
| 4-tolyl | 2-acetamido-4-pyridyl | 2,6-dichlorobenzyl |
| 3-tolyl | 2-acetamido-4-pyridyl | 2,6-dichlorobenzyl |
| 2-tolyl | 2-acetamido-4-pyridyl | 2,6-dichlorobenzyl |
| 4-trifluoromethylphenyl | 2-acetamido-4-pyridyl | 2,6-dichlorobenzyl |
| 3-trifluoromethylphenyl | 2-acetamido-4-pyridyl | 2,6-dichlorobenzyl |
| 2,6-dichlorophenyl | 2-acetamido-4-pyridyl | 2,6-dichlorobenzyl |
| 2,6-dimethylphenyl | 2-acetamido-4-pyridyl | 2,6-dichlorobenzyl |
| 3,4-dichlorophenyl | 2-acetamido-4-pyridyl | 2,6-dichlorobenzyl |
| 3,4-dimethylphenyl | 2-acetamido-4-pyridyl | 2,6-dichlorobenzyl |
| 2,4-dichlorophenyl | 2-acetamido-4-pyridyl | 2,6-dichlorobenzyl |
| 2,4-dimethylphenyl | 2-acetamido-4-pyridyl | 2,6-dichlorobenzyl |
| Phenyl | 2-amino-4-pyrimidinyl | 2,6-dichlorobenzyl |
| 4-fluorophenyl | 2-amino-4-pyrimidinyl | 2,6-dichlorobenzyl |
| 3-fluorophenyl | 2-amino-4-pyrimidinyl | 2,6-dichlorobenzyl |
| 2-fluorophenyl | 2-amino-4-pyrimidinyl | 2,6-dichlorobenzyl |
| 4-chlorophenyl | 2-amino-4-pyrimidinyl | 2,6-dichlorobenzyl |
| 3-chlorophenyl | 2-amino-4-pyrimidinyl | 2,6-dichlorobenzyl |
| 2-chlorophenyl | 2-amino-4-pyrimidinyl | 2,6-dichlorobenzyl |

-continued

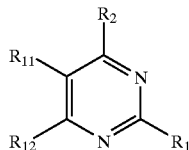

wherein $R^2$ is H and $R^{11}$, $R^{12}$, and $R^1$ are one of the combinations given in the following table:

| $R^{11}$ | $R^{12}$ | $R^1$ |
| --- | --- | --- |
| 4-tolyl | 2-amino-4-pyrimidinyl | 2,6-dichlorobenzyl |
| 3-tolyl | 2-amino-4-pyrimidinyl | 2,6-dichlorobenzyl |
| 2-tolyl | 2-amino-4-pyrimidinyl | 2,6-dichlorobenzyl |
| 4-trifluoromethylphenyl | 2-amino-4-pyrimidinyl | 2,6-dichlorobenzyl |
| 3-trifluoromethylphenyl | 2-amino-4-pyrimidinyl | 2,6-dichlorobenzyl |
| 2,6-dichlorophenyl | 2-amino-4-pyrimidinyl | 2,6-dichlorobenzyl |
| 2,6-dimethylphenyl | 2-amino-4-pyrimidinyl | 2,6-dichlorobenzyl |
| 3,4-dichlorophenyl | 2-amino-4-pyrimidinyl | 2,6-dichlorobenzyl |
| 3,4-dimethylphenyl | 2-amino-4-pyrimidinyl | 2,6-dichlorobenzyl |
| 2,4-dichlorophenyl | 2-amino-4-pyrimidinyl | 2,6-dichlorobenzyl |
| 2,4-dimethylphenyl | 2-amino-4-pyrimidinyl | 2,6-dichlorobenzyl |
| Phenyl | 4-pyridyl | 2-(2-chlorophenyl)ethylamino |
| 4-fluorophenyl | 4-pyridyl | 2-(2-chlorophenyl)ethylamino |
| 3-fluorophenyl | 4-pyridyl | 2-(2-chlorophenyl)ethylamino |
| 2-fluorophenyl | 4-pyridyl | 2-(2-chlorophenyl)ethylamino |
| 4-chlorophenyl | 4-pyridyl | 2-(2-chlorophenyl)ethylamino |
| 3-chlorophenyl | 4-pyridyl | 2-(2-chlorophenyl)ethylamino |
| 2-chlorophenyl | 4-pyridyl | 2-(2-chlorophenyl)ethylamino |
| 4-tolyl | 4-pyridyl | 2-(2-chlorophenyl)ethylamino |
| 3-tolyl | 4-pyridyl | 2-(2-chlorophenyl)ethylamino |
| 2-tolyl | 4-pyridyl | 2-(2-chlorophenyl)ethylamino |
| 4-trifluoromethylphenyl | 4-pyridyl | 2-(2-chlorophenyl)ethylamino |
| 3-trifluoromethylphenyl | 4-pyridyl | 2-(2-chlorophenyl)ethylamino |
| 2,6-dichlorophenyl | 4-pyridyl | 2-(2-chlorophenyl)ethylamino |
| 2,6-dimethylphenyl | 4-pyridyl | 2-(2-chlorophenyl)ethylamino |
| 3,4-dichlorophenyl | 4-pyridyl | 2-(2-chlorophenyl)ethylamino |
| 3,4-dimethylphenyl | 4-pyridyl | 2-(2-chlorophenyl)ethylamino |
| 2,4-dichlorophenyl | 4-pyridyl | 2-(2-chlorophenyl)ethylamino |
| 2,4-dimethylphenyl | 4-pyridyl | 2-(2-chlorophenyl)ethylamino |
| 4-fluorophenyl | 4-pyridyl | 3-(3-fluorophenyl)propylamino |
| 4-fluorophenyl | 2-amino-4-pyrimidinyl | 3-(3-fluorophenyl)propylamino |
| benzyl | 4-pyridyl | 3-phenylpropylamino |
| benzyl | 4-pyridyl | 2-(4-fluorophenyl)ethylamino |

-continued

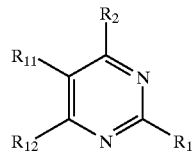

wherein $R^2$ is H and $R^{11}$, $R^{12}$, and $R^1$ are one of the combinations given in the following table:

| $R^{11}$ | $R^{12}$ | $R^1$ |
| --- | --- | --- |
| 2-thienyl | 4-pyridyl | 3-phenylpropylamino |
| 2-thienyl | 4-pyridyl | 2-(4-fluorophenyl)ethylamino |
| cyclohexyl | 4-pyridyl | 3-phenylpropylamino |
| cyclohexyl | 4-pyridyl | 2-(4-fluorophenyl)ethylamino |
| tert-butyl | 4-pyridyl | 3-phenylpropylamino |
| tert-butyl | 4-pyridyl | 2-(4-fluorophenyl)ethylamino |
| 4-fluorophenyl | 4-piperidinyl | 3-phenylpropylamino |
| 4-fluorophenyl | 4-piperidinyl | 2-(4-fluorophenyl)ethylamino |
| 4-fluorophenyl | 4-pyranyl | 3-phenylpropylamino |
| 4-fluorophenyl | 4-pyranyl | 2-(4-fluorophenyl)ethylamino |
| Phenyl | 2-amino-4-pyridyl | 2-(2-chlorophenyl)ethylamino |
| 4-fluorophenyl | 2-amino-4-pyridyl | 2-(2-chlorophenyl)ethylamino |
| 3-fluorophenyl | 2-amino-4-pyridyl | 2-(2-chlorophenyl)ethylamino |
| 2-fluorophenyl | 2-amino-4-pyridyl | 2-(2-chlorophenyl)ethylamino |
| 4-chlorophenyl | 2-amino-4-pyridyl | 2-(2-chlorophenyl)ethylamino |
| 3-chlorophenyl | 2-amino-4-pyridyl | 2-(2-chlorophenyl)ethylamino |
| 2-chlorophenyl | 2-amino-4-pyridyl | 2-(2-chlorophenyl)ethylamino |
| 4-tolyl | 2-amino-4-pyridyl | 2-(2-chlorophenyl)ethylamino |
| 3-tolyl | 2-amino-4-pyridyl | 2-(2-chlorophenyl)ethylamino |
| 2-tolyl | 2-amino-4-pyridyl | 2-(2-chlorophenyl)ethylamino |
| 4-trifluoromethylphenyl | 2-amino-4-pyridyl | 2-(2-chlorophenyl)ethylamino |
| 3-trifluoromethylphenyl | 2-amino-4-pyridyl | 2-(2-chlorophenyl)ethylamino |
| 2,6-dichlorophenyl | 2-amino-4-pyridyl | 2-(2-chlorophenyl)ethylamino |
| 2,6-dimethylphenyl | 2-amino-4-pyridyl | 2-(2-chlorophenyl)ethylamino |
| 3,4-dichlorophenyl | 2-amino-4-pyridyl | 2-(2-chlorophenyl)ethylamino |
| 3,4-dimethylphenyl | 2-amino-4-pyridyl | 2-(2-chlorophenyl)ethylamino |
| 2,4-dichlorophenyl | 2-amino-4-pyridyl | 2-(2-chlorophenyl)ethylamino |
| 2,4-dimethylphenyl | 2-amino-4-pyridyl | 2-(2-chlorophenyl)ethylamino |
| Phenyl | 2-acetamido-4-pyridyl | 2-(2-chlorophenyl)ethylamino |
| 4-fluorophenyl | 2-acetamido-4-pyridyl | 2-(2-chlorophenyl)ethylamino |
| 3-fluorophenyl | 2-acetamido-4-pyridyl | 2-(2-chlorophenyl)ethylamino |
| 2-fluorophenyl | 2-acetamido-4-pyridyl | 2-(2-chlorophenyl)ethylamino |
| 4-chlorophenyl | 2-acetamido-4-pyridyl | 2-(2-chlorophenyl)ethylamino |
| 3-chlorophenyl | 2-acetamido-4-pyridyl | 2-(2-chlorophenyl)ethylamino |

-continued

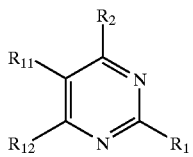

wherein $R^2$ is H and $R^{11}$, $R^{12}$, and $R^1$ are one of the combinations given in the following table:

| $R^{11}$ | $R^{12}$ | $R^1$ |
|---|---|---|
| 2-chlorophenyl | 2-acetamido-4-pyridyl | 2-(2-chlorophenyl)ethylamino |
| 4-tolyl | 2-acetamido-4-pyridyl | 2-(2-chlorophenyl)ethylamino |
| 3-tolyl | 2-acetamido-4-pyridyl | 2-(2-chlorophenyl)ethylamino |
| 2-tolyl | 2-acetamido-4-pyridyl | 2-(2-chlorophenyl)ethylamino |
| 4-trifluoromethylphenyl | 2-acetamido-4-pyridyl | 2-(2-chlorophenyl)ethylamino |
| 3-trifluoromethylphenyl | 2-acetamido-4-pyridyl | 2-(2-chlorophenyl)ethylamino |
| 2,6-dichlorophenyl | 2-acetamido-4-pyridyl | 2-(2-chlorophenyl)ethylamino |
| 2,6-dimethylphenyl | 2-acetamido-4-pyridyl | 2-(2-chlorophenyl)ethylamino |
| 3,4-dichlorophenyl | 2-acetamido-4-pyridyl | 2-(2-chlorophenyl)ethylamino |
| 3,4-dimethylphenyl | 2-acetamido-4-pyridyl | 2-(2-chlorophenyl)ethylamino |
| 2,4-dichlorophenyl | 2-acetamido-4-pyridyl | 2-(2-chlorophenyl)ethylamino |
| 2,4-dimethylphenyl | 2-acetamido-4-pyridyl | 2-(2-chlorophenyl)ethylamino |
| Phenyl | 2-amino-4-pyrimidinyl | 2-(2-chlorophenyl)ethylamino |
| 4-fluorophenyl | 2-amino-4-pyrimidinyl | 2-(2-chlorophenyl)ethylamino |
| 3-fluorophenyl | 2-amino-4-pyrimidinyl | 2-(2-chlorophenyl)ethylamino |
| 2-fluorophenyl | 2-amino-4-pyrimidinyl | 2-(2-chlorophenyl)ethylamino |
| 4-chlorophenyl | 2-amino-4-pyrimidinyl | 2-(2-chlorophenyl)ethylamino |
| 3-chlorophenyl | 2-amino-4-pyrimidinyl | 2-(2-chlorophenyl)ethylamino |
| 2-chlorophenyl | 2-amino-4-pyrimidinyl | 2-(2-chlorophenyl)ethylamino |
| 4-tolyl | 2-amino-4-pyrimidinyl | 2-(2-chlorophenyl)ethylamino |
| 3-tolyl | 2-amino-4-pyrimidinyl | 2-(2-chlorophenyl)ethylamino |
| 2-tolyl | 2-amino-4-pyrimidinyl | 2-(2-chlorophenyl)ethylamino |
| 4-trifluoromethylphenyl | 2-amino-4-pyrimidinyl | 2-(2-chlorophenyl)ethylamino |
| 3-trifluoromethylphenyl | 2-amino-4-pyrimidinyl | 2-(2-chlorophenyl)ethylamino |
| 2,6-dichlorophenyl | 2-amino-4-pyrimidinyl | 2-(2-chlorophenyl)ethylamino |
| 2,6-dimethylphenyl | 2-amino-4-pyrimidinyl | 2-(2-chlorophenyl)ethylamino |
| 3,4-dichlorophenyl | 2-amino-4-pyrimidinyl | 2-(2-chlorophenyl)ethylamino |
| 3,4-dimethylphenyl | 2-amino-4-pyrimidinyl | 2-(2-chlorophenyl)ethylamino |
| 2,4-dichlorophenyl | 2-amino-4-pyrimidinyl | 2-(2-chlorophenyl)ethylamino |
| 2,4-dimethylphenyl | 2-amino-4-pyrimidinyl | 2-(2-chlorophenyl)ethylamino |
| Phenyl | 4-pyridyl | 2-(4-fluorophenyl)ethylamino |
| 4-fluorophenyl | 4-pyridyl | 2-(4-fluorophenyl)ethylamino |

-continued

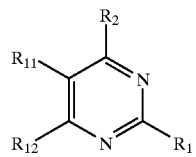

wherein $R^2$ is H and $R^{11}$, $R^{12}$, and $R^1$ are one of the combinations given in the following table:

| $R^{11}$ | $R^{12}$ | $R^1$ |
|---|---|---|
| 3-fluorophenyl | 4-pyridyl | 2-(4-fluorophenyl)ethylamino |
| 2-fluorophenyl | 4-pyridyl | 2-(4-fluorophenyl)ethylamino |
| 4-chlorophenyl | 4-pyridyl | 2-(4-fluorophenyl)ethylamino |
| 3-chlorophenyl | 4-pyridyl | 2-(4-fluorophenyl)ethylamino |
| 2-chlorophenyl | 4-pyridyl | 2-(4-fluorophenyl)ethylamino |
| 4-tolyl | 4-pyridyl | 2-(4-fluorophenyl)ethylamino |
| 3-tolyl | 4-pyridyl | 2-(4-fluorophenyl)ethylamino |
| 2-tolyl | 4-pyridyl | 2-(4-fluorophenyl)ethylamino |
| 4-trifluoromethylphenyl | 4-pyridyl | 2-(4-fluorophenyl)ethylamino |
| 3-trifluoromethylphenyl | 4-pyridyl | 2-(4-fluorophenyl)ethylamino |
| 2,6-dichlorophenyl | 4-pyridyl | 2-(4-fluorophenyl)ethylamino |
| 2,6-dimethylphenyl | 4-pyridyl | 2-(4-fluorophenyl)ethylamino |
| 3,4-dichlorophenyl | 4-pyridyl | 2-(4-fluorophenyl)ethylamino |
| 3,4-dimethylphenyl | 4-pyridyl | 2-(4-fluorophenyl)ethylamino |
| 2,4-dichlorophenyl | 4-pyridyl | 2-(4-fluorophenyl)ethylamino |
| 2,4-dimethylphenyl | 4-pyridyl | 2-(4-fluorophenyl)ethylamino |
| Phenyl | 2-amino-4-pyridyl | 2-(4-fluorophenyl)ethylamino |
| 4-fluorophenyl | 2-amino-4-pyridyl | 2-(4-fluorophenyl)ethylamino |
| 3-fluorophenyl | 2-amino-4-pyridyl | 2-(4-fluorophenyl)ethylamino |
| 2-fluorophenyl | 2-amino-4-pyridyl | 2-(4-fluorophenyl)ethylamino |
| 4-chlorophenyl | 2-amino-4-pyridyl | 2-(4-fluorophenyl)ethylamino |
| 3-chlorophenyl | 2-amino-4-pyridyl | 2-(4-fluorophenyl)ethylamino |
| 2-chlorophenyl | 2-amino-4-pyridyl | 2-(4-fluorophenyl)ethylamino |
| 4-tolyl | 2-amino-4-pyridyl | 2-(4-fluorophenyl)ethylamino |
| 3-tolyl | 2-amino-4-pyridyl | 2-(4-fluorophenyl)ethylamino |
| 2-tolyl | 2-amino-4-pyridyl | 2-(4-fluorophenyl)ethylamino |
| 4-trifluoromethylphenyl | 2-amino-4-pyridyl | 2-(4-fluorophenyl)ethylamino |
| 3-trifluoromethylphenyl | 2-amino-4-pyridyl | 2-(4-fluorophenyl)ethylamino |
| 2,6-dichlorophenyl | 2-amino-4-pyridyl | 2-(4-fluorophenyl)ethylamino |
| 2,6-dimethylphenyl | 2-amino-4-pyridyl | 2-(4-fluorophenyl)ethylamino |
| 3,4-dichlorophenyl | 2-amino-4-pyridyl | 2-(4-fluorophenyl)ethylamino |
| 3,4-dimethylphenyl | 2-amino-4-pyridyl | 2-(4-fluorophenyl)ethylamino |
| 2,4-dichlorophenyl | 2-amino-4-pyridyl | 2-(4-fluorophenyl)ethylamino |

-continued

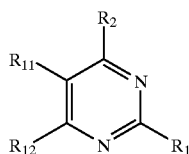

wherein $R^2$ is H and $R^{11}$, $R^{12}$, and $R^1$ are one of the combinations given in the following table:

| $R^{11}$ | $R^{12}$ | $R^1$ |
|---|---|---|
| 2,4-dimethylphenyl | 2-amino-4-pyridyl | 2-(4-fluorophenyl)ethylamino |
| Phenyl | 2-acetamido-4-pyridyl | 2-(4-fluorophenyl)ethylamino |
| 4-fluorophenyl | 2-acetamido-4-pyridyl | 2-(4-fluorophenyl)ethylamino |
| 3-fluorophenyl | 2-acetamido-4-pyridyl | 2-(4-fluorophenyl)ethylamino |
| 2-fluorophenyl | 2-acetamido-4-pyridyl | 2-(4-fluorophenyl)ethylamino |
| 4-chlorophenyl | 2-acetamido-4-pyridyl | 2-(4-fluorophenyl)ethylamino |
| 3-chlorophenyl | 2-acetamido-4-pyridyl | 2-(4-fluorophenyl)ethylamino |
| 2-chlorophenyl | 2-acetamido-4-pyridyl | 2-(4-fluorophenyl)ethylamino |
| 4-tolyl | 2-acetamido-4-pyridyl | 2-(4-fluorophenyl)ethylamino |
| 3-tolyl | 2-acetamido-4-pyridyl | 2-(4-fluorophenyl)ethylamino |
| 2-tolyl | 2-acetamido-4-pyridyl | 2-(4-fluorophenyl)ethylamino |
| 4-trifluoromethylphenyl | 2-acetamido-4-pyridyl | 2-(4-fluorophenyl)ethylamino |
| 3-trifluoromethylphenyl | 2-acetamido-4-pyridyl | 2-(4-fluorophenyl)ethylamino |
| 2,6-dichlorophenyl | 2-acetamido-4-pyridyl | 2-(4-fluorophenyl)ethylamino |
| 2,6-dimethylphenyl | 2-acetamido-4-pyridyl | 2-(4-fluorophenyl)ethylamino |
| 3,4-dichlorophenyl | 2-acetamido-4-pyridyl | 2-(4-fluorophenyl)ethylamino |
| 3,4-dimethylphenyl | 2-acetamido-4-pyridyl | 2-(4-fluorophenyl)ethylamino |
| 2,4-dichlorophenyl | 2-acetamido-4-pyridyl | 2-(4-fluorophenyl)ethylamino |
| 2,4-dimethylphenyl | 2-acetamido-4-pyridyl | 2-(4-fluorophenyl)ethylamino |
| Phenyl | 2-amino-4-pyrimidinyl | 2-(4-fluorophenyl)ethylamino |
| 4-fluorophenyl | 2-amino-4-pyrimidinyl | 2-(4-fluorophenyl)ethylamino |
| 3-fluorophenyl | 2-amino-4-pyrimidinyl | 2-(4-fluorophenyl)ethylamino |
| 2-fluorophenyl | 2-amino-4-pyrimidinyl | 2-(4-fluorophenyl)ethylamino |
| 4-chlorophenyl | 2-amino-4-pyrimidinyl | 2-(4-fluorophenyl)ethylamino |
| 3-chlorophenyl | 2-amino-4-pyrimidinyl | 2-(4-fluorophenyl)ethylamino |
| 2-chlorophenyl | 2-amino-4-pyrimidinyl | 2-(4-fluorophenyl)ethylamino |
| 4-tolyl | 2-amino-4-pyrimidinyl | 2-(4-fluorophenyl)ethylamino |
| 3-tolyl | 2-amino-4-pyrimidinyl | 2-(4-fluorophenyl)ethylamino |
| 2-tolyl | 2-amino-4-pyrimidinyl | 2-(4-fluorophenyl)ethylamino |
| 4-trifluoromethylphenyl | 2-amino-4-pyrimidinyl | 2-(4-fluorophenyl)ethylamino |
| 3-trifluoromethylphenyl | 2-amino-4-pyrimidinyl | 2-(4-fluorophenyl)ethylamino |
| 2,6-dichlorophenyl | 2-amino-4-pyrimidinyl | 2-(4-fluorophenyl)ethylamino |
| 2,6-dimethylphenyl | 2-amino-4-pyrimidinyl | 2-(4-fluorophenyl)ethylamino |
| 3,4-dichlorophenyl | 2-amino-4-pyrimidinyl | 2-(4-fluorophenyl)ethylamino |
| 3,4-dimethylphenyl | 2-amino-4-pyrimidinyl | 2-(4-fluorophenyl)ethylamino |
| 2,4-dichlorophenyl | 2-amino-4-pyrimidinyl | 2-(4-fluorophenyl)ethylamino |
| 2,4-dimethylphenyl | 2-amino-4-pyrimidinyl | 2-(4-fluorophenyl)ethylamino |
| Phenyl | 4-pyridyl | 3-phenylpropylamino |
| 4-fluorophenyl | 4-pyridyl | 3-phenylpropylamino |
| 3-fluorophenyl | 4-pyridyl | 3-phenylpropylamino |
| 2-fluorophenyl | 4-pyridyl | 3-phenylpropylamino |
| 4-chlorophenyl | 4-pyridyl | 3-phenylpropylamino |
| 3-chlorophenyl | 4-pyridyl | 3-phenylpropylamino |
| 2-chlorophenyl | 4-pyridyl | 3-phenylpropylamino |
| 4-tolyl | 4-pyridyl | 3-phenylpropylamino |
| 3-tolyl | 4-pyridyl | 3-phenylpropylamino |
| 2-tolyl | 4-pyridyl | 3-phenylpropylamino |
| 4-trifluoromethylphenyl | 4-pyridyl | 3-phenylpropylamino |
| 3-trifluoromethylphenyl | 4-pyridyl | 3-phenylpropylamino |
| 2,6-dichlorophenyl | 4-pyridyl | 3-phenylpropylamino |
| 2,6-dimethylphenyl | 4-pyridyl | 3-phenylpropylamino |
| 3,4-dichlorophenyl | 4-pyridyl | 3-phenylpropylamino |
| 3,4-dimethylphenyl | 4-pyridyl | 3-phenylpropylamino |
| 2,4-dichlorophenyl | 4-pyridyl | 3-phenylpropylamino |
| 2,4-dimethylphenyl | 4-pyridyl | 3-phenylpropylamino |
| Phenyl | 2-amino-4-pyridyl | 3-phenylpropylamino |
| 4-fluorophenyl | 2-amino-4-pyridyl | 3-phenylpropylamino |
| 3-fluorophenyl | 2-amino-4-pyridyl | 3-phenylpropylamino |
| 2-fluorophenyl | 2-amino-4-pyridyl | 3-phenylpropylamino |
| 4-chlorophenyl | 2-amino-4-pyridyl | 3-phenylpropylamino |
| 3-chlorophenyl | 2-amino-4-pyridyl | 3-phenylpropylamino |
| 2-chlorophenyl | 2-amino-4-pyridyl | 3-phenylpropylamino |
| 4-tolyl | 2-amino-4-pyridyl | 3-phenylpropylamino |
| 3-tolyl | 2-amino-4-pyridyl | 3-phenylpropylamino |
| 2-tolyl | 2-amino-4-pyridyl | 3-phenylpropylamino |
| 4-trifluoromethylphenyl | 2-amino-4-pyridyl | 3-phenylpropylamino |
| 3-trifluoromethylphenyl | 2-amino-4-pyridyl | 3-phenylpropylamino |
| 2,6-dichlorophenyl | 2-amino-4-pyridyl | 3-phenylpropylamino |
| 2,6-dimethylphenyl | 2-amino-4-pyridyl | 3-phenylpropylamino |
| 3,4-dichlorophenyl | 2-amino-4-pyridyl | 3-phenylpropylamino |

-continued

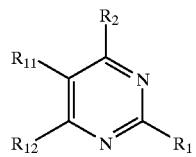

wherein $R^2$ is H and $R^{11}$, $R^{12}$, and $R^1$ are one of the combinations given in the following table:

| $R^{11}$ | $R^{12}$ | $R^1$ |
|---|---|---|
| 3,4-dimethylphenyl | 2-amino-4-pyridyl | 3-phenylpropylamino |
| 2,4-dichlorophenyl | 2-amino-4-pyridyl | 3-phenylpropylamino |
| 2,4-dimethylphenyl | 2-amino-4-pyridyl | 3-phenylpropylamino |
| Phenyl | 2-acetamido-4-pyridyl | 3-phenylpropylamino |
| 4-fluorophenyl | 2-acetamido-4-pyridyl | 3-phenylpropylamino |
| 3-fluorophenyl | 2-acetamido-4-pyridyl | 3-phenylpropylamino |
| 2-fluorophenyl | 2-acetamido-4-pyridyl | 3-phenylpropylamino |
| 4-chlorophenyl | 2-acetamido-4-pyridyl | 3-phenylpropylamino |
| 3-chlorophenyl | 2-acetamido-4-pyridyl | 3-phenylpropylamino |
| 2-chlorophenyl | 2-acetamido-4-pyridyl | 3-phenylpropylamino |
| 4-tolyl | 2-acetamido-4-pyridyl | 3-phenylpropylamino |
| 3-tolyl | 2-acetamido-4-pyridyl | 3-phenylpropylamino |
| 2-tolyl | 2-acetamido-4-pyridyl | 3-phenylpropylamino |
| 4-trifluoromethylphenyl | 2-acetamido-4-pyridyl | 3-phenylpropylamino |
| 3-trifluoromethylphenyl | 2-acetamido-4-pyridyl | 3-phenylpropylamino |
| 2,6-dichlorophenyl | 2-acetamido-4-pyridyl | 3-phenylpropylamino |
| 2,6-dimethylphenyl | 2-acetamido-4-pyridyl | 3-phenylpropylamino |
| 3,4-dichlorophenyl | 2-acetamido-4-pyridyl | 3-phenylpropylamino |
| 3,4-dimethylphenyl | 2-acetamido-4-pyridyl | 3-phenylpropylamino |
| 2,4-dichlorophenyl | 2-acetamido-4-pyridyl | 3-phenylpropylamino |
| 2,4-dimethylphenyl | 2-acetamido-4-pyridyl | 3-phenylpropylamino |
| Phenyl | 2-amino-4-pyrimidinyl | 3-phenylpropylamino |
| 4-fluorophenyl | 2-amino-4-pyrimidinyl | 3-phenylpropylamino |
| 3-fluorophenyl | 2-amino-4-pyrimidinyl | 3-phenylpropylamino |
| 2-fluorophenyl | 2-amino-4-pyrimidinyl | 3-phenylpropylamino |
| 4-chlorophenyl | 2-amino-4-pyrimidinyl | 3-phenylpropylamino |
| 3-chlorophenyl | 2-amino-4-pyrimidinyl | 3-phenylpropylamino |
| 2-chlorophenyl | 2-amino-4-pyrimidinyl | 3-phenylpropylamino |
| 4-tolyl | 2-amino-4-pyrimidinyl | 3-phenylpropylamino |
| 3-tolyl | 2-amino-4-pyrimidinyl | 3-phenylpropylamino |
| 2-tolyl | 2-amino-4-pyrimidinyl | 3-phenylpropylamino |
| 4-trifluoromethylphenyl | 2-amino-4-pyrimidinyl | 3-phenylpropylamino |
| 3-trifluoromethylphenyl | 2-amino-4-pyrimidinyl | 3-phenylpropylamino |

-continued

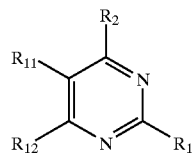

wherein $R^2$ is H and $R^{11}$, $R^{12}$, and $R^1$ are one of the combinations given in the following table:

| $R^{11}$ | $R^{12}$ | $R^1$ |
|---|---|---|
| 2,6-dichlorophenyl | 2-amino-4-pyrimidinyl | 3-phenylpropylamino |
| 2,6-dimethylphenyl | 2-amino-4-pyrimidinyl | 3-phenylpropylamino |
| 3,4-dichlorophenyl | 2-amino-4-pyrimidinyl | 3-phenylpropylamino |
| 3,4-dimethylphenyl | 2-amino-4-pyrimidinyl | 3-phenylpropylamino |
| 2,4-dichlorophenyl | 2-amino-4-pyrimidinyl | 3-phenylpropylamino |
| 2,4-dimethylphenyl | 2-amino-4-pyrimidinyl | 3-phenylpropylamino |
| Phenyl | 4-pyridyl | 3-imidazolylpropylamino |
| 4-fluorophenyl | 4-pyridyl | 3-imidazolylpropylamino |
| 3-fluorophenyl | 4-pyridyl | 3-imidazolylpropylamino |
| 2-fluorophenyl | 4-pyridyl | 3-imidazolylpropylamino |
| 4-chlorophenyl | 4-pyridyl | 3-imidazolylpropylamino |
| 3-chlorophenyl | 4-pyridyl | 3-imidazolylpropylamino |
| 2-chlorophenyl | 4-pyridyl | 3-imidazolylpropylamino |
| 4-tolyl | 4-pyridyl | 3-imidazolylpropylamino |
| 3-tolyl | 4-pyridyl | 3-imidazolylpropylamino |
| 2-tolyl | 4-pyridyl | 3-imidazolylpropylamino |
| 4-trifluoromethylphenyl | 4-pyridyl | 3-imidazolylpropylamino |
| 3-trifluoromethylphenyl | 4-pyridyl | 3-imidazolylpropylamino |
| 2,6-dichlorophenyl | 4-pyridyl | 3-imidazolylpropylamino |
| 2,6-dimethylphenyl | 4-pyridyl | 3-imidazolylpropylamino |
| 3,4-dichlorophenyl | 4-pyridyl | 3-imidazolylpropylamino |
| 3,4-dimethylphenyl | 4-pyridyl | 3-imidazolylpropylamino |
| 2,4-dichlorophenyl | 4-pyridyl | 3-imidazolylpropylamino |
| 2,4-dimethylphenyl | 4-pyridyl | 3-imidazolylpropylamino |
| Phenyl | 2-amino-4-pyridyl | 3-imidazolylpropylamino |
| 4-fluorophenyl | 2-amino-4-pyridyl | 3-imidazolylpropylamino |
| 3-fluorophenyl | 2-amino-4-pyridyl | 3-imidazolylpropylamino |
| 2-fluorophenyl | 2-amino-4-pyridyl | 3-imidazolylpropylamino |
| 4-chlorophenyl | 2-amino-4-pyridyl | 3-imidazolylpropylamino |
| 3-chlorophenyl | 2-amino-4-pyridyl | 3-imidazolylpropylamino |
| 2-chlorophenyl | 2-amino-4-pyridyl | 3-imidazolylpropylamino |
| 4-tolyl | 2-amino-4-pyridyl | 3-imidazolylpropylamino |
| 3-tolyl | 2-amino-4-pyridyl | 3-imidazolylpropylamino |
| 2-tolyl | 2-amino-4-pyridyl | 3-imidazolylpropylamino |
| 4-trifluoromethylphenyl | 2-amino-4-pyridyl | 3-imidazolylpropylamino |
| 3-trifluoromethylphenyl | 2-amino-4-pyridyl | 3-imidazolylpropylamino |
| 2,6-dichlorophenyl | 2-amino-4-pyridyl | 3-imidazolylpropylamino |

-continued

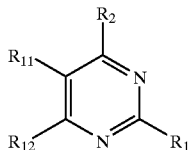

wherein R² is H and R¹¹, R¹², and R¹ are one of the combinations given in the following table:

| R¹¹ | R¹² | R¹ |
|---|---|---|
| 2,6-dimethylphenyl | 2-amino-4-pyridyl | 3-imidazolylpropylamino |
| 3,4-dichlorophenyl | 2-amino-4-pyridyl | 3-imidazolylpropylamino |
| 3,4-dimethylphenyl | 2-amino-4-pyridyl | 3-imidazolylpropylamino |
| 2,4-dichlorophenyl | 2-amino-4-pyridyl | 3-imidazolylpropylamino |
| 2,4-dimethylphenyl | 2-amino-4-pyridyl | 3-imidazolylpropylamino |
| Phenyl | 2-acetamido-4-pyridyl | 3-imidazolylpropylamino |
| 4-fluorophenyl | 2-acetamido-4-pyridyl | 3-imidazolylpropylamino |
| 3-fluorophenyl | 2-acetamido-4-pyridyl | 3-imidazolylpropylamino |
| 2-fluorophenyl | 2-acetamido-4-pyridyl | 3-imidazolylpropylamino |
| 4-chlorophenyl | 2-acetamido-4-pyridyl | 3-imidazolylpropylamino |
| 3-chlorophenyl | 2-acetamido-4-pyridyl | 3-imidazolylpropylamino |
| 2-chlorophenyl | 2-acetamido-4-pyridyl | 3-imidazolylpropylamino |
| 4-tolyl | 2-acetamido-4-pyridyl | 3-imidazolylpropylamino |
| 3-tolyl | 2-acetamido-4-pyridyl | 3-imidazolylpropylamino |
| 2-tolyl | 2-acetamido-4-pyridyl | 3-imidazolylpropylamino |
| 4-trifluoromethylphenyl | 2-acetamido-4-pyridyl | 3-imidazolylpropylamino |
| 3-trifluoromethylphenyl | 2-acetamido-4-pyridyl | 3-imidazolylpropylamino |
| 2,6-dichlorophenyl | 2-acetamido-4-pyridyl | 3-imidazolylpropylamino |
| 2,6-dimethylphenyl | 2-acetamido-4-pyridyl | 3-imidazolylpropylamino |
| 3,4-dichlorophenyl | 2-acetamido-4-pyridyl | 3-imidazolylpropylamino |
| 3,4-dimethylphenyl | 2-acetamido-4-pyridyl | 3-imidazolylpropylamino |
| 2,4-dichlorophenyl | 2-acetamido-4-pyridyl | 3-imidazolylpropylamino |
| 2,4-dimethylphenyl | 2-acetamido-4-pyridyl | 3-imidazolylpropylamino |
| Phenyl | 2-amino-4-pyrimidinyl | 3-imidazolylpropylamino |
| 4-fluorophenyl | 2-amino-4-pyrimidinyl | 3-imidazolylpropylamino |
| 3-fluorophenyl | 2-amino-4-pyrimidinyl | 3-imidazolylpropylamino |
| 2-fluorophenyl | 2-amino-4-pyrimidinyl | 3-imidazolylpropylamino |
| 4-chlorophenyl | 2-amino-4-pyrimidinyl | 3-imidazolylpropylamino |
| 3-chlorophenyl | 2-amino-4-pyrimidinyl | 3-imidazolylpropylamino |
| 2-chlorophenyl | 2-amino-4-pyrimidinyl | 3-imidazolylpropylamino |
| 4-tolyl | 2-amino-4-pyrimidinyl | 3-imidazolylpropylamino |
| 3-tolyl | 2-amino-4-pyrimidinyl | 3-imidazolylpropylamino |
| 2-tolyl | 2-amino-4-pyrimidinyl | 3-imidazolylpropylamino |
| 4-trifluoromethylphenyl | 2-amino-4-pyrimidinyl | 3-imidazolylpropylamino |
| 3-trifluoromethylphenyl | 2-amino-4-pyrimidinyl | 3-imidazolylpropylamino |
| 2,6-dichlorophenyl | 2-amino-4-pyrimidinyl | 3-imidazolylpropylamino |
| 2,6-dimethylphenyl | 2-amino-4-pyrimidinyl | 3-imidazolylpropylamino |
| 3,4-dichlorophenyl | 2-amino-4-pyrimidinyl | 3-imidazolylpropylamino |
| 3,4-dimethylphenyl | 2-amino-4-pyrimidinyl | 3-imidazolylpropylamino |
| 2,4-dichlorophenyl | 2-amino-4-pyrimidinyl | 3-imidazolylpropylamino |
| 2,4-dimethylphenyl | 2-amino-4-pyrimidinyl | 3-imidazolylpropylamino |
| 4-fluorophenyl | 4-pyridyl | 4-fluorobenzylamino |
| 4-fluorophenyl | 2-acetamido-4-pyridyl | 4-fluorobenzylamino |
| 4-fluorophenyl | 2-amino-4-pyrimidinyl | 4-fluorobenzylamino |
| 4-fluorophenyl | 4-pyridyl | 2-(2-chlorophenyl-1-methyl)ethyl)amino |
| 4-fluorophenyl | 2-acetamido-4-pyridyl | 2-(2-chlorophenyl-1-methyl)ethyl)amino |
| 4-fluorophenyl | 2-amino-4-pyrimidinyl | 2-(2-chlorophenyl-1-methyl)ethyl)amino |
| 4-fluorophenyl | 4-pyridyl | (3-(4-fluorophenyl)-propyl)amino |
| 4-fluorophenyl | 2-acetamido-4-pyridyl | (3-(4-fluorophenyl)-propyl)amino |
| 4-fluorophenyl | 2-amino-4-pyrimidinyl | (3-(4-fluorophenyl)-propyl)amino |
| 4-fluorophenyl | 4-pyridyl | (3-(4-fluorophenyl)-1-methyl-propyl)amino |
| 4-fluorophenyl | 2-acetamido-4-pyridyl | (3-(4-fluorophenyl)-1-methyl-propyl)amino |
| 4-fluorophenyl | 2-amino-4-pyrimidinyl | (3-(4-fluorophenyl)-1-methyl-propyl)amino |
| 4-fluorophenyl | 4-pyridyl | (1,1-dimethyl-3-(4-fluoro-phenyl)-propyl)amino |
| 4-fluorophenyl | 2-acetamido-4-pyridyl | (1,1-dimethyl-3-(4-fluoro-phenyl)-propyl)amino |
| 4-fluorophenyl | 2-amino-4-pyrimidinyl | (1,1-dimethyl-3-(4-fluoro-phenyl)-propyl)amino |
| 4-fluorophenyl | 4-pyridyl | (3-(2-fluorophenyl)-propyl)amino |
| 4-fluorophenyl | 2-acetamido-4-pyridyl | (3-(2-fluorophenyl)-propyl)amino |
| 4-fluorophenyl | 2-amino-4-pyrimidinyl | (3-(2-fluorophenyl)-propyl)amino |
| 4-fluorophenyl | 4-pyridyl | (3-methyl-3-phenylpropyl)amino |
| 4-fluorophenyl | 2-acetamido-4-pyridyl | (3-methyl-3-phenylpropyl)amino |
| 4-fluorophenyl | 2-amino-4-pyrimidinyl | (3-methyl-3-phenylpropyl)amino |
| 4-fluorophenyl | 4-pyridyl | (2-methyl-3-phenyl-propyl)amino |

-continued

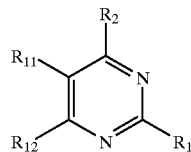

wherein R² is H and R¹¹, R¹², and R¹ are one of the combinations given in the following table:

| R¹¹ | R¹² | R¹ |
|---|---|---|
| 4-fluorophenyl | 2-acetamido-4-pyridyl | (2-methyl-3-phenyl-propyl)amino |
| 4-fluorophenyl | 2-amino-4-pyrimidinyl | (2-methyl-3-phenyl-propyl)amino |
| 3-fluorophenyl | 4-pyridyl | (S)-tetrahydroisoquinol-3-ylmethylenamino |
| 2-fluorophenyl | 2-amino-4-pyridyl | (S)-3-benzylpiperazinyl |
| 3-chlorophenyl | 2-acetamido-4-pyridyl | (S)-2-N-isopropylamino-3-phenylpropylamino |
| 2-chlorophenyl | 2-amino-4-pyrimidinyl | (S)-2-N-glycylamino-3-phenylpropylamino |
| 4-tolyl | 4-pyridyl | (S)-2-amino-3-phenylpropylamino |
| 3-tolyl | 2-amino-4-pyridyl | (R)-2-amino-3-phenylpropylamino |
| 2-tolyl | 2-acetamido-4-pyridyl | 3-amino-3-phenylpropyl amino |
| 4-trifluoro-methylphenyl | 2-amino-4-pyrimidinyl | (S)-2-amino-3-(2-fluorophenyl)propylamino |
| 3-trifluoro-methylphenyl | 4-pyridyl | (S)-2-amino-3-(2-methylphenyl)propylamino |
| 2,6-dichlorophenyl | 2-amino-4-pyridyl | 3-amino-3-(2-fluorophenyl)propylamino |
| 2,6-dimethyl phenyl | 2-acetamido-4-pyridyl | 3-amino-3-(2-methylphenyl)propylamino |
| 3,4-dichlorophenyl | 2-amino-4-pyrimidinyl | 2-amino-2-methyl-3-phenylpropylamino |
| 3,4-dimethyl phenyl | 4-pyridyl | 3-amino-2-methyl-3-phenylpropylamino |
| 3-fluorophenyl | 2-amino-4-pyridyl | (S)-2-amino-3-phenylpropylamino |
| 2-fluorophenyl | 2-acetamido-4-pyridyl | (S)-2-amino-3-(2-fluorophenyl)propylamino |
| 3-chlorophenyl | 2-amino-4-pyrimidinyl | (S)-2-amino-3-(2-methylphenyl)propylamino |
| 2-chlorophenyl | 4-pyridyl | (S)-2-N-isopropylamino-3-phenylpropylamino |
| 4-tolyl | 2-amino-4-pyridyl | (S)-2-N-glycylamino-3-phenylpropylamino |
| 3-tolyl | 2-acetamido-4-pyridyl | 2-amino-2-methyl-3-phenylpropylamino |
| 2-tolyl | 2-amino-4-pyrimidinyl | (R)-2-amino-3-phenylpropylamino |
| 4-trifluoro-methylphenyl | 4-pyridyl | 3-amino-3-phenylpropylamino |
| 3-trifluoro-methylphenyl | 2-amino-4-pyridyl | 3-amino-3-(2-fluorophenyl)propylamino |
| 2,6-dichlorophenyl | 2-acetamido-4-pyridyl | 3-amino-3-(2-methylphenyl)propylamino |
| 2,6-dimethyl phenyl | 2-amino-4-pyrimidinyl | 3-amino-2-methyl-3-phenylpropylamino |
| 3,4-dichlorophenyl | 4-pyridyl | (S)-tetrahydroisoquinol-3-ylmethylenamino |
| 3,4-dimethyl phenyl | 4-pyridyl | (S)-3-benzylpiperazinyl | and

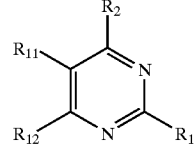

wherein R² is —OH and R¹¹, R¹², and R¹ are one of the combinations given in the following table:

| R¹¹ | R¹² | R¹ |
|---|---|---|
| Phenyl | 4-pyridyl | 4-pyridyl |
| 4-fluorophenyl | 4-pyridyl | 4-pyridyl |
| 3-fluorophenyl | 4-pyridyl | 4-pyridyl |
| 2-fluorophenyl | 4-pyridyl | 4-pyridyl |
| 4-chlorophenyl | 4-pyridyl | 4-pyridyl |
| 3-chlorophenyl | 4-pyridyl | 4-pyridyl |
| 2-chlorophenyl | 4-pyridyl | 4-pyridyl |
| 4-tolyl | 4-pyridyl | 4-pyridyl |
| 3-tolyl | 4-pyridyl | 4-pyridyl |
| 2-tolyl | 4-pyridyl | 4-pyridyl |
| 4-trifluoro-methylphenyl | 4-pyridyl | 4-pyridyl |
| 3-trifluoro-methylphenyl | 4-pyridyl | 4-pyridyl |
| 2,6-dichlorophenyl | 4-pyridyl | 4-pyridyl |
| 2,6-dimethyl phenyl | 4-pyridyl | 4-pyridyl |
| 3,4-dichlorophenyl | 4-pyridyl | 4-pyridyl |
| 3,4-dimethyl phenyl | 4-pyridyl | 4-pyridyl |
| 2,4-dichlorophenyl | 4-pyridyl | 4-pyridyl |
| 2,4-dimethyl phenyl | 4-pyridyl | 4-pyridyl |
| Phenyl | 2-amino-4-pyridyl | 4-pyridyl |
| 4-fluorophenyl | 2-amino-4-pyridyl | 4-pyridyl |
| 3-fluorophenyl | 2-amino-4-pyridyl | 4-pyridyl |
| 2-fluorophenyl | 2-amino-4-pyridyl | 4-pyridyl |
| 4-chlorophenyl | 2-amino-4-pyridyl | 4-pyridyl |
| 3-chlorophenyl | 2-amino-4-pyridyl | 4-pyridyl |
| 2-chlorophenyl | 2-amino-4-pyridyl | 4-pyridyl |
| 4-tolyl | 2-amino-4-pyridyl | 4-pyridyl |
| 3-tolyl | 2-amino-4-pyridyl | 4-pyridyl |
| 2-tolyl | 2-amino-4-pyridyl | 4-pyridyl |
| 4-trifluoro-methylphenyl | 2-amino-4-pyridyl | 4-pyridyl |
| 3-trifluoro-methylphenyl | 2-amino-4-pyridyl | 4-pyridyl |
| 2,6-dichlorophenyl | 2-amino-4-pyridyl | 4-pyridyl |
| 2,6-dimethyl phenyl | 2-amino-4-pyridyl | 4-pyridyl |
| 3,4-dichlorophenyl | 2-amino-4-pyridyl | 4-pyridyl |
| 3,4-dimethyl phenyl | 2-amino-4-pyridyl | 4-pyridyl |
| 2,4-dichlorophenyl | 2-amino-4-pyridyl | 4-pyridyl |
| 2,4-dimethyl phenyl | 2-amino-4-pyridyl | 4-pyridyl |
| Phenyl | 2-acetamido-4-pyridyl | 4-pyridyl |

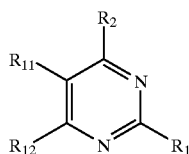

wherein $R^2$ is —OH and $R^{11}$, $R^{12}$, and $R^1$ are one of the combinations given in the following table:

| $R^{11}$ | $R^{12}$ | $R^1$ |
|---|---|---|
| 4-fluorophenyl | 2-acetamido-4-pyridyl | 4-pyridyl |
| 3-fluorophenyl | 2-acetamido-4-pyridyl | 4-pyridyl |
| 2-fluorophenyl | 2-acetamido-4-pyridyl | 4-pyridyl |
| 4-chlorophenyl | 2-acetamido-4-pyridyl | 4-pyridyl |
| 3-chlorophenyl | 2-acetamido-4-pyridyl | 4-pyridyl |
| 2-chlorophenyl | 2-acetamido-4-pyridyl | 4-pyridyl |
| 4-tolyl | 2-acetamido-4-pyridyl | 4-pyridyl |
| 3-tolyl | 2-acetamido-4-pyridyl | 4-pyridyl |
| 2-tolyl | 2-acetamido-4-pyridyl | 4-pyridyl |
| 4-trifluoromethylphenyl | 2-acetamido-4-pyridyl | 4-pyridyl |
| 3-trifluoromethylphenyl | 2-acetamido-4-pyridyl | 4-pyridyl |
| 2,6-dichlorophenyl | 2-acetamido-4-pyridyl | 4-pyridyl |
| 2,6-dimethylphenyl | 2-acetamido-4-pyridyl | 4-pyridyl |
| 3,4-dichlorophenyl | 2-acetamido-4-pyridyl | 4-pyridyl |
| 3,4-dimethylphenyl | 2-acetamido-4-pyridyl | 4-pyridyl |
| 2,4-dichlorophenyl | 2-acetamido-4-pyridyl | 4-pyridyl |
| 2,4-dimethylphenyl | 2-acetamido-4-pyridyl | 4-pyridyl |
| Phenyl | 2-amino-4-pyrimidinyl | 4-pyridyl |
| 4-fluorophenyl | 2-amino-4-pyrimidinyl | 4-pyridyl |
| 3-fluorophenyl | 2-amino-4-pyrimidinyl | 4-pyridyl |
| 2-fluorophenyl | 2-amino-4-pyrimidinyl | 4-pyridyl |
| 4-chlorophenyl | 2-amino-4-pyrimidinyl | 4-pyridyl |
| 3-chlorophenyl | 2-amino-4-pyrimidinyl | 4-pyridyl |
| 2-chlorophenyl | 2-amino-4-pyrimidinyl | 4-pyridyl |
| 4-tolyl | 2-amino-4-pyrimidinyl | 4-pyridyl |
| 3-tolyl | 2-amino-4-pyrimidinyl | 4-pyridyl |
| 2-tolyl | 2-amino-4-pyrimidinyl | 4-pyridyl |
| 4-trifluoromethylphenyl | 2-amino-4-pyrimidinyl | 4-pyridyl |
| 3-trifluoromethylphenyl | 2-amino-4-pyrimidinyl | 4-pyridyl |
| 2,6-dichlorophenyl | 2-amino-4-pyrimidinyl | 4-pyridyl |
| 2,6-dimethylphenyl | 2-amino-4-pyrimidinyl | 4-pyridyl |
| 3,4-dichlorophenyl | 2-amino-4-pyrimidinyl | 4-pyridyl |
| 3,4-dimethylphenyl | 2-amino-4-pyrimidinyl | 4-pyridyl |
| 2,4-dichlorophenyl | 2-amino-4-pyrimidinyl | 4-pyridyl |
| 2,4-dimethylphenyl | 2-amino-4-pyrimidinyl | 4-pyridyl |
| Phenyl | 4-pyridyl | 4-methyl sulfinylphenyl |
| 4-fluorophenyl | 4-pyridyl | 4-methyl sulfinylphenyl |
| 3-fluorophenyl | 4-pyridyl | 4-methyl sulfinylphenyl |
| 2-fluorophenyl | 4-pyridyl | 4-methyl sulfinylphenyl |
| 4-chlorophenyl | 4-pyridyl | 4-methyl sulfinylphenyl |
| 3-chlorophenyl | 4-pyridyl | 4-methyl sulfinylphenyl |
| 2-chlorophenyl | 4-pyridyl | 4-methyl sulfinylphenyl |
| 4-tolyl | 4-pyridyl | 4-methyl sulfinylphenyl |
| 3-tolyl | 4-pyridyl | 4-methyl sulfinylphenyl |
| 2-tolyl | 4-pyridyl | 4-methyl sulfinylphenyl |
| 4-trifluoromethylphenyl | 4-pyridyl | 4-methyl sulfinylphenyl |
| 3-trifluoromethylphenyl | 4-pyridyl | 4-methyl sulfinylphenyl |
| 2,6-dichlorophenyl | 4-pyridyl | 4-methyl sulfinylphenyl |
| 2,6-dimethylphenyl | 4-pyridyl | 4-methyl sulfinylphenyl |
| 3,4-dichlorophenyl | 4-pyridyl | 4-methyl sulfinylphenyl |
| 3,4-dimethylphenyl | 4-pyridyl | 4-methyl sulfinylphenyl |
| 2,4-dichlorophenyl | 4-pyridyl | 4-methyl sulfinylphenyl |
| 2,4-dimethylphenyl | 4-pyridyl | 4-methyl sulfinylphenyl |
| Phenyl | 2-amino-4-pyridyl | 4-methyl sulfinylphenyl |
| 4-fluorophenyl | 2-amino-4-pyridyl | 4-methyl sulfinylphenyl |
| 3-fluorophenyl | 2-amino-4-pyridyl | 4-methyl sulfinylphenyl |
| 2-fluorophenyl | 2-amino-4-pyridyl | 4-methyl sulfinylphenyl |
| 4-chlorophenyl | 2-amino-4-pyridyl | 4-methyl sulfinylphenyl |
| 3-chlorophenyl | 2-amino-4-pyridyl | 4-methyl sulfinylphenyl |
| 2-chlorophenyl | 2-amino-4-pyridyl | 4-methyl sulfinylphenyl |
| 4-tolyl | 2-amino-4-pyridyl | 4-methyl sulfinylphenyl |
| 3-tolyl | 2-amino-4-pyridyl | 4-methyl sulfinylphenyl |
| 2-tolyl | 2-amino-4-pyridyl | 4-methyl sulfinylphenyl |
| 4-trifluoromethylphenyl | 2-amino-4-pyridyl | 4-methyl sulfinylphenyl |
| 3-trifluoromethylphenyl | 2-amino-4-pyridyl | 4-methyl sulfinylphenyl |
| 2,6-dichlorophenyl | 2-amino-4-pyridyl | 4-methyl sulfinylphenyl |
| 2,6-dimethylphenyl | 2-amino-4-pyridyl | 4-methyl sulfinylphenyl |
| 3,4-dichlorophenyl | 2-amino-4-pyridyl | 4-methyl sulfinylphenyl |
| 3,4-dimethylphenyl | 2-amino-4-pyridyl | 4-methyl sulfinylphenyl |
| 2,4-dichlorophenyl | 2-amino-4-pyridyl | 4-methyl sulfinylphenyl |

-continued

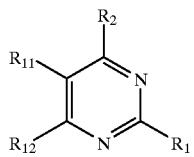

wherein $R^2$ is —OH and $R^{11}$, $R^{12}$, and $R^1$ are one of the combinations given in the following table:

| $R^{11}$ | $R^{12}$ | $R^1$ |
|---|---|---|
| 2,4-dimethylphenyl | 2-amino-4-pyridyl | 4-methyl sulfinylphenyl |
| Phenyl | 2-acetamido-4-pyridyl | 4-methyl sulfinylphenyl |
| 4-fluorophenyl | 2-acetamido-4-pyridyl | 4-methyl sulfinylphenyl |
| 3-fluorophenyl | 2-acetamido-4-pyridyl | 4-methyl sulfinylphenyl |
| 2-fluorophenyl | 2-acetamido-4-pyridyl | 4-methyl sulfinylphenyl |
| 4-chlorophenyl | 2-acetamido-4-pyridyl | 4-methyl sulfinylphenyl |
| 3-chlorophenyl | 2-acetamido-4-pyridyl | 4-methyl sulfinylphenyl |
| 2-chlorophenyl | 2-acetamido-4-pyridyl | 4-methyl sulfinylphenyl |
| 4-tolyl | 2-acetamido-4-pyridyl | 4-methyl sulfinylphenyl |
| 3-tolyl | 2-acetamido-4-pyridyl | 4-methyl sulfinylphenyl |
| 2-tolyl | 2-acetamido-4-pyridyl | 4-methyl sulfinylphenyl |
| 4-trifluoromethylphenyl | 2-acetamido-4-pyridyl | 4-methyl sulfinylphenyl |
| 3-trifluoromethylphenyl | 2-acetamido-4-pyridyl | 4-methyl sulfinylphenyl |
| 2,6-dichlorophenyl | 2-acetamido-4-pyridyl | 4-methyl sulfinylphenyl |
| 2,6-dimethylphenyl | 2-acetamido-4-pyridyl | 4-methyl sulfinylphenyl |
| 3,4-dichlorophenyl | 2-acetamido-4-pyridyl | 4-methyl sulfinylphenyl |
| 3,4-dimethylphenyl | 2-acetamido-4-pyridyl | 4-methyl sulfinylphenyl |
| 2,4-dichlorophenyl | 2-acetamido-4-pyridyl | 4-methyl sulfinylphenyl |
| 2,4-dimethylphenyl | 2-acetamido-4-pyridyl | 4-methyl sulfinylphenyl |
| Phenyl | 2-amino-4-pyrimidinyl | 4-methyl sulfinylphenyl |
| 4-fluorophenyl | 2-amino-4-pyrimidinyl | 4-methyl sulfinylphenyl |
| 3-fluorophenyl | 2-amino-4-pyrimidinyl | 4-methyl sulfinylphenyl |
| 2-fluorophenyl | 2-amino-4-pyrimidinyl | 4-methyl sulfinylphenyl |
| 4-chlorophenyl | 2-amino-4-pyrimidinyl | 4-methyl sulfinylphenyl |
| 3-chlorophenyl | 2-amino-4-pyrimidinyl | 4-methyl sulfinylphenyl |
| 2-chlorophenyl | 2-amino-4-pyrimidinyl | 4-methyl sulfinylphenyl |
| 4-tolyl | 2-amino-4-pyrimidinyl | 4-methyl sulfinylphenyl |
| 3-tolyl | 2-amino-4-pyrimidinyl | 4-methyl sulfinylphenyl |
| 2-tolyl | 2-amino-4-pyrimidinyl | 4-methyl sulfinylphenyl |
| 4-trifluoromethylphenyl | 2-amino-4-pyrimidinyl | 4-methyl sulfinylphenyl |
| 3-trifluoromethylphenyl | 2-amino-4-pyrimidinyl | 4-methyl sulfinylphenyl |
| 2,6-dichlorophenyl | 2-amino-4-pyrimidinyl | 4-methyl sulfinylphenyl |
| 2,6-dimethylphenyl | 2-amino-4-pyrimidinyl | 4-methyl sulfinylphenyl |

-continued

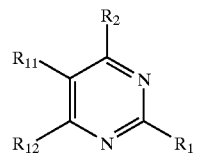

wherein $R^2$ is —OH and $R^{11}$, $R^{12}$, and $R^1$ are one of the combinations given in the following table:

| $R^{11}$ | $R^{12}$ | $R^1$ |
|---|---|---|
| phenyl | pyrimidinyl | |
| 3,4-dichlorophenyl | 2-amino-4-pyrimidinyl | 4-methyl sulfinylphenyl |
| 3,4-dimethylphenyl | 2-amino-4-pyrimidinyl | 4-methyl sulfinylphenyl |
| 2,4-dichlorophenyl | 2-amino-4-pyrimidinyl | 4-methyl sulfinylphenyl |
| 2,4-dimethylphenyl | 2-amino-4-pyrimidinyl | 4-methyl sulfinylphenyl |
| Phenyl | 4-pyridyl | 2,6-dichlorobenzyl |
| 4-fluorophenyl | 4-pyridyl | 2,6-dichlorobenzyl |
| 3-fluorophenyl | 4-pyridyl | 2,6-dichlorobenzyl |
| 2-fluorophenyl | 4-pyridyl | 2,6-dichlorobenzyl |
| 4-chlorophenyl | 4-pyridyl | 2,6-dichlorobenzyl |
| 3-chlorophenyl | 4-pyridyl | 2,6-dichlorobenzyl |
| 2-chlorophenyl | 4-pyridyl | 2,6-dichlorobenzyl |
| 4-tolyl | 4-pyridyl | 2,6-dichlorobenzyl |
| 3-tolyl | 4-pyridyl | 2,6-dichlorobenzyl |
| 2-tolyl | 4-pyridyl | 2,6-dichlorobenzyl |
| 4-trifluoromethylphenyl | 4-pyridyl | 2,6-dichlorobenzyl |
| 3-trifluoromethylphenyl | 4-pyridyl | 2,6-dichlorobenzyl |
| 2,6-dichlorophenyl | 4-pyridyl | 2,6-dichlorobenzyl |
| 2,6-dimethylphenyl | 4-pyridyl | 2,6-dichlorobenzyl |
| 3,4-dichlorophenyl | 4-pyridyl | 2,6-dichlorobenzyl |
| 3,4-dimethylphenyl | 4-pyridyl | 2,6-dichlorobenzyl |
| 2,4-dichlorophenyl | 4-pyridyl | 2,6-dichlorobenzyl |
| 2,4-dimethylphenyl | 4-pyridyl | 2,6-dichlorobenzyl |
| Phenyl | 2-amino-4-pyridyl | 2,6-dichlorobenzyl |
| 4-fluorophenyl | 2-amino-4-pyridyl | 2,6-dichlorobenzyl |
| 3-fluorophenyl | 2-amino-4-pyridyl | 2,6-dichlorobenzyl |
| 2-fluorophenyl | 2-amino-4-pyridyl | 2,6-dichlorobenzyl |
| 4-chlorophenyl | 2-amino-4-pyridyl | 2,6-dichlorobenzyl |
| 3-chlorophenyl | 2-amino-4-pyridyl | 2,6-dichlorobenzyl |
| 2-chlorophenyl | 2-amino-4-pyridyl | 2,6-dichlorobenzyl |
| 4-tolyl | 2-amino-4-pyridyl | 2,6-dichlorobenzyl |
| 3-tolyl | 2-amino-4-pyridyl | 2,6-dichlorobenzyl |
| 2-tolyl | 2-amino-4-pyridyl | 2,6-dichlorobenzyl |
| 4-trifluoromethylphenyl | 2-amino-4-pyridyl | 2,6-dichlorobenzyl |
| 3-trifluoromethylphenyl | 2-amino-4-pyridyl | 2,6-dichlorobenzyl |
| 2,6-dichlorophenyl | 2-amino-4-pyridyl | 2,6-dichlorobenzyl |
| 2,6-dimethylphenyl | 2-amino-4-pyridyl | 2,6-dichlorobenzyl |
| 3,4-dichlorophenyl | 2-amino-4-pyridyl | 2,6-dichlorobenzyl |

-continued

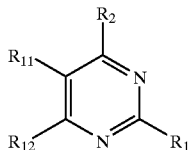

wherein $R^2$ is —OH and $R^{11}$, $R^{12}$, and $R^1$ are one of the combinations given in the following table:

| $R^{11}$ | $R^{12}$ | $R^1$ |
|---|---|---|
| 3,4-dimethyl phenyl | 2-amino-4-pyridyl | 2,6-dichlorobenzyl |
| 2,4-dichlorophenyl | 2-amino-4-pyridyl | 2,6-dichlorobenzyl |
| 2,4-dimethyl phenyl | 2-amino-4-pyridyl | 2,6-dichlorobenzyl |
| Phenyl | 2-acetamido-4-pyridyl | 2,6-dichlorobenzyl |
| 4-fluorophenyl | 2-acetamido-4-pyridyl | 2,6-dichlorobenzyl |
| 3-fluorophenyl | 2-acetamido-4-pyridyl | 2,6-dichlorobenzyl |
| 2-fluorophenyl | 2-acetamido-4-pyridyl | 2,6-dichlorobenzyl |
| 4-chlorophenyl | 2-acetamido-4-pyridyl | 2,6-dichlorobenzyl |
| 3-chlorophenyl | 2-acetamido-4-pyridyl | 2,6-dichlorobenzyl |
| 2-chlorophenyl | 2-acetamido-4-pyridyl | 2,6-dichlorobenzyl |
| 4-tolyl | 2-acetamido-4-pyridyl | 2,6-dichlorobenzyl |
| 3-tolyl | 2-acetamido-4-pyridyl | 2,6-dichlorobenzyl |
| 2-tolyl | 2-acetamido-4-pyridyl | 2,6-dichlorobenzyl |
| 4-trifluoro-methylphenyl | 2-acetamido-4-pyridyl | 2,6-dichlorobenzyl |
| 3-trifluoro-methylphenyl | 2-acetamido-4-pyridyl | 2,6-dichlorobenzyl |
| 2,6-dichlorophenyl | 2-acetamido-4-pyridyl | 2,6-dichlorobenzyl |
| 2,6-dimethyl phenyl | 2-acetamido-4-pyridyl | 2,6-dichlorobenzyl |
| 3,4-dichlorophenyl | 2-acetamido-4-pyridyl | 2,6-dichlorobenzyl |
| 3,4-dimethyl phenyl | 2-acetamido-4-pyridyl | 2,6-dichlorobenzyl |
| 2,4-dichlorophenyl | 2-acetamido-4-pyridyl | 2,6-dichlorobenzyl |
| 2,4-dimethyl phenyl | 2-acetamido-4-pyridyl | 2,6-dichlorobenzyl |
| Phenyl | 2-amino-4-pyrimidinyl | 2,6-dichlorobenzyl |
| 4-fluorophenyl | 2-amino-4-pyrimidinyl | 2,6-dichlorobenzyl |
| 3-fluorophenyl | 2-amino-4-pyrimidinyl | 2,6-dichlorobenzyl |
| 2-fluorophenyl | 2-amino-4-pyrimidinyl | 2,6-dichlorobenzyl |
| 4-chlorophenyl | 2-amino-4-pyrimidinyl | 2,6-dichlorobenzyl |
| 3-chlorophenyl | 2-amino-4-pyrimidinyl | 2,6-dichlorobenzyl |
| 2-chlorophenyl | 2-amino-4--pyrimidinyl | 2,6-dichlorobenzyl |
| 4-tolyl | 2-amino-4-pyrimidinyl | 2,6-dichlorobenzyl |
| 3-tolyl | 2-amino-4-pyrimidinyl | 2,6-dichlorobenzyl |
| 2-tolyl | 2-amino-4-pyrimidinyl | 2,6-dichlorobenzyl |
| 4-trifluoro-methylphenyl | 2-amino-4-pyrimidinyl | 2,6-dichlorobenzyl |
| 3-trifluoro-methylphenyl | 2-amino-4-pyrimidinyl | 2,6-dichlorobenzyl |
| 2,6-dichlorophenyl | 2-amino-4-pyrimidinyl | 2,6-dichlorobenzyl |
| 2,6-dimethyl phenyl | 2-amino-4-pyrimidinyl | 2,6-dichlorobenzyl |
| 3,4-dichlorophenyl | 2-amino-4-pyrimidinyl | 2,6-dichlorobenzyl |
| 3,4-dimethyl phenyl | 2-amino-4-pyrimidinyl | 2,6-dichlorobenzyl |
| 2,4-dichlorophenyl | 2-amino-4-pyrimidinyl | 2,6-dichlorobenzyl |
| 2,4-dimethyl phenyl | 2-amino-4-pyrimidinyl | 2,6-dichlorobenzyl |
| Phenyl | 4-pyridyl | 2-(4-fluorophenyl)ethylamino |
| 4-fluorophenyl | 4-pyridyl | 2-(4-fluorophenyl)ethylamino |
| 3-fluorophenyl | 4-pyridyl | 2-(4-fluorophenyl)ethylamino |
| 2-fluorophenyl | 4-pyridyl | 2-(4-fluorophenyl)ethylamino |
| 4-chlorophenyl | 4-pyridyl | 2-(4-fluorophenyl)ethylamino |
| 3-chlorophenyl | 4-pyridyl | 2-(4-fluorophenyl)ethylamino |
| 2-chlorophenyl | 4-pyridyl | 2-(4-fluorophenyl)ethylamino |
| 4-tolyl | 4-pyridyl | 2-(4-fluorophenyl)ethylamino |
| 3-tolyl | 4-pyridyl | 2-(4-fluorophenyl)ethylamino |
| 2-tolyl | 4-pyridyl | 2-(4-fluorophenyl)ethylamino |
| 4-trifluoro-methylphenyl | 4-pyridyl | 2-(4-fluorophenyl)ethylamino |
| 3-trifluoro-methylphenyl | 4-pyridyl | 2-(4-fluorophenyl)ethylamino |
| 2,6-dichlorophenyl | 4-pyridyl | 2-(4-fluorophenyl)ethylamino |
| 2,6-dimethyl phenyl | 4-pyridyl | 2-(4-fluorophenyl)ethylamino |
| 3,4-dichlorophenyl | 4-pyridyl | 2-(4-fluorophenyl)ethylamino |
| 3,4-dimethyl phenyl | 4-pyridyl | 2-(4-fluorophenyl)ethylamino |
| 2,4-dichlorophenyl | 4-pyridyl | 2-(4-fluorophenyl)ethylamino |
| 2,4-dimethyl phenyl | 4-pyridyl | 2-(4-fluorophenyl)ethylamino |
| Phenyl | 2-amino-4-pyridyl | 2-(4-fluorophenyl)ethylamino |
| 4-fluorophenyl | 2-amino-4-pyridyl | 2-(4-fluorophenyl)ethylamino |
| 3-fluorophenyl | 2-amino-4-pyridyl | 2-(4-fluorophenyl)ethylamino |
| 2-fluorophenyl | 2-amino-4-pyridyl | 2-(4-fluorophenyl)ethylamino |
| 4-chlorophenyl | 2-amino-4-pyridyl | 2-(4-fluorophenyl)ethylamino |
| 3-chlorophenyl | 2-amino-4-pyridyl | 2-(4-fluorophenyl)ethylamino |
| 2-chlorophenyl | 2-amino-4-pyridyl | 2-(4-fluorophenyl)ethylamino |
| 4-tolyl | 2-amino-4-pyridyl | 2-(4-fluorophenyl)ethylamino |

-continued

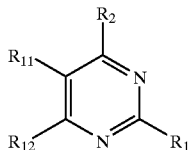

wherein R² is —OH and R¹¹, R¹², and R¹ are one of the combinations given in the following table:

| R¹¹ | R¹² | R¹ |
|---|---|---|
| 3-tolyl | 2-amino-4-pyridyl | 2-(4-fluorophenyl)ethylamino |
| 2-tolyl | 2-amino-4-pyridyl | 2-(4-fluorophenyl)ethylamino |
| 4-trifluoromethylphenyl | 2-amino-4-pyridyl | 2-(4-fluorophenyl)ethylamino |
| 3-trifluoromethylphenyl | 2-amino-4-pyridyl | 2-(4-fluorophenyl)ethylamino |
| 2,6-dichlorophenyl | 2-amino-4-pyridyl | 2-(4-fluorophenyl)ethylamino |
| 2,6-dimethylphenyl | 2-amino-4-pyridyl | 2-(4-fluorophenyl)ethylamino |
| 3,4-dichlorophenyl | 2-amino-4-pyridyl | 2-(4-fluorophenyl)ethylamino |
| 3,4-dimethylphenyl | 2-amino-4-pyridyl | 2-(4-fluorophenyl)ethylamino |
| 2,4-dichlorophenyl | 2-amino-4-pyridyl | 2-(4-fluorophenyl)ethylamino |
| 2,4-dimethylphenyl | 2-amino-4-pyridyl | 2-(4-fluorophenyl)ethylamino |
| Phenyl | 2-acetamido-4-pyridyl | 2-(4-fluorophenyl)ethylamino |
| 4-fluorophenyl | 2-acetamido-4-pyridyl | 2-(4-fluorophenyl)ethylamino |
| 3-fluorophenyl | 2-acetamido-4-pyridyl | 2-(4-fluorophenyl)ethylamino |
| 2-fluorophenyl | 2-acetamido-4-pyridyl | 2-(4-fluorophenyl)ethylamino |
| 4-chlorophenyl | 2-acetamido-4-pyridyl | 2-(4-fluorophenyl)ethylamino |
| 3-chlorophenyl | 2-acetamido-4-pyridyl | 2-(4-fluorophenyl)ethylamino |
| 2-chlorophenyl | 2-acetamido-4-pyridyl | 2-(4-fluorophenyl)ethylamino |
| 4-tolyl | 2-acetamido-4-pyridyl | 2-(4-fluorophenyl)ethylamino |
| 3-tolyl | 2-acetamido-4-pyridyl | 2-(4-fluorophenyl)ethylamino |
| 2-tolyl | 2-acetamido-4-pyridyl | 2-(4-fluorophenyl)ethylamino |
| 4-trifluoromethylphenyl | 2-acetamido-4-pyridyl | 2-(4-fluorophenyl)ethylamino |
| 3-trifluoromethylphenyl | 2-acetamido-4-pyridyl | 2-(4-fluorophenyl)ethylamino |
| 2,6-dichlorophenyl | 2-acetamido-4-pyridyl | 2-(4-fluorophenyl)ethylamino |
| 2,6-dimethylphenyl | 2-acetamido-4-pyridyl | 2-(4-fluorophenyl)ethylamino |
| 3,4-dichlorophenyl | 2-acetamido-4-pyridyl | 2-(4-fluorophenyl)ethylamino |
| 3,4-dimethylphenyl | 2-acetamido-4-pyridyl | 2-(4-fluorophenyl)ethylamino |
| 2,4-dichlorophenyl | 2-acetamido-4-pyridyl | 2-(4-fluorophenyl)ethylamino |
| 2,4-dimethylphenyl | 2-acetamido-4-pyridyl | 2-(4-fluorophenyl)ethylamino |
| Phenyl | 2-amino-4-pyrimidinyl | 2-(4-fluorophenyl)ethylamino |
| 4-fluorophenyl | 2-amino-4-pyrimidinyl | 2-(4-fluorophenyl)ethylamino |
| 3-fluorophenyl | 2-amino-4-pyrimidinyl | 2-(4-fluorophenyl)ethylamino |
| 2-fluorophenyl | 2-amino-4-pyrimidinyl | 2-(4-fluorophenyl)ethylamino |

-continued wherein R² is —OH and R¹¹, R¹², and R¹ are one of the combinations given in the following table:

| R¹¹ | R¹² | R¹ |
|---|---|---|
| 4-chlorophenyl | 2-amino-4-pyrimidinyl | 2-(4-fluorophenyl)ethylamino |
| 3-chlorophenyl | 2-amino-4-pyrimidinyl | 2-(4-fluorophenyl)ethylamino |
| 2-chlorophenyl | 2-amino-4-pyrimidinyl | 2-(4-fluorophenyl)ethylamino |
| 4-tolyl | 2-amino-4-pyrimidinyl | 2-(4-fluorophenyl)ethylamino |
| 3-tolyl | 2-amino-4-pyrimidinyl | 2-(4-fluorophenyl)ethylamino |
| 2-tolyl | 2-amino-4-pyrimidinyl | 2-(4-fluorophenyl)ethylamino |
| 4-trifluoromethylphenyl | 2-amino-4-pyrimidinyl | 2-(4-fluorophenyl)ethylamino |
| 3-trifluoromethylphenyl | 2-amino-4-pyrimidinyl | 2-(4-fluorophenyl)ethylamino |
| 2,6-dichlorophenyl | 2-amino-4-pyrimidinyl | 2-(4-fluorophenyl)ethylamino |
| 2,6-dimethylphenyl | 2-amino-4-pyrimidinyl | 2-(4-fluorophenyl)ethylamino |
| 3,4-dichlorophenyl | 2-amino-4-pyrimidinyl | 2-(4-fluorophenyl)ethylamino |
| 3,4-dimethylphenyl | 2-amino-4-pyrimidinyl | 2-(4-fluorophenyl)ethylamino |
| 2,4-dichlorophenyl | 2-amino-4-pyrimidinyl | 2-(4-fluorophenyl)ethylamino |
| 2,4-dimethylphenyl | 2-amino-4-pyrimidinyl | 2-(4-fluorophenyl)ethylamino |
| Phenyl | 4-pyridyl | 3-phenyl-propylamino |
| 4-fluorophenyl | 4-pyridyl | 3-phenyl-propylamino |
| 3-fluorophenyl | 4-pyridyl | 3-phenyl-propylamino |
| 2-fluorophenyl | 4-pyridyl | 3-phenyl-propylamino |
| 4-chlorophenyl | 4-pyridyl | 3-phenyl-propylamino |
| 3-chlorophenyl | 4-pyridyl | 3-phenyl-propylamino |
| 2-chlorophenyl | 4-pyridyl | 3-phenyl-propylamino |
| 4-tolyl | 4-pyridyl | 3-phenyl-propylamino |
| 3-tolyl | 4-pyridyl | 3-phenyl-propylamino |
| 2-tolyl | 4-pyridyl | 3-phenyl-propylamino |
| 4-trifluoromethylphenyl | 4-pyridyl | 3-phenyl-propylamino |
| 3-trifluoromethylphenyl | 4-pyridyl | 3-phenyl-propylamino |
| 2,6-dichlorophenyl | 4-pyridyl | 3-phenyl-propylamino |
| 2,6-dimethylphenyl | 4-pyridyl | 3-phenyl-propylamino |
| 3,4-dichlorophenyl | 4-pyridyl | 3-phenyl-propylamino |
| 3,4-dimethylphenyl | 4-pyridyl | 3-phenyl-propylamino |
| 2,4-dichlorophenyl | 4-pyridyl | 3-phenyl-propylamino |
| 2,4-dimethylphenyl | 4-pyridyl | 3-phenyl-propylamino |
| Phenyl | 2-amino-4-pyridyl | 3-phenyl-propylamino |
| 4-fluorophenyl | 2-amino-4-pyridyl | 3-phenyl-propylamino |
| 3-fluorophenyl | 2-amino-4-pyridyl | 3-phenyl-propylamino |
| 2-fluorophenyl | 2-amino-4-pyridyl | 3-phenyl-propylamino |
| 4-chlorophenyl | 2-amino-4-pyridyl | 3-phenyl-propylamino |
| 3-chlorophenyl | 2-amino-4-pyridyl | 3-phenyl-propylamino |

-continued

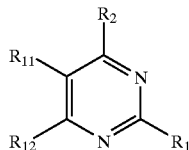

wherein R² is —OH and R¹¹, R¹², and R¹ are one of the combinations given in the following table:

| R¹¹ | R¹² | R¹ |
|---|---|---|
| 2-chlorophenyl | 2-amino-4-pyridyl | 3-phenyl-propylamino |
| 4-tolyl | 2-amino-4-pyridyl | 3-phenyl-propylamino |
| 3-tolyl | 2-amino-4-pyridyl | 3-phenyl-propylamino |
| 2-tolyl | 2-amino-4-pyridyl | 3-phenyl-propylamino |
| 4-trifluoromethylphenyl | 2-amino-4-pyridyl | 3-phenyl-propylamino |
| 3-trifluoromethylphenyl | 2-amino-4-pyridyl | 3-phenyl-propylamino |
| 2,6-dichlorophenyl | 2-amino-4-pyridyl | 3-phenyl-propylamino |
| 2,6-dimethylphenyl | 2-amino-4-pyridyl | 3-phenyl-propylamino |
| 3,4-dichlorophenyl | 2-amino-4-pyridyl | 3-phenyl-propylamino |
| 3,4-dimethylphenyl | 2-amino-4-pyridyl | 3-phenyl-propylamino |
| 2,4-dichlorophenyl | 2-amino-4-pyridyl | 3-phenyl-propylamino |
| 2,4-dimethylphenyl | 2-amino-4-pyridyl | 3-phenyl-propylamino |
| Phenyl | 2-acetamido-4-pyridyl | 3-phenyl-propylamino |
| 4-fluorophenyl | 2-acetamido-4-pyridyl | 3-phenyl-propylamino |
| 3-fluorophenyl | 2-acetamido-4-pyridyl | 3-phenyl-propylamino |
| 2-fluorophenyl | 2-acetamido-4-pyridyl | 3-phenyl-propylamino |
| 4-chlorophenyl | 2-acetamido-4-pyridyl | 3-phenyl-propylamino |
| 3-chlorophenyl | 2-acetamido-4-pyridyl | 3-phenyl-propylamino |
| 2-chlorophenyl | 2-acetamido-4-pyridyl | 3-phenyl-propylamino |
| 4-tolyl | 2-acetamido-4-pyridyl | 3-phenyl-propylamino |
| 3-tolyl | 2-acetamido-4-pyridyl | 3-phenyl-propylamino |
| 2-tolyl | 2-acetamido-4-pyridyl | 3-phenyl-propylamino |
| 4-trifluoromethylphenyl | 2-acetamido-4-pyridyl | 3-phenyl-propylamino |
| 3-trifluoromethylphenyl | 2-acetamido-4-pyridyl | 3-phenyl-propylamino |
| 2,6-dichlorophenyl | 2-acetamido-4-pyridyl | 3-phenyl-propylamino |
| 2,6-dimethylphenyl | 2-acetamido-4-pyridyl | 3-phenyl-propylamino |
| 3,4-dichlorophenyl | 2-acetamido-4-pyridyl | 3-phenyl-propylamino |
| 3,4-dimethylphenyl | 2-acetamido-4-pyridyl | 3-phenyl-propylamino |
| 2,4-dichlorophenyl | 2-acetamido-4-pyridyl | 3-phenyl-propylamino |
| 2,4-dimethylphenyl | 2-acetamido-4-pyridyl | 3-phenyl-propylamino |
| Phenyl | 2-amino-4-pyrimidinyl | 3-phenyl-propylamino |

-continued

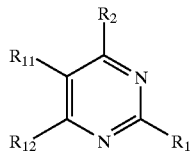

wherein R² is —OH and R¹¹, R¹², and R¹ are one of the combinations given in the following table:

| R¹¹ | R¹² | R¹ |
|---|---|---|
| 4-fluorophenyl | 2-amino-4-pyrimidinyl | 3-phenyl-propylamino |
| 3-fluorophenyl | 2-amino-4-pyrimidinyl | 3-phenyl-propylamino |
| 2-fluorophenyl | 2-amino-4-pyrimidinyl | 3-phenyl-propylamino |
| 4-chlorophenyl | 2-amino-4-pyrimidinyl | 3-phenyl-propylamino |
| 3-chlorophenyl | 2-amino-4-pyrimidinyl | 3-phenyl-propylamino |
| 2-chlorophenyl | 2-amino-4-pyrimidinyl | 3-phenyl-propylamino |
| 4-tolyl | 2-amino-4-pyrimidinyl | 3-phenyl-propylamino |
| 3-tolyl | 2-amino-4-pyrimidinyl | 3-phenyl-propylamino |
| 2-tolyl | 2-amino-4-pyrimidinyl | 3-phenyl-propylamino |
| 4-trifluoromethylphenyl | 2-amino-4-pyrimidinyl | 3-phenyl-propylamino |
| 3-trifluoromethylphenyl | 2-amino-4-pyrimidinyl | 3-phenyl-propylamino |
| 2,6-dichlorophenyl | 2-amino-4-pyrimidinyl | 3-phenyl-propylamino |
| 2,6-dimethylphenyl | 2-amino-4-pyrimidinyl | 3-phenyl-propylamino |
| 3,4-dichlorophenyl | 2-amino-4-pyrimidinyl | 3-phenyl-propylamino |
| 3,4-dimethylphenyl | 2-amino-4-pyrimidinyl | 3-phenyl-propylamino |
| 2,4-dichlorophenyl | 2-amino-4-pyrimidinyl | 3-phenyl-propylamino |
| 2,4-dimethylphenyl | 2-amino-4-pyrimidinyl | 3-phenyl-propylamino |
| Phenyl | 4-pyridyl | (1-methyl-3-phenyl)propylamino |
| 4-fluorophenyl | 4-pyridyl | (1-methyl-3-phenyl)propylamino |
| 3-fluorophenyl | 4-pyridyl | (1-methyl-3-phenyl)propylamino |
| 2-fluorophenyl | 4-pyridyl | (1-methyl-3-phenyl)propylamino |
| 4-chlorophenyl | 4-pyridyl | (1-methyl-3-phenyl)propylamino |
| 3-chlorophenyl | 4-pyridyl | (1-methyl-3-phenyl)propylamino |
| 2-chlorophenyl | 4-pyridyl | (1-methyl-3-phenyl)propylamino |
| 4-tolyl | 4-pyridyl | (1-methyl-3-phenyl)propylamino |
| 3-tolyl | 4-pyridyl | (1-methyl-3-phenyl)propylamino |
| 2-tolyl | 4-pyridyl | (1-methyl-3-phenyl)propylamino |
| 4-trifluoromethylphenyl | 4-pyridyl | (1-methyl-3-phenyl)propylamino |
| 3-trifluoromethylphenyl | 4-pyridyl | (1-methyl-3-phenyl)propylamino |
| 2,6-dichlorophenyl | 4-pyridyl | (1-methyl-3-phenyl)propylamino |
| 2,6-dimethylphenyl | 4-pyridyl | (1-methyl-3-phenyl)propylamino |
| 3,4-dichlorophenyl | 4-pyridyl | (1-methyl-3-phenyl)propylamino |
| 3,4-dimethylphenyl | 4-pyridyl | (1-methyl-3-phenyl)propylamino |

-continued

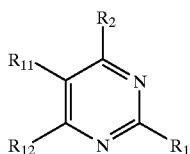

wherein R² is —OH and R¹¹, R¹², and R¹ are one of the combinations given in the following table:

| R¹¹ | R¹² | R¹ |
|---|---|---|
| 2,4-dichlorophenyl | 4-pyridyl | (1-methyl-3-phenyl)propylamino |
| 2,4-dimethylphenyl | 4-pyridyl | (1-methyl-3-phenyl)propylamino |
| Phenyl | 2-amino-4-pyridyl | (1-methyl-3-phenyl)propylamino |
| 4-fluorophenyl | 2-amino-4-pyridyl | (1-methyl-3-phenyl)propylamino |
| 3-fluorophenyl | 2-amino-4-pyridyl | (1-methyl-3-phenyl)propylamino |
| 2-fluorophenyl | 2-amino-4-pyridyl | (1-methyl-3-phenyl)propylamino |
| 4-chlorophenyl | 2-amino-4-pyridyl | (1-methyl-3-phenyl)propylamino |
| 3-chlorophenyl | 2-amino-4-pyridyl | (1-methyl-3-phenyl)propylamino |
| 2-chlorophenyl | 2-amino-4-pyridyl | (1-methyl-3-phenyl)propylamino |
| 4-tolyl | 2-amino-4-pyridyl | (1-methyl-3-phenyl)propylamino |
| 3-tolyl | 2-amino-4-pyridyl | (1-methyl-3-phenyl)propylamino |
| 2-tolyl | 2-amino-4-pyridyl | (1-methyl-3-phenyl)propylamino |
| 4-trifluoromethylphenyl | 2-amino-4-pyridyl | (1-methyl-3-phenyl)propylamino |
| 3-trifluoromethylphenyl | 2-amino-4-pyridyl | (1-methyl-3-phenyl)propylamino |
| 2,6-dichlorophenyl | 2-amino-4-pyridyl | (1-methyl-3-phenyl)propylamino |
| 2,6-dimethylphenyl | 2-amino-4-pyridyl | (1-methyl-3-phenyl)propylamino |
| 3,4-dichlorophenyl | 2-amino-4-pyridyl | (1-methyl-3-phenyl)propylamino |
| 3,4-dimethylphenyl | 2-amino-4-pyridyl | (1-methyl-3-phenyl)propylamino |
| 2,4-dichlorophenyl | 2-amino-4-pyridyl | (1-methyl-3-phenyl)propylamino |
| 2,4-dimethylphenyl | 2-amino-4-pyridyl | (1-methyl-3-phenyl)propylamino |
| Phenyl | 2-acetamido-4-pyridyl | (1-methyl-3-phenyl)propylamino |
| 4-fluorophenyl | 2-acetamido-4-pyridyl | (1-methyl-3-phenyl)propylamino |
| 3-fluorophenyl | 2-acetamido-4-pyridyl | (1-methyl-3-phenyl)propylamino |
| 2-fluorophenyl | 2-acetamido-4-pyridyl | (1-methyl-3-phenyl)propylamino |
| 4-chlorophenyl | 2-acetamido-4-pyridyl | (1-methyl-3-phenyl)propylamino |
| 3-chlorophenyl | 2-acetamido-4-pyridyl | (1-methyl-3-phenyl)propylamino |
| 2-chlorophenyl | 2-acetamido-4-pyridyl | (1-methyl-3-phenyl)propylamino |
| 4-tolyl | 2-acetamido-4-pyridyl | (1-methyl-3-phenyl)propylamino |
| 3-tolyl | 2-acetamido-4-pyridyl | (1-methyl-3-phenyl)propylamino |
| 2-tolyl | 2-acetamido-4-pyridyl | (1-methyl-3-phenyl)propylamino |
| 4-trifluoromethylphenyl | 2-acetamido-4-pyridyl | (1-methyl-3-phenyl)propylamino |
| 3-trifluoromethylphenyl | 2-acetamido-4-pyridyl | (1-methyl-3-phenyl)propylamino |
| 2,6-dichlorophenyl | 2-acetamido-4-pyridyl | (1-methyl-3-phenyl)propylamino |
| 2,6-dimethylphenyl | 2-acetamido-4-pyridyl | (1-methyl-3-phenyl)propylamino |
| 3,4-dichlorophenyl | 2-acetamido-4-pyridyl | (1-methyl-3-phenyl)propylamino |
| 3,4-dimethylphenyl | 2-acetamido-4-pyridyl | (1-methyl-3-phenyl)propylamino |
| 2,4-dichlorophenyl | 2-acetamido-4-pyridyl | (1-methyl-3-phenyl)propylamino |
| 2,4-dimethylphenyl | 2-acetamido-4-pyridyl | (1-methyl-3-phenyl)propylamino |
| Phenyl | 2-amino-4-pyrimidinyl | (1-methyl-3-phenyl)propylamino |
| 4-fluorophenyl | 2-amino-4-pyrimidinyl | (1-methyl-3-phenyl)propylamino |
| 3-fluorophenyl | 2-amino-4-pyrimidinyl | (1-methyl-3-phenyl)propylamino |
| 2-fluorophenyl | 2-amino-4-pyrimidinyl | (1-methyl-3-phenyl)propylamino |
| 4-chlorophenyl | 2-amino-4-pyrimidinyl | (1-methyl-3-phenyl)propylamino |
| 3-chlorophenyl | 2-amino-4-pyrimidinyl | (1-methyl-3-phenyl)propylamino |
| 2-chlorophenyl | 2-amino-4-pyrimidinyl | (1-methyl-3-phenyl)propylamino |
| 4-tolyl | 2-amino-4-pyrimidinyl | (1-methyl-3-phenyl)propylamino |
| 3-tolyl | 2-amino-4-pyrimidinyl | (1-methyl-3-phenyl)propylamino |
| 2-tolyl | 2-amino-4-pyrimidinyl | (1-methyl-3-phenyl)propylamino |
| 4-trifluoromethylphenyl | 2-amino-4-pyrimidinyl | (1-methyl-3-phenyl)propylamino |
| 3-trifluoromethylphenyl | 2-amino-4-pyrimidinyl | (1-methyl-3-phenyl)propylamino |
| 2,6-dichlorophenyl | 2-amino-4-pyrimidinyl | (1-methyl-3-phenyl)propylamino |
| 2,6-dimethylphenyl | 2-amino-4-pyrimidinyl | (1-methyl-3-phenyl)propylamino |
| 3,4-dichlorophenyl | 2-amino-4-pyrimidinyl | (1-methyl-3-phenyl)propylamino |
| 3,4-dimethylphenyl | 2-amino-4-pyrimidinyl | (1-methyl-3-phenyl)propylamino |
| 2,4-dichlorophenyl | 2-amino-4-pyrimidinyl | (1-methyl-3-phenyl)propylamino |
| 2,4-dimethylphenyl | 2-amino-4-pyrimidinyl | (1-methyl-3-phenyl)propylamino |
| 4-fluorophenyl | 4-pyridyl | 4-fluorobenzylamino |
| 4-fluorophenyl | 2-acetamido-4-pyridyl | 4-fluorobenzylamino |
| 4-fluorophenyl | 2-amino-4-pyrimidinyl | 4-fluorobenzylamino |
| 4-fluorophenyl | 4-pyridylnyl | (2-(4-fluorophenyl)-1-methyl-ethyl)amino |
| 4-fluorophenyl | 2-acetamido-4-pyridyl | (2-(4-fluorophenyl)-1-methyl-ethyl)amino |
| 4-fluorophenyl | 2-amino-4-pyrimidinyl | (2-(4-fluorophenyl)-1-methyl-ethyl)amino |
| 4-fluorophenyl | 4-pyridyl | (1,1-dimethyl-2-(4-fluorophenyl)-ethyl)amino |
| 4-fluorophenyl | 2-acetamido-4-pyridyl | (1,1-dimethyl-2-(4-fluorophenyl)-ethyl)amino |
| 4-fluorophenyl | 2-amino-4-pyrimidinyl | (1,1-dimethyl-2-(4-fluorophenyl)-ethyl)amino |

-continued

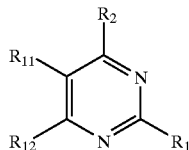

wherein $R^2$ is —OH and $R^{11}$, $R^{12}$, and $R^1$ are one of the combinations given in the following table:

| $R^{11}$ | $R^{12}$ | $R^1$ |
|---|---|---|
| 4-fluorophenyl | 4-pyridyl | 2-(4-fluorophenyl)-2-methyl-ethylamino |
| 4-fluorophenyl | 2-acetamido-4-pyridyl | 2-(4-fluorophenyl)-2-methyl-ethyl)amino |
| 4-fluorophenyl | 2-amino-4-pyrimidinyl | 2-(4-fluorophenyl)-2-methyl-ethyl)amino |
| 4-fluorophenyl | 4-pyridyl | (2-methyl-2-phenylethyl)amino |
| 4-fluorophenyl | 2-acetamido-4-pyridyl | (2-methyl-2-phenylethyl)amino |
| 4-fluorophenyl | 2-amino-4-pyrimidinyl | (2-methyl-2-phenylethyl)amino |
| 4-fluorophenyl | 4-pyridyl | methyl-(2-phenylethyl)amino |
| 4-fluorophenyl | 2-acetamido-4-pyridyl | methyl-(2-phenylethyl)amino |
| 4-fluorophenyl | 2-amino-4-pyrimidinyl | methyl-(2-phenylethyl)amino |
| 4-fluorophenyl | 4-pyridyl | (2-(4-trifluoromethylphenyl)ethyl)amino |
| 4-fluorophenyl | 2-acetamido-4-pyridyl | (2-(4-trifluoromethylphenyl)ethyl)amino |
| 4-fluorophenyl | 2-amino-4-pyrimidinyl | (2-(4-trifluoromethylphenyl)ethyl)amino |
| 4-fluorophenyl | 4-pyridyl | 2-(4-tolyl)ethylamino |
| 4-fluorophenyl | 2-acetamido-4-pyridyl | 2-(4-tolyl)ethylamino |
| 4-fluorophenyl | 2-amino-4-pyrimidinyl | 2-(4-tolyl)ethylamino |
| 4-fluorophenyl | 4-pyridyl | (2-(3-fluorophenyl)ethyl)amino |
| 4-fluorophenyl | 2-acetamido-4-pyridyl | (2-(3-fluorophenyl)ethyl)amino |
| 4-fluorophenyl | 2-amino-4-pyrimidinyl | (2-(3-fluorophenyl)ethyl)amino |
| 4-fluorophenyl | 4-pyridyl | (2-(2-fluorophenyl)ethyl)amino |
| 4-fluorophenyl | 2-acetamido-4-pyridyl | (2-(2-fluorophenyl)ethyl)amino |
| 4-fluorophenyl | 2-amino-4-pyrimidinyl | (2-(2-fluorophenyl)ethyl)amino |
| 4-fluorophenyl | 4-pyridyl | methyl-(2-(2-pyridyl)ethyl)amino |
| 4-fluorophenyl | 2-acetamido-4-pyridyl | methyl-(2-(2-pyridyl)ethyl)amino |
| 4-fluorophenyl | 2-amino-4-pyrimidinyl | methyl-(2-(2-pyridyl)ethyl)amino |
| 4-fluorophenyl | 4-pyridyl | (1,1-dimethyl-3-phenyl-propyl)amino |
| 4-fluorophenyl | 2-acetamido-4-pyridyl | (1,1-dimethyl-3-phenyl-propyl)amino |
| 4-fluorophenyl | 2-amino-4-pyrimidinyl | (1,1-dimethyl-3-phenyl-propyl)amino |
| 4-fluorophenyl | 4-pyridyl | (3-(4-fluorophenyl)-propyl)amino |
| 4-fluorophenyl | 2-acetamido-4-pyridyl | (3-(4-fluorophenyl)-propyl)amino |
| 4-fluorophenyl | 2-amino-4-pyrimidinyl | (3-(4-fluorophenyl)-propyl)amino |
| 4-fluorophenyl | 4-pyridyl | (3-(4-fluorophenyl)-1-methyl-propyl)amino |
| 4-fluorophenyl | 2-acetamido-4-pyridyl | (3-(4-fluorophenyl)-1-methyl-propyl)amino |
| 4-fluorophenyl | 2-amino-4-pyrimidinyl | (3-(4-fluorophenyl)-1-methyl-propyl)amino |

-continued

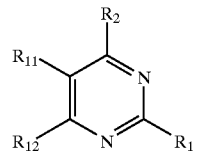

wherein $R^2$ is —OH and $R^{11}$, $R^{12}$, and $R^1$ are one of the combinations given in the following table:

| $R^{11}$ | $R^{12}$ | $R^1$ |
|---|---|---|
| 4-fluorophenyl | 4-pyridyl | (1,1-dimethyl-3-(4-fluorophenyl)-propyl)amino |
| 4-fluorophenyl | 2-acetamido-4-pyridyl | (1,1-dimethyl-3-(4-fluorophenyl)-propyl)amino |
| 4-fluorophenyl | 2-amino-4-pyrimidinyl | (1,1-dimethyl-3-(4-fluorophenyl)-propyl)amino |
| 4-fluorophenyl | 4-pyridyl | (3-(2-fluorophenyl)-propyl)amino |
| 4-fluorophenyl | 2-acetamido-4-pyridyl | (3-(2-fluorophenyl)-propyl)amino |
| 4-fluorophenyl | 2-amino-4-pyrimidinyl | (3-(2-fluorophenyl)-propyl)amino |
| 4-fluorophenyl | 4-pyridyl | (3-methyl-3-phenyl-propyl)amino |
| 4-fluorophenyl | 2-acetamido-4-pyridyl | (3-methyl-3-phenyl-propyl)amino |
| 4-fluorophenyl | 2-amino-4-pyrimidinyl | (3-methyl-3-phenyl-propyl)amino |
| 4-fluorophenyl | 4-pyridyl | (2-methyl-3-phenyl-propyl)amino |
| 4-fluorophenyl | 2-acetamido-4-pyridyl | (2-methyl-3-phenyl-propyl)amino |
| 4-fluorophenyl | 2-amino-4-pyrimidinyl | (2-methyl-3-phenyl-propyl)amino |
| 4-fluorophenyl | 4-pyridyl | (3,3-dimethylbutyl)amino |
| 4-fluorophenyl | 2-acetamido-4-pyridyl | (3,3-dimethylbutyl)amino |
| 4-fluorophenyl | 2-amino-4-pyrimidinyl | (3,3-dimethylbutyl)amino |
| 4-fluorophenyl | 4-pyridyl | isoamylamino |
| 4-fluorophenyl | 2-acetamido-4-pyridyl | isoamylamino |
| 4-fluorophenyl | 2-amino-4-pyrimidinyl | isoamylamino |
| 4-fluorophenyl | 4-pyridyl | amylamino |
| 4-fluorophenyl | 2-acetamido-4-pyridyl | amylamino |
| 4-fluorophenyl | 2-amino-4-pyrimidinyl | amylamino |
| 4-fluorophenyl | 4-pyridyl | (2,5-dimethyl)pentylamino |
| 4-fluorophenyl | 2-acetamido-4-pyridyl | (2,5-dimethyl)pentylamino |
| 4-fluorophenyl | 2-amino-4-pyrimidinyl | (2,5-dimethyl)pentylamino |
| 4-fluorophenyl | 4-pyridyl | piperazinyl |
| 4-fluorophenyl | 2-acetamido-4-pyridyl | piperazinyl |
| 4-fluorophenyl | 2-amino-4-pyrimidinyl | piperazinyl |
| 4-fluorophenyl | 4-pyridyl | (3-(3-fluorophenyl)-propyl)amino |
| 4-fluorophenyl | 2-acetamido-4-pyridyl | (3-(3-fluorophenyl)-propyl)amino |
| 4-fluorophenyl | 2-amino-4-pyrimidinyl | (3-(3-fluorophenyl)-propyl)amino |
| benzyl | 4-pyridyl | 3-phenylpropylamino |
| benzyl | 4-pyridyl | 2-(4-fluorophenyl)ethylamino |
| 2-thienyl | 4-pyridyl | 3-phenypropylamino |
| 2-thienyl | 4-pyridyl | 2-(4-fluorophenyl)ethylamino |
| cyclohexyl | 4-pyridyl | 3-phenylpropylamino |
| cyclohexyl | 4-pyridyl | 2-(4-fluorophenyl)ethylamino |
| tert-butyl | 4-pyridyl | 3-phenylpropylamino |

-continued

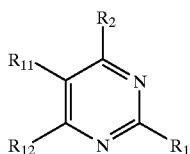

wherein $R^2$ is —OH and $R^{11}$, $R^{12}$, and $R^1$ are one of the combinations given in the following table:

| $R^{11}$ | $R^{12}$ | $R^1$ |
|---|---|---|
| tert-butyl | 4-pyridyl | 2-(4-fluorophenyl)ethylamino |
| 4-fluorophenyl | 4-piperidinyl | 3-phenylpropylamino |
| 4-fluorophenyl | 4-piperidinyl | 2-(4-fluorophenyl)ethylamino |
| 4-fluorophenyl | 4-pyranyl | 3-phenylpropylamino |
| 4-fluorophenyl | 4-pyranyl | 2-(4-fluorophenyl)ethylamino |
| Phenyl | 4-pyridyl | 3-phenyl-2-amino-propylamino |
| 4-fluorophenyl | 4-pyridyl | 3-phenyl-2-amino-propylamino |
| 3-fluorophenyl | 4-pyridyl | 3-phenyl-2-amino-propylamino |
| 2-fluorophenyl | 4-pyridyl | 3-phenyl-2-amino-propylamino |
| 4-chlorophenyl | 4-pyridyl | 3-phenyl-2-amino-propylamino |
| 3-chlorophenyl | 4-pyridyl | 3-phenyl-2-amino-propylamino |
| 2-chlorophenyl | 4-pyridyl | 3-phenyl-2-amino-propylamino |
| 4-tolyl | 4-pyridyl | 3-phenyl-2-amino-propylamino |
| 3-tolyl | 4-pyridyl | 3-phenyl-2-amino-propylamino |
| 2-tolyl | 4-pyridyl | 3-phenyl-2-amino-propylamino |
| 4-trifluoromethylphenyl | 4-pyridyl | 3-phenyl-2-amino-propylamino |
| 3-trifluoromethylphenyl | 4-pyridyl | 3-phenyl-2-amino-propylamino |
| 2,6-dichlorophenyl | 4-pyridyl | 3-phenyl-2-amino-propylamino |
| 2,6-dimethylphenyl | 4-pyridyl | 3-phenyl-2-amino-propylamino |
| 3,4-dichlorophenyl | 4-pyridyl | 3-phenyl-2-amino-propylamino |
| 3,4-dimethylphenyl | 4-pyridyl | 3-phenyl-2-amino-propylamino |
| 2,4-dichlorophenyl | 4-pyridyl | 3-phenyl-2-amino-propylamino |
| 2,4-dimethylphenyl | 4-pyridyl | 3-phenyl-2-amino-propylamino |
| Phenyl | 4-pyridyl | 3-phenyl-3-amino-propylamino |
| 4-fluorophenyl | 4-pyridyl | 3-phenyl-3-amino-propylamino |
| 3-fluorophenyl | 4-pyridyl | 3-phenyl-3-amino-propylamino |
| 2-fluorophenyl | 4-pyridyl | 3-phenyl-3-amino-propylamino |
| 4-chlorophenyl | 4-pyridyl | 3-phenyl-3-amino-propylamino |
| 3-chlorophenyl | 4-pyridyl | 3-phenyl-3-amino propylamino |
| 2-chlorophenyl | 4-pyridyl | 3-phenyl-3-amino-propylamino |
| 4-tolyl | 4-pyridyl | 3-phenyl-3-amino-propylamino |
| 3-tolyl | 4-pyridyl | 3-phenyl-3-amino-propylamino |
| 2-tolyl | 4-pyridyl | 3-phenyl-3-amino-propylamino |

-continued

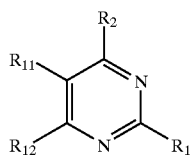

wherein $R^2$ is —OH and $R^{11}$, $R^{12}$, and $R^1$ are one of the combinations given in the following table:

| $R^{11}$ | $R^{12}$ | $R^1$ |
|---|---|---|
| 4-trifluoromethylphenyl | 4-pyridyl | 3-phenyl-3-amino-propylamino |
| 3-trifluoromethylphenyl | 4-pyridyl | 3-phenyl-3-amino-propylamino |
| 2,6-dichlorophenyl | 4-pyridyl | 3-phenyl-3-amino-propylamino |
| 2,6-dimethylphenyl | 4-pyridyl | 3-phenyl-3-amino-propylamino |
| 3,4-dichlorophenyl | 4-pyridyl | 3-phenyl-3-amino-propylamino |
| 3,4-dimethylphenyl | 4-pyridyl | 3-phenyl-3-amino-propylamino |
| 2,4-dichlorophenyl | 4-pyridyl | 3-phenyl-3-amino-propylamino |
| 2,4-dimethylphenyl | 4-pyridyl | 3-phenyl-3-amino-propylamino |
| 3-fluorophenyl | 4-pyridyl | (S)-tetrahydroisoquinol-3-ylmethylenamino |
| 2-fluorophenyl | 2-amino-4-pyridyl | (S)-3-benzylpiperazinyl |
| 3-chlorophenyl | 2-acetamido-4-pyridyl | (S)-2-N-isopropylamino-3-phenylpropylamino |
| 2-chlorophenyl | 2-amino-4-pyrimidinyl | (S)-2-N-glycylamino-3-phenylpropylamino |
| 4-tolyl | 4-pyridyl | (S)-2-amino-3-phenylpropylamino |
| 3-tolyl | 2-amino-4-pyridyl | (R)-2-amino-3-phenylpropylamino |
| 2-tolyl | 2-acetamido-4-pyridyl | 3-amino-3-phenylpropylamino |
| 4-trifluoromethylphenyl | 2-amino-4-pyrimidinyl | (S)-2-amino-3-(2-fluorophenyl)propylamino |
| 3-trifluoromethylphenyl | 4-pyridyl | (S)-2-amino-3-(2-methylphenyl)propylamino |
| 2,6-dichlorophenyl | 2-amino-4-pyridyl | 3-amino-3-(2-fluorophenyl)propylamino |
| 2,6-dimethylphenyl | 2-acetamido-4-pyridyl | 3-amino-3-(2-methylphenyl)propylamino |
| 3,4-dichlorophenyl | 2-amino-4-pyrimidinyl | 2-amino-2-methyl-3-phenylpropylamino |
| 3,4-dimethylphenyl | 4-pyridyl | 3-amino-2-methyl-3-phenylpropylamino |
| 3-fluorophenyl | 2-amino-4-pyridyl | (S)-2-amino-3-phenylpropylamino |
| 2-fluorophenyl | 2-acetamido-4-pyridyl | (S)-2-amino-3-(2-fluorophenyl)propylamino |
| 3-chlorophenyl | 2-amino-4-pyrimidinyl | (S)-2-amino-3-(2-methylphenyl)propylamino |
| 2-chlorophenyl | 4-pyridyl | (S)-2-N-isopropylamino-3-phenylpropylamino |
| 4-tolyl | 2-amino-4-pyridyl | (S)-2-N-glycylamino-3-phenylpropylamino |
| 3-tolyl | 2-acetamido-4-pyridyl | 2-amino-2-methyl-3-phenylpropylamino |
| 2-tolyl | 2-amino-4-pyridyl | (R)-2-amino-3-phenylpropylamino |
| 4-trifluoromethylphenyl | 4-pyridyl | 3-amino-3-phenylpropylamino |
| 3-trifluoromethylphenyl | 2-amino-4-pyridyl | 3-amino-3-(2-fluorophenyl)propylamino |
| 2,6-dichlorophenyl | 2-acetamido-4-pyridyl | 3-amino-3-(2-methylphenyl)propylamino |
| 2,6-dimethylphenyl | 2-amino-4-pyrimidinyl | 3-amino-2-methyl-3-phenylpropylamino |
| 3,4- | 4-pyridyl | (S)-tetrahydroisoquinol- |

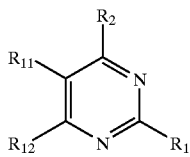

wherein $R^2$ is —OH and $R^{11}$, $R^{12}$, and $R^1$ are one of the combinations given in the following table:

| $R^{11}$ | $R^{12}$ | $R^1$ |
|---|---|---|
| dichlorophenyl | | 3-ylmethylenamino |
| 3,4-dimethyl phenyl | 4-pyridyl | (S)-3-benzylpiperazinyl |

Additional preferred compounds are listed in the Examples, infra.

As utilized herein, the following terms shall have the following meanings:

"Alkyl", alone or in combination, means a straight-chain or branched-chain alkyl radical containing preferably 1–15 carbon atoms ($C_1$–$C_{15}$), more preferably 1–8 carbon atoms ($C_1$–$C_8$), even more preferably 1–6 carbon atoms ($C_1$–$C_6$), yet more preferably 1–4 carbon atoms ($C_1$–$C_4$), still more preferably 1–3 carbon atoms ($C_1$–$C_3$), and most preferably 1–2 carbon atoms ($C_1$–$C_2$). Examples of such radicals include methyl, ethyl, n-propyl, isopropyl, n-butyl, isobutyl, sec-butyl, tert-butyl, pentyl, iso-amyl, hexyl, octyl and the like.

"Hydroxyalkyl", alone or in combination, means an alkyl radical as defined above wherein at least one hydrogen radical is replaced with a hydroxyl radical, preferably 1–3 hydrogen radicals are replaced by hydroxyl radicals, more preferably 1–2 hydrogen radicals are replaced by hydroxyl radicals, and most preferably one hydrogen radical is replaced by a hydroxyl radical. Examples of such radicals include hydroxymethyl, 1-, 2-hydroxyethyl, 1-, 2-, 3-hydroxypropyl, 1,3-dihydroxy-2-propyl, 1,3-dihydroxybutyl, 1,2,3,4,5,6-hexahydroxy-2-hexyl and the like.

"Alkenyl", alone or in combination, means a straight-chain or branched-chain hydrocarbon radical having one or more double bonds, preferably 1–2 double bonds and more preferably one double bond, and containing preferably 2–15 carbon atoms ($C_2$–$C_{15}$), more preferably 2–8 carbon atoms ($C_2$–$C_8$), even more preferably 2–6 carbon atoms ($C_2$–$C_6$), yet more preferably 2–4 carbon atoms ($C_2$–$C_4$), and still more preferably 2–3 carbon atoms ($C_2$–$C_3$). Examples of such alkenyl radicals include ethenyl, propenyl, 2-methylpropenyl, 1,4-butadienyl and the like.

"Alkoxy", alone or in combination, means a radical of the type "R—O—" wherein "R" is an alkyl radical as defined above and "O" is an oxygen atom. Examples of such alkoxy radicals include methoxy, ethoxy, n-propoxy, isopropoxy, n-butoxy, iso-butoxy, sec-butoxy, tert-butoxy and the like.

"Alkoxycarbonyl", alone or in combination, means a radical of the type "R—O—C(O)—" wherein "R—O—" is an alkoxy radical as defined above and "C(O)" is a carbonyl radical.

"Alkoxycarbonylamino", alone or in combination, means a radical of the type "R—O—C(O)—NH—" wherein "R—O—C(O)" is an alkoxycarbonyl radical as defined above, wherein the amino radical may optionally be substituted, such as with alkyl, aryl, aralkyl, cycloalkyl, cycloalkylalkyl and the like.

"Alkylthio", alone or in combination, means a radical of the type "R—S—" wherein "R" is an alkyl radical as defined above and "S" is a sulfur atom. Examples of such alkylthio radicals include methylthio, ethylthio, n-propylthio, isopropylthio, n-butylthio, iso-butylthio, sec-butylthio, tert-butylthio and the like.

"Alkylsulfinyl", alone or in combination, means a radical of the type "R—S(O)—" wherein "R" is an alkyl radical as defined above and "S(O)" is a mono-oxygenated sulfur atom. Examples of such alkylsulfinyl radicals include methylsulfinyl, ethylsulfinyl, n-propylsulfinyl, isopropylsulfinyl, n-butylsulfinyl, iso-butylsulfinyl, sec-butylsulfinyl, tert-butylsulfinyl and the like.

"Alkylsulfonyl", alone or in combination, means a radical of the type "R—S(O)$_2$—" wherein "R" is an alkyl radical as defined above and "S(O)$_2$" is a di-oxygenated sulfur atom. Examples of such alkylsulfonyl radicals include methylsulfonyl, ethylsulfonyl, n-propylsulfonyl, isopropylsulfonyl, n-butylsulfonyl, iso-butylsulfonyl, sec-butylsulfonyl, tert-butylsulfonyl and the like.

"Aryl", alone or in combination, means a phenyl or biphenyl radical, which is optionally benzo fused or heterocyclo fused and which is optionally substituted with one or more substituents selected from alkyl, alkoxy, halogen, hydroxy, amino, azido, nitro, cyano, haloalkyl, carboxy, alkoxycarbonyl, cycloalkyl, alkanoylamino, amido, amidino, alkoxycarbonylamino, N-alkylamidino, alkylamino, dialkylamino, aminoalkyl, alkylaminoalkyl, dialkylaminoalkyl, N-alkylamido, N,N-dialkylamido, aralkoxycarbonylamino, alkylthio, alkylsulfinyl, alkylsulfonyl, oxo and the like. Examples of aryl radicals are phenyl, o-tolyl, 4-methoxyphenyl, 2-(tert-butoxy)phenyl, 3-methyl-4-methoxyphenyl, 2-$CF_3$-phenyl, 2-fluorophenyl, 2-chlorophenyl, 3-nitrophenyl, 3-aminophenyl, 3-acetamidophenyl, 2-amino-3-(aminomethyl)phenyl, 6-methyl-3-acetamidophenyl, 6-methyl-2-aminophenyl, 6-methyl-2,3-diaminophenyl, 2-amino-3-methylphenyl, 4,6-dimethyl-2-aminophenyl, 4-hydroxyphenyl, 3-methyl-4-hydroxyphenyl, 4-(2-methoxyphenyl)phenyl, 2-amino-1-naphthyl, 2-naphthyl, 3-amino-2-naphthyl, 1-methyl-3-amino-2-naphthyl, 2,3-diamino-1-naphthyl, 4,8-dimethoxy-2-naphthyl and the like.

"Aralkyl", and "arylalkyl", alone or in combination, means an alkyl radical as defined above in which at least one hydrogen atom, preferably 1–2, is replaced by an aryl radical as defined above, such as benzyl, 1-, 2-phenylethyl, dibenzylmethyl, hydroxyphenylmethyl, methylphenylmethyl, diphenylmethyl, dichlorophenylmethyl, 4-methoxyphenylmethyl and the like.

"Aralkoxy", alone or in combination, means an alkoxy radical as defined above in which at least one hydrogen atom, preferably 1–2, is replaced by an aryl radical as defined above, such as benzyloxy, 1-, 2-phenylethoxy, dibenzylmethoxy, hydroxyphenylmethoxy, methylphenylmethoxy, dichlorophenylmethoxy, 4-methoxyphenylmethoxy and the like.

"Aralkoxycarbonyl", alone or in combination, means a radical of the type "R—O—C(O)—" wherein "R—O—" is an aralkoxy radical as defined above and "—C(O)—" is a carbonyl radical.

"Alkanoyl", alone or in combination, means a radical of the type "R—C(O)—" wherein "R" is an alkyl radical as defined above and "—C(O)—" is a carbonyl radical. Examples of such alkanoyl radicals include acetyl, trifluoroacetyl, hydroxyacetyl, propionyl, butyryl, valeryl, 4-methylvaleryl, and the like.

"Alkanoylamino", alone or in combination, means a radical of the type "R—C(O)—NH—" wherein "R—C(O)—" is an alkanoyl radical as defined above, wherein the amino radical may optionally be substituted, such as with alkyl, aryl, aralkyl, cycloalkyl, cycloalkylalkyl and the like.

"Aminocarbonyl", alone or in combination, means an amino substituted carbonyl (carbamoyl) radical, wherein the amino radical may optionally be mono- or di-substituted, such as with alkyl, aryl, aralkyl, cycloalkyl, cycloalkylalkyl, alkanoyl, alkoxycarbonyl, aralkoxycarbonyl and the like.

"Aminosulfonyl", alone or in combination, means an amino substituted sulfonyl radical.

"Benzo", alone or in combination, means the divalent radical $C_6H_4$=derived from benzene. "Benzo fused" forms a ring system in which benzene and a cycloalkyl or aryl group have two carbons in common, for example tetrahydronaphthylene and the like.

"Bicyclic" as used herein is intended to include both fused ring systems, such as naphthyl and β-carbolinyl, and substituted ring systems, such as biphenyl, phenylpyridyl and diphenylpiperazinyl.

"Cycloalkyl", alone or in combination, means a saturated or partially saturated, preferably one double bond, monocyclic, bicyclic or tricyclic carbocyclic alkyl radical, preferably monocyclic, containing preferably 5–12 carbon atoms ($C_5$–$C_{12}$), more preferably 5–10 carbon atoms ($C_5$–$C_{10}$), even more preferably 5–7 carbon atoms ($C_5$–$C_7$), which is optionally benzo fused or heterocyclo fused and which is optionally substituted as defined herein with respect to the definition of aryl. Examples of such cycloalkyl radicals include cyclopentyl, cyclohexyl, dihydroxycyclohexyl, ethylenedioxycyclohexyl, cycloheptyl, octahydronaphthyl, tetrahydronaphthyl, octahydroquinolinyl, dimethoxytetrahydronaphthyl, 2,3-dihydro-1H-indenyl, azabicyclo[3.2.1]octyl and the like.

"Heteroatoms" means nitrogen, oxygen and sulfur heteroatoms.

"Heterocyclo fused" forms a ring system in which a heterocyclyl or heteroaryl group of 5–6 ring members and a cycloalkyl or aryl group have two carbons in common, for example indole, isoquinoline, tetrahydroquinoline, methylenedioxybenzene and the like.

"Heterocyclyl" means a saturated or partially unsaturated, preferably one double bond, monocyclic or bicyclic, preferably monocyclic, heterocycle radical containing at least one, preferably 1 to 4, more preferably 1 to 3, even more preferably 1–2, nitrogen, oxygen or sulfur atom ring member and having preferably 3–8 ring members in each ring, more preferably 5–8 ring members in each ring and even more preferably 5–6 ring members in each ring. "Heterocyclyl" is intended to include sulfone and sulfoxide derivatives of sulfur ring members and N-oxides of tertiary nitrogen ring members, and carbocyclic fused, preferably 3–6 ring carbon atoms and more preferably 5–6 ring carbon atoms, and benzo fused ring systems. "Heterocyclyl" radicals may optionally be substituted on at least one, preferably 1–4, more preferably 1–3, even more preferably 1–2, carbon atoms by halogen, alkyl, alkoxy, hydroxy, oxo, thioxo, aryl, aralkyl, heteroaryl, heteroaralkyl, amidino, N-alkylamidino, alkoxycarbonylamino, alkylsulfonylamino and the like, and/ or on a secondary nitrogen atom by hydroxy, alkyl, aralkoxycarbonyl, alkanoyl, alkoxycarbonyl, heteroaralkyl, aryl or aralkyl radicals. More preferably, "heterocyclyl", alone or in combination, is a radical of a monocyclic or bicyclic saturated heterocyclic ring system having 5–8 ring members per ring, wherein 1–3 ring members are oxygen, sulfur or nitrogen heteroatoms, which is optionally partially unsaturated or benzo-fused and optionally substituted by 1–2 oxo or thioxo radicals. Examples of such heterocyclyl radicals include pyrrolidinyl, piperidinyl, piperazinyl, morpholinyl, thiamorpholinyl, 4-benzyl-piperazin-1-yl, pyrimidinyl, tetrahydrofuryl, pyrazolidonyl, pyrazolinyl, pyridazinonyl, pyrrolidonyl, tetrahydrothienyl and its sulfoxide and sulfone derivatives, 2,3-dihydroindolyl, tetrahydroquinolinyl, 1,2,3,4-tetrahydroisoquinolinyl, 1,2,3, 4-tetrahydro-1-oxo-isoquinolinyl, 2,3-dihydrobenzofuryl, benzopyranyl, methylenedioxyphenyl, ethylenedioxyphenyl and the like.

"Heteroaryl" means a monocyclic or bicyclic, preferably monocyclic, aromatic heterocycle radical, having at least one, preferably 1 to 4, more preferably 1 to 3, even more preferably 1–2, nitrogen, oxygen or sulfur atom ring members and having preferably 5–6 ring members in each ring, which is optionally saturated carbocyclic fused, preferably 3–4 carbon atoms ($C_3$–$C_4$) to form 5–6 ring membered rings and which is optionally substituted as defined above with respect to the definitions of aryl. Examples of such heteroaryl groups include imidazolyl, 1-benzyloxycarbonylimidazol-4-yl, pyrrolyl, pyrazolyl, pyridyl, 3-(2-methyl)pyridyl, 3-(4-trifluoromethyl)pyridyl, pyrimidinyl, 5-(4-trifluoromethyl)pyrimidinyl, pyrazinyl, triazolyl, furyl, thienyl, oxazolyl, thiazolyl, indolyl, quinolinyl, 5,6,7,8-tetrahydroquinolyl, 5,6,7,8-tetrahydroisoquinolinyl, quinoxalinyl, benzothiazolyl, benzofuryl, benzimidazolyl, benzoxazolyl and the like.

"Heteroaralkyl" and "heteroarylalkyl," alone or in combination, means an alkyl radical as defined above in which at least one hydrogen atom, preferably 1–2, is replaced by a heteroaryl radical as defined above, such as 3-furylpropyl, 2-pyrrolyl propyl, chloroquinolinylmethyl, 2-thienylethyl, pyridylmethyl, 1-imidazolylethyl and the like.

"Halogen" and "halo", alone or in combination, means fluoro, chloro, bromo or iodo radicals.

"Haloalkyl", alone or in combination, means an alkyl radical as defined above in which at least one hydrogen atom, preferably 1–3, is replaced by a halogen radical, more preferably fluoro or chloro radicals. Examples of such haloalkyl radicals include 1,1,1-trifluoroethyl, chloromethyl, 1-bromoethyl, fluoromethyl, difluoromethyl, trifluoromethyl, bis(trifluoromethyl)methyl and the like.

"4(3H)-pyrimidinone" (A) and "4-hydroxy-pyrimidine" (B) are names of two tautomers of the same compound which may be used interchangeably. It is intended that the use of one of these terms inherently includes the other.

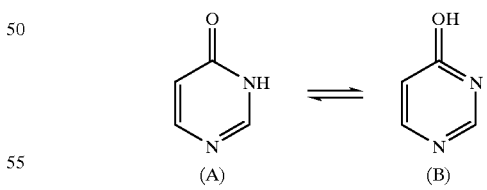

"Pharmacologically acceptable salt" means a salt prepared by conventional means, and are well known by those skilled in the art. The "pharmacologically acceptable salts" include basic salts of inorganic and organic acids, including but not limited to hydrochloric acid, hydrobromic acid, sulphuric acid, phosphoric acid, methanesulphonic acid, ethanesulfonic acid, malic acid, acetic acid, oxalic acid, tartaric acid, citric acid, lactic acid, fumaric acid, succinic acid, maleic acid, salicylic acid, benzoic acid, phenylacetic acid, mandelic acid and the like. When compounds of the invention include an acidic function such as a carboxy group, then suitable pharmaceutically acceptable cation pairs for the carboxy group are well known to those skilled in the art and include alkaline, alkaline earth, ammonium, quaternary ammonium cations and the like. For additional examples of "pharmacologically acceptable salts," see infra and Berge et al, *J. Pharm. Sci.* 66, 1 (1977).

"Cytokine" means a secreted protein that affects the functions of other cells, particularly as it relates to the modulation of interactions between cells of the immune system or cells involved in the inflammatory response. Examples of cytokines include but are not limited to interleukin 1 (IL-1), preferably IL-1β, interleukin 6 (IL-6), interleukin 8 (IL-8) and TNF, preferably TNF-α (tumor necrosis factor-α).

"TNF, IL-1, IL-6, and/or IL-8 mediated disease or disease state" means all disease states wherein TNF, IL-1, IL-6, and/or IL-8 plays a role, either directly as TNF, IL-1, IL-6, and/or IL-8 itself, or by TNF, IL-1, IL-6, and/or IL-8 inducing another cytokine to be released. For example, a disease state in which IL-1 plays a major role, but in which the production of or action of IL-1 is a result of TNF, would be considered mediated by TNF.

"Leaving group" generally refers to groups readily displaceable by a nucleophile, such as an amine, a thiol or an alcohol nucleophile. Such leaving groups are well known in the art. Examples of such leaving groups include, but are not limited to, N-hydroxysuccinimide, N-hydroxybenzotriazole, halides, triflates, tosylates and the like. Preferred leaving groups are indicated herein where appropriate.

"Protecting group" generally refers to groups well known in the art which are used to prevent selected reactive groups, such as carboxy, amino, hydroxy, mercapto and the like, from undergoing undesired reactions, such as nucleophilic, electrophilic, oxidation, reduction and the like. Preferred protecting groups are indicated herein where appropriate. Examples of amino protecting groups include, but are not limited to, aralkyl, substituted aralkyl, cycloalkenylalkyl and substituted cycloalkenyl alkyl, allyl, substituted allyl, acyl, alkoxycarbonyl, aralkoxycarbonyl, silyl and the like. Examples of aralkyl include, but are not limited to, benzyl, ortho-methylbenzyl, trityl and benzhydryl, which can be optionally substituted with halogen, alkyl, alkoxy, hydroxy, nitro, acylamino, acyl and the like, and salts, such as phosphonium and ammonium salts. Examples of aryl groups include phenyl, naphthyl, indanyl, anthracenyl, 9-(9-phenylfluorenyl), phenanthrenyl, durenyl and the like. Examples of cycloalkenylalkyl or substituted cycloalkyenylalkyl radicals, preferably have 6–10 carbon atoms, include, but are not limited to, cyclohexenyl methyl and the like. Suitable acyl, alkoxycarbonyl and aralkoxycarbonyl groups include benzyloxycarbonyl, t-butoxycarbonyl, iso-butoxycarbonyl, benzoyl, substituted benzoyl, butyryl, acetyl, tri-fluoroacetyl, tri-chloro acetyl, phthaloyl and the like. A mixture of protecting groups can be used to protect the same amino group, such as a primary amino group can be protected by both an aralkyl group and an aralkoxycarbonyl group. Amino protecting groups can also form a heterocyclic ring with the nitrogen to which they are attached, for example, 1,2-bis(methylene)benzene, phthalimidyl, succinimidyl, maleimidyl and the like and where these heterocyclic groups can further include adjoining aryl and cycloalkyl rings. In addition, the heterocyclic groups can be mono-, di- or tri-substituted, such as nitrophthalimidyl. Amino groups may also be protected against undesired reactions, such as oxidation, through the formation of an addition salt, such as hydrochloride, toluene-sulfonic acid, trifluoroacetic acid and the like. Many of the amino protecting groups are also suitable for protecting carboxy, hydroxy and mercapto groups. For example, aralkyl groups. Alkyl groups are also sutiable groups for protecting hydroxy and mercapto groups, such as tert-butyl.

Silyl protecting groups are silicon atoms optionally substituted by one or more alkyl, aryl and aralkyl groups. Suitable silyl protecting groups include, but are not limited to, trimethylsilyl, triethylsilyl, tri-isopropylsilyl, tert-butyldimethylsilyl, dimethylphenylsilyl, 1,2-bis(dimethylsilyl)benzene, 1,2-bis(dimethylsilyl)ethane and diphenylmethylsilyl. Silylation of an amino groups provide mono- or di-silylamino groups. Silylation of aminoalcohol compounds can lead to a N,N,O-tri-silyl derivative. Removal of the silyl function from a silyl ether function is readily accomplished by treatment with, for example, a metal hydroxide or ammonium flouride reagent, either as a discrete reaction step or in situ during a reaction with the alcohol group. Suitable silylating agents are, for example, trimethylsilyl chloride, tert-buty-dimethylsilyl chloride, phenyldimethylsilyl chloride, diphenylmethyl silyl chloride or their combination products with imidazole or DMF. Methods for silylation of amines and removal of silyl protecting groups are well known to those skilled in the art. Methods of preparation of these amine derivatives from corresponding amino acids, amino acid amides or amino acid esters are also well known to those skilled in the art of organic chemistry including amino acid/amino acid ester or aminoalcohol chemistry.

Protecting groups are removed under conditions which will not affect the remaining portion of the molecule. These methods are well known in the art and include acid hydrolysis, hydrogenolysis and the like. A preferred method involves removal of a protecting group, such as removal of a benzyloxycarbonyl group by hydrogenolysis utilizing palladium on carbon in a suitable solvent system such as an alcohol, acetic acid, and the like or mixtures thereof. A t-butoxycarbonyl protecting group can be removed utilizing an inorganic or organic acid, such as HCl or trifluoroacetic acid, in a suitable solvent system, such as dioxane or methylene chloride. The resulting amino salt can readily be neutralized to yield the free amine. Carboxy protecting group, such as methyl, ethyl, benzyl, tert-butyl, 4-methoxyphenylmethyl and the like, can be removed under hydroylsis and hydrogenolysis conditions well known to those skilled in the art.

The symbols used above have the following meanings:

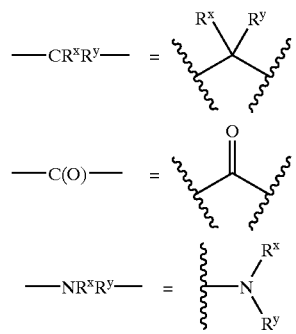

-continued

—C(NR)— = 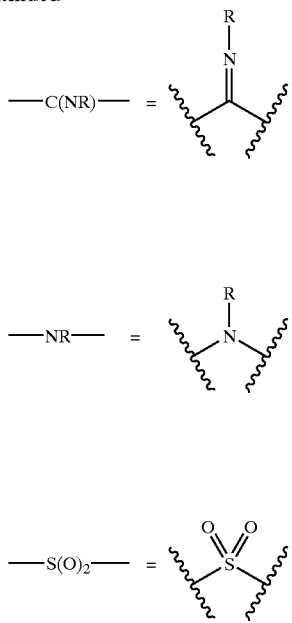

—NR— =

—S(O)₂— =

Prodrugs of the compounds of this invention are also contemplated by this invention. A prodrug is an active or inactive compound that is modified chemically through in vivo physiological action, such as hydrolysis, metabolism and the like, into a compound of this invention following adminstration of the prodrug to a patient. The suitability and techniques involved in making and using prodrugs are well known by those skilled in the art. For a general discussion of prodrugs involving esters see Svensson and Tunek Drug Metabolism Reviews 165 (1988) and Bundgaard Design of Prodrugs, Elsevier (1985). Examples of a masked carboxylate anion include a variety of esters, such as alkyl (for example, methyl, ethyl), cycloalkyl (for example, cyclohexyl), aralkyl (for example, benzyl, p-methoxybenzyl), and alkylcarbonyloxyalkyl (for example, pivaloyloxymethyl). Amines have been masked as arylcarbonyloxymethyl substituted derivatives which are cleaved by esterases in vivo releasing the free drug and formaldehyde (Bungaard J. Med. Chem. 2503 (1989)). Also, drugs containing an acidic NH group, such as imidazole, imide, indole and the like, have been masked with N-acyloxymethyl groups (Bundgaard Design of Prodrugs, Elsevier (1985)). Hydroxy groups have been masked as esters and ethers. EP 039,051 (Sloan and Little, Apr. 11, 1981) discloses Mannich-base hydroxamic acid prodrugs, their preparation and use.

Compounds according to the invention can be synthesized according to one or more of the following methods. It should be noted that the general procedures are shown as it relates to preparation of compounds having unspecified stereochemistry. However, such procedures are generally applicable to those compounds of a specific stereochemistry, e.g., where the stereochemistry about a group is (S) or (R). In addition, the compounds having one stereochemistry (e.g., (R)) can often be utilized to produce those having opposite stereochemistry (i.e., (S)) using well-known methods, for example, by inversion.

Pyrimidines

A general method for the preparation of compounds of formula I involves the condensation of an 1,3-dicarbonyl intermediate IV with an N—C—N containing structure such as an amidine V, a guanidine VI or urea VII (Scheme 1; for a review of synthetic methods see D. J. Brown, Heterocyclic Compounds: the Pyrimidines, Chapter 3, 1994, John Wiley & Sons).

Scheme 1

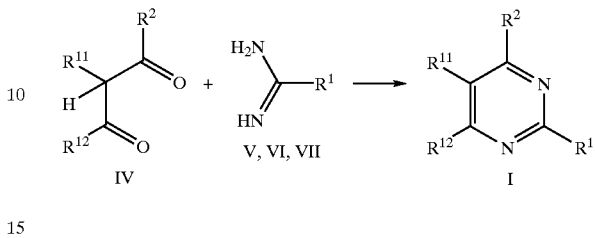

Additionally, as a 1,3-dicarbonyl synthon, a b-dimethylamino-a,b-unsaturated ketone IX can be reacted with amidines V or guanidines VI as described (G. B. Bennett et al., J. Med. Chem. 21, 623–628, 1978). (Scheme 2). Such b-dimethylamino-a,b-unsaturated ketones IX can be prepared by aminoformylation of an active methylene ketone VIII with Bredereck's reagent, namely, bis (dimethylamino)methoxymethane (H. Bredereck et al., Chem. Ber. 101, 41–50 (1968); G. B. Bennett et al., J. Org. Chem. 43, 221–225 (1977)).

Scheme 2

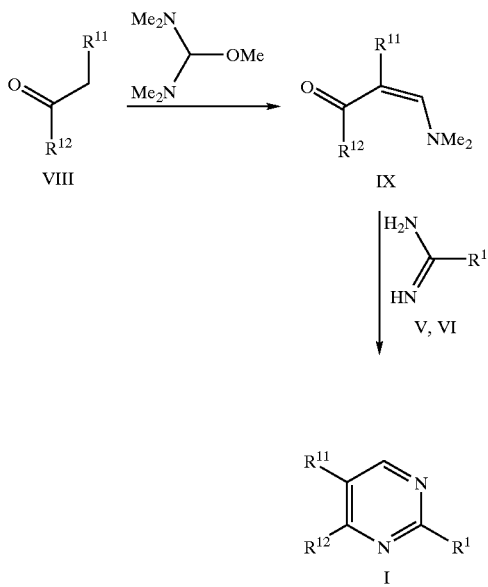

Scheme 3

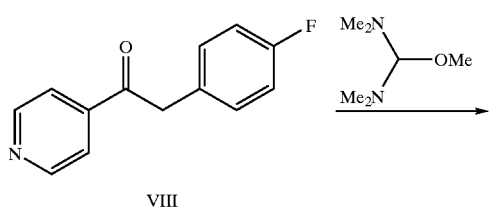

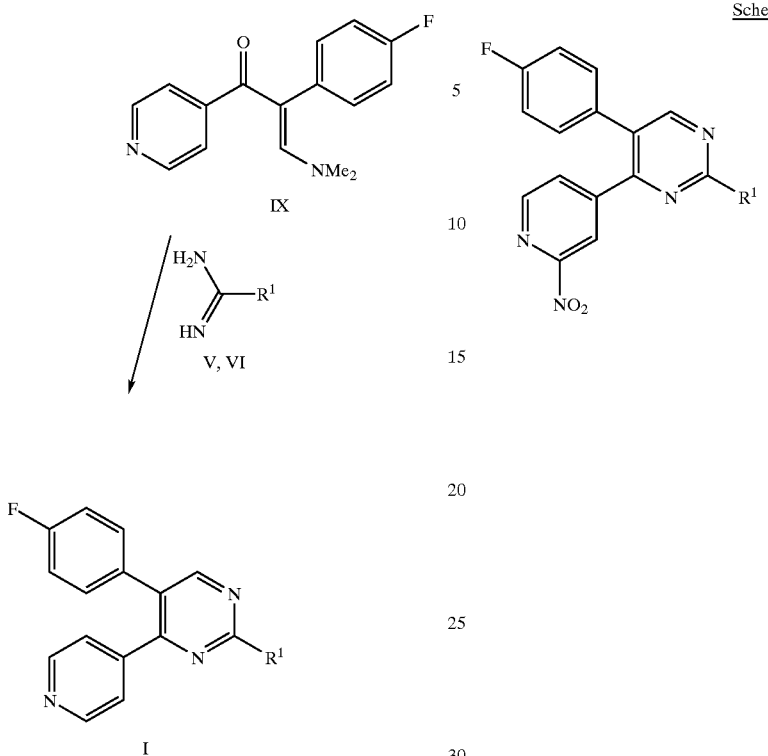

According to this approach, Scheme 3 illustrates the conversion of 2-(4-fluorophenyl)-1-(4-pyridyl)ethanone (VIII; Sheldrake, *Synthetic Communications* 23, 1967 (1993)) into the enamine IX. Intermediate IX may be condensed with a variety of amidines V and guanidines VI to provide 2-substituted 5-(4-fluorophenyl)-4-(4-pyridyl)-pyrimidines I.

Further ketones VIII may be prepared (e.g., according to Sheldrake, Synthetic communications 23, 1967–1971 (1993)), by employing other heteroaryl carboxaldehydes as the starting material, such as 2-methylpyridine-4-carboxaldehyde, 2,6-dimethylpyridine-4-carboxaldehyde (Mathes and Sauermilch, *Chem. Ber.* 88, 1276–1283 (1955)), quinoline-4-carboxaldehyde, pyrimidine-4-carboxaldehyde, 6-methylpyrimidine-4-carboxaldehyde, 2-methylpyrimidine-4-carboxaldehyde, 2,6-dimethylpyrimidine-4-carboxaldehyde (Bredereck et al., *Chem. Ber.* 97, 3407–3417 (1964)). Furthermore, 2-nitropyridin-4-carboxaldehyde may be prepared from 2-nitro-4-methylpyridine (Stanonis, *J. Org. Chem.* 22, 475 (1957)) by oxidation of the methyl group (Venemalm et al., *Tet. Lett.* 34, 5495–5496 (1993)). Its further conversion via a ketone VIII would lead to a 2-nitro-4-pyridyl derivative I (Scheme 4). Catalytic reduction of the nitro group to an amino group would provide a derivative of I with $R^{12}$ represented by a 2-amino-4-pyridyl group. Conventional acetylation of the amino group then leads to the 2-acetamido-4-pyridyl derivative.

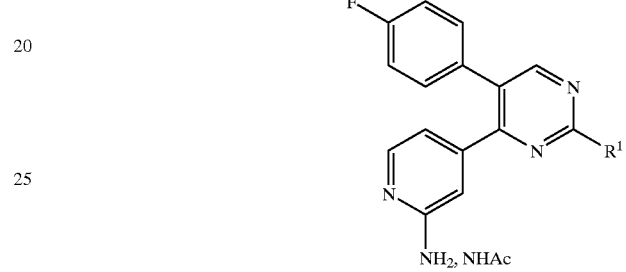

As displayed in Scheme 5, intermediate IX may also be condensed with urea VII to give the 2(1H)-pyrimidinone derivative X. X is transformed into chloride XI by reaction with a halogenating agent such as phosphorous oxychloride. Treatment of chloride XI with primary and secondary amines, thiolates or alcoholates allows the preparation of further pyrimidines I with $R^1$ represented by a substituted N, S or O groups, as recited above. Likewise, hydrazines may be reacted with chloride XI to provide 2-hydrazino substituted pyrimidines I.

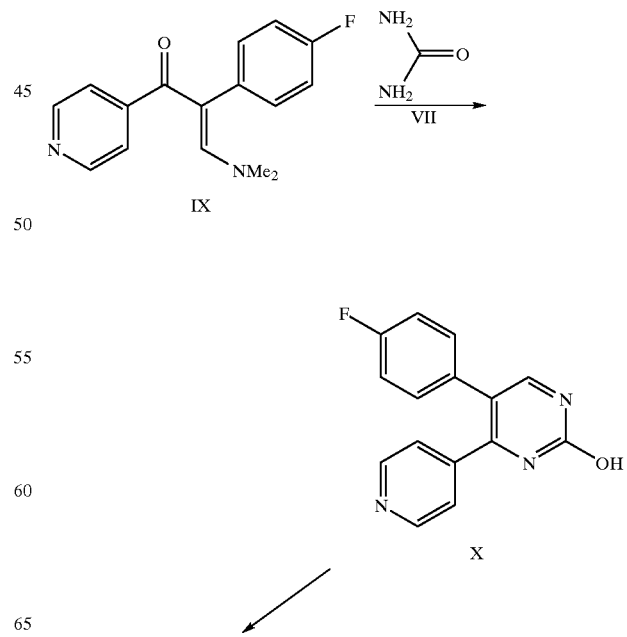

-continued

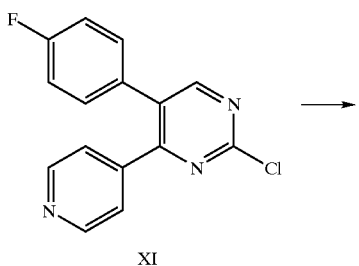

XI

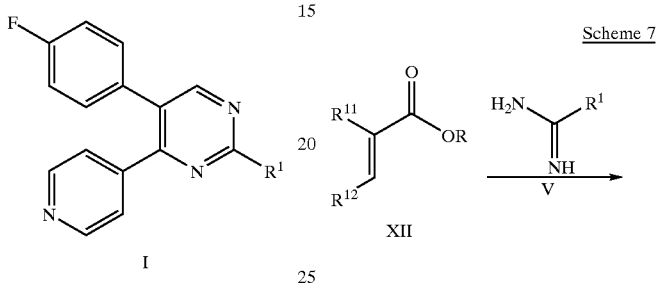

Scheme 6

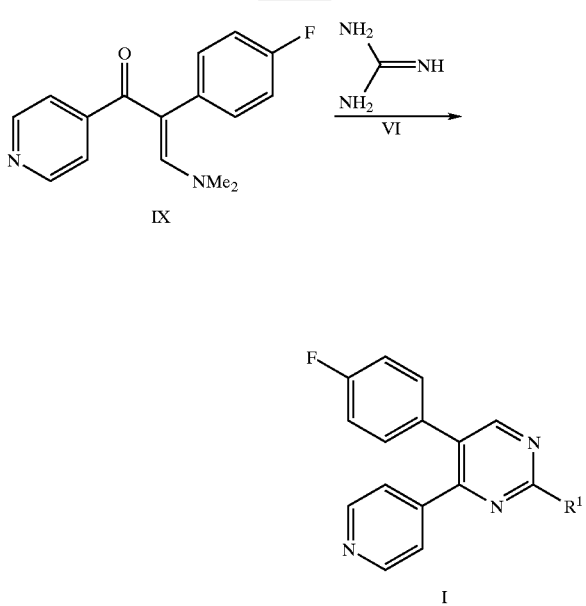

$R^1$ = $NH_2$
$R^1$ = $NR^{22}C(O)R^{21}$
$R^1$ = $NR^{22}SO_2R^{20}$

Palladium or nickel catalyzed cross couplings of chloride XI with arylboronic acids or arylzinc halides provide compounds of formula I wherein $R^1$ is aryl or heteroaryl.

Scheme 6 illustrates the reaction of intermediate IX with guanidine VI to give 2-amino substituted I. 2-Amino I is a useful intermediate for further acylations and sulfonylations of the 2-amino group to give acylamido and sulfonamido derivatives.

For the synthesis of 4-hydroxy-pyrimidines II, the approach displayed in Scheme 7 may be followed (for a review of synthetic methods see: D. J. Brown, Heterocyclic Compounds: the Pyrimidines, supra). This approach involves the cyclization reaction between an acrylic acid ester XII and an amidine V followed by oxidation of the resulting dihydropyrimidinone XIII to give II.

Scheme 7

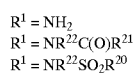

For the synthesis of 2-substituted 5-(4-fluorophenyl)-6-(4-pyridyl)-4-hydroxy-pyrimidines II (Scheme 8), the disubstituted acrylic acid ester XII may be prepared conveniently by condensation of pyridine-4-carboxaldehyde with 4-fluorophenylacetic acid followed by esterification. XII may be reacted with a variety of amidines V at elevated temperature. As a dehydrogenating agent for the conversion of XIII to II, sodium nitrite/acetic acid is suitable.

Accordingly, further compounds of formula II may be obtained in which $R^{12}$ is any other heteroaryl ring within the definition of $R^{12}$ by the appropriate choice of starting material. Such starting materials include but are not limited to 2-methylpyridine-4-carboxaldehyde, 2,6-dimethylpyridine-4-carboxaldehyde (Mathes and Sauermilch, *Chem. Ber.* 88, 1276–1283 (1955)), quinoline-4-carboxaldehyde, pyrimidine-4-carboxaldehyde, 6-methylpyrimidine-4-carbox-aldehyde, 2-methylpyrimidine-4-carboxaldehyde, 2,6-dimethylpyrimidine-4-carboxalde-hyde (Bredereck et al., *Chem. Ber.* 97, 3407–3417 (1964)). The use of 2-nitropyridine-4-carboxaldehyde would lead to a derivative of formula II with $R^{12}$ represented by a 2-nitro-4-pyridyl group. Catalytic reduction of the nitro to an amino group would provide the 2-amino-4-pyridyl derivative of II. The approach displayed in Scheme 8 is applicable to the use of other aryl acetic acids leading to compounds of formula II with different aryl groups as $R^{11}$.

Scheme 8

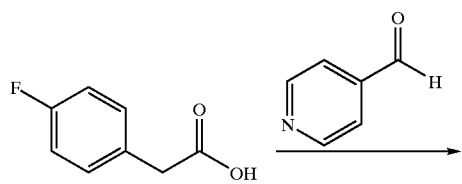
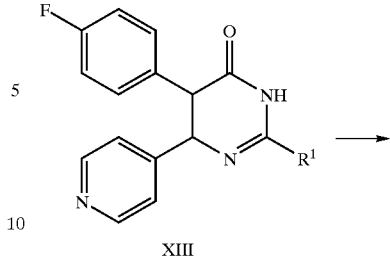
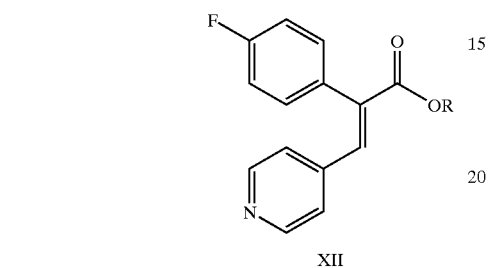
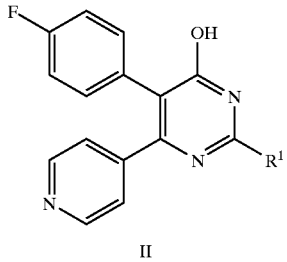
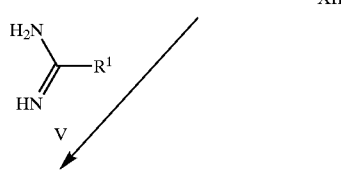

Another approach (Scheme 9) leading to 5,6-diaryl-4-hydroxy-pyrimidines involves the cyclization of the b-keto ester XIV with thiourea to give the thiouracil derivative XV. XV can be S-monomethylated to XVI. Reaction of XVI with primary and secondary amines leads to 2-amino substituted 4-hydroxy-pyrimidines II. Further 2-thioether derivatives of II with $R^1 = SR^{21}$ can be obtained, for example by alkylation of XV with alkyl halides. Treatment of XV or XVI with Raney nickel and $H_2$ provides compounds of structure II wherein $R^1$ is H.

Scheme 9

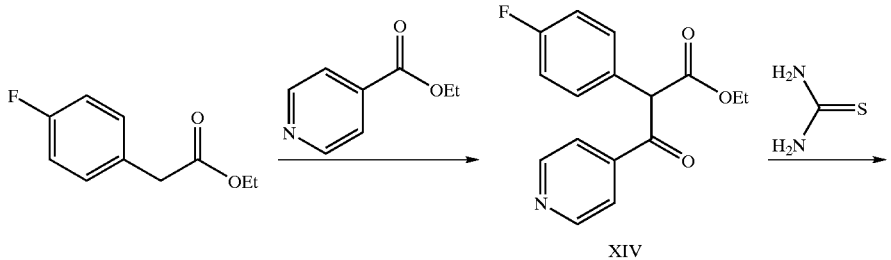
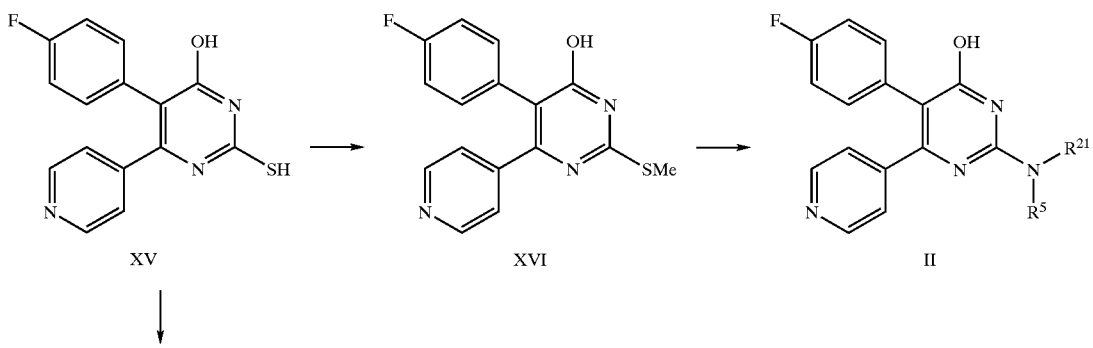

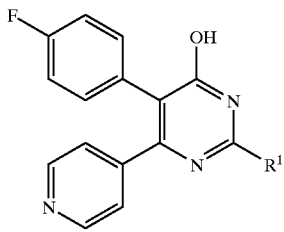

$R^1 = SR^{21}$

Although Scheme 9 illustrates syntheses in which $R^{12}$ is 4-pyridyl, this approach may be equally applied to any other heteroaryl ring within the definition of $R^{12}$ by the appropriate choice of the starting material. Such starting materials include but are not limited to ethyl 2-methyl isonicotinate (Efimovsky and Rumpf, *Bull. Soc. Chim. FR.* 648–649 (1954)), methyl pyrimidine-4-carboxylate, methyl 2-methylpyrimidine-4-carboxylate, methyl 6-methylpyrimidine-4-carboxylate and methyl 2,6-dimethylpyrimidine-4-carboxylate (Sakasi et al., *Heterocycles* 13, 235 (1978)). Likewise, methyl 2-nitroisonicotinate (Stanonis, *J. Org. Chem.* 22, 475 (1957)) may be reacted with an aryl acetic acid ester followed by cyclization of the resultant b-keto ester with thiourea analogously to Scheme 9. Subsequent catalytic reduction of the nitro group to an amino group would give a 4-hydroxy-pyrimidine II in which $R^{12}$ is represented by a 2-amino-4-pyridyl group (Scheme 10).

Scheme 10

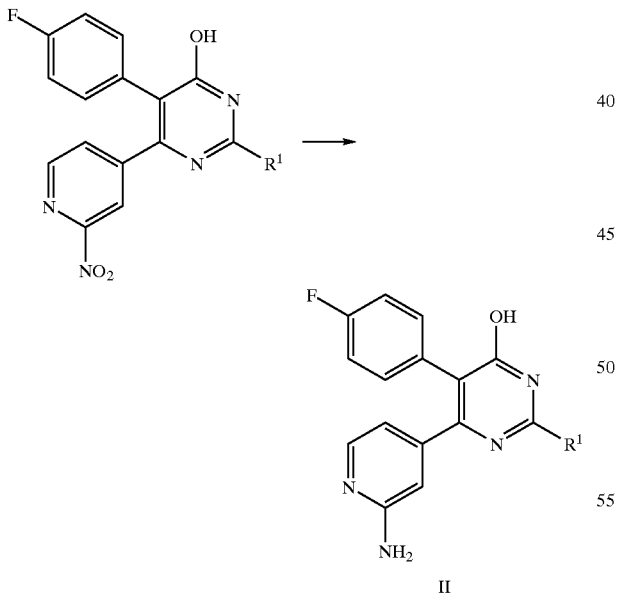

Furthermore, methyl 2-acetamido isonicotinate (Scheme 11) may be reacted analogously to Scheme 9 after appropriate protection of the amide nitrogen with e.g. a tert-butyldimethylsilyloxymethyl group (Benneche et al., *Acta Chem. Scand.* B 42 384–389 (1988)), a tert-butyldimethylsilyl group, a benzyloxymethyl group, a benzyl group or the like ($P_1$).

Scheme 11

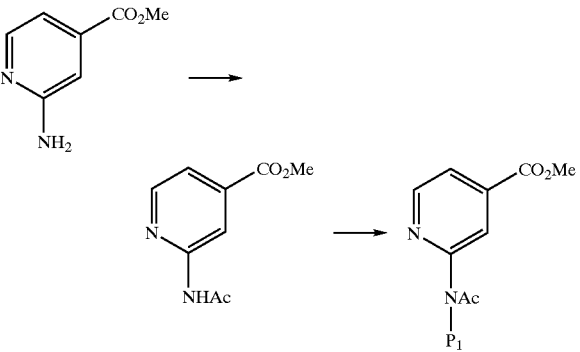

Removal of the protecting group $P_1$ of the resulting pyrimidine II with a suitable reagent (e.g., tetrabutylammonium fluoride in the case where $P_1$ is t-butyldimethylsilyloxymethyl) would then lead to a pyrimidine II with $R^{12}$ represented by a 2-acetamido-4-pyridyl group. Needless to say, ethyl p-fluorophenyl acetate may be substituted by any alkyl arylacetate in the procedure illustrated in Scheme 9 thus providing compounds of formula II with different $R^{11}$ aryl substituents.

In a further process, compounds of pyrimidines II may be prepared by coupling a suitable derivative of XVIII (L is a leaving group, such as halogen radical and the like, and $P^2$ is a protecting group, such as benzyl and the like) with an appropriate aryl equivalent.

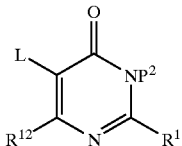

XVIII

Such aryl/heteroaryl couplings are well known to those skilled in the art and involve an organic-metallic component for reaction with a reactive derivative, e.g., a halogeno derivative, of the second compound in the presence of a catalyst. The metallo-organic species may be provided either by the pyrimidinone in which case the aryl component provides the reactive halogen equivalent or the pyrimidinone may be in the form of a reactive 5-halogeno derivative for reaction with a metallo organic aryl compound. Accordingly, 5-bromo and 5-iodo derivatives of XVIII (L=Br, I) may be treated with arylalkyl tin compounds, e.g., trimethylstannylbenzene, in an inert solvent such as tetrahydrofuran in the presence of a palladium catalyst, such as di(triphenylphosphine)palladium(II)dichloride. (Peters et al., *J. Heterocyclic Chem.* 27, 2165–2173, (1990). Alternatively, the halogen derivative of XVIII may be converted into a trialkyltin derivative (L=Bu₃Sn) by reaction with e.g. tributylstannyl chloride following lithiation with butyllithium and may then be reacted with an aryl halide in the presence of a catalyst. (Sandosham and Undheim, *Acta Chem. Scand.* 43, 684–689 (1989). Both approaches would lead to pyrimidines II in which $R^{11}$ is represented by aryl and heteroaryl groups.

As reported in the literature (Kabbe, *Lieb. Ann. Chem.* 704, 144 (1967); German Patent 1271116 (1968)) and displayed in Scheme 12, 5-aryl-2,6-dipyridyl-4-hydroxy-pyrimidines II may be prepared in a one step synthesis by reaction of the cyanopyridine with an arylacetyl ester, such as ethyl phenylacetate in the presence of sodium methoxide.

Scheme 12

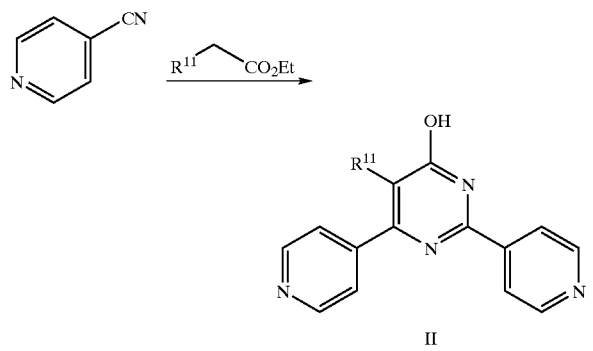

Analogously, as reported (Kabbe, supra) and displayed in Scheme 13, 4-amino-5-(aryl)-2,6-dipyridyl-pyrimidines XIX are obtained in a one step synthesis by reaction of cyanopyridine with arylacetonitrile, such as 4-fluorophenylacetonitrile.

Scheme 13

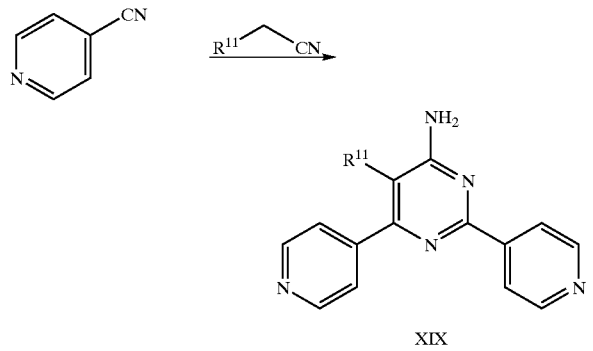

Modification at the 4-position ($R^2$ of formula I) of pyrimidine II is possible by conversion into the chloro derivative XX by reaction with phosphorous oxychloride (Scheme 14). A 4-alkoxy derivative XXI may be prepared from chloro derivative XX by nucleophilic substitution with alkoxide. Alternatively, in stead of the chloro group, other leaving groups, such as tosylates, mesylates and the like, can be used. Also, such leaving groups can also be displaced by amino, thiolates, alcoholates, and the like nucleophiles. For example, the chloro derivative XX may be reduced by catalytic hydrogenation to give a pyrimidine I where $R^2$ is H, or may be reacted with an alkyl or aryl boronic acid or an alkyl or aryl zinc halide to provide a pyrimidine I where $R^2$ is alkyl or aryl.

Scheme 14

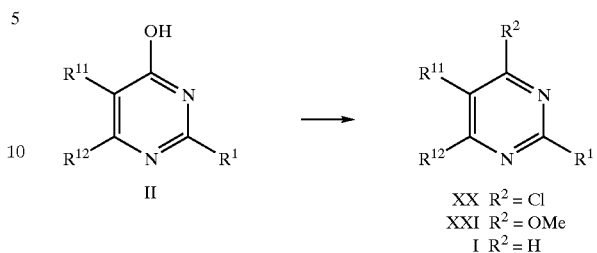

XX $R^2 = Cl$
XXI $R^2 = OMe$
I $R^2 = H$

In Scheme 15, compounds of the present invention of formula XXX can be readily prepared by reacting the methylthio intermediate XXXI with the amine $NHR^5R^{21}$, for example by heating the mixture preferably at a temperature greater than 100° C., more preferably 150–210° C. Alternatively, compounds of formula XXX can be readily prepared by reacting the methylsulfonyl intermediate XXXII with the amine $NHR^5R^{21}$, for example by heating the mixture preferably at a temperature greater than 40° C., more preferably 50–210° C.

Scheme 15

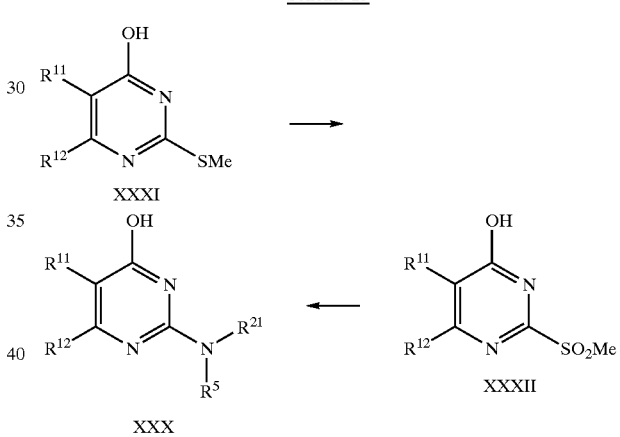

Amines of formula $NHR^5R^{21}$ are commercially available or can be readily prepared by those skilled in the art from commercially available starting materials. For example, an amide, nitro or cyano group can be reduced under reducing conditions, such as in the prescence of a reducing agent like lithium aluminum hydride and the like, to form the corresponding amine. Alkylation and acylation of amino groups are well known in the art. Chiral and achiral substituted amines can be prepared from chiral amino acids and amino acid amides (for example, alkyl, aryl, heteroaryl, cycloalkyl, arylalkyl, heteroarylalkyl, cycloalkylalkyl and the like substituted glycine, β-alanine and the like) using methods well known in the art, such as H. Brunner, P. Hankofer, U. Holzinger, B. Treittinger and H. Schoenenberger, Eur. J. Med. Chem. 25, 35–44, 1990; M. Freiberger and R. B. Hasbrouck, J. Am. Chem. Soc. 82, 696–698, 1960; Dornow and Fust, Chem. Ber. 87, 984, 1954; M. Kojima and J. Fujita, Bull. Chem. Soc. Jpn. 55, 1454–1459, 1982; W. Wheeler and D. O'Bannon, Journal of Labelled Compounds and Radiopharmaceuticals XXXI, 306, 1992; and S. Davies, N. Garrido, O. Ichihara and I. Walters, J. Chem. Soc., Chem. Commun. 1153, 1993.

The following Examples are presented for illustrative purposes only and are not intended, nor should they be

EXAMPLES

Example 1

General Procedure for the Preparation of 2-substituted 5-(4-fluorophenyl)-4-(4-pyridyl)-pyrimidines a. 3-(Dimethylamino)-2-(4-fluorophenyl)-1-(4-pyridyl)-3-propene-1-one (According to Bennett et al., J. Org. Chem. 43, 221 (1977)).

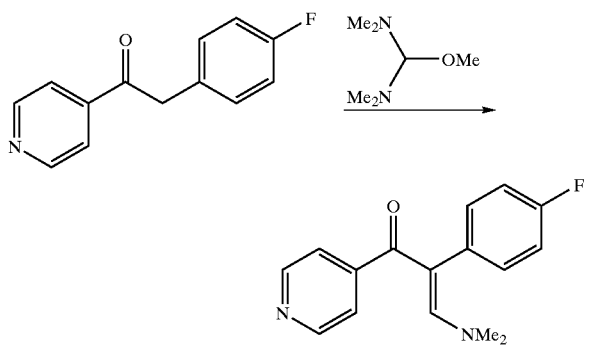

A mixture of 2-(4-fluorophenyl)-1-(4-pyridinyl)ethanone (300 mg, 1.39 mmol) and bis(dimethylamino)methoxymethane (300 mml, 1.95 mmol) was heated at 110° C. for 1.5 h under argon. It was evaporated and the yellow, crystallizing residue dried in an oil pump vacuum before used in the succeeding reaction. MS (m/z): 270.8 (M+H)+; $C_{16}H_{15}FN_2O$ requir. 270.3. $^1$H-NMR (CDCl$_3$): d 8.57, 7.25 (2 m, each 2H, Pyrid.), 7.36 (s, 1H, CH=), 7.13, 6.99 (2 m, each 2H, PhF), 3.00 (bs, 6H, 2CH$_3$).

b. General Procedure (According to Bennett et al., J. Med. Chem. 21, 623 (1978)).

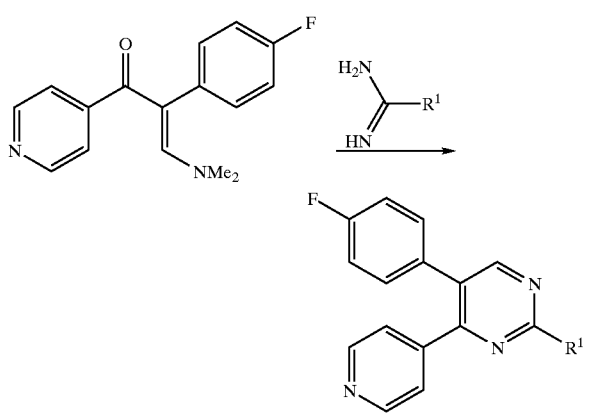

A solution of 3-(dimethylamino)-2-(4-fluorophenyl)-1-(4-pyridinyl)-3-propene-1-one (1.39 mmol) in absol. ethanol (9 ml) was transferred into a solution of the $R^1$—C(NH)NH$_2$ (1.67 mmol) in ethanol (2 ml) prepared from sodium (1.67 mmol) and the amidine or guanidine hydrochloride (1.67 mmol). After heating under reflux for 1.5 to 24 h, it was evaporated and the resulting material was applied either directly to a column of silica gel (1–5% methanol/dichloromethane) or was taken up in dichloromethane followed by washing with water, drying of the organic solution and evaporation prior to column chromatography.

The following pyrimidines were prepared according to this general procedure by reacting 3-(dimethylamino)-2-(4-fluorophenyl)-1-(4-pyridinyl)-3-propene-1-one with amidines:

1-1 5-(4-Fluorophenyl)-2-methyl-4-(4-pyridyl)-pyrimidine

MS (m/z): 266.0 (M+H)+; $C_{16}H_{12}FN_3$ requir. 265.3. $^1$H-NMR (CDCl$_3$): d 8.70 (d, 1H, H-6, Pyrim.), 8.59, 7.32 (2 m, each 2H, Pyrid.), 7.20–7.00 (m, 4H, PhF), 2.88 (s, 3H, CH$_3$).

$R_1$=CH$_3$—

1-2 5-(4-Fluorophenyl)-2-isopropyl-4-(4-pyridyl)-pyrimidine

MS (m/z): 294.4 (M+H)+; $C_{18}H_{16}FN_3$ requir. 293.4. $^1$H-NMR (CDCl$_3$): d 8.73 (s, 1H, H-6, Pyrim.), 8.60, 7.35 (2 m, each 2H, Pyrid.), 7.20–7.04 (m, 4H, PhF), 3.37 (m, 1H, CH(CH$_3$)$_2$), 1.50, 1.47 (2s, each 3H, 2CH$_3$).

$R_1$=(CH$_3$)$_2$CH—

1-3 2-tert-Butyl-5-(4-fluorophenyl)-4-(4-pyridyl)-pyrimidine

MS (m/z): 307.8 (M+H)+; $C_{19}H_{18}FN_3$ requir. 307.4. $^1$H-NMR (CDCl$_3$): d 8.72 (S, 1H, H-6, Pyrim.), 8.59, 7.38 (2 m, each 2H, Pyrid.), 7.21–7.06 (m, 4H, PhF), 1.52 (s, 9H, 3CH$_3$).

$R_1$=(CH$_3$)$_3$C—

1-4 2-(1-Chloro-2-methoxyethyl)-5-(4-fluorophenyl)-4-(4-pyridyl)-pyrimidine

MS (m/z): 344.2 (M+H)+; $C_{18}H_{15}ClFN_3O$ requir. 343.8. $^1$H-NMR (CDCl$_3$): d 8.81 (s, 1H, H-6, Pyrim.), 8.61, 7.35 (2 m, each 2H, Pyrid.), 7.22–7.08 (m, 4H, PhF), 5.29 (dd, 1H, CHCl), 4.31, 4.04 (2 dd, each 1H, CH$_2$O), 3.47 (s, 3H, CH$_3$O).

$R_1$=CH$_3$OCH$_2$CH(Cl)—

1-5 2-(Cyclopropyl)-5-(4-fluorophenyl)-4-(4-pyridyl)-pyrimidine

MS (m/z): 292.0 (M+H)+; $C_{18}H_{14}FN_3$ requir. 291.3. $^1$H-NMR (CDCl$_3$): d 8.60 (s, 1H, H-6, Pyrim.), 8.57, 7.32 (2 d, each 2H, Pyrid.), 7.16–7.00 (m, 4H, PhF), 2.32 (m, 1H, —CH—), 1.2, 1.1 (2 m, each 2H, 2CH$_2$).

1-6 2-(Adamant-1-yl)-5-(4-fluorophenyl)-4-(4-pyridyl)-pyrimidine

MS (m/z): 386.0 (M+H)+; $C_{25}H_{24}FN_3$ requir. 385.5. $^1$H-NMR (CDCl$_3$): d 8.76 (s, 1H, H-6, Pyrim.), 8.61, 7.51 (2 m, each 2H, Pyrid.), 7.22–7.08 (m, 4H, PhF), ~1.9–1.5 (broad, 15H, CH$_2$, CH).

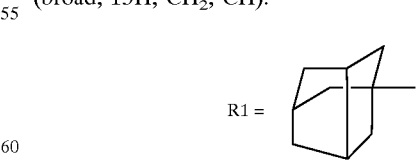

1-7 2-Benzyl-5-(4-fluorophenyl)-4-(4-pyridyl)-pyrimidine

MS (m/z): 342.2 (M+H)+; $C_{22}H_{16}FN_3$ requir. 341.4. $^1$H-NMR (CDCl$_3$): d 8.71 (s, 1H, H-6, Pyrim.), 8.60, 7.48 (2 m, each 2H, Pyrid.), 7.42–7.04 (m, 9H, PhF, Ph), 4.42 (s, 2H, CH$_2$Ph).

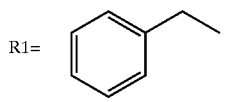

1-8 2-(2,6-Dichlorobenzyl)-5-(4-fluorophenyl)-4-(4-pyridyl)-pyrimidine

MS (m/z): 410.2 (M)+; $C_{22}H_{14}Cl_2FN_3$ requir. 410.3. $^1$H-NMR (CDCl$_3$): d 8.68 (s, 1H, H-6, Pyrim.), 8.57 (d, 2H, Pyrid.), 7.44–7.03 (m, 9H, Pyrid., PhF, PhCl$_2$), 4.93 (s, 2H, CH$_2$).

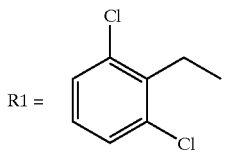

1-9 5-(4-Fluorophenyl)-2-phenoxymethyl-4-(4-pyridyl)-pyrimidine

MS (m/z): 358.2 (M+H)+; $C_{22}H_{16}FN_3O$ requir. 357.4. $^1$H-NMR (CDCl$_3$): d 8.83 (s, 1H, H-6, Pyrim.), 8.60 (m, 2H, Pyrid.), 7.36–6.98 (m, 11H, Pyrid., PhF, Ph), 5.43 (s, 2H, CH$_2$).

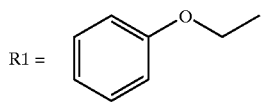

1-10 5-(4-Fluorophenyl)-2-phenylthiomethyl-4-(4-pyridinyl)-pyrimidine

MS (m/z): 374.2 (M+H)+; $C_{22}H_{16}FN_3S$ requir. 373.5. $^1$H-NMR (CDCl$_3$): d 8.72 (s, 1H, Pyrim.), 8.56, 7.49 (2 m each 2H, Pyrid.), 7.32–7.02 (m, 9H, PhF, Ph), 4.50 (s, 2H, CH$_2$).

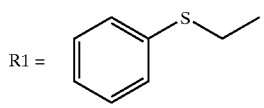

1-11 5-(4-Fluorophenyl)-2-phenyl-4-(4-pyridyl)-pyrimidine

MS (m/z): 328.2 (M+H)+; $C_{21}H_{14}FN_3$ requir. 327.4. $^1$H-NMR (CDCl$_3$): d 8.85 (s, 1H, H-6, Pyrim.), 8.63, 7.4 (2 m, each 2H, Pyrid.), 8.56, 7.6–7.5, 7.25–7.05 (m, 9H, PhF, Ph).

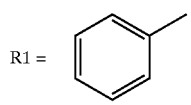

1-12 5-(4-Fluorophenyl)-2-(4-hydroxyphenyl)-4-(4-pyridyl)-pyrimidine

MS (m/z): 344.2 (M+H)+; $C_{21}H_{14}FN_3O$ requir. 343.4. $^1$H-NMR (DMSO-d$_6$): d 10.2 (bs, 1H, OH), 8.90 (s, 1H, H-6, Pyrim., Pyrim.), 8.60, 7.42 (2 m, each 2H, Pyrid.), 8.35, 7.40–6.92 (m, 8H, PhF, PhOH).

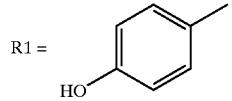

1-13 5-(4-Fluorophenyl)-2-(4-aminophenyl)-4-(4-pyridyl)-pyrimidine

MS (m/z): 343.2 (M+H)+; $C_{21}H_{15}FN_4$ requir. 342.4. $^1$H-NMR (CDCl$_3$): d 8.75 (s, 1H, H-6, Pyrim.), 8.60, 7.41 (2 m, each 2H, Pyrid.), 8,40, 7.22–6.79 (m, 8H, PhF, Ph), 4.00 (bs, 2H, NH$_2$)

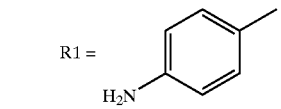

1-14 5-(4-Fluorophenyl)-2-(3-pyridyl)-4-(4-pyridyl)-pyrimidine

MS (m/z): 329.0 (M+H)+; $C_{20}H_{13}FN_4$ requir. 328.4. $^1$H-NMR (CDCl$_3$): d 9.80 (bs, H-2, 3-Pyrid.), 8.90 (s, 1H, H-6, Pyrim.), 8.84, 8.80 (2 m, each 1H, 3-Pyrid.), 8.66, 7.45 (2 m, each 2H, 4-Pyrid.), 7.50 (m, 1H, 3-Pyrid.), 7.28–7.10 (m, 4H, PhF).

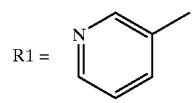

1-15 5-(4-Fluorophenyl)-2-(2-pyridyl)-4-(4-pyridyl)-pyrimidine

MS (m/z): 329.0 (M+H)+; $C_{20}H_{13}FN_4$ requir. 328.4. $^1$H-NMR (CDCl$_3$): d 9.01 (s, 1H, H-6, Pyrim.), 8.92, 8.66, 7.94, 7.48 (4 m, each 1H, 2-Pyrid.), 8.66, 7.47 (2 m, each 2H, 4-Pyrid.), 7.26, 7.14 (2 m, each 2H, PhF).

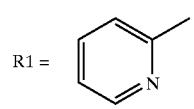

1-16 5-(4-Fluorophenyl)-2-(2-pyrazinyl)-4-(4-pyridyl)-pyrimidine

MS (m/z): 330.2 (M+H)+; $C_{19}H_{12}FN_5$ requir. 329.3. $^1$H-NMR (CDCl$_3$): 9.84 (m, 1H, H-3, Pyraz.), 9.01 (s, 1H, H-6, Pyrim.), 8.84, 8.76 (2 m, each 1H, H-5, H-6, Pyraz.), 8.65, 7.44 (2 m, each 2H, Pyrid.), 7.26, 7.13 (2 m, each 2H, PhF).

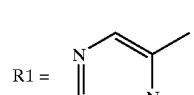

1-17 5-(4-Fluorophenyl)-2-(2-methylthiazol-4-yl)-4-(4-pyridyl)-pyrimidine

MS (m/z): 349.0 (M+H)+; $C_{19}H_{13}FN_4S$ requir. 348.4. $^1$H-NMR (CDCl$_3$): d 8.90 (s, 1H, H-6, Pyrim.), 8.63, 7.42 (2 m, each 2H, Pyrid.), 8.32 (s, 1H, H-5, Thiaz.), 7.22, 7.10 (2 m, each 2H, PhF), 2.88 (s, 3H, CH$_3$).

R1 = 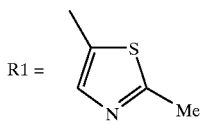

1-18 5-(4-Fluorophenyl)-4-(4-pyridyl)-2-(2-thienyl)-pyrimidine
MS (m/z): 334.2 (M+H)⁺; $C_{19}H_{12}FN_3S$ requir. 333.4.
¹H-NMR (CDCl₃): d 8.74 (S, 1H, H-6, Pyrim.), 8.63, 7.41 (2 m, each 2H, Pyrid.), 8.13, 7.55 (2 m, each 1H, Thioph.), 7.20 (m, 3H, PhF, Thioph.). 7.10 (m, 2H, PhF).

R1 = 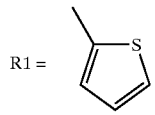

The following pyrimidines were prepared according to the general procedure by reacting 3-(dimethylamino)-2-(4-fluorophenyl)-1-(4-pyridinyl)-3-propene-1-one with guanidines:
1-19 2-Amino-5-(4-fluorophenyl)-4-(4-pyridyl)-pyrimidine
MS (m/z): 267.0 (M+H)⁺; $C_{15}H_{11}FN_4$ requir. 266.3.
¹H-NMR (DMSO-d₆): d 8.54, 7.26 (2 m, each 2H, Pyrid.), 8.35 (s, 1H, H-6, Pyrim.), 7.22–7.12 (m, 4H, PhF), 6.97 (s, 2H, NH₂).
R1=NH₂—
1-20 2-Ethylamino-5-(4-fluorophenyl)-4-(4-pyridyl)-pyrimidine
MS (m/z): 295.0 (M+H)⁺; $C_{17}H_{15}FN_4$ requir. 294.3.
¹H-NMR (CDCl₃): d 8.56, 7.32 (m, each 2H, Pyrid.), 8.36 (s, 1H, H-6, Pyrim.), 7.12–6.99 (m, 4H, PhF), 5.33 (unresolv.t, 1H, NH), 3.58 (m, 2H, CH₂), 1.32 (t, 3H, CH₃).
R1=CH₃CH₂—NH—
1-21 5-(4-Fluorophenyl)-4-(4-pyridyl)-2-(2-sulfoethylamino)-pyrimidine
MS (m/z): 375.2 (M+H)⁺; $C_{17}H_{15}FN_4O_3S$ requir. 374.4.
¹H-NMR (DMSO-d₆): d 8.51, 7.25 (2 d, each 2H, Pyrid.), 8.36 (s, 1H, H-6, Pyrim.), 7.32 (t, 1H, NH), 7.2–7.1 (m, 4H, PhF), 3.62 (q, 2H, CH₂N), 2.72 (t, 2H, CH₂).
R1=HO₃S—CH₂—CH₂—NH—
1-22 2-(2-Diethylaminoethylamino)-5-(4-fluorophenyl)-4-(4-pyridyl)-pyrimidine
MS (m/z): 365.8 (M+H)⁺; $C_{21}H_{24}FN_5$ requir. 365.5.
¹H-NMR (CDCl₃): d 8.55, 7.28 (2 m, each 2H, Pyrid.), 8.34 (s, 1H, H-6, Pyrim.), 7.08, 7.01 (2 m, each 2H, PhF), 5.95 (bs, 1H, NH), 3.60 (q, 2H, CH₂N), 2.76 (t, 2H, CH₂), 2.65 (q, 4H, 2CH₂CH₃), 1.08 (t, 6H, 2CH₃).
R1=(CH₃CH₂)₂NCH₂CH₂NH—
1-23 (4-Fluorophenyl)-4-(4-pyridyl)-2-(thioureido)-pyrimidine
MS (m/z): 326.2 (M+H)⁺; $C_{16}H_{12}FN_5S$ requir. 325.4.
¹H-NMR (DMSO-d₆): d 10.84, 10.11, 9.20 (3 s, each 1H, NH, SH), 8.75 (s, 1H, H-6, Pyrim.), 8.59, 7.32 (2 m, each 2H, Pyrid.), 7.28, 7.21 (2 m, each 2H, Ph)F.

R1 = 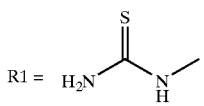

1-24 2-(2,6-Dichlorophenylamino)-5-(4-fluorophenyl)-4-(4-pyridyl)-pyrimidine
MS (m/z): 410.8 (M)⁺; $C_{21}H_{13}Cl_2FN_4$ requir. 411.3.
¹H-NMR (CDCl₃): d 8.54, 7.30 (2 m, each 2H, Pyrid.), 8.45 (s, 1H, H-6, Pyrim.), 7.45 (d, 2H, PhCl₂), 7.21 (t, 1H, PhCl₂), 7.12, 7.04 (2 m, each 2H, PhF).

R1 = 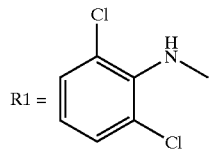

1-25 2-(2,6-Dimethylphenylamino)-5-(4-fluorophenyl)-4-(4-pyridyl)-pyrimidine
MS (m/z): 371.0 (M+H)⁺; $C_{23}H_{19}FN_4$ requir. 370.4.
¹H-NMR (CDCl₃): d 8.56, 7.32 (2 d, each 2H, Pyrid.), 8.40 (s, 1H, H-6, Pyrim.), 7.20 (s, 3H, PhCl₂), 7.11, 7.04 (2 m, each 2H, PhF), 6.66 (s, 1H, NH), 2.20 (s, 6H, 2CH₃).

R1 = 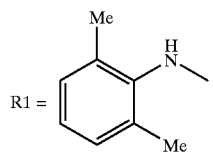

1-26 5-(4-Fluorophenyl)-4-(4-pyridyl)-pyrimidine
MS (m/z): 373.0 (M+H)⁺; $C_{22}H_{17}FN_4O$ requir. 372.4.
¹H-NMR (CDCl₃): d 8.62, 7.40 (2 m, each 2H, Pyrid.), 8.60 (m, 1H, PhOMe), 8.52 (s, 1H, H-6, Pyrim.), 7.99 (s, 1H, NH), 7.18–6.94 (m, 7H, PhF, PhOMe), 3.96 (s, 3H, CH₃O).

R1 = 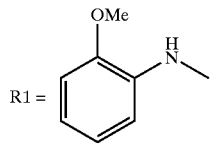

1-27 5-(4-Fluorophenyl)-2-(4-fluorophenylamino)-4-(4-pyridyl)-pyrimidine
MS (m/z): 361.0 (M+H)⁺; $C_{21}H_{14}F_2N_4$ requir. 360.4.
¹H-NMR (CDCl₃): d 8.58, 7.32 (m, 2H, Pyrid.), 8.46 (s, 1H, H-6, Pyrim.), 7.62 (m, 2H, PhF), 7.24 (bs, 1H, NH), 7.13–7.00 (m, 6H, PhF).

R1 = 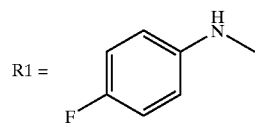

1-28 2-(4-Ethylphenylamino)-5-(4-fluorophenyl)-4-(4-pyridyl)-pyrimidine
MS (m/z): 371.2 (M+H)⁺; $C_{23}H_{19}FN_4$ requir. 370.4.
¹H-NMR (CDCl₃): d 8.61, 7.41 (2 m, each 2H, Pyrid.), 8.49 (s, 1H, H-6, Pyrim.), 7.60, 7.23 (2 d, each 2H, PhEth), ~7.28 (NH), 7.13, 7.06 (2 m, each 2H, PhF), 2.67 (q, 2H, CH₂), 1.27 (t, 3H, CH₃).

R1 = 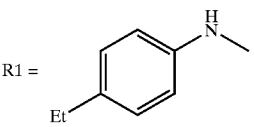

1-29 5-(4-Fluorophenyl)-4-(4-pyridyl)-2-(3-trifluoromethylphenylamino)-pyrimidine
MS (m/z): 411.0 (M+H)⁺; $C_{22}H_{14}F_4N_4$ requir. 410.4.
¹H-NMR (CDCl₃): d 8.60, 7.35 (2 m, each 2H, Pyrid.), 8.52

(s, 1H, H-6, Pyrim.), 8.23, 7.73, 7.46 (s, dd, t, each 1H, PhCF₃), 7.44 (s, 1H, NH), 7.31 (dd, 1H, PhCF₃), 7.13, 7.05 (2 m, each 2H, PhF).

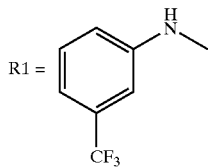

1-30 2-(Benzylamino)-5-(4-fluorophenyl)-4-(4-pyridyl)-pyrimidine

MS (m/z): 357.0 (M+H)⁺; $C_{22}H_{17}FN_4$ requir. 356.4. ¹H-NMR (CDCl₃): d 8.55, 7.28 (2 m, each 2H, Pyrid.), 8.36 (s, 1H, H-6, Pyrim.), 7.44–7.28 (m, 5H, Ph), 7.09, 7.02 (2 m, each 2H, PhF),5.71 (t, 1H, NH), 4.75 (d, 1H, CH₂)

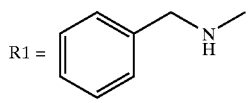

1-31 5-(4-Fluorophenyl)-2-(2-phenylethylamino)-4-(4-pyridyl)-pyrimidine

MS (m/z): 371.0 (M+H)⁺; $C_{23}H_{19}FN_4$ requir. 370.4. ¹H-NMR (CDCl₃): d 8.56 (m, 2H, Pyrid.), 8.35 (s, 1H, H-6, Pyrim.), 7.38–7.22 (m, 7H, Ph, Pyrid.), 7.08, 7.02 (2 m, each 2H, PhF), 5.32 (t, 1H, NH), 3.80 (q, 2H, CH₂N), 2.92 (t, 2H, CH₂).

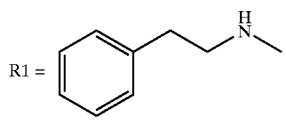

1-32 5-(4-Fluorophenyl)-4-(4-pyridyl)-2-pyrrolidino-pyrimidine

MS (m/z): 321.2 (M+H)⁺; $C_{19}H_{17}FN_4$ requir. 320.4. ¹H-NMR (CDCl₃): d 8.54, 7.32 (2 d, each 2H, Pyrid.), 8.37 (s, 1H, H-6, Pyrim.), 7.06, 7.00 (2 m, each 2H, PhF), 3.68, 2.05 (2 m, each 4H, 4CH₂)

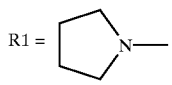

1-33 5-(4-Fluorophenyl)-2-morpholino-4-(4-pyridyl)-pyrimidine

MS (m/z): 337.2 (M+H)⁺; $C_{19}H_{17}FN_4O$ requir. 336.4. ¹H-NMR (CDCl₃): d 8.56, 7.31 (2 m, each 2H, Pyrid.), 8.40 (s, 1H, H-6, Pyrim.), 7.10, 7.03 (2 m, each 2H, PhF), 3.94, 3.83 (2 m, each 4H, 4CH₂).

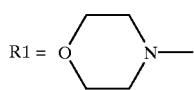

1-34 2-(3,5-Dimethylpyrazolyl)-5-(4-fluorophenyl)-4-(4-pyridyl)-pyrimidine

MS (m/z): 346.0 (M+H)⁺; $C_{20}H_{16}FN_5$ requir. 345.4. ¹H-NMR (CDCl₃): d 8.80 (s, 1H, H-6, Pyrim.), 8.60, 7.35 (2 m, each 2H, Pyrid.), 7.18, 7.08 (2 m, each 2H, PhF), 6.08 (s, 1H, Pyraz.), 2.70, 2.30 (2 s, each 3H, 2CH₃)

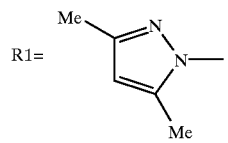

1-35 5-(4-Fluorophenyl)-4-(4-pyridyl)-2-(3,5-bis (trifluoromethyl)benzenesulfamoyl)-pyrimidine MS (m/z): 542.8 (M+H)⁺; $C_{23}H_{13}F_7N_4O_2S$ requir. 542.4. ¹H-NMR (DMSO-d₆): d 8.63 (s, 1H, H-6, Pyrim.), 8.56 (m, 2H, Pyrid.), 8.49, 8.43 (2 s, 2H, 1H, Ph(CF₃)₂), 7.26–7.15 (m, 6H, PhF, Pyrid.).

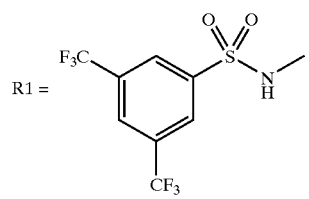

1-36 2-(4-Aminobenzenesulfamoyl)-5-(4-fluorophenyl)-4-(4-pyridyl)-pyrimidine

MS (m/z): 421.8 (M+H)⁺; $C_{21}H_{16}FN_5O_2S$ requir. 421.5. ¹H-NMR (DMSO-d₆) d 8.58 (s, 1H, H-6, Pyrim.), 8.575 (m, 2H, Pyrid.), 7.64, 6.56 (2 d, each 2H, PhNH₂), 7.28–7.15 (m, 6H, PhF, Pyrid.), 5.99 (s, 2H, NH₂).

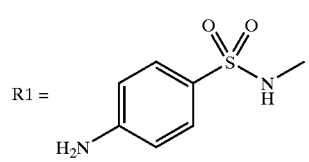

1-37 2-(2-Dimethylaminoethylthio)-5-(4-fluorophenyl)-4-(4-pyridyl)-pyrimidine was prepared according to the general procedure by reacting 3-(dimethylamino)-2-(4-fluorophenyl)-1-(4-pyridinyl)-3-propene-1-one with S-(2-dimethylaminoethyl)isothiourea. MS (m/z): 355.2 (M+H)⁺; $C_{19}H_{19}FN_4S$ requir. 354.5. ¹H-NMR (CDCl₃): d 8.59, 7.32 (2 m, each 2H, Pyrid.), 8.58 (s, 1H, H-6, Pyrim.), 7.16, 7.08 (2 m, each 2H, PhF), 3.40, 2.76 (2 m, each 2H, 2CH₂), 2.37 (s, 6H, 2CH₃).

R1=(CH₃)₂NCH₂CH₂S—

Example 2

General Procedure for the Preparation of 2-N Substituted 2-amino-5-(4-fluorophenyl)-4-(4-pyridyl)-pyrimidines a. 5-(4-Fluorophenyl)-4-(4-pyridyl)-2(1H)-pyrimidinone

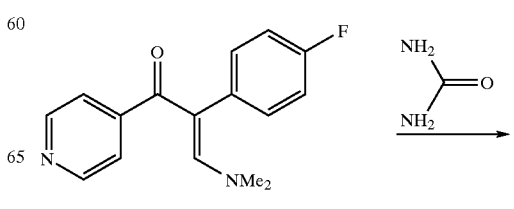

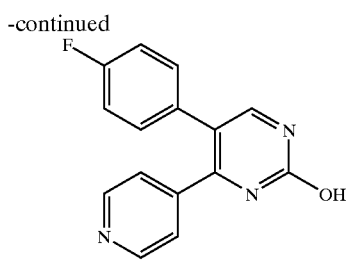

Urea (0.67 g, 11.15 mmol) was added to a stirred ethanolic 0.62 N sodium ethoxide solution (15 ml). An ethanolic solution (60 ml) of 3-(dimethylamino)-2-(4-fluorophenyl)-1-(4-pyridinyl)-3-propene-1-one (9.29 mmol) was added and the mixture was refluxed overnight. It was evaporated followed by column chromatography (5% methanol/dichloromethane to 100% methanol). Crystals (presumably urea) obtained on treating the resultant product with dichloromethane/methanol were filtered. The filtrate was evaporated and the remainder rechromatographed on a column of silica gel (chloroform/methanol/water=70:20:1) to yield the title compound as a yellowish foam.

MS (m/z): 268.2 (M+H)$^+$; $C_{15}H_{10}FN_3O$ requir. 267.3. $^1$H-NMR (DMSO-d$_6$): d 8.55, 7.24 (2 m, each 2H, Pyrid.), 8.22 (bs, 1H, H-6, Pyrim.), 7.20–7.10 (m, 4H, PhF).

b. 2-Chloro-5-(4-fluorophenyl)-4-(4-pyridyl)-pyrimidine

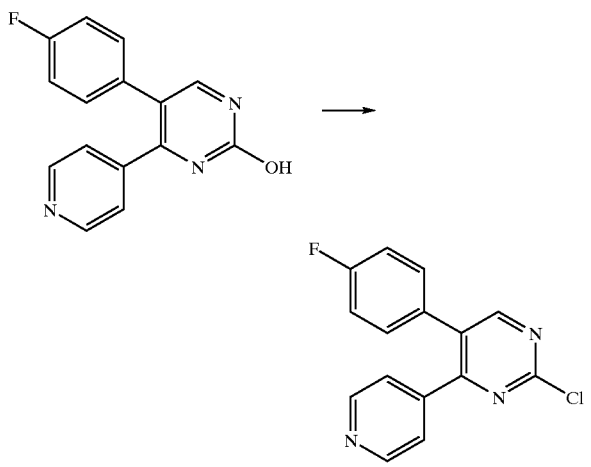

A mixture of 5-(4-fluorophenyl)-4-(4-pyridyl)-2-(1H)-pyrimidinone (2.41 mmol) and phosphorus oxychloride (3 ml) was heated at reflux for 45 min. It was evaporated to dryness at a bath temperature of >500° C. The flask was cooled in an ice-bath and ice-water was added. If the pH value was found still acidic, then the mixture was neutralized with aqueous 5% ammonium hydroxide. It was extracted with dichloromethane, followed by washing of the organic solution with aqueous sodium chloride, drying and evaporation to yield the title compound as a yellowish foam which was used without further purification.

MS (m/z): 286.1 (M+H)$^+$; $C_{15}H_{19}ClFN_3$ requir. 285.7. $^1$H-NMR (CDCl$_3$): d 8.68 (s, 1H, H-6, Pyrim.), 8.62, 7.42 (2 m, each 2H, Pyrid.), 7.23–7.10 (m, 4H, PhF). Alternatively, 2-chloro-5-(3-methylphenyl)-4-(4-pyridyl)-pyrimidine (MS (m/z): 282 (M+H)$^+$; $C_{16}H_{12}ClN_3$ requir. 281.7) and 2-chloro-4-(4-pyridyl)-5-(3-trifluoro methylphenyl)-pyrimidine (MS (m/z): 336.0 (M)$^+$; $C_{16}H_9ClF_3N_3$ requir. 335.7) have been synthesized by the same reaction sequence, but starting from 2-(3-methyl phenyl)-1-(4-pyridinyl)ethanone (prepared according to: I. Lantos et al., J. Org. Chem. 53, 4223–4227, 1988) and 1-(4-pyridinyl)-2-(3-trifluoromethylphenyl)ethanone (prepared according to: P. W. Sheldrake, Synth. Commun. 23 (24), 1967–1971, 1993); and WO 97/12876). Also, thionyl chloride/N,N-dimethylformamide (excess/3 equivalents, reflux) can be used instead of phosphorus oxychloride.

c. General Procedure

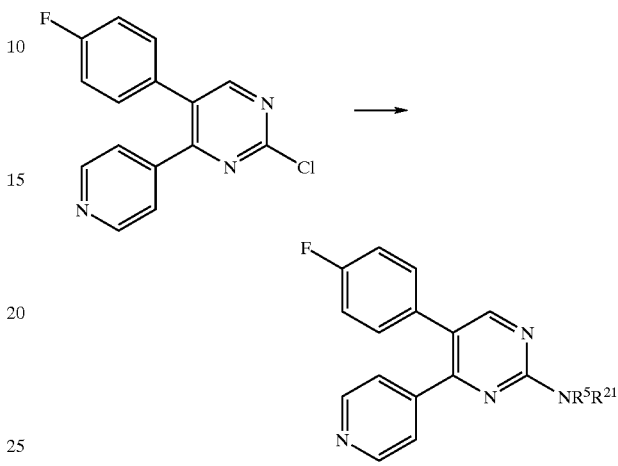

Typically, a mixture of 2-chloro-5-(4-fluoro phenyl)-4-(4-pyridyl)-pyrimidine (50–120 mg, 0.18–0.42 mmol) and the amine, HNR$^5$R$^{21}$, (0.5–5.5 mmol) was heated at 50–100° C. for 5–60 min (thin layer chromatography check). The mixture was applied directly to a column of silica gel which was developed with dichloromethane/methanol or dichloromethane/methanol/conc. ammonium hydroxide.

An alternate procedure using ethanol as a solvent was used in case of Examples 2–6, 2–11, 2–12, 2–20 and 2–26 as described.

The following pyrimidines were prepared according to this procedure using the appropriate amine and substituted 2-chloropyrimidine:

2-1 2-(2-Aminoethylamino)-5-(4-fluorophenyl)-4-(4-pyridyl)-pyrimidine hydrochloride MS (m/z): 310.2 (M+H)$^+$; $C_{17}H_{16}FN_5$—HCl requir. 309.4+36.5. $^1$H-NMR (CD$_3$OD): d 8.84, 8.10 (2 m, each 2H, Pyrid.), 8.58 (s, 1H, H-6, Pyrim.), 7.28, 7.15 (2 m, each 2H, PhF), 3.83 (t, 2H, CH$_2$), 3.27 (t, 2H, CH$_2$).

R1=NH$_2$CH$_2$CH$_2$NH—

2-2 2-(3-Aminopropylamino)-5-(4-fluorophenyl)-4-(4-pyridyl)-pyrimidine hydrochloride MS (m/z): 324.0 (M+H)$^+$; $C_{18}H_{18}FN_5$-HCl requir. 323.4+36.5. $^1$H-NMR (CD$_3$OD): d 8.85, 8.10 (m, 2H, Pyrid.), 8.54 (s, 1H, H-6, Pyrim.), 7.27, 7.14 (2 m, each 2H, PhF), 3.84, 3.68 (2 t, each 2H, 2CH$_2$N), 2.18 (m, 2H, CH$_2$).

R1=NH$_2$CH$_2$CH$_2$CH$_2$NH—

2-3 2-(4-Aminobutylamino)-5-(4-fluorophenyl)-4-(4-pyridyl)-pyrimidine hydrochloride MS (m/z): 338.0 (M+H)$^+$; $C_{19}H_{20}FN_5$—HCl requir. 337.4+36.5. $^1$H-NMR (CD$_3$OD): d 8.80, 8.05 (2 m, each 2H, Pyrid.), 8.50 (s, 1H, H-6, Pyrim.), 7.25, 7.14 (2 m, each 2H, PhF), 3.58 (bt, 2H, CH$_2$), 3.02 (bt, 1H, CH$_2$), 1.80 (m, 4H, 2CH$_2$)

R1=NH$_2$CH$_2$CH$_2$CH$_2$CH$_2$NH—

2-4 2-(2-Dimethylaminoethylamino)-5-(4-fluorophenyl)-4-(4-pyridyl)-pyrimidine

MS (m/z): 338.2 (M+H)$^+$; $C_{19}H_{20}FN_5$ requir. 337.4. $^1$H-NMR (CDCl$_3$): d 8.57, 7.30 (2 m, each 2H, Pyrid.), 8.37 (s, 1H, H-6, Pyrim.), 7.10, 7.03 (2 m, each 2H, PhF), 6.00

(t, 1H, NH), 3.66 (q, 2H, CH$_2$), 2.71 (t, 2H, CH$_2$), 2.41 (s, 6H, 2CH$_3$).

R1=(CH$_3$)$_2$NCH$_2$CH$_2$NH—

2-5 5-(4-Fluorophenyl)-2-(2-phenylaminoethylamino)-4-(4-pyridyl)-pyrimidine

MS (m/z): 386 (M+H)$^+$; C$_{23}$H$_{20}$FN$_5$ requir. 385.5. $^1$H-NMR (CDCl$_3$): d 8.57, 7.28 (m, 2H, Pyrid.), 8.36 (s, 1H, H-6, Pyrim.), 7.18 (t, 2H, Ph), 7.08, 7.02 (2 m, each 2H, PhF), 6.73 (t, 1H, Ph), 6.64 (d, 2H, Ph), 5.62 (bt, 1H, NH), 3.80 (q, 2H, CH$_2$), 3.47 (t, 2H, CH$_2$).

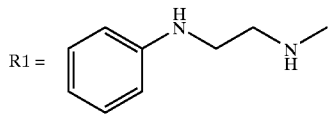

2-6 5-(4-Fluorophenyl)-2-(2-(4-fluorophenylamino)-ethylamino)-4-(4-pyridyl)-pyrimidine A solution of 2-chloro-5-(4-fluorophenyl)-4-(4-pyridyl)-pyrimidine (103 mg, 0.36 mmol) and N-(4-fluorophenyl) ethylendiamine (1 ml) in ethanol (1 ml) was heated to reflux for 3 h. Evaporation was followed by column chromatography (3% methanol/dichloromethane) to provide the title compound as a yellowish solid. MS (m/z): 404.2 (M+H)$^+$; C$_{23}$H$_{19}$F$_2$N$_5$ requir. 403.4. $^1$H-NMR (CDCl$_3$): 8.60 7.31 (2 m, each 2H, Pyrid.), 8.40 (s, 1H, H-6, Pyrim.), 7.11–7.02 (2 m, each 2H, PhF), 6.90, 6.60 (t, dd, each 2H, PhF), 5.62 (t, 1H, NH), 3.82 (q, 2H, CH$_2$), 3.44 (t, 2H, CH$_2$).

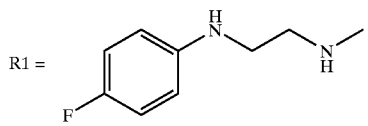

2-7 5-(4-Fluorophenyl)-2-(4-methylbenzylamino)-4-(4-pyridyl)-pyrimidine

MS (m/z): 371.2 (M+H)$^+$; C$_{23}$H$_{19}$FN$_4$ requir. 370.4. $^1$H-NMR (CDCl$_3$): d 8.55, 7.34 (2 m, each 2H, Pyrid.), 8.36 (s, 1H, H-6, Pyrim.), 7.30, 7.18 (2 d, each 2H, PhMe), 7.08, 7.02 (2 m, each 2H, PhF), 5.69 (bs, 1H, NH), 4.69 (d, 2H, CH$_2$), 2.36 (s, 3H, CH$_3$)

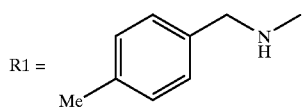

2-8 5-(4-Fluorophenyl)-2-(2-(4-fluorophenyl)-ethylamino)-4-(4-pyridyl)-pyrimidine MS (m/z): 389.2 (M+H)$^+$; C$_{23}$H$_{18}$F$_2$N$_4$ requir. 388.4. $^1$H-NMR (CDCl$_3$): d 8.57 (m, 2H, Pyrid.), 8.36 (s, 1H, H-6, Pyrim.), 7.32–7.20, 7.12–6.98 (2 m, 10H, 2 PhF, Pyrid.), 5.37 (bt, 1H, NH), 3.79 (q, 2H, CH$_2$N), 2.97 (t, 2H, CH$_2$).

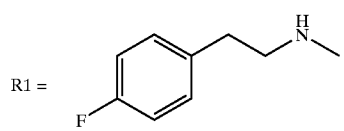

2-9 2-(2-(4-Chlorophenyl)-ethylamino)-5-(4-fluorophenyl)-4-(4-pyridyl)-pyrimidine MS (m/z): 405.0 (M+H)$^+$; C$_{23}$H$_{18}$ClFN$_4$ requir. 404.9. $^1$H-NMR (CDCl$_3$): d 8.56 (bs, 2H, Pyrid.), 8.34 (s, 1H, H-6, Pyrim.), 7.29 (m, d, 4H, Pyrid., PhCl), 7.20 (d, 2H, PhCl), 7.08, 7.02 (2 m, each 2H, PhF), 5.35 (t, 1H, NH), 3.78 (q, CH$_2$N), 2.96 (t, 2H, CH$_2$)

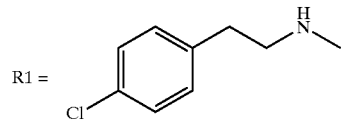

2-10 2-(2-(4-Bromophenyl)-ethylamino)-5-(4-fluorophenyl)-4-(4-pyridyl)-pyrimidine MS (m/z): 449.0 (M)$^+$; C$_{23}$H$_{18}$BrFN$_4$ requir. 449.3. $^1$H-NMR (CDCl$_3$): d 8.58, 7.47 (m, 2H, Pyrid.), 8.37 (s, 1H, H-6, Pyrim.), 7.29, 7.17 (2 d, each 2H, PhCl), 7.10, 7.02 (2 d, each 2H, PhF), 5.34 (t, 1H, NH), 3.80 (q, 2H, CH$_2$N), 2.97 (t, 2H, CH$_2$).

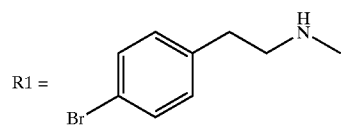

2-11 5-(4-Fluorophenyl)-2-(2-(4-hydroxyphenyl)-ethylamino)-4-(4-pyridyl)-pyrimidine A mixture of 2-chloro-5-(4-fluorophenyl)-4-(4-pyridyl)-pyrimidine (61 mg, 0.21 mmol), tyramine hydrochloride (186 mg, 1.01 mmol) and sodium hydrogencarbonate (90 mg, 1.07 mmol) in aqueous ethanol (1 ml) was heated to reflux for 1 h. Solvent evaporation and subsequent column chromatography (5% methanol/dichloromethane) provided the title compound as a yellow solid. MS (m/z): 387.2 (M+H)$^+$; C$_{23}$H$_{19}$FN$_4$O requir. 386.4. $^1$H-NMR (DMSO-d$_6$): d 9.12 (bs, 1H, OH), 8.54, 7.26 (2 m, each 2H, Pyrid.), 8.38 (s, 1H, H-6, Pyrim.), 7.52 (t, 1H, NH), 7.20–7.10 (m, 4H, PhF), 7.05, 6.69 (2 d, each 2H, PhOH), 3.52 (q, 2H, CH$_2$N), 2.78 (t, 2H, CH$_2$).

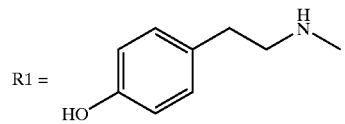

2-12 2-(2-(4-Aminophenyl)-ethylamino)-5-(4-fluorophenyl)-4-(4-pyridyl)-pyrimidine A solution of 2-chloro-5-(4-fluorophenyl)-4-(4-pyridyl)-pyrimidine (71 mg, 0.25 mmol) and 2-(4-aminophenyl) ethylamine (0.5 ml, 3.80 mmol) in ethanol (1.5 ml) was heated to reflux for 20 min. Evaporation and subsequent chromatography on a column of silica gel (2% methanol/dichloromethane) provided the title compound as a yellow syrup. MS (m/z): 386.4 (M+H)$^+$; C$_{23}$H$_{20}$FN$_5$ requir. 385.5. $^1$H-NMR (CDCl$_3$): d 8.56, 7.32 (2 m, each 2H, Pyrid.), 8.35 (s, 1H, H-6, Pyrim.), 7.12–6.99 (m, 6H, PhF, PhNH$_2$), 6.68 (d, 2H, PhNH$_2$), 5.37 (t, 1H, NH), 3.75 (q, 2H, CH$_2$N), 2.88 (t, 2H, CH$_2$).

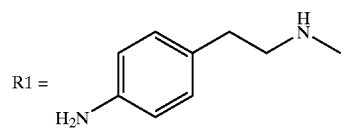

2-13 5-(4-Fluorophenyl)-2-(2-(2-fluorophenyl)-ethylamino)-4-(4-pyridyl)-pyrimidine MS (m/z): 389.2 (M+H)$^+$; C$_{23}$H$_{18}$F$_2$N$_4$ requir. 388.4. $^1$H-NMR (CDCl$_3$): 8.57 (m, 2H, Pyrid.), 8.35 (s, 1H, H-6, Pyrim.), 7.34–7.20, 7.14–7.00 (2 m, 10H, 2 PhF, Pyrid.), 5.42 (bt, 1H, NH), 3.82 (q, 2H, CH$_2$N), 3.05 (t, 2H, CH$_2$)

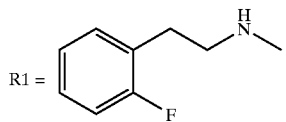

2-14 2-(2-(2-Chlorophenyl)-ethylamino))-5-(4-fluorophenyl)-4-(4-pyridyl)-pyrimidine
MS (m/z): 405.0 (M+H)$^+$; C$_{23}$H$_{18}$ClFN$_4$ requir. 404.9.
$^1$H-NMR (CDCl$_3$): d 8.57 (m, 2H, Pyrid.), 8.36 (s, 1H, H-6, Pyrim.), 7.40–7.00 (m, 10H, PhF, PhCl$_2$, Pyrid.), 5.44 (bt, 1H, NH), 3.84 (q, 2H, CH$_2$N), 3.15 (t, 2H, CH$_2$).

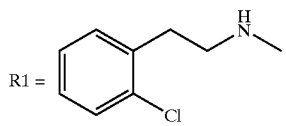

2-15 5-(4-Fluorophenyl)-2-(2-(2-methoxyphenyl)-ethylamino)-4-(4-pyridyl)-pyrimidine
MS (m/z): 401.2 (M+H)$^+$; C$_{24}$H$_{21}$FN$_4$O requir. 400.5
$^1$H-NMR (CDCl$_3$): d 8.56, 7.30 (2 m, each 2H, Pyrid.), 8.34 (s, 1H, H-6, Pyrim.), 7.24, 7.08, 7.02, 6.92 (4 m, each 2H, PhF, PhOMe), 5.50 (bt, 1H, NH), 3.87 (s, 3H, CH$_3$), 3.78 (q, 2H, CH$_2$N), 3.02 (t, 2H, CH$_2$).

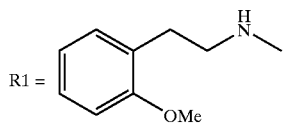

2-16 2-(2-(2,4-Dichlorophenyl)-ethylamino)-5-(4-fluorophenyl)-4-(4-pyridyl)-pyrimidine
MS (m/z): 439.0 (M)$^+$; C$_{23}$H$_{17}$Cl$_2$FN$_4$ requir. 439.3.
$^1$H-NMR (CDCl$_3$): 8.56 (bs, 2H, Pyrid.), 8.34 (s, 1H, H-6, Pyrim.), 7.37 (s, 1H, PhCl), 7.30 (bd, 2H, Pyrid.), 7.22–7.15 (m, 2H, PhCl), 7.08, 7.05 (2 m, each 2H, PhF), 5.40 (t, 1H, NH), 3.80 (q, 2H, CH$_2$N), 3.10 (t, 2H, CH$_2$).

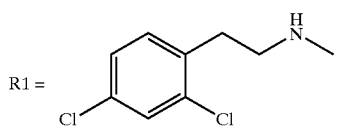

2-17 2-(2-(2,6-Dichlorophenyl)-ethylamino)-5-(4-fluorophenyl)-4-(4-pyridyl)-pyrimidine
MS (m/z): 439.0 (M)$^+$; C$_{23}$H$_{17}$Cl$_2$FN$_4$ requir. 439.3.
$^1$H-NMR (CDCl$_3$): 8.57 (m, 2H, Pyrid.), 8.36 (s, 1H, H-6, Pyrim.), 7.35 (d, 2H, PhCl), 7.11 (m, 3H, PhF, PhCl), 7.03 (m, 2H, PhF), 5.45 (t, 1H, NH), 3.86 (q, 2H, CH$_2$N), 3.38 (t, 2H, CH$_2$).

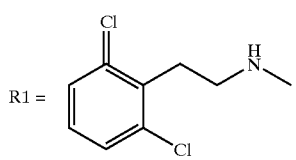

2-18 5-(4-Fluorophenyl)-2-(2-(3-methoxyphenyl)-ethylamino)-4-(4-pyridyl)-pyrimidine
MS (m/z): 401.2 (M+H)$^+$; C$_{24}$H$_{21}$FN$_4$O requir. 400.5.
H-NMR (CDCl$_3$): d 8.56 (m, 2H, Pyrid.), 8.34 (s, 1H, H-6, Pyrim.), 7.32–7.22, 7.11–6.98, 6.89–6.77 (3 m, 10H, PhF, PhOMe, Pyrid.), 5.38 (t, 1H, NH), 3.82 (m, 5H, CH$_2$N, CH$_3$), 2.96 (t, 2H, CH$_2$)

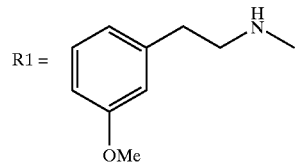

2-19 2-(2-(3-Chlorophenyl)-ethylamino))-5-(4-fluorophenyl)-4-(4-pyridyl)-pyrimidine
MS (m/z): 405.4 (M+H)$^+$; C$_{23}$H$_{18}$ClFN$_4$ requir. 404.9.
$^1$H-NMR (CDCl$_3$): d 8.60 (d, 2H, Pyrid.), 8.38 (s, 1H, H-6, Pyrim.), 7.32–7.24 (m, 5H, Pyrid., PhCl), 7.18 (m, 1H, PhCl), 7.11, 7.04 (2 m, each 2H, PhF), 5.35 (t, 1H, NH), 3.83 (q, 2H, CH$_2$N), 3.00 (t, 2H, CH$_2$)

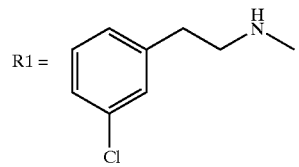

2-20 5-(4-Fluorophenyl)-2-((2-hydroxy-2-phenyl)-ethylamino)-4-(4-pyridyl)-pyrimidine
A mixture of 2-chloro-5-(4-fluorophenyl)-4-(4-pyridyl)-pyrimidine (87 mg, 0.31 mmol) and 2-amino-1-phenylethanol (300 mg, 2.19 mmol) in ethanol (2 ml) was heated to reflux for 2 h. Evaporation and subsequent chromatography on a column of silica gel (4% methanol/dichloromethane) provided the title compound as as yellow foam. MS (m/z): 387.0 (M+H)$^+$; C$_{23}$H$_{19}$FN$_4$O requir. 386.4.
$^1$H-NMR (CDCl$_3$): d 8.58 (d, 2H, Pyrid.), 8.38 (s, 1H, H-6, Pyrim.), 7.47 (d, 2H, Ph), 7.41 (t, 2H, Ph), 7.34 (t, 1H, Ph), 7.28 (d, 2H, Pyrid.), 7.10, 7.02 (2 m, 2H, PhF), 5.72 (t, 1H, NH), 5.06 (m CHOH)), 4.02–3.92 (m, 2H, OH, 1CH$_2$), 3.72 (ddd, 1H, 1CH$_2$)

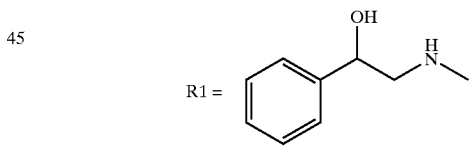

2-21 5-(4-Fluorophenyl)-2-(methyl-(2-phenylethyl)-amino)-4-(4-pyridyl)-pyrimidine
MS (m/z): 385.0 (M+H)$^+$; C$_{24}$H$_{21}$FN$_4$ requir. 384.5.
$^1$H-NMR (CDCl$_3$): d 8.57, 7.35 (2 m, each 2H, Pyrid.), 8.40 (s, 1H, H-6, Pyrim.), 7.34–7.21 (m, 5H, Ph), 7.10, 7.03 (2 m, each 2H, PhF), 3.96 (t, 2H, CH$_2$N), 3.23 (s, 3H, CH$_3$), 3.00 (t, 2H, CH$_2$).

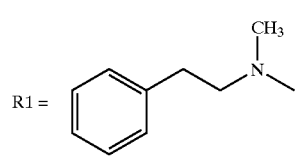

2-22 5-(4-Fluorophenyl)-2-((3-phenylpropyl)-amino)-4-(4-pyridyl)-pyrimidine

MS (m/z): 385.2 (M+H)+; C₂₄H₂₁FN₄ requir. 384.5.
¹H-NMR (CDCl₃): d 8.56 (m, 2H, Pyrid.), 8.34 (s, 1H, H-6, Pyrim.), 7.34–7.20 (m, 7H, Ph, Pyrid.), 7.08, 7.01 (2 m, each 2H, PhF), 5.38 (t, 1H, NH), 3.58 (q, 2H, CH₂N), 2.78 (t, 2H, CH₂), 2.03 (m, 2H, CH₂).

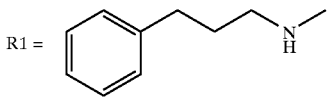

2-23 5-(4-Fluorophenyl)-2-((1-methyl-3-phenylpropyl)-amino)-4-(4-pyridyl)-pyrimidine MS (m/z): 399.0 (M+H)+; C₂₅H₂₃FN₄ requir. 398.5.
¹H-NMR (CDCl₃): d 8.56 (m, 2H, Pyrid.), 8.32 (s, 1H, H-6, Pyrim.), 7.32–7.17 (m, 7H, Pyrid., Ph), 7.09–7.02 (2 m, each 2H, PhF), 5.16 (d, 1H, NH), 4.28 (m, 1H, CH), 2.77 (m, 2H, CH₂), 1.94 (m, 2H, CH₂), 1.34 (d, 3H, CH₃).

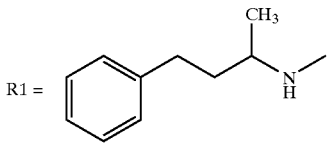

2-24 5-(4-Fluorophenyl)-2-((3-imidazolylpropyl)-amino)-4-(4-pyridyl)-pyrimidine

MS (m/z) 375.0 (M+H)+; C₂₁H₁₉FN₆ requir. 374.4.
¹H-NMR (CDCl₃) d 8.57, 7.26 (2 m, each 2H, Pyrid.), 8.36 (s, 1H, H-6, Pyrim.), 7.56 (s, 1H, Imid.), 7.16–6.96 (m, 6H, PhF, Imid.), 5.38 (bt, 1H, NH), 4.12 (t, 2H, CH₂N), 3.56 (q, 2H, CH₂NH), 2.20 (m, 2H, CH₂).

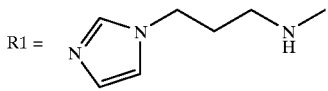

2-25 5-(4-Fluorophenyl)-2-((4-phenyl-n-butyl)-amino)-4-(4-pyridyl)-pyrimidine

MS (m/z): 399.0 (M+H)+; C₂₅H₂₃FN₄ requir. 398.5.
¹H-NMR (CDCl₃): d 8.56 (m, 2H, Pyrid.), 8.34 (s, 1H, H-6, Pyrim.), 7.33–7.17 (m, 7H, Ph, Pyrid.), 7.08, 7.02 (2 m, each 2H, PhF), 5.33 (bt, 1H, NH), 3.56 (q, 2H, CH₂N), 2.71 (t, 2H, CH₂), 1.76 (m, 4H, 2CH₂).

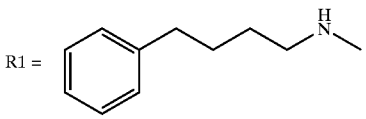

2-26 5-(4-Fluorophenyl)-2-(1-piperazinyl)-4-(4-pyridyl)-pyrimidine

A mixture of 2-chloro-5-(4-fluorophenyl)-4-(4-pyridyl)-pyrimidine (71 mg, 0.25 mmol) and piperazine (214 mg, 2.48 mmol) in ethanol (1 ml) was heated to reflux for 5 min. Evaporation and subsequent chromatography on a column of silica gel (5% methanol/dichloromethane) provided the title compound as as yellow solid. MS (m/z): 336.2 (M+H)+; C₁₉H₁₈FN₅ requir. 335.4. ¹H-NMR (CDCl₃): d 8.54, 7.29 (2 m, each 2H, Pyrid.), 8.37 (s, 1H, H-6, Pyrim.), 7.08, 7.00 (2 m, each 2H, PhF), 3.95 (t, 4H, 2CH₂), 3.01 (t, 4H, 2CH₂).

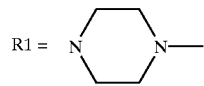

2-27 5-(4-Fluorophenyl)-2-(1-piperidinyl)-4-(4-pyridyl)-pyrimidine

MS (m/z): 335.2 (M+H)+; C₂₀H₁₉FN₄ requir. 334.4.
¹H-NMR (CDCl₃): d 8.55, 7.30 (2 m, each 2H, Pyrid.), 8.36 (s, 1H, H-6, Pyrim.), 7.08, 7.01 (2 m, 2H, PhF), 3.91 (t, 4H, 2CH₂N), 1.74, 1.68 (2 m, 6H, 3CH₂).

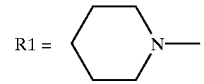

2-28 5-(4-Fluorophenyl)-2-(4-methyl-1-piperazinyl)-4-(4-pyridyl)-pyrimidine

MS (m/z): 350.0 (M+H)+; C₂₀H₂₀FN₅ requir. 349.4.
¹H-NMR (CDCl₃): d 8.58, 7.32 (2 m, each 2H, Pyrid.), 8.40 (s, 1H, H-6, Pyrim.), 7.10, 7.04 (2 m, each 2H, PhF), 4.00 (t, 4H, 2CH₂), 2.57 (t, 4H, 2CH₂), 2.42 (s, 3H, CH₃).

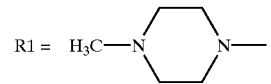

2-29 5-(4-Fluorophenyl)-2-(4-phenyl-1-piperazinyl)-4-(4-pyridyl)-pyrimidine

MS (m/z): 412.2 (M+H)+; C₂₅H₂₂FN₅ requir. 411.5.
¹H-NMR (CDCl₃): d 8.58 (bd, 2H, Pyrid.), 8.42 (s, 1H, H-6, Pyrim.), 7.38–7.30 (m, 4H, Pyrid., Ph), 7.15–7.00 (m, 6H, PhF, Ph), 6.94 (t, 1H, Ph), 4.13 (t, 4H, 2CH₂), 3.33 (t, 4H, 2CH₂).

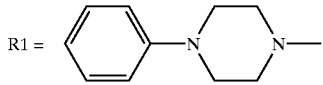

2-30 5-(4-Fluorophenyl)-2-(2-morpholinoethylamino)-4-(4-pyridyl)-pyrimidine

MS (m/z): 380.4 (M+H)+; C₂₁H₂₂FN₅O requir. 379.4.
¹H-NMR (CDCl₃): d 8.58, 7.30 (2 m, each 2H, Pyrid.), 8.38 (s, 1H, H-6,Pyrim.), 7.10, 7.03 (2m, each 2H, PhF), 5.91 (bs, 1H, NH), 3.79 (bs, 4H, 2CH₂), 3.66 (bs, 2H, CH₂), 2.71 (bs, 2H, CH₂), 2.59 (bs, 4H, 2CH₂).

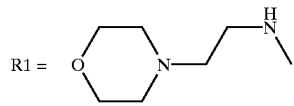

2-31 5-(4-Fluorophenyl)-2-(2-piperidinoethylamino)-4-(4-pyridyl)-pyrimidine

MS (m/z): 378.2 (M+H)+; C₂₂H₂₄FN₅ requir. 377.5
¹H-NMR (CDCl₃): d 8.54, 7.27 (2 d, each 2H, Pyrid.), 8.34 (s, 1H, H-6, Pyrim.), 7.06, 7.00 (2 m, each 2H, PhF), 6.04 (bt, 1H, NH), 3.66 (q, 2H, CH₂NH), 2.74 (t, 2H, CH₂), 2.61 (bs, 4H, 2CH₂), 1.68 (m, 4H, 2CH₂), 1.50 (m, 2H, CH₂).

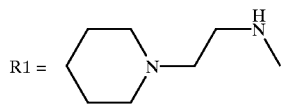

2-32 5-(4-Fluorophenyl)-4-(4-pyridyl)-2-(2-pyrrolidinoethylamino)-pyrimidine

MS (m/z): 364.0 (M+H)$^+$; $C_{21}H_{22}FN_5$ requir. 363.4 $^1$H-NMR (CDCl$_3$): d 8.55, 7.28 (2 m, each 2H, Pyrid.), 8.36 (s, 1H, H-6, Pyrim.), 7.08, 7.02 (2 m, each 2H, PhF), 6.28 (t, 1H, NH), 3.86 (q, 2H, CH$_2$NH), 3.18 (t, 2H, CH$_2$N), 3.10 (bs, 4H, 2CH$_2$N), 2.02 (bs, 4H, 2CH$_2$).

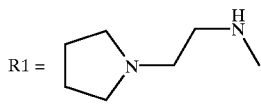

2-33 5-(4-Fluorophenyl)-2-(3-morpholinopropylamino)-4-(4-pyridyl)-pyrimidine

MS (m/z): 394.2 (M+H)$^+$; $C_{22}H_{24}FN_5O$ requir. 393.5. $^1$H-NMR (CDCl$_3$): d 8.54, 7.27 (2 m, each 2H, Pyrid.), 8.33 (s, 1H, H-6, Pyrim.), 7.06, 7.00 (2 m, each 2H, PhF), 6.00 (t, 1H, NH), 3.76 (t, 4H, 2CH$_2$O), 3.60 (q, 2H, CH$_2$NH), 2.52 (t, 2H, CH$_2$N), 2.50 (m, 4H, CH$_2$N), 1.86 (m, 2H, CH$_2$).

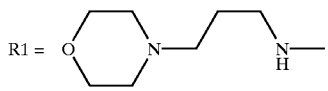

2-34 5-(4-Fluorophenyl)-2-(3-(2-pyrrolidinon-1-yl)-propylamino)-4-(4-pyridyl)-pyrimidine

MS (m/z): 392.2 (M+H)$^+$; $C_{22}H_{22}FN_5O$ requir. 391.5. $^1$H-NMR (CDCl$_3$): d 8.58, 7.30 (m, 2H, Pyrid.), 8.36 (s, 1H, H-6, Pyrim.), 7.10, 7.04 (m, 2H, PhF), 5.88 (t, 1H, NH), 3.56 (q, 2H, CH$_2$NH), 3.48, 3.45 (2 t, each 2H, 2CH$_2$), 2.46 (t, 2H, CH$_2$), 2.08 (m, 2H, CH$_2$), 1.90 (m, 2H, CH$_2$).

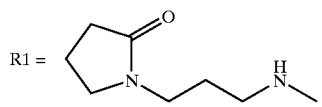

2-35 2-(((S)-2-Amino-3-phenylpropyl)-amino)-5-(4-fluorophenyl)-4-(4-pyridyl)-pyrimidine hydrochloride

MS (m/z): 400.1 (M+H)$^+$; $C_{24}H_{22}FN_5$ requir. 399.5 (free base).

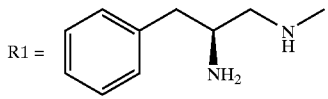

2-36 2-(((S)-2-Amino-3-phenylpropyl)-amino)-4-(4-pyridyl)-5-(3-trifluoromethylphenyl)-pyrimidine hydrochloride

2-Chloro-4-(4-pyridyl)-5-(3-trifluoromethylphenyl)-pyrimidine and (S)-1,2-benzylethylendiamine were reacted according to the General Procedure, Step C (70° C. for 75 min) to give the title compound. MS (m/z): 450.4 (M+H)$^+$; $C_{25}H_{22}F_3N_5$ requir. 4449.5 (free base).

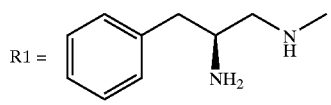

2-37 2-(((S)-2-Amino-3-phenylpropyl)-amino)-5-(3-methylphenyl)-4-(4-pyridyl)-pyrimidine hydrochloride

2-Chloro-5-(3-methylphenyl)-4-(4-pyridyl)-pyrimidine and (S)-1,2-benzylethylendiamine were reacted according to the General Procedure, Step C (100° C. for 20 min) to give the title compound. MS (m/z): 396.2 (M+H)$^+$; $C_{25}H_{25}N_5$ requir. 395.5 (free base).

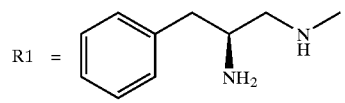

2-38 2-(((S)-2-N,N-Dimethylamino-3-phenylpropyl)-amino)-5-(4-fluorophenyl)-4-(4-pyridyl)-pyrimidine

2-Chloro-5-(4-fluorophenyl)-4-(4-pyridyl)-pyridimine and (S)-2-N,N-dimethylamino-3-phenylpropylamine were reacted according to the General Procedure, Step C (100° C. for 45 min) to give the title compound. MS (m/z): 427.8 (M+H)$^+$; $C_{26}H_{26}FN_5$ requir. 427.5.

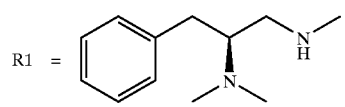

2-39 2-(((S)-2-N,N-Dimethylamino-3-phenylpropyl)-amino)-5-(3-methylphenyl)-4-(4-pyridyl)-pyrimidine

2-Chloro-5-(3-methylphenyl)-4-(4-pyridyl)-pyrimidine and (S)-2-N,N-dimethylamino-3-phenylpropylamine were reacted according to the General Procedure, Step C (100° C. for 30 min) to give the title compound. MS (m/z): 424.2 (M+H)$^+$; $C_{27}H_{29}FN_5$ requir. 423.6.

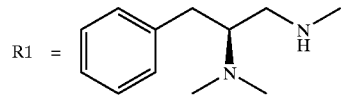

2-40 2-((3-Amino-3-phenylpropyl)-amino)-5-(4-fluorophenyl)-4-(4-pyridyl)-pyrimidine hydrochloride

2-Chloro-5-(4-fluorophenyl)-4-(4-pyridyl)-pyrimidine and 1-phenyl-1,3-propanediamine were reacted according to the General Procedure, Step C (100° C. for 30 min) to give the title compound. MS (m/z): 4001. (M+H)$^+$; $C_{24}H_{22}FN_5$ requir. 399.5 (free base).

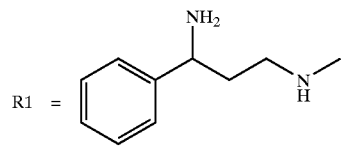

2-41 2-((3-Amino-3-phenylpropyl)-amino)-4-(4-pyridyl)-5-(3-trifluoromethylphenyl)-pyrimidine hydrochloride

2-Chloro-4-(4-pyridyl)-5-(3-trifluoromethylphenyl)-pyrimidine and 1-phenyl-1,3-propanediamine were reacted according to the General Procedure, Step C (100° C. for 1 h) to give the title compound. MS (m/z): 450.3 (M+H)$^+$; $C_{25}H_{22}F_3N_5$ requir. 449.5 (free base).

R1 = 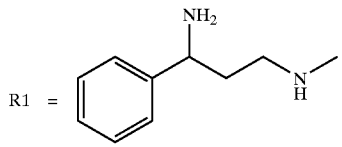

2-42 2-((3-Amino-3-(2-fluorophenyl)propyl)-amino)-4-(4-pyridyl)-5-(3-trifluoromethylphenyl)-pyrimidine hydrochloride 2-Chloro-4-(4-pyridyl)-5-(3-trifluoromethylphenyl)-pyrimidine and 1-(2-fluorophenyl)-1,3-propanediamine were reacted according to the General Procedure, Step C (100° C. for 30 min) to give the title compound. MS (m/z): 468.4 (M+H)$^+$; $C_{25}H_{21}F_4N_5$ requir. 467.5 (free base).

R1 = 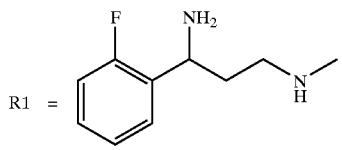

2-43 2-((3-Amino-3-phenylpropyl)-amino)-5-(3-methylphenyl)-4-(4-pyridyl)-pyrimidine hydrochloride 2-Chloro-5-(3-methylphenyl)-4-(4-pyridyl)-pyrimidine and 1-phenyl-1,3-propanediamine were reacted according to the General Procedure, Step C (100° C. for 30 min) to give the title compound. MS (m/z): 396.1 (M+H)$^+$; $C_{25}H_{25}N_5$ requir. 395.5 (free base).

R1 = 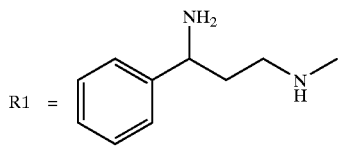

2-44 2-((2-Amino-2-methyl-3-phenylpropyl)-amino)-5-(3-methylphenyl)-4-(4-pyridyl)-pyrimidine hydrochloride 2-Chloro-5-(3-methylphenyl)-4-(4-pyridyl)-pyrimidine and 2-amino-2-methyl-3-phenylpropylamine were reacted according to the General Procedure, Step C (100° C. for 30 min) to give the title compound. MS (m/z): 410.2 (M+H)$^+$; $C_{26}H_{27}N_5$ requir. 409.5 (free base).

R1 = 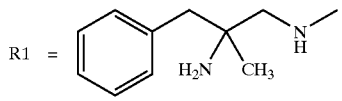

2-45 2-((3-Hydroxy-3-phenylpropyl)-amino) 5-(3-methylphenyl)-4-(4-pyridyl)-pyrimidine 2-Chloro-5-(3-methylphenyl)-4-(4-pyridyl)-pyrimidine and 3-hydroxy-3-phenylpropylamine were reacted according to the General Procedure, Step C (100° C. for 30 min) to give the title compound. MS (m/z): 397.2 (M+H)$^+$; $C_{25}H_{24}N_4O$ requir. 396.5.

R1 = 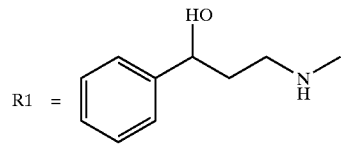

2-46 2-(((2R,3R)-3-Amino-2-methyl-3-phenylpropyl)-amino)-4-(4-pyridyl)-5-(3-trifluoromethylphenyl)-pyrimidine hydrochloride 2-Chloro-4-(4-pyridyl)-5-(3-trifluoromethylphenyl)-pyrimidine and (1R,2R)-2-methyl-1-phenyl-1,3-propanediamine were reacted according to the General Procedure, Step C (50° C. for 1 h) to give the title compound. MS (m/z): 464.4 (M+H)$^+$; $C_{26}H24F_3N_5$ requir. 463.5 (free base).

R1 = 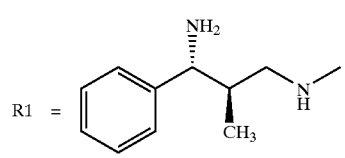

2-47 2-(((2S,3S)-3-Amino-2-methyl-3-phenylpropyl)-amino)-4-(4-pyridyl)-5-(3-trifluoromethylphenyl)-pyrimidine hydrochloride 2-Chloro-4-(4-pyridyl)-5-(3-trifluoromethylphenyl)-pyrimidine and (1S,2S)-2-methyl-1-phenyl-1,3-propanediamine were reacted according to the General Procedure, Step C (90° C. for 45 min) to give the title compound. MS (m/z): 464.1 (M+H)$^+$; $C_{26}H_{24}F_3N_5$ requir. 463.5 (free base).

R1 = 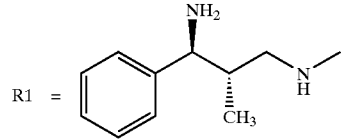

2-48 2-((S)-3-Benzylpiperazinyl)-4-(4-pyridyl)-5-(3-trifluoromethylphenyl)-pyrimidine hydrochloride 2-Chloro-4-(4-pyridyl)-5-(3-trifluoromethylphenyl)-pyrimidine and (S)-2-benzylpiperazine were reacted according to the General Procedure, Step C (70° C. for 30 min) to give the title compound. MS (m/z): 475.5 (M+H)$^+$; $C_{27}H_{24}F_3N_5$ requir. 476.1 (free base).

R1 = 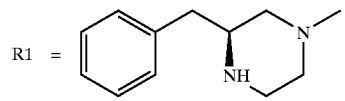

2-49 4-(4-Pyridyl)-2-(((S)-tetrahydroisoquinol-3-ylmethylen)amino)-5-(3-trifluoromethylphenyl)-pyrimidine hydrochloride 2-Chloro-4-(4-pyridyl)-5-(3-trifluoromethylphenyl)-pyrimidine and (S)-tetrahydroisoquinol-3-ylmethylenamine were reacted according to the General Procedure, Step C (50° C. for 1.5 h) to give the title compound. MS (m/z): 462.4 (M+H)$^+$; $C_{26}H_{22}F_3N_5$ requir. 461.5 (free base).

R1 = [structure: tetrahydroisoquinoline with CH2-NH-CH3]

2-50 5-(3-Methylphenyl)-4-(4-pyridyl)-2-(((S)-tetrahydroisoquinol-3-ylmethylen)amino)-pyrimidine hydrochloride 2-Chloro-5-(3-methylphenyl)-4-(4-pyridyl)-pyrimidine and (S)-tetrahydroisoquinol-3-ylmethylenamine were reacted according to the General Procedure, Step C (100° C. for 45 min) to give the title compound. MS (m/z): 408.2 (M+H)$^+$; $C_{26}H_{25}N_5$ requir. 407.5 (free base).

R1 = [structure: tetrahydroisoquinoline with CH2-NH-]

Example 3

General Procedure for the Preparation of 2-acylamino-5-(4-fluorophenyl)-4-(4-pyridyl)-pyrimidines

[reaction scheme]

The chlorocarbonyl R—C(O)Cl (0.57 mmol) was added dropwise to a solution of 2-amino-5-(4-fluorophenyl)-4-(4-pyridyl)-pyrimidine (0.38 mmol) in pyridine (3 ml) at ice-bath temperature. It was stirred for 3 h at room temperature, monitored by thin layer chromatography, poured into ice-water, extracted with dichloromethane, dried and evaporated. The crude product can be purified by silica gel column chromatography (hexane-acetone) and recrystallized from a suitable solvent such as ethyl acetate.

The following compounds were prepared using the appropriate acid chloride according to this procedure:

3-1 2-Acetamido-5-(4-fluorophenyl)-4-(4-pyridyl)-pyrimidine

MS (m/z): 309.0 (M+H)$^+$; $C_{17}H_{13}FN_4O$ requir. 308.3. $^1$H-NMR (CDCl$_3$): d 8.63 (s, 1H, H-6, Pyrim.), 8.60, 7.29 (2 m, each 2H, Pyrid.), 8.26 (bs, 1H, NH), 7.14, 7.08 (2 m, each 2H, PhF), 2.58 (s, 3H, CH$_3$CO).

R=CH$_3$—

3-2 2-Butyramido-5-(4-fluorophenyl)-4-(4-pyridyl)-pyrimidine

MS (m/z): 337.2 (M+H)$^+$; $C_{19}H_{17}FN_4O$ requir. 336.4. $^1$H-NMR (CDCl$_3$): d 8.64, (s, 1H, H-6, Pyrim.), 8.60, 7.31 (2 m, each 2H, Pyrid.), 8.17 (bs, 1H, NH), 7.14, 7.08 (2 m, each 2H, PhF), 2.80 (t, 2H, CH$_2$CO), 1.82 (m, 2H, CH$_2$), 1.06 (t, 3H, CH$_3$).

R=CH$_3$CH$_2$CH$_2$—

3-3 5-(4-Fluorophenyl)-2-pivalamido-4-(4-pyridyl)-pyrimidine

MS (m/z): 351.0 (M+H)$^+$; $C_{20}H_{19}FN_4O$ requir. 350.4. $^1$H-NMR (CDCl$_3$): d 8.69 (s, 1H, H-6, Pyrim.), 8.60, 7.35 (2 m, each 2H, Pyrid.), 8.25 (bs, 1H, NH), 7.15, 7.08 (2 m, each 2H, PhF), 1.4 (s, 9H, 3CH$_3$).

R=(CH$_3$)$_3$C—

3-4 2-Benzamido-5-(4-fluorophenyl)-4-(4-pyridyl)-pyrimidine

MS (m/z): 371.0 (M+H)$^+$; $C_{22}H_{15}FN_4O$ requir. 370.4. $^1$H-NMR (CDCl$_3$): d 8.75 (s, 2H, NH, H-6, Pyrim.), 8.61, 7.36 (2 m, each 2H, Pyrid.), 8.00, 7.63, 7.55 (d, t, t, 2H, 1H, 2H, Ph), 7.18, 7.10 (2 m, each 2H, PhF).

R = [phenyl]

3-5 5-(4-Fluorophenyl)-2-phenylacetamido-4-(4-pyridyl)-pyrimidine

MS (m/z): 385.0 (M+H)$^+$; $C_{23}H_{17}FN_4O$ requir. 384.4. $^1$H-NMR (CDCl$_3$): d 8.66 (s, 1H, H-6, Pyrim.), 8.59, 7.28 (2 m, each 2H, Pyrid.), 8.21 (bs, 1H, NH), 7.43–7.30 (m, 5H, Ph), 7.14, 7.08 (2 m, each 2H, PhF), 4.13 (s, 2H, CH$_2$)

R = [benzyl]

3-6 5-(4-Fluorophenyl)-2-hydrocinnamamido-4-(4-pyridyl)-pyrimidine

MS (m/z): 399.2 (M+H)$^+$; $C_{24}H_{19}FN_4O$ requir. 398.4. $^1$H-NMR (CDCl$_3$): d 8.60 (s, 1H, H-6, Pyrim.), 8.54 (m, 2H, Pyrid.), 8.20 (bs, 1H, NH), 7.31–7.16 (m, 7H, Ph, Pyrid.), 7.11, 7.05 (2 m, each 2H, PhF), 3.20, 3.09 (2 t, each 2H, 2CH$_2$).

R = [phenylpropyl]

Example 4

General Procedure for the Preparation of 2-substituted 5-(4-fluorophenyl)-6-(4-pyridyl)-4 (3H)-pyrimidones

[reaction scheme]

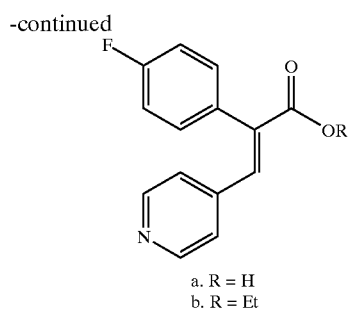

a. R = H
b. R = Et

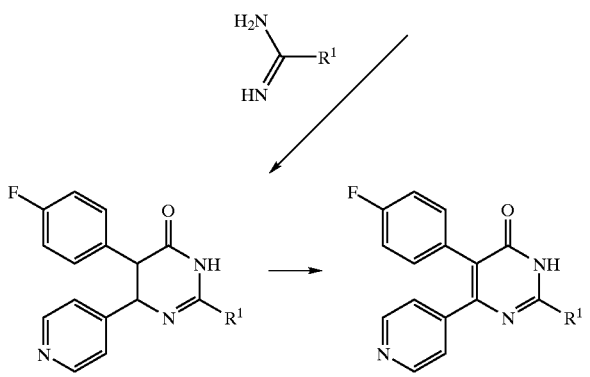

a. 2-(4-Fluorophenyl)-3-(4-pyridyl)-acrylic acid

A mixture of 4-fluorophenylacetic acid (9 g, 58.4 mmol), 4-pyridinecarboxaldehyde (5.6 ml, 58.6 mmol), pyridine (6 ml) and acetic anhydride (6 ml) was heated at 150° C. for 1 h followed by evaporation and co-distillation with water. The resulting material crystallized on addition of ethanol. The solids were filtered and washed with ethanol and ethyl acetate to provide the title compound.

MS (m/z): 244.0 (M+H)$^+$; $C_{14}H_{10}FNO_2$ requir. 243.2
$^1$H-NMR (DMSO-d$_6$): d 8.43, 6.98 (2 d, each 2H, Pyrid.), 7.73 (s, 1H, CH=), 7.21 (d, 4H, PhF).

b. Ethyl 2-(4-fluorophenyl)-3-(4-pyridyl)-acrylate

Conc. sulfuric acid (2.2 ml) was added carefully to a suspension of 2-(4-fluorophenyl)-3-(4-pyridyl)-acrylic acid (6.7 g, 27.5 mmol) in ethanol (120 ml) and the mixture was heated at reflux for 24 h. The solvent was evaporated, the remainder was taken up in dichloromethane and the organic solution was washed with aqueous sodium hydrogencarbonate and water, followed by drying and evaporation. Flash column chromatography on silica gel (hexane-acetone=2:1) provided the pure title compound. MS (m/z): 271.8 (M+H)$^+$; $C_{16}H_{14}FNO_2$ requir. 271.3 $^1$H-NMR (CDCl$_3$): 8.44, 6.88 (2 m, each 2H, Pyrid.), 7.72 (s, 1H, CH=), 7.16, 7.06 (2 m, each 2H, PhF), 4.28 (q, 2H, CH$_2$), 1.28 (t, 3H, CH$_3$).

c. General Procedure

A stirred mixture of ethyl 2-(4-fluorophenyl)-3-(4-pyridyl)-acrylate (357 mg, 1.38 mmol), the amidine hydrochloride (2.61 mmol) and sodium methoxide (250 mg, 4.62 mmol) in ethanol (5 ml) was heated in a sealed tube at 120° C. for 3 h. It was neutralized with 2N hydrochloric acid prior to evaporation. The residue was taken up in acetic acid (25 ml) and treated with sodium nitrite (670 mg, 9.71 mmol) at 44° C. for 20 min. After evaporation, the resultant product was taken up in dichloromethane and the solution was washed with aqueous sodium hydrogencarbonate and water before drying and evaporation. The product was purified by recrystallization from methanol. If the crude product of nitrite oxidation was water soluble, as was found for 5-(4-fluorophenyl)-2-methyl-6-(4-pyridyl)-4(3H)-pyrimidinone, then no aqueous work up was done, but the material obtained on evaporation was applied to a column of silica gel (5% methanol/dichloromethane) prior to recrystallization.

The following compounds were prepared accordingly using the appropriate amidine hydrochloride:

4-1 5-(4-Fluorophenyl)-2-methyl-6-(4-pyridyl)-4(3H)-pyrimidinone

MS (m/z): 282.2 (M+H)$^+$; $C_{16}H_{12}FN_3O$ requir. 281.3
$^1$H-NMR (DMSO-d$_6$): d 8.46 (m 2H, Pyrid.), 7.2–7.03 (m, 6H, PhF, Pyrid.). 2.38 (s, 3H, CH$_3$).

R1=CH$_3$—

4-2 5-(4-Fluorophenyl)-2-isopropyl-6-(4-pyridyl)-4(3H)-pyrimidinone

MS (m/z): 310.0 (M+H)$^+$; $C_{18}H_{16}FN_3O$ requir. 309.4
$^1$H-NMR (DMSO-d$_6$): 8.45 (m, 2H, Pyrid.), 7.21–7.03 (m, 6H, PhF, Pyrid.), 2.90 (m, 1H, CH(CH$_3$)$_2$,) 1.26, 1.24 (2s, each 3H, 2CH$_3$)

R1=(CH$_3$)$_2$CH—

4-3 2-(2,6-Dichlorobenzyl)-5-(4-fluorophenyl)-6-(4-pyridyl)-4(3H)-pyrimidinone

MS (m/z): 426.0 (M)$^+$; $C_{22}H_{14}Cl_2FN_3O$ requir. 426.3
$^1$H-NMR (DMSO-d$_6$): d 8.37 (m, 2H, Pyrid.), 7.50 (d, 2H, PhCl$_2$), 7.35 (t, 1H, PhCl $_2$), 7.18–7.08 (m, 4H, PhF), 6.96 (m, 2H, Pyrid.), 4.36 (s, 2H, CH$_2$)

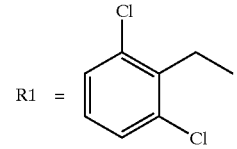

4-4 5-(4-Fluorophenyl)-2-phenyl-6-(4-pyridyl)-4(3H)-pyrimidinone

MS (m/z): 344.2 (M+H)$^+$; $C_{21}H_{14}FN_3O$ requir. 343.4
$^1$H-NMR (DMSO-d$_6$): d 8.49 (d, 2H, Pyrid.), 8,20 (d, 2H, Ph), 7.66–7.50 (m, 3H, Pyrid., Ph), 7.32–7.11 (m, 6H, PhF, Ph).

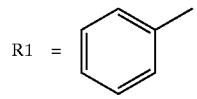

4-5 5-(4-Fluorophenyl)-2-(4-phenylbutyl)-6-(4-pyridyl)-4(3H)-pyrimidinone

Ethyl 2-(4-fluorophenyl)-3-oxo-3-(4-pyridyl)-propionate (293 mg, 1.02 mmol), 4-phenylbutanecarboxamidine (315 mg, 1.79 mmol) and pyridinium p-toluenesulfonate (10 mg) were suspended in p-xylene (10 ml). With efficient stirring, the mixture was heated to reflux using a Dean-Stark apparatus with continuous removal of water. After 16 h, the solvent was evaporated and the product purified by column chromatography on silica gel (3% methanol/dichloromethane) followed by recrystallization from acetone. MS (m/z): 400.3 (M+H)$^+$; $C_{25}H_{22}FN_3O$ requir. 399.5

R1=Ph(CH$_2$)$_4$—

Example 5

General Procedure for the Preparation of 5-(4-fluorophenyl)-6-(4-pyridyl)-2-thioalkyl-4(3H)-pyrimidinones Step A. Ethyl 2-(4-fluorophenyl)-3-oxo-3-(4-pyridyl)-propionate

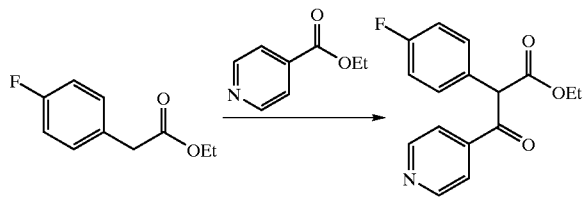

(According to: Legrand and Lozac'h, *Bull. Soc. Chim. Fr.*, 79–81 (1955)).

A mixture of ethyl 4-fluorophenylacetate (13 g, 71.35 mmol), ethyl isonicotinate (10.7 ml, 71.4 mmol) and sodium spheres (1.64 g, 71.34 mmol) was heated at 90–95° C. under argon. The mixture started to reflux and gradually turned into a solid. After 2.5 h, the mixture was neutralized with dil. acetic acid with cooling followed by extraction with dichloromethane. The organic solution was washed with water, dried and evaporated. Flash chromatography on a column of silica gel (hexane-acetone=4:1, 3:1, 2:1) provided the title compound as an oil. MS (m/z): 287.8 (M+H)$^+$; $C_{16}H_{14}FNO_3$ requir. 287.3 $^1$H-NMR (CDCl$_3$), (ketone:enole=1:0.33): d 13.50 (s, 0.3H, OH-E), 8.81 (m, 2H, Pyrid.-K), 8.48 (m, 0.66 H, Pyrid.-E), 7.72 (m, 2H, Pyrid.-K), 7.38 (m, 2H, PhF-K), 7.14–7.04 (m, 2H, PhF-K; ~0.65H, Pyrid.-E; ~0.65H, PhF-E), 6.96 (t, 0.64H, PhF-E), 5.51 (s, 1H, CH—K), 4.23–4.2-(m, CH$_2$—K,E), 1.26 (t, CH$_3$—K,E).

Step B. 5-(4-fluorophenyl)-6-(4-pyridyl)-2-thiouracil

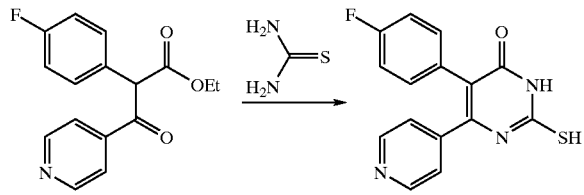

A stirred mixture of ethyl 2-(4-fluorophenyl)-3-oxo-3-(4-pyridyl)-propionate (22.3 g, 77.6 mmol) and thiourea (5.9 g, 77.6 mmol) was reacted at 190° C. under argon for 40 min. The reaction mixture was allowed to reach room temperature, taken up in acetone and the precipitate was filtered to provide the title compound.

MS (m/z): 300.2 (M+H)$^+$; $C_{15}H_{10}FN_3OS$ requir. 299.3 $^1$H-NMR (DMSO-d$_6$): d 12.74, 12.65 (2s, 2H), 8.51 (m, 2H, Pyrid.), 7.26 (m, 2H, Pyrid.), 7.09 and 7.03 (2 m, each 2H, PhF).

Alternatively, ethyl 2-(4-fluorophenyl)-3-oxo-3-(4-pyridyl)-propionate (2.87 g, 10 mmol) and thiourea (2.28 g, 30 mmol) were suspended in anhydrous p-xylene (50 ml) with very efficient stirring. To the mixture pyridinium p-toluenesulfonate (100 mg) was added and refluxed for 12–16 h using a Dean-Stark apparatus with continuous removal of water (0.2 ml). Reaction mixture was cooled and a dark brown solid was filtered using a Buchner funnel. The collected solid was suspended in acetone (25 ml) and filtered. The acetone washed product contained a trace of thiourea, which was removed by trituration with hot water (20–30 ml). The product was filtered and airdried.

Step C. General Procedure

The arylalkyl bromide (0.36 mmol) was added dropwise to a stirring mixture of 5-(4-fluorophenyl)-6-(4-pyridyl)-2-thiouracil (100 mg, 0.33 mmol) and potassium carbonate (46 mg, 0.33 mmol) in N,N-dimethylformamide (4.6 ml). Stirring was continued for 3 h followed by evaporation. Flash chromatography on a column of silica gel (hexane-acetone=3:1, 2:1, 1:1) and recrystallization from hot methanol provided the target compound.

The following compounds were obtained using the appropriate arylalkyl bromide according to the above procedure:

5-1 5-(4-Fluorophenyl)-2-(2-phenylethyl)thio-6-(4-pyridyl)-4(3H)-pyrimidinone

MS (m/z): 404.2 (M+H)$^+$; $C_{23}H_{18}FN_3OS$ requir. 403.4. $^1$H-NMR (DMSO-d$_6$): d 13.08 (bs, 0.7H), 8.49 (m, 2H, Pyrid.), 7.30–7.06 (m, 11H, Pyrid., Ph, PhF), 3.41 (dd, 2H, CH$_2$S), 3.00 (t, 2H, CH$_2$).

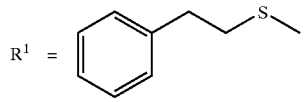

5-2 5-(4-Fluorophenyl)-2-(3-phenylpropyl)thio-6-(4-pyridyl)-4(3H)-pyrimidinone

MS (m/z): 418.0 (M+H)$^+$; $C_{24}H_{20}FN_3OS$ requir. 417.5. $^1$H-NMR (DMSO-d$_6$): d 13.10 (bs, 0.7H), 8.47 (m, 2H, Pyrid.), 7.29–7.06 (m, 11H, Pyrid., Ph, PhF), 3.18 (t, 2H, CH$_2$S), 2.71 (t, 2H, CH$_2$Ph), 2.03 (m, 2H, CH$_2$).

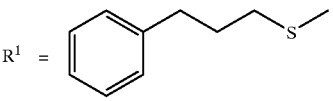

5-3 5-(4-Fluorophenyl)-2-(2-phenoxyethyl)thio-6-(4-pyridyl)-4(3H)-pyrimidinone

MS (m/z): 420.0 (M+H)$^+$; $C_{23}H_{18}FN_3O_2S$ requir. 419.5. $^1$H-NMR (DMSO-d$_6$): d 13.20 (bs, 0.7H), 8.46 (m, 2H, Pyrid.), 7.24–7.07 (m, 8H, Pyrid., PhF, Ph), 6.95 (d, 2H, Ph), 6.92 (t, overlapped, 1H, Ph), 4.30 (t, 2H, CH$_2$O), 3.58 (t, 2H, CH$_2$S).

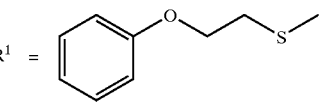

5-4 5-(4-Fluorophenyl)-2-(2-phenylaminoethyl)thio-6-(4-pyridyl)-4(3H)-pyrimidinone MS (m/z): 419.0 (M+H)$^+$; $C_{23}H_{19}FN_4OS$ requir. 418.5. $^1$H-NMR (DMSO-d$_6$): d 13.20 (bs, 0.8H), 8.48, 7.22 (2 m, each 2H, Pyrid.), 7.16, 7.10 (2 m, each 2H, PhF), 6.89 (t, 2H, Ph), 6.54 (d, 2H, Ph), 6.48 (t, 1H, Ph), 5.90 (bs, 0.6H, NH), 3.43–3.25 (m, 2CH$_2$).

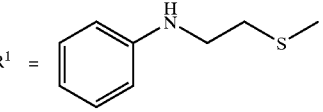

Example 6

General Procedure for the Preparation of 2-N Substituted 2-amino-5-(4-fluorophenyl)-6-(4-pyridyl)-4 (3H)-pyrimidinones Step A. 5-(4-Fluorophenyl)-2-methylthio-6-(4-pyridyl)-4 (3H)-pyrimidinone

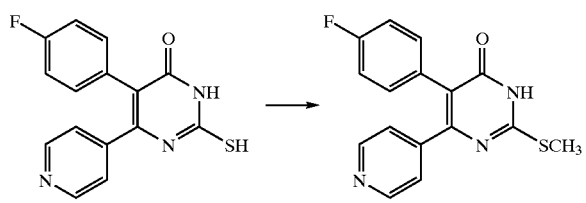

Methyl iodide (90 ml, 1.44 mmol) was added dropwise to a stirred mixture of 5-(4-fluorophenyl)-6-(4-pyridyl)-2-thiouracil (430 mg, 1.44 mmol) and potassium carbonate (198 mg, 1.43 mmol) in N,N-dimethylformamide (13 ml) at ice-bath temperature. After 40 min, it was evaporated and the crude product purified by flash chromatography on a column of silica gel (hexane-acetone=2:1, 1:1, 1:2) to provide the title compound as a solid. MS (m/z): 314.2 (M+H)$^+$; $C_{16}H_{12}FN_3OS$ requir. 313.3. $^1$H-NMR (DMSO-d$_6$): d 13.10 (bs), 8.47, 7.22 (2 m, each 2H, Pyrid.), 7.16, 7.10 (2 m, each 2H, PhF), 2.56 (s, 3H, CH$_3$).

Step B. General Procedure

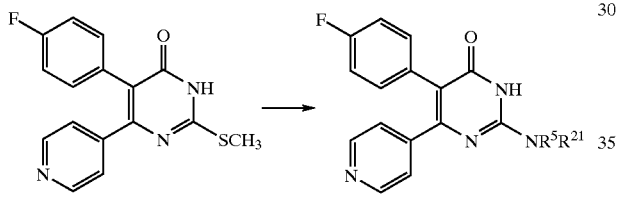

A mixture of 5-(4-fluorophenyl)-2-methylthio-6-(4-pyridyl)-4(3H)-pyrimidinone (100 mg, 0.32 mmol) and an amine HNR$^5$R$^{21}$ (1 mmol) was heated at 180° C. for 2 h. The resulting product was purified by flash chromatography on a column of silica gel (hexane-acetone or methanol-dichloromethane or dichloromethane-methanol-conc. ammonium hydroxide) to provide the target compound.

The following compounds were prepared using the general procedure outlined above and an appropriate amine:

6-1 2-(2-(2-Chlorophenyl)ethyl-amino)-5-(4-fluorophenyl)-6-(4-pyridyl)-4(3H)-pyrimidinone MS (m/z): 421.2 (M+H)$^+$; $C_{23}H_{18}ClFN_4O$ requir. 420.9. $^1$H-NMR (DMSO-d$_6$): d 11.24 (bs), 8.44, 7.16 (2 m, each 2H, Pyrid.), 7.43, 7.38 (2 dd, each 1H, PhCl), 7.30, 7.26 (2 dt, each 1H, PhCl), 7.10–7.00 (m, 2H, PhF), 6.74 (bs, 1H, NH), 3.60 (q, 2H, CH$_2$N), 3.03 (t, 2H, CH$_2$)

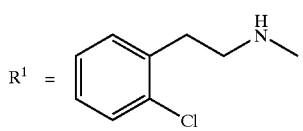

6-2 5-(4-Fluorophenyl)-2-((3-phenylpropyl)-amino)-6-(4-pyridyl)-4(3H)-pyrimidinone MS(m/z): 401.2 (M+H)$^+$; $C_{24}H_{21}FN_4O$ requir. 400.5. $^1$H-NMR (DMSO-d$_6$): d 11.16 (bs), 8.44, 7.14 (2 m, each 2H, Pyrid.), 7.32–7.01 (m, 9H, Ph, PhF), 6.78 (bs, NH), 3.36 (q, 2H, CH$_2$N), 2.67 (t, 2H, CH$_2$Ph), 1.89 (m, 2H, CH$_2$)

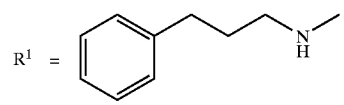

6-3 5-(4-Fluorophenyl)-2-((1-methyl-3-phenylpropyl)-amino)-6-(4-pyridyl)-4(3H)-pyrimidinone A reaction time of 15 h at 180° C. was required. MS (m/z): 415.0 (M+H)$^+$; $C_{25}H_{23}FN_4O$ requir. 414.5. $^1$H-NMR (CDCl$_3$): d 8.48 (m, 2H, Pyrid.), 7.28–7.08 (m, 9H, Pyrid., Ph, PhF), 6.94 (m, 2H, PhF), 5.67 (bs, 1H, NH), 4.08 (m, 1H, CHCH$_3$), 2.61 (t, 2H, CH$_2$Ph), 1.67 (m, 2H, CH$_2$), 1.08 (d, 3H, CH$_3$).

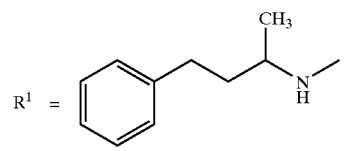

6-4 5-(4-Fluorophenyl)-2-((3-imidazolylpropyl)-amino)-6-(4-pyridyl)-4(3H)-pyrimidinone MS (m/z): 391.0 (M+H)$^+$; $C_{21}H_{19}FN_6O$ requir. 390.4. $^1$H-NMR (DMSO-d$_6$): d 11.24 (bs), 8.42, 7.12 (2 m, each 2H, Pyrid.), 7.62, 7.18 (2s, each 1H, Imid.), 7.08–6.99 (m, 4H, PhF), 6.88 (s, 1H, Imid.), 4.02 (t, 2H, CH$_2$N), 3.28 (overlapped by water signal, CH$_2$NH), 2.00 (m, 2H, CH$_2$).

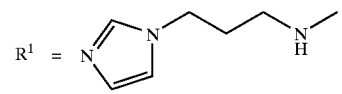

6-5 2-(((S)-2-Amino-3-phenylpropyl)-amino)-5-(4-fluorophenyl)-6-(4-pyridyl)-4(3H)-pyrimidinone hydrochloride The reaction was done at 170° C. for 7 h. MS (m/z): 416.1 (M+H)$^+$; $C_{26}H_{22}FN_5O$ requir. 415.5.

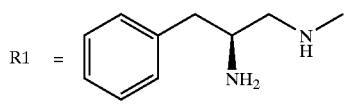

Example 7

5-(4-Fluorophenyl)-2-hydrazino-6-(4-pyridyl)-4 (3H)-pyrimidinone

A mixture of 5-(4-fluorophenyl)-6-(4-pyridyl)-2-thiouracil (500 mg, 1.66 mmol) and hydrazine hydrate (800 ml, ~14 mmol) was heated at 120° C. for 60 min. It was evaporated and the reaction product was recrystallized from hot methanol to provide the title compound. MS (m/z): 298.0 (M+H)$^+$; $C_{15}H_{12}FN_5O$ requir. 297.3. $^1$H-NMR (DMSO-d$_6$): d 8.41, 7.12 (2 m, each 2H, Pyrid.), 7.05, 7.00 (2 m, each 2H, PhF).

R$^1$=NH—NH$_2$

Example 8

General Procedure for the Preparation of 5-aryl-2,6-dipyridyl-(3H)-pyrimidinones

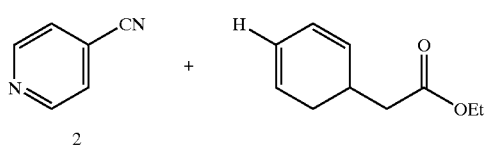

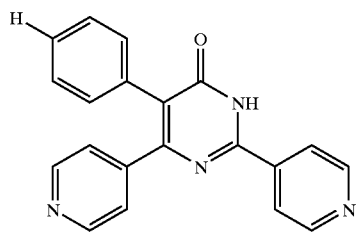
8-1

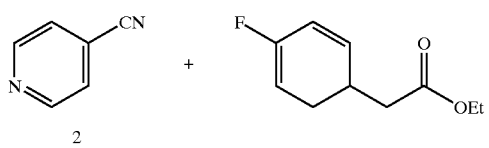

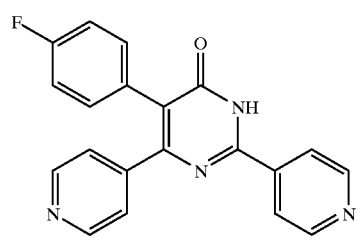
8-2

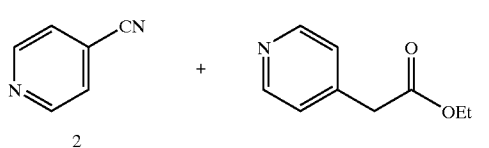

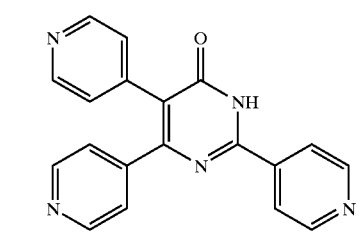
8-3

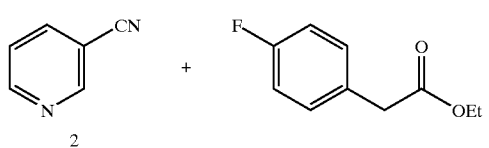

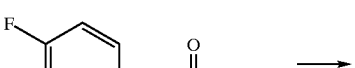

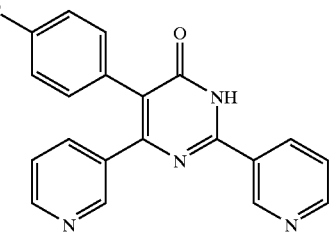

These compounds were prepared according to the literature (Kabbe, supra; German Patent 1271116 (1968)) as follows:

A stirred mixture of the ethyl phenylacetate (3.13 mmol), cyanopyridine (6.24 mmol) and sodium methoxide (3.5 mmol) in n-butanol (1.2 ml) was heated at 110° C. for 2 h. The reaction mixture was concentrated and dissolved in water (4 ml), followed by the addition of aqueous sat. ammonium chloride (2 ml). The precipitate was filtered and recrystallized from hot methanol.

The following compounds were prepared according to this procedure using the appropriate starting materials:

8-1 5-Phenyl-2,6-bis-(4-pyridyl)-4-(3H)pyrimidinone

MS (m/z): 327.2 (M+H)$^+$; $C_{20}H_{14}N_4O$ requir. 326.4. $^1$H-NMR (DMSO-d$_6$): d 8.78, 8.47, 8.13 (3 m, each 2H, Pyrid.), 7.40–7.14 (m, 7H, Ph, Pyrid.).

8-2 5-(4-Fluorophenyl)-2,6-bis-(4-pyridyl)-4(3H)-pyrimidinone

MS (m/z): 345.2 (M+H)$^+$; $C_{20}H_{13}FN_4O$ requir. 344.4. $^1$H-NMR (DMSO-d$_6$): d 8.80, 8.49, 8.13 (3 m, each 2H, Pyrid.), 7.40–7.08 (m, 6H, PhF, Pyrid.).

8-3 2,5,6-Tris-(4-pyridyl)-4(3H)-pyrimidinone was prepared according to the general procedure by reacting ethyl 4-pyridylacetate and 4-cyanopyridine in the presence of sodium methoxide. MS (m/z): 328.2 (M+H)$^+$; $C_{19}H_{13}N_5O$ requir. 327.4 $^1$H-NMR (DMSO-d$_6$): 8.65, 8.45, 8.35, 8.18, 7.25, 7.13 (6 m, each 2H, Pyrid.).

8-4 5-(4-Fluorophenyl)-2,6-bis-(3-pyridyl)-4(3H)-pyrimidinone

MS (m/z): 345.2 (M+H)$^+$; $C_{20}H_{13}FN_4O$ requir. 344.4 $^1$H-NMR (DMSO-d$_6$): d 9.34, 8.77, 8.54, 8.48, 7.78, 7.60, 7.34 (7 m, 3×1H, 2H, 3×1H, Pyrid.), 7.26, 7.15 (2 m, each 2H, PhF).

Example 9

4-Amino-5-(4-fluorophenyl)-2,6-bis-(4-pyridyl)-pyrimidine

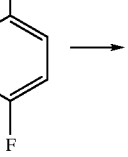

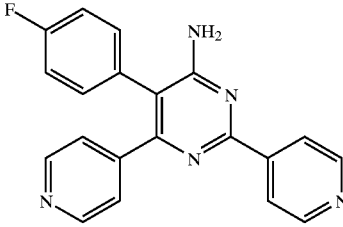

4-Amino-5-(4-fluorophenyl)-2,6-bis-(4-pyridyl)-pyrimidine was prepared according to the literature (Kabbe, supra):

Sodium methoxide (180 mg, 3.33 mmol) was added to a stirred solution of 4-cyanopyridine (650 mg, 6.24 mmol) and 4-fluorophenylacetonitrile (375 mml, 3.12 mmol) in n-butanol (1.5 ml). The mixture was stirred for 20 min at room temperature before heating it at 110° C. for 1.5 h. It was allowed to reach room temperature and ethanol (2.5 ml) was added. The precipitate was filtered and recrystallized from acetic acid/water (3.5/10 ml) to provide the title compound. MS (m/z): 344.2 (M+H)$^+$; $C_{20}H_{14}FN_5$ requir. 343.4 $^1$H-NMR (DMSO-$d_6$): 8.76, 8.47, 8.22 (3 m, each 2H, Pyrid.), 7.4–7.16 (m, 6H, PhF, Pyrid.).

Example 10

4-Methoxy-5-phenyl-2,6-bis-(4-pyridyl)-pyrimidine

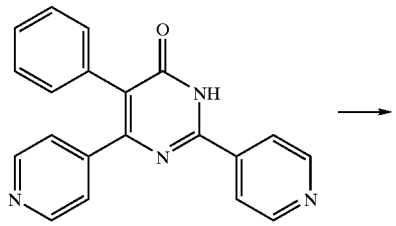

R = Cl
R = OMe

A mixture of 5-phenyl-2,6-bis-(4-pyridyl)-4(3H)-pyrimidinone (360 mg, 1.10 mmol) and phosphorus oxychloride (2 ml) was heated at reflux for 1.5 h. Work-up was done as described for the preparation of 2-chloro-5-(4-fluorophenyl)-4-(4-pyridyl)-pyrimidine. To a solution of the crude 4-chloro-5-phenyl-2,6-bis-(4-pyridyl)-pyrimidine (250 mg, 0.73 mmol) in methanol (5 ml) was added methanolic 0.5 N sodium methoxide (1.45 ml, 0.73 mmol) and it was heated at reflux for 1 h. After evaporation, the resultant material was partitioned between ethyl acetate and water. The organic solution was washed with water, dried and evaporated. Chromatography of the crude product on a column of silica gel (ethyl acetate) provided the title compound. MS (m/z): 341.2 (M+H)$^+$; $C_{21}H_{16}N_4O$ requir. 340.4 $^1$H-NMR (CDCl$_3$): 8.82, 8.54, 8.40 (3 m, each 2H, Pyrid.), 7.40–7.18 (m, 7H, Ph, Pyrid.), 4.15 (s, 3H, CH$_3$O).

Example 11

Procedure for the Preparation of 5-(4-Fluorophenyl)-2,4-bis-(4-pyridyl)-pyrimidine Step A. 4-Chloro-5-(4-fluorophenyl)-2,6-bis-(4-pyridyl)-pyrimidine

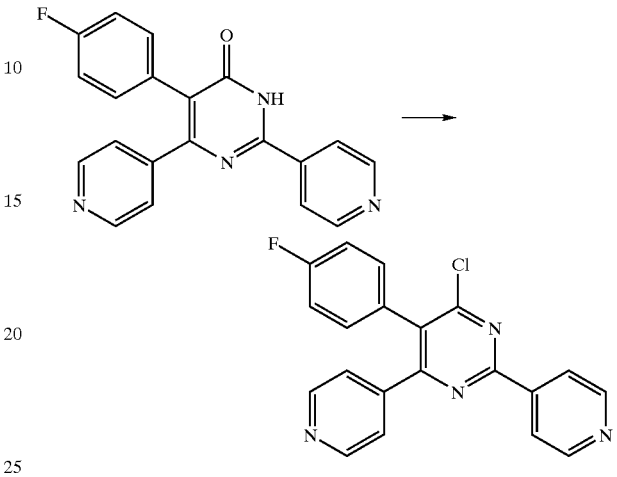

A mixture of 5-(4-fluorophenyl)-2,6-bis-(4-pyridyl)-4(3H)-pyrimidinone (760 mg, 2.21 mmol) in phosphorus oxychloride (3 ml) was heated at reflux for 1 h. Work-up was done as described for the preparation of 2-chloro-5-(4-fluorophenyl)-4-(4-pyridyl)-pyrimidine. A portion (290 mg) of the resulting product (495 mg) was purified by flash chromatography (ethyl acetate, trace triethylamine) on silica gel. MS (m/z): 363.2 (M+H)$^+$; $C_{20}H_{12}ClFN_4$ requir. 362.8 $^1$H-NMR (CDCl$_3$): d 8.84, 8.60, 8.38, 7.30 (4 m, each 2H, Pyrid.), 7.22, 7.13 (2 m, each 2H, PhF).

Step B. 5-(4-Fluorophenyl)-2,4-bis-(4-pyridyl)-pyrimidine

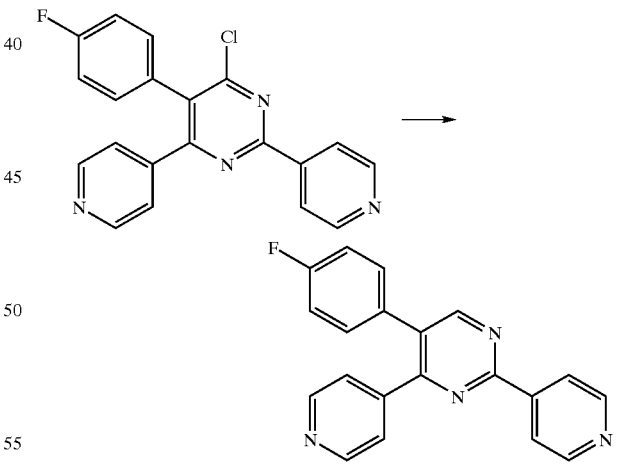

A stirred mixture of 4-chloro-5-(4-fluorophenyl)-2,6-bis-(4-pyridyl)-pyrimidine (99 mg, 0.27 mmol) and 10% palladium-on-carbon (70 mg) in ethanol (10 ml) was hydrogenated under an atmosphere of hydrogen for 28 h. Filtration and evaporation of the solvent was followed by flash chromatography (ethyl acetate) on a column of silica gel to provide the title compound. MS (m/z): 329.2 (M+H)$^+$; $C_{20}H_{13}FN_4$ requir. 328.4. $^1$H-NMR (CDCl$_3$): d 8.91 (s, 1H, H-6, Pyrim.), 8.83, 8.65, 8.40, 7.45 (4 m, each 2H, Pyrid.), 7.30–7.06 (m, 4H, PhF).

Example 12

Procedure for the Preparation of 2-(((S)-2-N-Glycylamino-3-phenylpropyl)-amino)-4-(4-pyridyl)-5-(3-trifluoromethylphenyl)-pyrimidine Hydrochloride

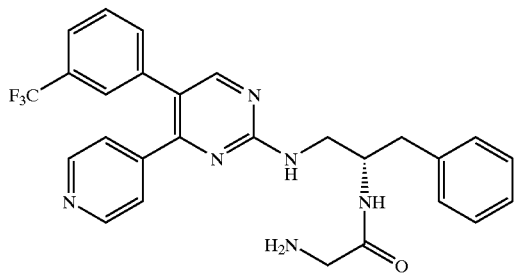

12-1 2-(((S)-2-N-Glycylamino-3-phenylpropyl)-amino)-4-(4-pyridyl)-5-(3-trifluoromethylphenyl)-pyrimidine hydrochloride Ethyl chloroformate (86 •l, 0.901 mmol) was added at ice-bath temperature to a stirring mixture of N-(tert.-butoxycarbonyl)glycine (160 mg, 0.911 mmol) and 4-methylmorpholine (110 •l, 1.00 mmol) in tetrahydrofuran (10 ml). After 40 min, a solution 2-(((S)-2-amino-3-phenylpropyl)-amino)-4-(4-pyridyl)-5-(3-trifluoromethylphenyl)-pyrimidine (409 mg, 0.911 mmol) in tetrahydrofuran (15 ml) was added at ice-bath temperature. Within 1 h, the mixture was allowed to reach room temperature. It was diluted with dichloromethane, washed with aqueous sodium hydrogencarbonate, followed by drying of the organic solution and evaporation. The resulting material was purified on a column of silica gel (5% methanol/dichloromethane), then dissolved in methanol (2 ml) and 4N hydrogen chloride/dioxane (2 ml) was added. After 1 h at room temperature, it was evaporated and the remainder taken up in dichloromethane followed by washing with aqueous sodium hydrogencarbonate, drying of the organic solution and evaporation. Column chromatography on silica gel (dichloromethane-methanol-conc. ammonium hydroxide=95:5:0; 90:10:0.6) provided the title compound as the free base which was converted into the hydrochloride by the addition of 4N hydrogen chloride/dioxane (85 •l) to its methanolic solution (3 ml) followed by evaporation. MS (m/z): 507.4 (M+H)$^+$; $C_{27}H_{25}F_3N_6O$ requir. 506.5 (free base).

The following compound was prepared using the above procedure and the appropriate starting materials:
12-2 2-(((S)-2-N-Glycylamino-3-phenylpropyl)-amino)-5-(3-methylphenyl)-4-(4-pyridyl)-pyrimidine hydrochloride
MS (m/z): 453.2 (M+H)$^+$; $C_{27}H_{28}N_6O$ requir. 452.6 (free base).

Example 13

Procedure for the Preparation of (S)-1,2-Benzylethylendiamine

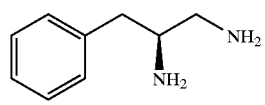

(S)-1,2-Benzylethylendiamine
The diamine was prepared according to the literature (H. Brunner, P. Hankofer, U. Holzinger, B. Treittinger and H. Schoenenberger, Eur. J. Med. Chem. 25, 35–44, (1990)) by reduction of L-phenylalanine amide with lithium aluminium hydride. The (R)-enantiomer was prepared in the same manner from D-phenylalanine amide.

Example 14

Procedure for the Preparation of 2-(((S)-2-Acetamido-3-phenylpropyl)-amino)-5-(4-fluorophenyl)-3-methyl-6-(4-pyridyl)-4(3H)-pyrimidinone

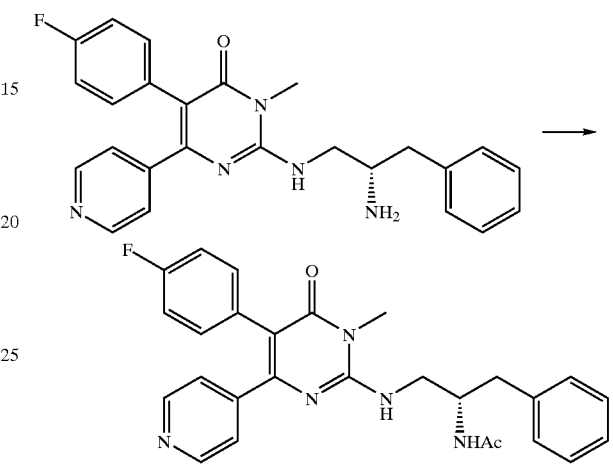

2-(((S)-2-Acetamido-3-phenylpropyl)-amino)-5-(4-fluorophenyl)-3-methyl-6-(4-pyridyl)-4(3H)-pyrimidinone
A solution of 2-(((S)-2-amino-3-phenylpropyl)-amino)-5-(4-fluorophenyl)-3-methyl-6-(4-pyridyl)-4(3H)-pyrimidinone (25 mg, 0.058 mmol) and acetic anhydride (200 ml) in methanol (2 ml) was kept at room temperature for 1 h. Evaporation followed by chromatography of the resultant product on a column of silica gel (10% methanol/dichloromethane) provided the title compound.
MS (m/z): 472.3 (M+H)$^+$; $C_{27}H_{26}FN_5O_2$ requir. 471.5.

Example 15

Procedure for the Preparation of 2-(((S)-2-N-Isopropylamino-3-phenylpropyl)-amino)-4-(4-pyridyl)-5-(3-trifluoromethylphenyl)-pyrimidine Hydrochloride

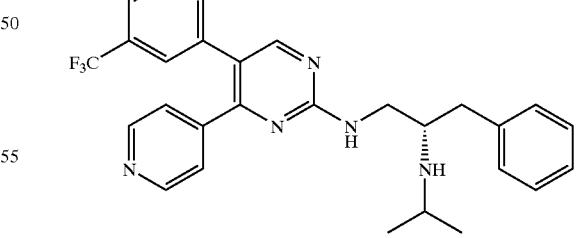

15-1 2-(((S)-2-N-Isopropylamino-3-phenylpropyl)-amino)-4-(4-pyridyl)-5-(3-trifluoromethylphenyl)-pyrimidine hydrochloride Sodium triacetoxyborohydride (184 mg, 0.868 mmol) was added to a stirring mixture of 2-(((S)-2-amino-3-phenylpropyl)-amino)-4-(4-pyridyl)-5-(3-trifluoromethylphenyl)-pyrimidine (300 mg, 0.668 mmol) and acetone (50 •l, 0.675 mmol) in 1,2-dichloroethane (4 ml). After 16 h, the reaction was quenched by the addition of sat. aqu. sodium hydrogencarbonate, followed by extraction with dichloromethane, drying of the organic solution and evaporation. Chromatography on a column of silica gel (5% methanol/chloroform) provided the title compound as a free base which was converted into the monohydrochloride by the addition of 6N hydrochloric acid (73 •l) to its methanolic solution (3 ml) and subsequent evaporation. MS (m/z): 491.7 (M)$^+$; $C_{28}H_{28}F_3N_5$ requir. 491.6 (free base).

The following compounds were prepared using the above procedure and the appropriate starting materials:

15-2 2-(((S)-2-N-Cyclohexylamino-3-phenylpropyl)-amino)-4-(4-pyridyl)-5-(3-trifluoromethylphenyl)-pyrimidine hydrochloride MS (m/z): 532.0 (M+H)$^+$; $C_{31}H_{32}F_3N_5$ requir. 531.6 (free base).

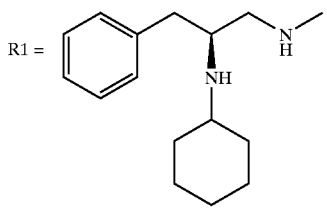

15-3 2-(((S)-2-N-Isopropylamino-3-phenylpropyl)-amino)-5-(3-methylphenyl)-4-(4-pyridyl)-pyrimidine hydrochloride MS (m/z): 439.1 (M+H)$^+$; $C_{28}H_{31}N_5$ requir. 437.6 (free base).

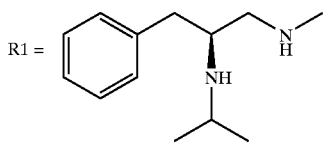

15-4 2-(((S)-2-N-Butylamino-3-phenylpropyl)-amino)-5-(3-methylphenyl)-4-(4-pyridyl)-pyrimidine hydrochloride MS (m/z): 452.1 (M+H)$^+$; $C_{29}H_{33}N_5$ requir. 451.6 (free base).

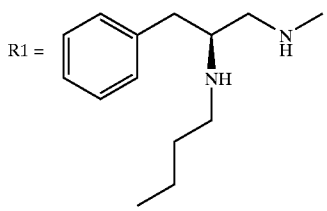

15-5 2-(((S)-2-N-Cyclohexylamino-3-phenylpropyl)-amino)-5-(3-methylphenyl)-4-(4-pyridyl)-pyrimidine hydrochloride MS (m/z): 478.3 (M+H)$^+$; $C_{31}H_{35}N_5$ requir. 477.7 (free base).

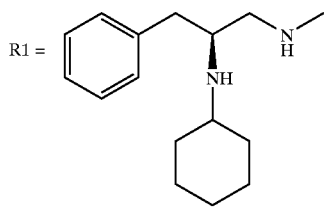

15-6 5-(4-Fluorophenyl)-2-(((S)-2-N-isopropylamino-3-phenylpropyl)-amino)-4-(4-pyridyl)-pyrimidine hydrochloride MS (m/z): 442.1 (M+H)$^+$; $C_{27}H_{28}FN_5$ requir. 441.6 (free base).

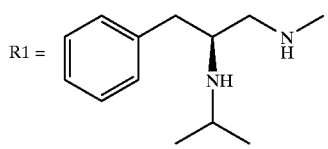

15-7 5-(4-Fluorophenyl)-2-((3-N-isopropylamino-3-phenylpropyl)-amino)-4-(4-pyridyl)-pyrimidine hydrochloride MS (m/z): 442.2 (M+H)$^+$; $C_{27}H_{28}FN_5$ requir. 441.6 (free base).

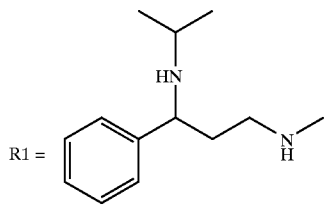

Example 16

Procedure for the Preparation of 2-(((S)-2-Amino-3-phenylpropyl)-amino)-5-(3-chloro-4-fluorophenyl)-4-(4-pyridyl)-pyrimidine Hydrochloride

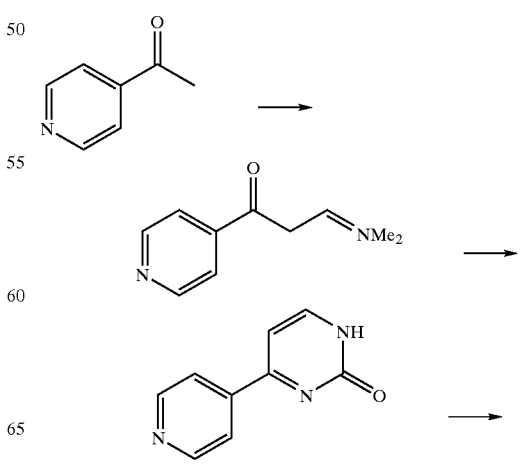

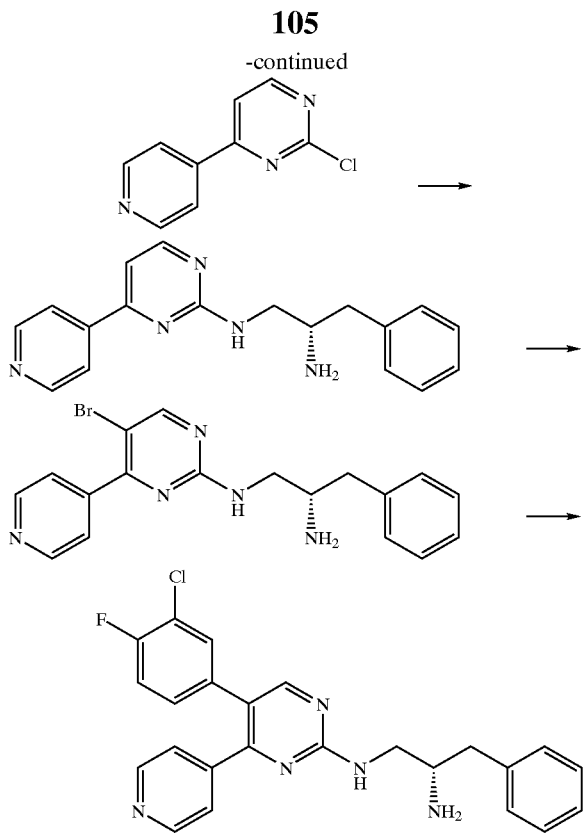

Step A: 4-(4-Pyridyl)-2(1H)-pyrimidinone

A mixture of 4-acetylpyridine (25 ml, 226.0 mmol) and bis(dimethylamino)methoxymethane (44 ml, 293.8 mmol) was heated at 85° C. for 30 min followed by evaporation to dryness to recover a solid of 3-(dimethylamino)-1-(4-pyridyl)-3-propen-1-one. Its ethanolic solution (200 ml) was transferred into ethanolic 1.13 N sodium ethoxide (200 ml) containing urea (16.3 g, 271 mmol). The mixture was heated to reflux overnight, then cooled down to ice-bath temperature. The precipitate was filtered, dissolved in a minimal amount of water and the aqueous solution was washed with dichloromethane. The title compound was precipitated from the aqueous solution by neutralization with 6N hydrochloric acid and filtered. More material was obtained from the original reaction filtrate which was concentrated, diluted with a minimal amount of water and washed with dichloromethane. The aqueous solution was neutralized with 6N hydrochloric acid and the precipitate filtered. MS (m/z): 174.1 (M+H)$^+$; C$_9$H$_7$N$_3$O requir. 173.2.

Step B: 2-Chloro-4-(4-pyridyl)-pyrimidine

With ice-bath cooling under argon, 4-(4-pyridyl)-2(1H)-pyrimidinone (13.45 g, 77.7 mmol) and thionyl chloride (92 ml) were combined. N,N-Dimethylformamide (13.2 ml, 170.5 mmol) was added slowly and the mixture was heated to reflux for 1 h. It was evaporated and co-distilled with toluene. At 0° C., water was added to the remainder, then 10% ammonium hydroxide until neutral followed by extraction with dichloromethane. Drying of the organic solution was followed by evaporation and the resultant solid was recrystallized from acetone. MS (m/z): 192.1,194.0 (M+H)$^+$; C$_9$H$_6$ClN$_3$ requir. 191.6.

Step C: 2-(((S)-2-Amino-3-phenylpropyl)-amino)-4-(4-pyridyl)-pyrimidine

A mixture of 2-chloro-4-(4-pyridyl)-pyrimidine (4.5 g, 23.7 mmol) and (S)-1,2-benzylethylendiamine (8.0 g, 53.3 mmol) was heated at 100° C. for 25 min. Column chromatography on silica gel (dichloromethane-methanol-conc. ammonium hydroxide=95:5:0.4) provided the title compound. MS (m/z): 306.5 (M+H)$^+$; C$_{18}$H$_{19}$N$_5$ requir. 305.4.

Step D: 2-(((S)-2-Amino-3-phenylpropyl)-amino)-5-bromo-4-(4-pyridyl)-pyrimidine

Bromine (787 •l, 15.28 mmol) was added to a stirring solution of 2-(((S)-2-amino-3-phenylpropyl)-amino)-4-(4-pyridyl)-pyrimidine (2.33 g, 7.64 mmol) in chloroform (25 ml). Stirring was continued for 2 d. The mixture was partitioned between dichloromethane and aqueous sodium hydrogencarbonate. The organic solution was washed with brine, dried and evaporated. The resultant product was purified on a column of silica gel (dichloromethane-methanol-conc. ammonium hydroxide=92:8:0.6). MS (m/z): 384.0, 386.0 (M+H)$^+$; C$_{18}$H$_{18}$BrN$_5$ requir. 384.3.

Step E: 2-(((S)-2-Amino-3-phenylpropyl)amino)-5-(3-chloro-4-fluorophenyl)-4-(4-pyridyl)-pyrimidine hydrochloride A mixture of 2-((2(S)-amino-3-phenyl propyl)amino)-5-bromo-4-(4-pyridyl)-pyrimidine (204 mg, 0.53 mmol), aqueous 2M sodium carbonate (1.66 ml, 3.32 mmol) and 3-chloro-4-fluorobenzene boronic acid (103 mg, 0.637 mmol) in toluene (5 ml) was stirred for 10 min under argon. The mixture was thoroughly degassed (10 times), before the addition of tetrakis (triphenylphosphine) palladium(0) (18 mg, 0.016 mmol). After heating at reflux for 16 h, the reaction mixture was diluted with toluene and washed with brine. The organic solution was dried and evaporated. Subsequent column chromatography on silica gel (dichloromethane-methanol-conc. ammonium hydroxide=95:5:04) provided the title compound which was converted into the hydrochloride by the addition of 6N hydrochloric acid (64 •l) to its methanolic solution (2 ml) followed by evaporation. MS (m/z): 434.1 (M)$^+$; C$_{24}$H$_{21}$ClFN$_5$ requir. 433.9 (free base).

The following compounds were prepared according to Step E of this procedure by using the appropriate boronic acid and 5-bromopyrimidine:

16-2 2-(((S)-2-Amino-3-phenylpropyl)-amino)-5-(3-fluorophenyl)-4-(4-pyridyl)-pyrimidine hydrochloride MS (m/z): 400.1 (M+H)$^+$; C$_{24}$H$_{22}$FN$_5$ requir. 399.5 (free base).

16-3 2-(((S)-2-Amino-3-phenylpropyl)-amino)-5-(3-isopropylphenyl)-4-(4-pyridyl)-pyrimidine hydrochloride MS (m/z): 424.2 (M+H)$^+$; C$_{27}$H$_{29}$N$_5$ requir. 423.6 (free base).

16-4 5-(3-Acetamidophenyl)-2-(((S)-2-amino-3-phenylpropyl)-amino)-4-(4-pyridyl)-pyrimidine hydrochloride MS (m/z): 439.1 (M+H)$^+$; C$_{26}$H$_{26}$N$_6$O requir. 438.5 (free base).

16-5 2-(((S)-2-Amino-3-phenylpropyl)-amino)-5-(4-chlorophenyl)-4-(4-pyridyl)-pyrimidine hydrochloride MS (m/z): 416.3 (M+H)$^+$; C$_{24}$H$_{22}$ClN$_5$ requir. 415.9 (free base).

16-6 2-(((S)-2-Amino-3-phenylpropyl)-amino)-5-(benzothienyl)-4-(4-pyridyl)-pyrimidine hydrochloride MS (m/z): 438.3 (M+H)$^+$; C$_{26}$H$_{23}$N$_5$S requir. 437.6 (free base).

16-7 2-(((S)-2-Amino-3-phenylpropyl)-amino)-5-(2-naphthyl)-4-(4-pyridyl)-pyrimidine hydrochloride MS (m/z): 432.5 (M+H)$^+$; C$_{28}$H$_{25}$N$_5$ requir. 431.5 (free base).

Example 17

Procedure for the Preparation of (S)-2-Benzylpiperazine

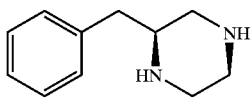

(S)-2-Benzylpiperazine

At ice-bath temperature, lithium aluminium hydride (1.6 g, 42.16 mmol) was added in portions to a stirring mixture of (S)-2-benzyl piperazine-3,6-dione (3.0 g, 14.70 mmol) and tetrahydrofuran (80 ml). After 30 min at ice-bath temperature, the mixture was refluxed for 4 h with stirring. The reaction was quenched by the portionwise addition of sodium sulfate decahydrate and some methanol until hydrogen evolution ceased. It was filtered and the solids were washed several times with dichloromethane. The combined filtrates were evaporated to leave a white solid. MS (m/z): 177.1 (M+H)$^+$; $C_{11}H_{16}N_2$ requir. 176.3.

Example 18

Procedure for the Preparation of (S)-2-N,N-Dimethylamino-3-phenylpropylamine

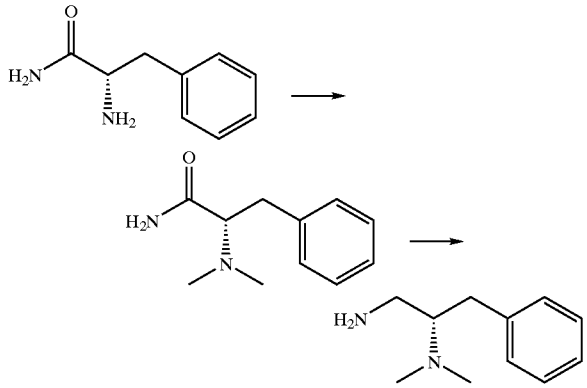

(S)-2-N,N-Dimethylamino-3-phenylpropylamine

Sodium triacetoxyhydride (13.0 g, 61.3 mmol) was added to a stirring mixture of phenylalanine amide (3.6 g, 21.9 mmol) and 37% formaldehyde solution (4.4 ml, 58.7 mmol) in 1,2-dichloroethane (77 ml). After stirring for 2 h, the reaction was quenched by the addition of sat. aqu. sodium hydrogencarbonate. Then potassium hydroxide pellets were added followed by extraction with dichloromethane, drying of the organic solution and evaporation. The resulting (S)-2-N,N-dimethylamino-3-phenylpropylamide was reduced with lithium aluminium hydride according to the literature (H. Brunner, P. Hankofer, U. Holzinger, B. Treittinger and H. Schoenenberger, Eur. J. Med. Chem. 25, 35–44, (1990)) to provide the title compound.

Example 19

Procedure for the Preparation of 2-(((S)-2-N,N-Dimethylamino-3-phenylpropyl)-amino)-5-(4-fluorophenyl-3-methyl-6-(4-pyridyl)-4(3H)-pyrimidinone Hydrochloride

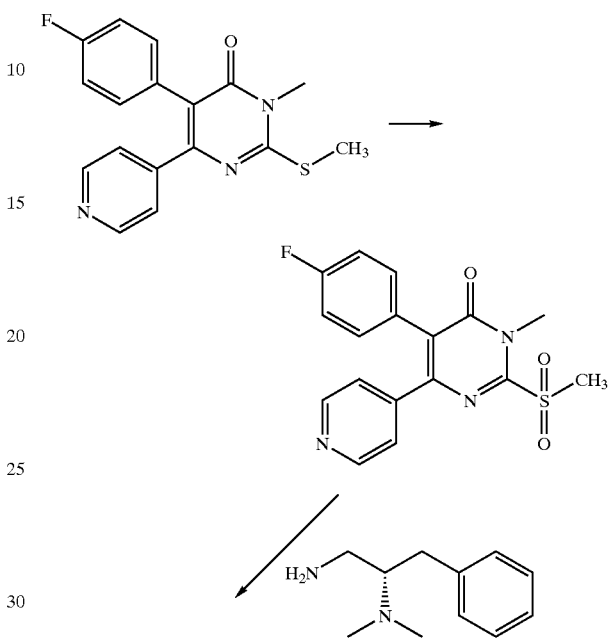

Step A. 5-(4-Fluorophenyl)-3-methyl-2-methylsulfonyl-6-(4-pyridyl)-4(3H)-pyrimidinone A mixture of 5-(4-fluorophenyl)-3-methyl-2-methylthio-6-(4-pyridyl)-4(3H)-pyrimidinone (400 mg, 1.22 mmol) and Oxone® (potassium peroxymonosulfate, 2.3 g, 3.74 mmol) in methanol (100 ml) and water (45 ml) was stirred for 13 h. The solvent was concentrated to about 50 ml, followed by extraction with dichloromethane, drying of the organic solution and evaporation. The resulting white solid was used without purification in the next step.

Step B. 2-(((S)-2-N,N-Dimethylamino-3-phenylpropyl)-amino)-5-(4-fluorophenyl-3-methyl-6-(4-pyridyl)-4(3H)-pyrimidinone hydrochloride A mixture of crude 5-(4-fluorophenyl)-3-methyl-2-methylsulfonyl-6-(4-pyridyl)-4(3H)-pyrimidinone (430 mg g, 1.19 mmol) and (S)-2-N,N-dimethylamino-3-phenylpropylamine (600 mml, ~3.4 mmol) was stirred at room temperature for 1 h and then briefly warmed at 50° C. Column chromatography on silica gel (3–5% methanol/chloroform) provided the title compound as a free base which was converted into the monohydrochloride by the addition of 4N hydrochloric acid/dioxane (160 mml, 0.64 mmol) to its methanolic solution (4 ml) and subsequent evaporation. MS (m/z): 458.0 (M+H)$^+$; $C_{27}H_{28}FN_5O$ requir. 457.5 (free base).

Example 20

5-(4-fluorophenyl)-6-(4-(2-acetamido)-pyridyl)-2-thioalkyl-4 (3H)-pyrimidinones Step A. Ethyl 2-(4-fluorophenyl)-3-oxo-3-(4-(2-acetamido)-pyridyl))-propionate A solution of 2-chloroisonicotinic acid (25.0 g, 0.16 mol) in 65 mL of concentrated ammonium hydroxide was warmed to 205 Celsius in a steel bomb for 72 h. After cooling to 23 C., the solution was acidified to a pH of 1 using 6N HCl and subsequently filtered to remove unreacted starting material. The solution was concentrated to one fourth the original volume (approx 200 mL) in vacuo, and carefully adjusted to a pH of 6 using 1 N NaOH. After storing the cloudy solution at 0 C. for 20 h, the desired 2-aminoisonicotinic acid was filtered off. To a suspension of 2-aminoisonicotinic acid in ethanol (600 mL) was added 47.1 mL of 4 N anhdrous HCl in dioxane. After warming to achieve reflux for 20 h, an additional 47.1 mL of 4 N anhdrous HCl in dioxane was added and the reaction was warmed to reflux for an additional 20 h. Concentration with a stream of nitrogen in the hood was followed by further concentration in vacuo, the remaining solid was diluted with saturated bicarbonate (200 mL), extracted with ethyl acetate (2×200 mL), dried (Na2SO4). After concentration in vacuo, the desired ethyl 2-aminoisonicotinate was obtained. To a solution of ethyl 2-aminoisonicotinic acid in pyridine (45 mL) at 0 C. undr an argon atmosphere was added acetyl chloride dropwise over 5 min. After 2 h at 0 C., the reaction was pored into over ice 300 g, extracted with ethyl acetate (2×300 mL), washed with water (2×100 ml) followed by brine (2×100 mL), and dried (Na2SO4). After concentration in vacuo, the residue was purified by application of flash chromatography (step gradient ethyl acetate:hexane 1:4 then ethyl acetate:hexane 1:1) to afford ethyl 2-acetamidoisonicotinate.

To a solution of diisopropylamine (14.15 mL, 101 mmol) and THF (40 mL) at −78 C. was added n-butyl lithium (38.1 mL, 95 mmol) dropwise over 5 min. After 10 min, ethyl 4-fluorophenylacetate (17.3 g, 95 mmol) was added in 40 mL of dry THF. After 10 min, ethyl 2-acetamidoisonicotinate (6.0 g, 29 mmol) was added in 20 ml of dry THF. The reaction was allowed to warm to 23 C. overnight, and then acetic acid (95 mmol) was added in one portion. The reaction was concentrated in vacuo, then partitioned repeatedly between saturated bicarbonate (200 ml) and ether (300 mL), the combined bicarbonate layers were neutralized with 10% citric acid, and extracted with ethyl acetate (2×300 mL). The organic layers were dried (Na2SO4), concentrated in vacuo to afford the Ethyl 2-(4-fluorophenyl)-3-oxo-3-(4-(2-acetamido)-pyridyl)-propionate.

Step B. 5-(4-fluorophenyl)-6-(4-(2-acetamido)pyridyl))-2-thiouracil

Ethyl 2-(4-fluorophenyl)-3-oxo-3-(4-(2-acetamido) pyridyl)-propionate (1.3 g, 3.78 mmol) and thiourea (863 mg, 11.3 mmol) were suspended in anhydrous p-xylene (15 ml) with very efficient stirring. To the mixture pyridinium p-toluenesulfonate (38 mg) was added and refluxed for 12–16 h using a Dean-Stark apparatus with continuous removal of water (0.1 ml). Reaction mixture was cooled and a dark brown solid was filtered using a Buchner funnel. The collected solid was suspended in acetone (25 ml) and filtered. The acetone washed product contained a trace of thiourea, which was removed by trituration with hot water (20–30 ml). The product was filtered and air dried followed by azeotroping with toluene.

Example 21

Procedure for the Preparation of (S)-2-N-Ethylamino-3-phenylpropylamine

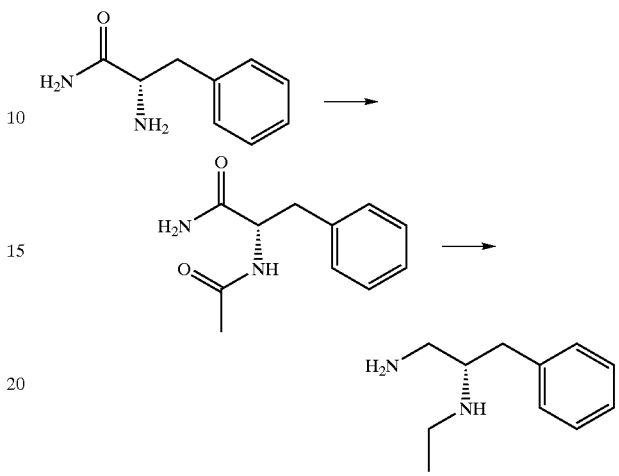

(S)-2-N-Ethylamino-3-phenylpropylamine

Acetic anhydride (1.2 ml, 12.7 mmol) was added to a stirring solution of L-phenylalanine amide (1.0 g, 6.10 mmol) in methanol (25 ml). After 1.5 h at room temperature, it was evaporated followed by drying in an oil pump vacuum. The resultant L-N-ethylphenylalanine amide (6.1 mmol) was reduced with lithium aluminium hydride (570 mg, 15.0 mmol) in tetrahydrofuran (65 mml) at 55° C. for 4 h. The reaction mixture was poured into sat. aqu. sodium hydrogencarbonate followed by extraction with dichloromethane, drying and evaporation. Column chromatography on silica gel (chloroform:methanol:triethylamine= 90:7:3) provided the amine as a yellowish oil. MS (m/z): 179.1 (M+H)$^+$; $C_{11}H_{18}N_2$ requir. 178.3.

Example 22

Procedure for the Preparation of 2-Amino-2-methyl-3-phenylpropylamine

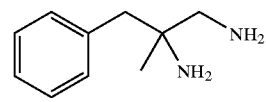

2-Amino-2-methyl-3-phenylpropylamine

A solution of commercially available D,L-α-methyl phenylalanine methyl ester (5.0 g, 25.7 mmol) in aqu. 28% ammonium hydroxide (50 ml) was kept at room temperature for 3 d. The resulting white precipitate of D,L-α-methyl phenylalanine amide was filtered and dried (2.5 g). This material (2.0 g, 11.22 mmol) was reduced with lithium aluminium hydride (1.3 g, 34.26 mmol) in boiling tetrahydrofuran for 24 h. The reaction was quenched by the addition of sodium sulfate decahydrate at ice-bath temperature. The salts were filtered off, followed by evaporation to leave the title compound as an oil. MS (m/z): 165.1 (M+H)$^+$; $C_{10}H_{16}N_2$ requir. 164.2. An alternative preparation was reported by M. Freiberger and R. B. Hasbrouck, J. Am. Chem. Soc. 82, 696–698 (1960).

Example 23

Procedure for the Preparation of 2-Methyl-3-phenylpropylamine

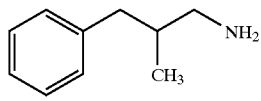

2-Methyl-3-phenylpropylamine

A mixture of commercially available 2-methyl-3-phenylpropylamide (4.32 g, 26.5 mmol) and lithium aluminium hydride (1.3 g, 34.3 mmol) in tetrahydrofuran (184 ml) was stirred at room temperature for 5 h. It was poured into aqu. sat. sodium sulfate and extracted with dichloromethane followed by drying of the organic solution and evaporation to provide the amine as an oil. Other syntheses have been reported, e.g. Dornow and Fust, Chem. Ber. 87, 984 (1954).

Example 24

Procedure for the Preparation of 5-(4-Fluorophenyl)-3-methyl-2-((2-methy-3-phenylpropyl)amino)-6-(4-pyridyl)-4(3H)-pyrimidinone Hydrochloride

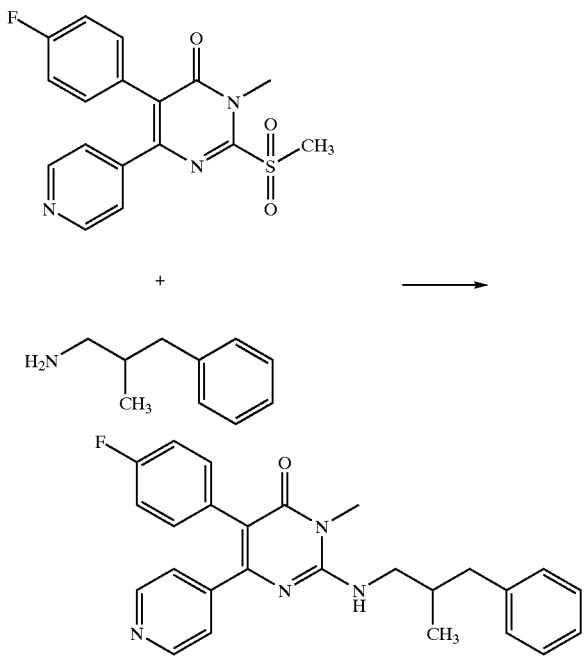

5-(4-Fluorophenyl)-3-methyl-2-((2-methy-3-phenylpropyl)amino)-6-(4-pyridyl)-4(3H)-pyrimidinone hydrochloride A mixture of crude 5-(4-fluorophenyl)-3-methyl-2-methylsulfonyl-6-(4-pyridyl)-4(3H)-pyrimidinone (520 mg g, 1.45 mmol) and 2-methyl-3-phenylpropylamine (1.5 g, 10.1 mmol) was heated at 50° C. for 30 min. Column chromatography on silica gel (2–5% methanol/dichloromethane; hexane-acetone=2:1) provided the title compound. MS (m/z): 429.4 (M+H)$^+$; $C_{26}H_{25}FN_4O$ requir. 428.5 (free base).

Example 25

Procedure for the Preparation of 1-Phenyl-1,3-propanediamine

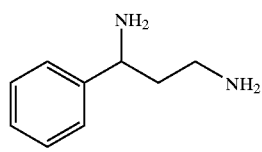

1-Phenyl-1.3-propanediamine

3-Phenyl-3-aminopropionic acid (S. G. Cohen and S. Y. Weinstein, J. Am. Chem. Soc. 86, 725–728, 1964) was converted into 1-phenyl-1,3-propanediamine as reported in the literature (M. Kojima and J. Fujita, Bull. Chem. Soc. Jpn. 55, 1454–1459 (1982)).

Analogously, 1-(2-fluorophenyl)-1,3-propanediamine, 1-(2-methylphenyl)-1,3-propanediamine and 1-(2-chlorophenyl)-1,3-propanediamine have been prepared by using the above procedure and the appropriate starting material.

Example 26

Procedure for the Preparation of 3-Ethyl-5-(4-fluorophenyl)-2-methylthio-6-(4-pyridyl)-4(3H)-pyrimidinone

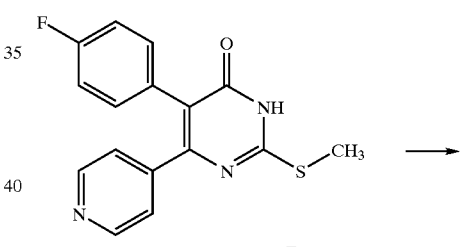

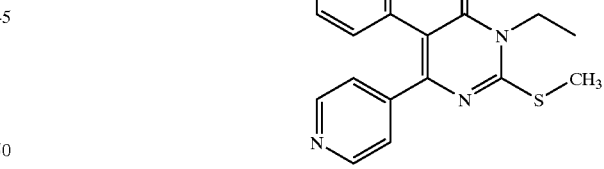

3-Ethyl-5-(4-fluorophenyl)-2-methylthio-6-(4-pyridyl)-4(3H)-pyrimidinone

Ethyl bromide (600 ml, 8.03 mmol) was added to a stirred mixture of 5-(4-fluorophenyl)-2-methylthio-6-(4-pyridyl)-4(3H)-pyrimidinone (1.8 g, 5.97 mmol) and sodium hydride (60% oily suspension, 320 mg, 8 mmol) in N,N-dimethylformamide (60 ml) at room temperature. More ethyl bromide (2×600 ml, 2×8.03 mmol) was added after 2 and 3.5 h. After 8 h, the reaction mixture was neutralized with acetic acid and evaporated. The remainder was taken up in dichloromethane, the organic solution was washed with water, dried and evaporated. Flash chromatography on a column of silica gel (hexane-acetone=3:1, 2:1). provided in the second main fraction the title compound as a solid.

Example 27

Procedure for the Preparation of 3-Ethyl-5-(4-fluorophenyl)-2-methylsulfonyl-6-(4-pyridyl)-4(3H)-pyrimidinone

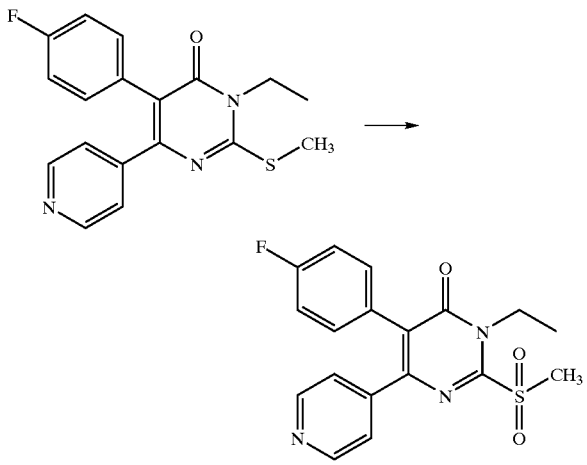

3-Ethyl-5-(4-fluorophenyl)-2-methylsulfonyl-6-(4-pyridyl)-4(3H)-pyrimidinone

A mixture of 3-ethyl-5-(4-fluorophenyl)-2-methylthio-6-(4-pyridyl)-4(3H)-pyrimidinone (300 mg, 0.88 mmol) and Oxone® (potassium peroxymonosulfate, 2.54 g, 4.14 mmol) in methanol (71 ml) and water (33 ml) was stirred for 14 h. The solvent was concentrated to about 35 ml, followed by extraction with dichloromethane, drying and evaporation. The resulting white solid was used without purification in the next step.

Example 28

Procedure for the Preparation of 2-(((S)-2-Amino-3-phenylpropyl)-amino)-3-ethyl-5-(4-fluorophenyl)-6-(4-pyridyl)-4(3H)-pyrimidinone Hydrochloride

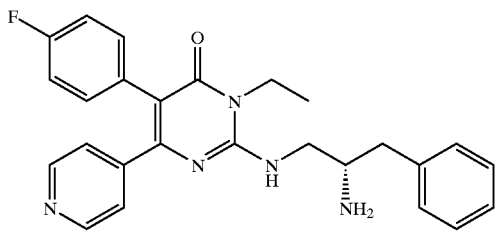

2-(((S)-2-Amino-3-phenylpropyl)-amino)-3-ethyl-5-(4-fluorophenyl)-6-(4-pyridyl)-4(3H)-pyrimidinone hydrochloride A mixture of 3-ethyl-5-(4-fluorophenyl)-2-methylthio-6-(4-pyridyl)-4(3H)-pyrimidinone (150 mg, 0.44 mmol) and (S)-1,2-benzylethylendiamine (200 ml, ~1.3 mmol) was heated at 190° C. for 4.5 h. Column chromatography on Iatrobeads® (chloroform:methanol:triethylamine=90:7:3) provided the title compound as a free base which was converted into the crystallizing monohydrochloride by the addition of 2N hydrochloric acid (165 ml, 0.33 mmol) and methanol (1.5 ml). Filtration provided the title compound. MS (m/z): 444.0 (M+H)$^+$; $C_{265}H_{27}FN_5O$ requir. 443.5 (free base).

Example 29

Procedure for the Preparation of 3-Ethyl-5-(4-fluorophenyl)-2-((2-methy-3-phenylpropyl)amino)-6-(4-pyridyl)-4(3H)-pyrimidinone Hydrochloride

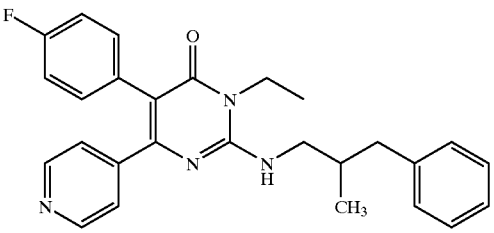

3-Ethyl-5-(4-fluorophenyl)-2-((2-methy-3-phenylpropyl)amino)-6-(4-pyridyl)-4(3H)-pyrimidinone hydrochloride A mixture of crude 3-ethyl-5-(4-fluorophenyl)-2-methylsulfonyl-6-(4-pyridyl)-4(3H)-pyrimidinone (320 mg g, 0.89 mmol) and 2-methyl-3-phenylpropylamine (600 ml, ~4 mmol) was heated at 60° C. for 2 h. Column chromatography on silica gel (hexane-acetone=2:1; 2–5% methanol/dichloromethane) provided the title compound. MS (m/z): 443.2 (M+H)$^+$; $C_{27}H_{27}FN_4O$ requir. 442.5.

Example 30

Procedure for the Preparation of 3-(2-Methylphenyl)propylamine

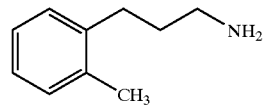

3-(2-Methylphenyl)propylamine

Diethyl cyanomethylphosphonate (5.0 ml, 30.9 mmol) was added to a stirring suspension of sodium hydride (60% oily suspension, 1.24 g, 31 mmol) in tetrahydrofuran (50 ml) under argon. After 30 min, 2-methylbenzaldehyde (3.6 ml, 31.1 mmol) was added and stirring continued for 1 h. The reaction was quenched by the addition of water and extracted with dichloromethane followed by drying and evaporation of the organic solution. Column chromatography (hexane; hexane:ethylacetate=3:1) provided 2-(2-methylphenyl)acrylonitrile as an oil. This material (3.8 g), 10% palladium on carbon (3.8 g) and 12 N hydrochloric acid (11.8 ml, 142 mmol) in methanol (125 ml) were hydrogenated with hydrogen at atmospheric pressure for 2 d. The catalyst was removed by filtration and the solvent was evaporated. The resultant material was partitioned between dichloromethane and water. The aqueous layer was made basic with 10 N sodium hydroxide and extracted with dichloromethane, followed by drying and evaporation. The resultant material was purified on a silica gel column (chloroform:methaol:triethylamine=85:10:5) to provide the title compound as an oil.

Example 31

Procedure for the Preparation of 2-amino-3-(2-fluorophenyl)-propylamine

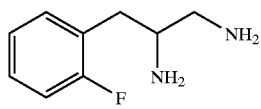

Step A. Methyl 2-amino-3-(2-fluorophenyl)propionate 5 g (27.3 mmol) of (D,L)-(2-fluoro-phenyl)alanine was suspended in 50 ml methanolic HCl and stirred at room temperature for 3 days. The reaction mixture was concentrated in vacuo and dried to give a yellow oil.
MS (m/z): 198 (M+H)$^+$; $C_{10}H_{12}FNO_2$ requir. 197.2.

Step B. 2-Amino-3-(2-fluorophenyl)propionamide

Methyl 2-amino-3-(2-fluorophenyl) propionate was suspended in 50 ml 30% ammonium hydroxide and stirred at room temperature for 18 hrs. The mixture was filtered, washed with cold water and 2-amino-3-(2-fluorophenyl) propionamide was collected as a white solid. MS (m/z): 183.1 (M+H)$^+$; $C_9H_{11}FN_2O$ requir. 182.2.

Step C. 2-Amino-3-(2-fluorophenyl)-propylamine

2-Amino-3-(2-fluorophenyl)propionamide was added carefully to a chilled (5°) mixture of LAH (1.0 g, 26.3 mmol) and 20 ml THF under argon. The reaction was then heated at reflux for 10 hrs. The reaction was cooled to 5° C. and carefully treated with $Na_2SO_4.10$ $H_2O$. The resulting mixture was stirred for 18 hrs, then filtered to remove the solids. The filtrate was concentrated in vacuo to give an amber oil. MS (m/z): 169 (M+H)$^+$; $C_9H_{13}FN_2$ requir. 168.19

Example 32

Procedure for the Preparation of (1R,2R)-2-Methyl-1-phenyl-1,3-propanediamine

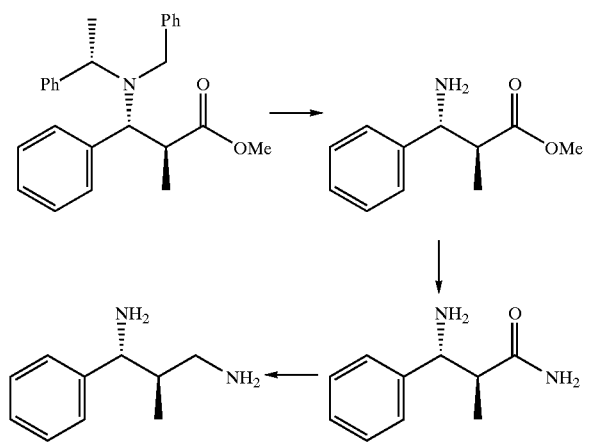

Step A: Methyl (2S,3R,•S)-3-(N-benzyl-N-•-methylbenzylamino)-2-methyl-3-phenylpropionate was prepared as reported for the 2R,3S,•R-enantiomer (S). G. Davies and I. A. S. Walters, J. Chem. Soc. Perkin Trans.I, 1129–1139 (1994).

Step B: Methyl (2S,3R)-3-amino-2-methyl-3-phenylpropionate

A mixture of methyl (2S,3R,•S)-3-(N-benzyl-N-•-methylbenzylamino)-2-methyl-3-phenylpropionate (13.0 g, 33.55 mmol) and 10% palladium-on-carbon (13.0 g) in glacial acetic acid (260 ml) was hydrogenated under a balloon of hydrogen for 24 h. The catalyst was removed by filtration followed by evaporation and co-distillation with toluene to provide the title compound as a white solid. MS (m/z): 194.2 (M+H)$^+$; $C_{11}H_{15}NO_2$ requir. 193.3.

Step C: (2S,3R)-3-Amino-2-methyl-3-phenylpropionamide

A solution of methyl (2S,3R)-3-amino-2-methyl-3-phenylpropionate (6.3 g, 33 mmol) in 2N methanolic ammonia (20 ml) and ammonium hydroxide (28–30%, 40 ml) was stirred at room temperature. After 4 d, it was evaporated followed by chromatography on a short column of silica gel (dichloromethane-methanol-conc. ammonium hydroxide= 93:7:0.7; 90:10:0.8) to provide the amide as a white solid. MS (m/z): 179.2 (M+H)$^+$; $C_{10}H_{14}N_2O$ requir. 178.2.

Step D: (1R,2R)-2-methyl-1-phenyl-1,3-propanediamine

Lithium aluminium hydride (2.3 g, 60.60 mmol) was added in portions to a stirring solution of (2S,3R)-3-amino-2-methyl-3-phenylpropionamide (2.6 g, 14.59 mmol) in tetrahydrofuran (54 ml) at ice-bath temperature. After 45 min, the mixture was heated at reflux for 16 h. With ice-bath cooling, the reaction was quenched by the portionwise addition of sodium sulfate decahydrate and some methanol until hydrogen evolution ceased. The solids were removed by filtration and washed with dichloromethane. The combined filtrates were evaporated to provide the title compound. MS (m/z): 165.2 (M+H)$^+$; $C_{10}H_{16}N_2$ requir. 164.3.

Analogously, the enantiomer (1S,2S)-2-methyl-1-phenyl-1,3-propanediamine was prepared from methyl (2R,3S,•R)-3-(N-benzyl-N-•-methylbenzylamino)-2-methyl-3-phenylpropionate. MS (m/z): 165.3 (M+H)$^+$; $C_{10}H_{16}N_2$ requir. 164.3.

Analogously, the enantiomers (1S,2R)-2-methyl-1-phenyl-1,3-propanediamine and (1R,2S)-2-methyl-1-phenyl-1,3-propanediamine may be prepared from tert.butyl (2S,3S,•R)- and -(2R,3R,•S)-3-(N-benzyl-N-•-methylbenzylamino)-2-methyl-3-phenylpropionate (Davies et al., J. Chem. Soc. Chem. Commun. 1153–1155, 1993).

Example 33

Procedure for the Preparation of 5-(4-fluorophenyl)-2-(4-phenylbutyl)-6-(4-pyridyl)-4(3H)-pyrimidinone

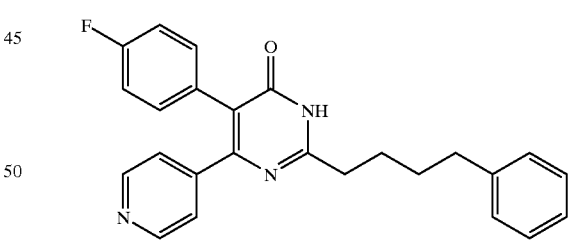

5-(4-Fluorophenyl)-2-(4-phenylbutyl)-6-(4-pyridyl)-4(3H)-pyrimidinone

Ethyl 2-(4-fluorophenyl)-3-oxo-3-(4-pyridyl)-propionate (293 mg, 1.02 mmol), 4-phenylbutanecarboxamidine (315 mg, 1.79 mmol) and pyridinium p-toluenesulfonate (10 mg) were suspended in p-xylene (10 ml). With efficient stirring, the mixture was heated to reflux using a Dean-Stark apparatus with continuous removal of water. After 16 h, the solvent was evaporated and the product purified by column chromatography on silica gel (3% methanol/dichloromethane) followed by recrystallization from acetone. MS (m/z): 400.3 (M+H)$^+$; $C_{25}H_{22}FN_3O$ requir. 399.5.

Example 34
Procedure for the Preparation of 5-(4-fluorophenyl)-2-(N-methyl-N-(2-phenylethyl)amino)-6-(4-pyridyl)-4(3H)-pyrimidinone
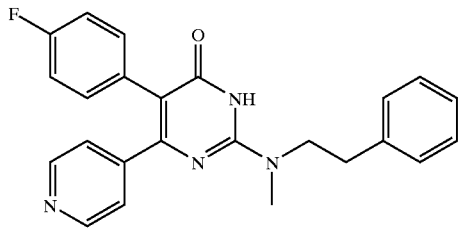
5-(4-Fluorophenyl)-2-(N-methyl-N-(2-phenylethyl)amino)-6-(4-pyridyl)-4(3H)-pyrimidinone was prepared using the methods described above. MS (m/z): 401.2 (M+H)$^+$; $C_{24}H_{21}FN_4O$ requir. 400.5.
Example 35
The compounds shown in Tables I–II can be prepared using the procedures of Examples 1–33.
TABLE I
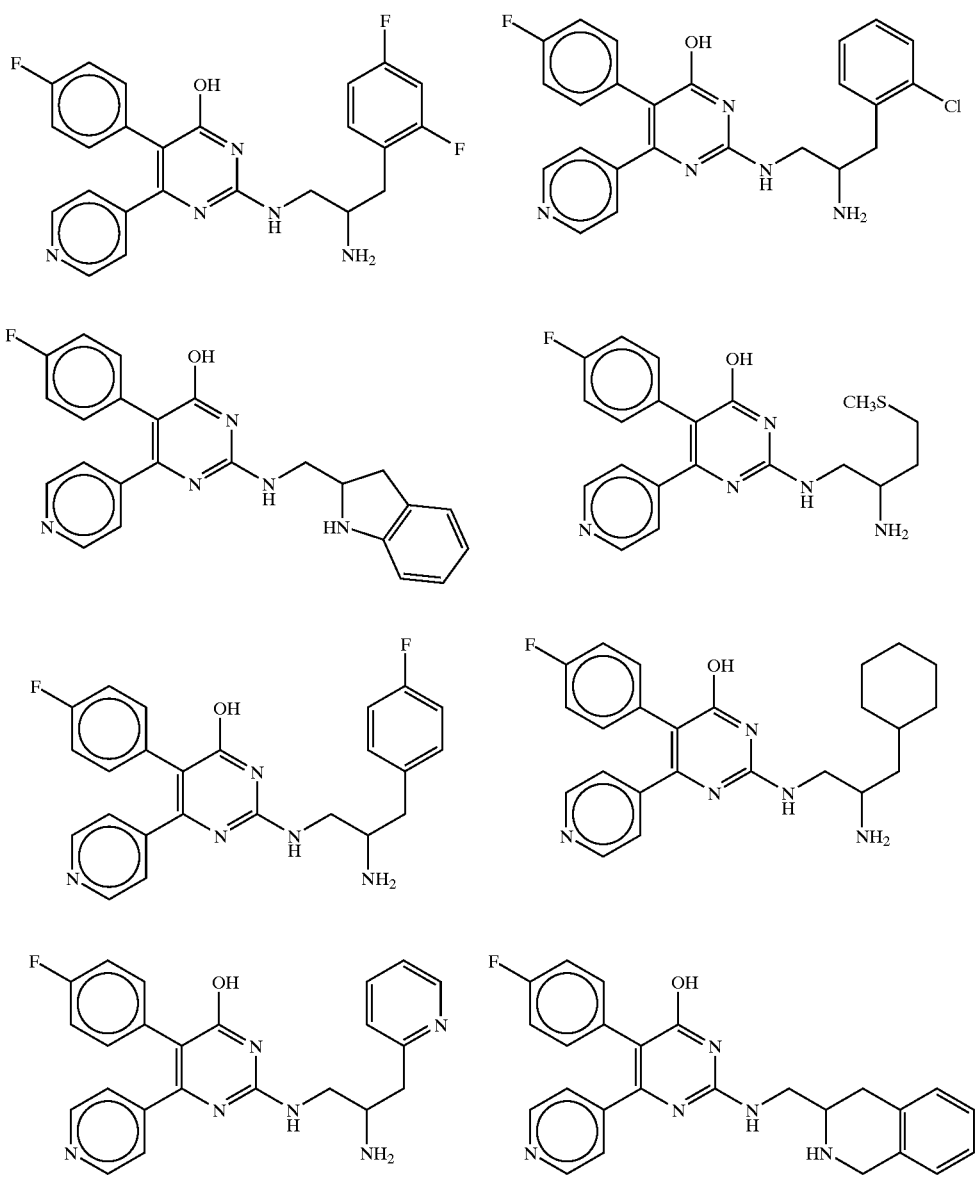

TABLE I-continued
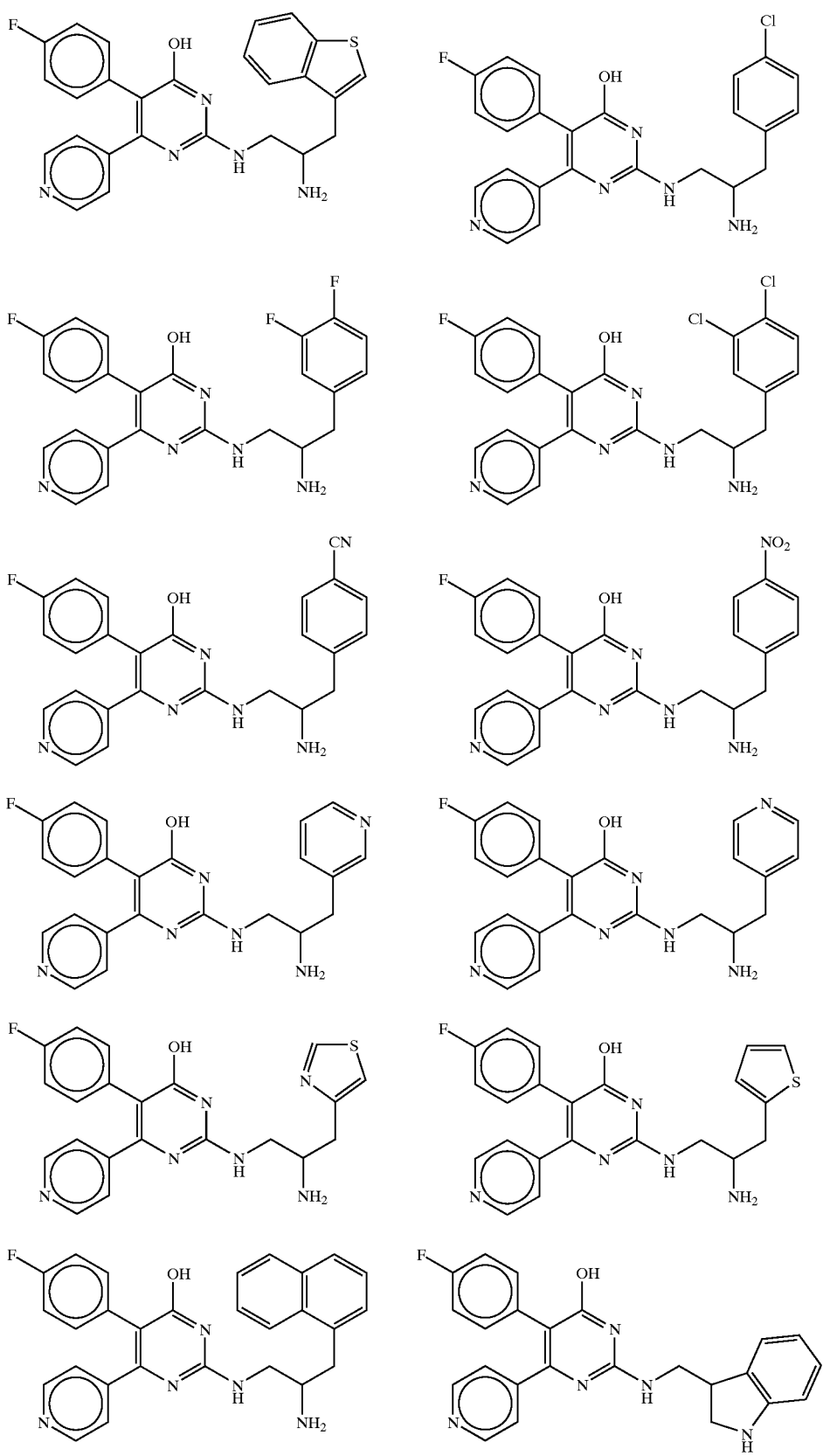

TABLE I-continued
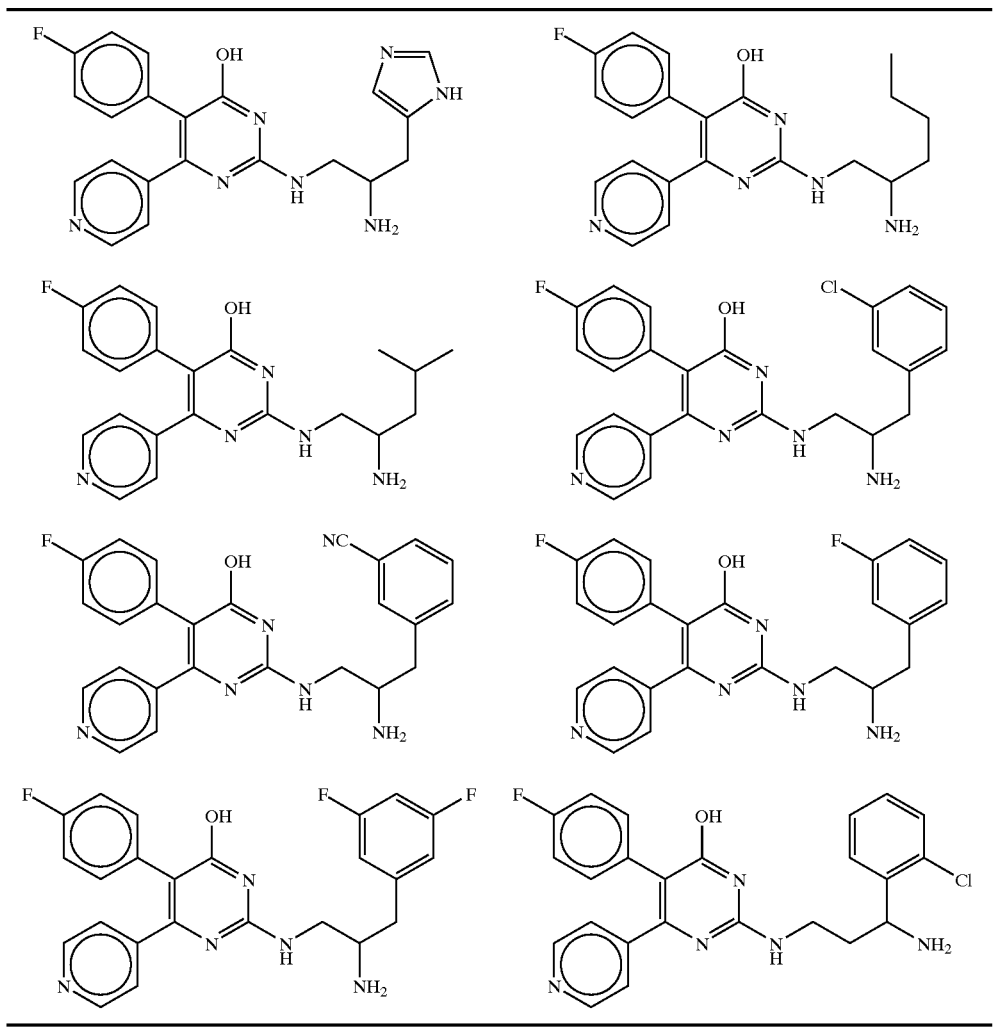
TABLE II
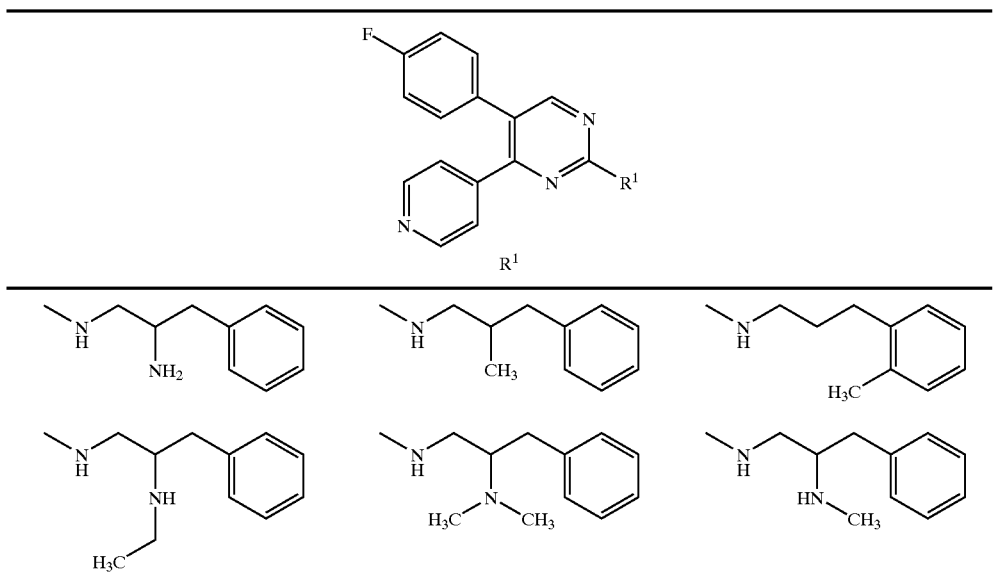

TABLE II-continued
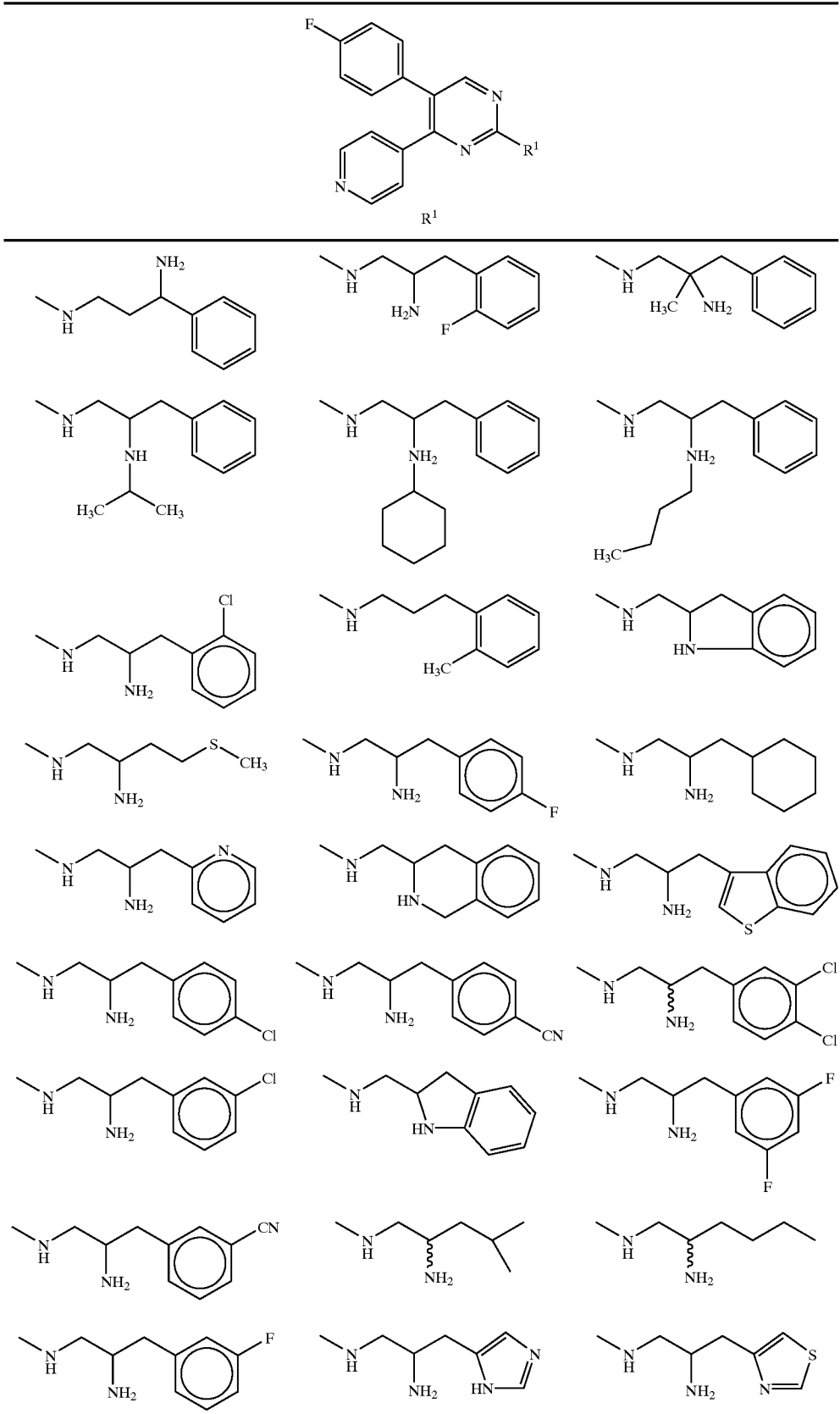

TABLE II-continued

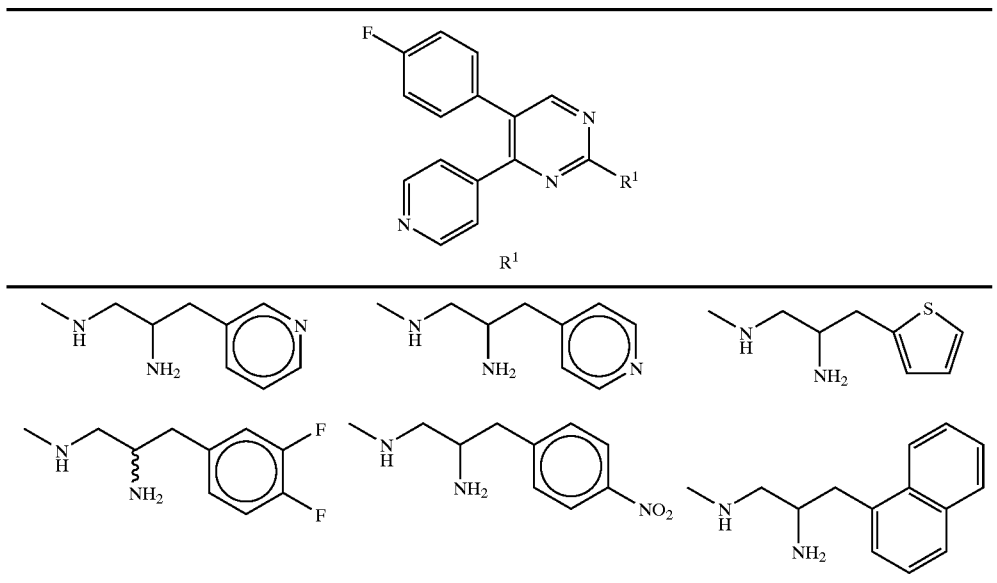

Example 36

Biological Assays

The following assays were used to characterize the ability of compounds of the invention to inhibit the production of TNF-α and IL-1-β. The second assay measured the inhibition of TNF-α and/or IL-1-β in mice after oral administration of the test compounds. The third assay, a glucagon binding inhibition in vitro assay, can be used to characterize the ability of compounds of the invention to inhibit glucagon binding. The fourth assay, a Cyclooxygenase enzyme (COX-1 and COX-2) inhibition activity in vitro assay, can be used to characterize the ability of compounds of the invention to inhibit COX-1 and/or COX-2.

Lipopolysaccharide-activated Monocyte TNF Production Assay

Isolation of Monocytes

Test compounds were evaluated in vitro for the ability to inhibit the production of TNF by monocytes activated with bacterial lipopolysaccharide (LPS). Fresh residual source leukocytes (a byproduct of plateletpheresis) were obtained from a local blood bank, and peripheral blood mononuclear cells (PBMCS) were isolated by density gradient centrifugation on Ficol-Paque Plus (Pharmacia). PBMCs were suspended at $2\times10^6$/ml in DMEM supplemented to contain 2% FCS, 10 mM, 0.3 mg/ml glutamate, 100 U/ml penicillin G and 100 mg/ml streptomycin sulfate (complete media). Cells were plated into Falcon flat bottom, 96 well culture plates (200 µl/well) and cultured overnight at 37° C. and 6% $CO_2$. Non-adherent cells were removed by washing with 200 µl/well of fresh medium. Wells containing adherent cells (~70% monocytes) were replenished with 100 µl of fresh medium.

Preparation of Test Compound Stock Solutions

Test compounds were dissolved in DMZ. Compound stock solutions were prepared to an initial concentration of 10–50 µM. Stocks were diluted initially to 20–200 µM in complete media. Nine two-fold serial dilutions of each compound were then prepared in complete medium.

Treatment of Cells with Test Compounds and Activation of TNF Production with Lipopolysaccharide One hundred microliters of each test compound dilution were added to microtiter wells containing adherent monocytes and 100 µl complete medium. Monocytes were cultured with test compounds for 60 min at which time 25 µl of complete medium containing 30 ng/ml lipopolysaccharide from E. coli K532 were added to each well. Cells were cultured an additional 4 hrs. Culture supernatants were then removed and TNF presence in the supernatants was quantified using an ELISA.

TNF ELISA

Flat bottom, 96 well Corning High Binding ELISA plates were coated overnight (4° C.) with 150 µL/well of 3 µg/ml murine anti-human TNF-α MAb (R&D Systems #MAB210). Wells were then blocked for 1 hr at room temperature with 200 µL/well of $CaCl_2$-free ELISA buffer supplemented to contain 20 mg/ml BSA (standard ELISA buffer: 20 mM, 150 mM NaCl, 2 mM $CaCl_2$, 0.15 mM thimerosal, pH 7.4). Plates were washed and replenished with 100 µl of test supernatants (diluted 1:3) or standards. Standards consisted of eleven 1.5-fold serial dilutions from a stock of 1 ng/ml recombinant human TNF (R&D Systems). Plates were incubated at room temperature for 1 hr on orbital shaker (300 rpm), washed and replenished with 100 µl/well of 0.5 µg/ml goat anti-human TNF-α (R&D systems #AB-210-NA) biotinylated at a 4:1 ratio. Plates were incubated for 40 min, washed and replenished with 100 µl/well of alkaline phosphatase-conjugated streptavidin (Jackson ImmunoResearch #016-050-084) at 0.02 µg/ml. Plates were incubated 30 min, washed and replenished with 200 µl/well of 1 mg/ml of p-nitrophenyl phosphate. After 30 min, plates were read at 405 nm on a $V_{max}$ plate reader.

Data Analysis

Standard curve data were fit to a second order polynomial and unknown TNF-α concentrations determined from their OD by solving this equation for concentration. TNF concentrations were then plotted vs. test compound concentration using a second order polynomial. This equation was then used to calculate the concentration of test compounds causing a 50% reduction in TNF production.

Compounds of the invention can also be shown to inhibit LPS-induced release of IL-1β, IL-6 and/or IL-8 from monocytes by measuring concentrations of IL-1β, IL-6 and/or IL-8 by methods well known to those skilled in the art. In a similar manner to the above described assay involving the LPS induced release of TNF•• from monocytes, compounds of this invention can also be shown to inhibit LPS induced release of IL-1β, IL-6 and/or IL-8 from monocytes by measuring concentrations of IL-1β, IL-6 and/or IL-8 by methods well known to those skilled in the art. Thus, the compounds of the invention may lower elevated levels of TNF-α, IL-1, IL-6, and IL-8 levels. Reducing elevated levels of these inflammatory cytokines to basal levels or below is favorable in controlling, slowing progression, and alleviating many disease states. All of the compounds are useful in the methods of treating disease states in which TNF-α, IL-1β, IL-6, and IL-8 play a role to the full extent of the definition of TNF-α-mediated diseases described herein.

Inhibition of LPS-Induced TNF-α Production in Mice

Male DBA/1LACJ mice were dosed with vehicle or test compounds in a vehicle (the vehicle consisting of 0.5% tragacanth in 0.03 N HCl) 30 minutes prior to lipopolysaccharide (2 mg/kg, I.V.) injection. Ninety minutes after LPS injection, blood was collected and the serum was analyzed by ELISA for TNF levels.

The following compounds exhibit activities in the monocyte assay (LPS induced TNF release) with $IC_{50}$ values of 20 μM or less:

5-(4-Fluorophenyl)-2-(4-pyridyl)-4-(4-pyridyl)-pyrimidine
5-(4-Fluorophenyl)-2-(2-methylthiazol-4-yl)-4-(4-pyridyl)-pyrimidine
5-(4-Fluorophenyl)-4-(4-pyridyl)-2-(2-thienyl)-pyrimidine
2-(2-Diethylaminoethylamino)-5-(4-fluorophenyl)-4-(4-pyridyl)-pyrimidine
2-(2-Aminoethylamino)-5-(4-fluorophenyl)-4-(4-pyridyl)-pyrimidine
2-(3-Aminopropylamino)-5-(4-fluorophenyl)-4-(4-pyridyl)-pyrimidine
2-(4-Aminobutylamino)-5-(4-fluorophenyl)-4-(4-pyridyl)-pyrimidine
2-(2,6-Dichlorobenzyl)-5-(4-fluorophenyl)-4-(4-pyridyl)-pyrimidine
2-(2,6-Dichlorophenylamino)-5-(4-fluorophenyl)-4-(4-pyridyl)-pyrimidine
2-(2,6-Dimethylphenylamino)-5-(4-fluorophenyl)-4-(4-pyridyl)-pyrimidine
5-(4-Fluorophenyl)-2-(2-methoxyphenylamino)-4-(4-pyridyl)-pyrimidine
5-(4-Fluorophenyl)-2-(4-fluorophenylamino)-4-(4-pyridyl)-pyrimidine
5-(4-Fluorophenyl)-2-phenylthiomethyl-4-(4-pyridinyl)-pyrimidine
2-(Benzylamino)-5-(4-fluorophenyl)-4-(4-pyridyl)-pyrimidine
5-(4-Fluorophenyl)-2-(2-phenylethylamino)-4-(4-pyridyl)-pyrimidine
5-(4-Fluorophenyl)-2-(methyl-(2-phenylethyl)-amino)-4-(4-pyridyl)-pyrimidine
5-(4-Fluorophenyl)-2-((2-hydroxy-2-phenyl-ethyl)amino)-4-(4-pyridyl)-pyrimidine
5-(4-Fluorophenyl)-2-(2-(4-hydroxyphenyl)ethyl-amino)-4-(4-pyridyl)-pyrimidine
2-(2-(4-Aminophenyl)ethyl-amino)-5-(4-fluorophenyl)-4-(4-pyridyl)-pyrimidine
5-(4-Fluorophenyl)-2-(2-(4-fluorophenyl)ethyl-amino)-4-(4-pyridyl)-pyrimidine
5-(4-Fluorophenyl)-2-(2-(2-fluorophenyl)ethyl-amino)-4-(4-pyridyl)-pyrimidine
2-(2-(2-Chlorophenyl)ethyl-amino))-5-(4-fluorophenyl)-4-(4-pyridyl)-pyrimidine
2-(2-(4-Chlorophenyl)ethyl-amino)-5-(4-fluorophenyl)-4-(4-pyridyl)-pyrimidine
2-(2-(3-Chlorophenyl)ethyl-amino))-5-(4-fluorophenyl)-4-(4-pyridyl)-pyrimidine
2-(2-(2,4-Dichlorophenyl)ethyl-amino)-5-(4-fluorophenyl)-4-(4-pyridyl)-pyrimidine
2-(2-(4-Bromophenyl)ethyl-amino)-5-(4-fluorophenyl)-4-(4-pyridyl)-pyrimidine
5-(4-Fluorophenyl)-2-(2-(2-methoxyphenyl)ethyl-amino)-4-(4-pyridyl)-pyrimidine
5-(4-Fluorophenyl)-2-(2-(3-methoxyphenyl)ethyl-amino)-4-(4-pyridyl)-pyrimidine
5-(4-Fluorophenyl)-2-((3-phenylpropyl)amino)-4-(4-pyridyl)-pyrimidine
5-(4-Fluorophenyl)-2-((l-methyl-3-phenylpropyl)-amino)-4-(4-pyridyl)-pyrimidine
2-(((S)-2-Amino-3-phenylpropyl)-amino)-5-(4-fluorophenyl)-4-(4-pyridyl)-pyrimidine
5-(4-Fluorophenyl)-2-(2-phenylaminoethylamino)-4-(4-pyridyl)-pyrimidine
5-(4-Fluorophenyl)-2-((3-imidazolylpropyl)-amino)-4-(4-pyridyl)-pyrimidine
5-(4-Fluorophenyl)-2-((4-phenylbutyl)-amino)-4-(4-pyridyl)-pyrimidine
5-(4-Fluorophenyl)-4-(4-pyridyl)-2-pyrrolidino-pyrimidine
5-(4-Fluorophenyl)-2-morpholino-4-(4-pyridyl)-pyrimidine
5-(4-Fluorophenyl)-2-(1-piperazinyl)-4-(4-pyridyl)-pyrimidine
5-(4-Fluorophenyl)-4-(4-pyridyl)-2-(2-pyrrolidinoethylamino)-pyrimidine
5-(4-Fluorophenyl)-2-(2-morpholinoethylamino)-4-(4-pyridyl)-pyrimidine
5-(4-Fluorophenyl)-2-(2-piperidinoethylamino)-4-(4-pyridyl)-pyrimidine
5-(4-Fluorophenyl)-2-(3-(2-pyrrolidinon-1-yl)propyl-amino)-4-(4-pyridyl)-pyrimidine
2-(2,6-Dichlorobenzyl)-5-(4-fluorophenyl)-6-(4-pyridyl)-4(3H)-pyrimidinone
5-(4-Fluorophenyl)-2-(2-phenylethyl)thio-6-(4-pyridyl)-4(3H)-pyrimidinone
5-(4-Fluorophenyl)-2-(3-phenylpropyl)thio-6-(4-pyridyl)-4(3H)-pyrimidinone
5-(4-Fluorophenyl)-2-(2-phenoxyethyl)thio-6-(4-pyridyl)-4(3H)-pyrimidinone
5-(4-Fluorophenyl)-2-(2-phenylaminoethyl)thio-6-(4-pyridyl)-4(3H)-pyrimidinone
2-(2-(2-Chlorophenyl)ethyl-amino)-5-(4-fluorophenyl)-6-(4-pyridyl)-4(3H)-pyrimidinone
5-(4-Fluorophenyl)-2-((3-phenylpropyl)amino)-6-(4-pyridyl)-4(3H)-pyrimidinone
5-(4-Fluorophenyl)-2-((l-methyl-3-phenylpropyl)-amino)-6-(4-pyridyl)-4(3H)-pyrimidinone
5-(4-Fluorophenyl)-2-((3-imidazolylpropyl)amino)-6-(4-pyridyl)-4(3H)-pyrimidinone
2-(((S)-2-Amino-3-phenylpropyl)-amino)-4-(4-pyridyl)-5-(3-trifluoromethylphenyl)-pyrimidine
2-(((S)-2-Amino-3-phenylpropyl)-amino)-5-(3-methylphenyl)-4-(4-pyridyl)-pyrimidine
2-(((S)-2-N,N-Dimethylamino-3-phenylpropyl)-amino)-5-(4-fluorophenyl)-4-(4-pyridyl)-pyrimidine
2-(((S)-2-N,N-Dimethylamino-3-phenylpropyl)-amino)-5-(3-methylphenyl)-4-(4-pyridyl)-pyrimidine
2-((3-Amino-3-phenylpropyl)-amino)-5-(4-fluorophenyl)-4-(4-pyridyl)-pyrimidine 2-((3-Amino-3-phenylpropyl)-amino)-4-(4-pyridyl)-5-(3-trifluoromethylphenyl)-pyrimidine 2-((3-Amino-3-(2-fluorophenyl)propyl)-amino)-4-(4-pyridyl)-5-(3-trifluoromethylphenyl)-pyrimidine 2-((3-Amino-3-phenylpropyl)-amino)-5-(3-methylphenyl)-4-(4-pyridyl)-pyrimidine 2-((2-Amino-2-methyl-3-phenylpropyl)-amino)-5-(3-methylphenyl)-4-(4-pyridyl)-pyrimidine 2-((3-Hydroxy-3-phenylpropyl)-amino)-5-(3-methylphenyl)-4-(4-pyridyl)-pyrimidine 2-(((2S,3S)-3-Amino-2-methyl-3-phenylpropyl)-amino)-4-(4-pyridyl)-5-(3-trifluoromethylphenyl)-pyrimidine 2-(((2R,3R)-3-Amino-2-methyl-3-phenylpropyl)-amino)-4-(4-pyridyl)-5-(3-trifluoromethylphenyl)-pyrimidine 2-((S)-3-Benzylpiperazinyl)-4-(4-pyridyl)-5-(3-trifluoromethylphenyl)-pyrimidine 4-(4-Pyridyl)-2-(((S)-tetrahydroisoquinol-3-ylmethylen)amino)-5-(3-trifluoromethylphenyl)-pyrimidine 5-(3-Methylphenyl)-4-(4-pyridyl)-2-(((S)-tetrahydroisoquinol-3-ylmethyl)amino)-pyrimidine 2-(((S)-2-N-Isopropylamino-3-phenylpropyl)-amino)-4-(4-pyridyl)-5-(3-trifluoromethylphenyl)-pyrimidine 2-(((S)-2-N-Cyclohexylamino-3-phenylpropyl)-amino)-4-(4-pyridyl)-5-(3-trifluoromethylphenyl)-pyrimidine 2-(((S)-2-N-Isopropylamino-3-phenylpropyl)-amino)-5-(3-methylphenyl)-4-(4-pyridyl)-pyrimidine 2-(((S)-2-N-Butylamino-3-phenylpropyl)-amino)-5-(3-methylphenyl)-4-(4-pyridyl)-pyrimidine 2-(((S)-2-N-Cyclohexylamino-3-phenylpropyl)-amino)-5-(3-methylphenyl)-4-(4-pyridyl)-pyrimidine 5-(4-Fluorophenyl)-2-(((S)-2-N-isopropylamino-3-phenylpropyl)-amino)-4-(4-pyridyl)-pyrimidine 5-(4-Fluorophenyl)-2-((3-N-isopropylamino-3-phenylpropyl)-amino)-4-(4-pyridyl)-pyrimidine 2-(((S)-2-N-Glycylamino-3-phenylpropyl)-amino)-4-(4-pyridyl)-5-(3-trifluoromethylphenyl)-pyrimidine 2-(((S)-2-N-Glycylamino-3-phenylpropyl)-amino)-5-(3-methylphenyl)-4-(4-pyridyl)-pyrimidine 2-(((S)-2-Amino-3-phenylpropyl)-amino)-5-(3-chloro-4-fluorophenyl)-4-(4-pyridyl)-pyrimidine 2-(((S)-2-Amino-3-phenylpropyl)-amino)-5-(3-fluorophenyl)-4-(4-pyridyl)-pyrimidine 2-(((S)-2-Amino-3-phenylpropyl)-amino)-5-(3-isopropylphenyl)-4-(4-pyridyl)-pyrimidine 5-(3-Acetamidophenyl)-2-(((S)-2-amino-3-phenylpropyl)-amino)-4-(4-pyridyl)-pyrimidine 2-(((S)-2-Amino-3-phenylpropyl)-amino)-5-(4-chlorophenyl)-4-(4-pyridyl)-pyrimidine 2-(((S)-2-Amino-3-phenylpropyl)-amino)-5-(benzothienyl)-4-(4-pyridyl)-pyrimidine 2-(((S)-2-Amino-3-phenylpropyl)-amino)-5-(2-naphthyl)-4-(4-pyridyl)-pyrimidine 2-(((S)-2-Amino-3-phenylpropyl)-amino)-5-(4-fluorophenyl)-6-(4-pyridyl)-4(3H)-pyrimidinone.

The following compounds exhibit activities in the monocyte assay (LPS induced TNF release) with IC$_{50}$ values of 5 μM or less:

2-(2-Aminoethylamino)-5-(4-fluorophenyl)-4-(4-pyridyl)-pyrimidine 2-(3-Aminopropylamino)-5-(4-fluorophenyl)-4-(4-pyridyl)-pyrimidine 2-(Benzylamino)-5-(4-fluorophenyl)-4-(4-pyridyl)-pyrimidine 5-(4-Fluorophenyl)-2-(2-phenylethylamino)-4-(4-pyridyl)-pyrimidine 5-(4-Fluorophenyl)-2-(N-methyl-N-(2-phenylethyl)amino)-4-(4-pyridyl)-pyrimidine 5-(4-Fluorophenyl)-2-(2-hydroxy-2-phenyl-ethyl)amino-4-(4-pyridyl)-pyrimidine 5-(4-Fluorophenyl)-2-(2-(4-hydroxyphenyl)ethylamino)-4-(4-pyridyl)-pyrimidine 5-(4-Fluorophenyl)-2-(2-(4-fluorophenyl)ethylamino)-4-(4-pyridyl)-pyrimidine 5-(4-Fluorophenyl)-2-(2-(2-fluorophenyl)ethylamino)-4-(4-pyridyl)-pyrimidine 2-(2-(2-Chlorophenyl)ethylamino))-5-(4-fluorophenyl)-4-(4-pyridyl)-pyrimidine 2-(2-(4-Chlorophenyl)ethylamino)-5-(4-fluorophenyl)-4-(4-pyridyl)-pyrimidine 2-(2-(2,4-Dichlorophenyl)ethylamino)-5-(4-fluorophenyl)-4-(4-pyridyl)-pyrimidine 5-(4-Fluorophenyl)-2-(3-phenylpropyl)amino-4-(4-pyridyl)-pyrimidine 2-((S)-2-Amino-3-phenylpropyl)amino-5-(4-fluorophenyl)-4-(4-pyridyl)-pyrimidine 5-(4-Fluorophenyl)-2-(2-phenylaminoethylamino)-4-(4-pyridyl)-pyrimidine 5-(4-Fluorophenyl)-2-(3-imidazolylpropyl)amino-4-(4-pyridyl)-pyrimidine 5-(4-Fluorophenyl)-4-(4-pyridyl)-2-pyrrolidino-pyrimidine 5-(4-Fluorophenyl)-2-(1-piperazinyl)-4-(4-pyridyl)-pyrimidine 5-(4-Fluorophenyl)-2-(2-phenylethyl)thio-6-(4-pyridyl)-4(3H)-pyrimidinone 5-(4-Fluorophenyl)-2-(3-phenylpropyl)thio-6-(4-pyridyl)-4(3H)-pyrimidinone 2-(2-(2-Chlorophenyl)ethyl-amino)-5-(4-fluorophenyl)-6-(4-pyridyl)-4(3H)-pyrimidinone 5-(4-Fluorophenyl)-2-(3-phenylpropyl)amino-6-(4-pyridyl)-4(3H)-pyrimidinone 5-(4-Fluorophenyl)-2-(1-methyl-3-phenylpropyl)amino-6-(4-pyridyl)-4(3H)-pyrimidinone 2-(((S)-2-Amino-3-phenylpropyl)-amino)-4-(4-pyridyl)-5-(3-trifluoromethylphenyl)-pyrimidine 2-(((S)-2-Amino-3-phenylpropyl)-amino)-5-(3-methylphenyl)-4-(4-pyridyl)-pyrimidine 2-(((S)-2-N,N-Dimethylamino-3-phenylpropyl)-amino)-5-(4-fluorophenyl)-4-(4-pyridyl)-pyrimidine 2-(((S)-2-N,N-Dimethylamino-3-phenylpropyl)-amino)-5-(3-methylphenyl)-4-(4-pyridyl)-pyrimidine 2-((3-Amino-3-phenylpropyl)-amino)-5-(4-fluorophenyl)-4-(4-pyridyl)-pyrimidine 2-((3-Amino-3-phenylpropyl)-amino)-4-(4-pyridyl)-5-(3-trifluoromethylphenyl)-pyrimidine 2-((3-Amino-3-(2-fluorophenyl)propyl)-amino)-4-(4-pyridyl)-5-(3-trifluoromethylphenyl)-pyrimidine 2-((3-Amino-3-phenylpropyl)-amino)-5-(3-methylphenyl)-4-(4-pyridyl)-pyrimidine 2-((2-Amino-2-methyl-3-phenylpropyl)-amino)-5-(3-methylphenyl)-4-(4-pyridyl)-pyrimidine 2-((3-Hydroxy-3-phenylpropyl)-amino)-5-(3-methylphenyl)-4-(4-pyridyl)-pyrimidine 2-(((2S,3S)-3-Amino-2-methyl-3-phenylpropyl)-amino)-4-(4-pyridyl)-5-(3-trifluoromethylphenyl)-pyrimidine 2-(((2R,3R)-3-Amino-2-methyl-3-phenylpropyl)-amino)-4-(4-pyridyl)-5-(3-trifluoromethylphenyl)-pyrimidine 2-((S)-3-Benzylpiperazinyl)-4-(4-pyridyl)-5-(3-trifluoromethylphenyl)-pyrimidine 4-(4-Pyridyl)-2-(((S)-tetrahydroisoquinol-3-ylmethyl)amino)-5-(3-trifluoromethylphenyl)-pyrimidine 5-(3-Methylphenyl)-4-(4-pyridyl)-2-(((S)-tetrahydroisoquinol-3-ylmethylen)amino)-pyrimidine 2-(((S)-2-N-Isopropylamino-3-phenylpropyl)-amino)-4-(4-pyridyl)-5-(3-trifluoromethylphenyl)-pyrimidine 2-(((S)-2-N-Cyclohexylamino-3-phenylpropyl)-amino)-4-(4-pyridyl)-5-(3-trifluoromethylphenyl)-pyrimidine
2-(((S)-2-N-Isopropylamino-3-phenylpropyl)-amino)-5-(3-methylphenyl)-4-(4-pyridyl)-pyrimidine
2-(((S)-2-N-Butylamino-3-phenylpropyl)-amino)-5-(3-methylphenyl)-4-(4-pyridyl)-pyrimidine
2-(((S)-2-N-Cyclohexylamino-3-phenylpropyl)-amino)-5-(3-methylphenyl)-4-(4-pyridyl)-pyrimidine
5-(4-Fluorophenyl)-2-(((S)-2-N-isopropylamino-3-phenylpropyl)-amino)-4-(4-pyridyl)-pyrimidine
5-(4-Fluorophenyl)-2-((3-N-isopropylamino-3-phenylpropyl)-amino)-4-(4-pyridyl)-pyrimidine
2-(((S)-2-N-Glycylamino-3-phenylpropyl)-amino)-4-(4-pyridyl)-5-(3-trifluoromethylphenyl)-pyrimidine
2-(((S)-2-N-Glycylamino-3-phenylpropyl)-amino)-5-(3-methylphenyl)-4-(4-pyridyl)-pyrimidine
2-(((S)-2-Amino-3-phenylpropyl)-amino)-5-(3-chloro-4-fluorophenyl)-4-(4-pyridyl)-pyrimidine
2-(((S)-2-Amino-3-phenylpropyl)-amino)-5-(3-fluorophenyl)-4-(4-pyridyl)-pyrimidine
2-(((S)-2-Amino-3-phenylpropyl)-amino)-5-(3-isopropylphenyl)-4-(4-pyridyl)-pyrimidine
5-(3-Acetamidophenyl)-2-(((S)-2-amino-3-phenylpropyl)-amino)-4-(4-pyridyl)-pyrimidine
2-(((S)-2-Amino-3-phenylpropyl)-amino)-5-(4-chlorophenyl)-4-(4-pyridyl)-pyrimidine
2-(((S)-2-Amino-3-phenylpropyl)-amino)-5-(benzothienyl)-4-(4-pyridyl)-pyrimidine
2-(((S)-2-Amino-3-phenylpropyl)-amino)-5-(2-naphthyl)-4-(4-pyridyl)-pyrimidine
2-(((S)-2-Amino-3-phenylpropyl)-amino)-5-(4-fluorophenyl)-6-(4-pyridyl)-4-(3H)pyrimidinone.

Compounds of the invention may be shown to have anti-inflammatory properties in animal models of inflammation, including carageenan paw edema, collagen induced arthritis and adjuvant arthritis, such as the carageenan paw edema model (C. A. Winter et al Proc. Soc. Exp. Biol. Med. (1962) vol 111, p 544; K. F. Swingle, in R. A. Scherrer and M. W. Whitehouse, Eds., Antiinflammatory Agents, Chemistry and Pharmacology, Vol. 13-II, Academic, New York, 1974, p. 33) and collagen induced arthritis (D. E. Trentham et al J. Exp. Med. (1977) vol. 146, p 857; J. S. Courtenay, Nature (New Biol.) (1980), Vol 283, p 666).

$^{125}$I-Glucagon Binding Screen with CHO/hGLUR Cells

The assay is described in WO 97/16442, which is incorporated herein by reference in its entirety.
Reagents The reagents can be prepared as follows: (a) prepare fresh 1M o-Phenanthroline (Aldrich) (198.2 mg/ml ethanol); (b) prepare fresh 0.5M DTT (Sigma); (c) Protease Inhibitor Mix (1000×): 5 mg leupeptin, 10 mg benzamidine, 40 mg bacitracin and 5 mg soybean trypsin inhibitor per ml DMSO and store aliquots at −20° C.; (d) 250 μM human glucagon (Peninsula): solubilize 0.5 mg vial in 575 μl 0.1N acetic acid (1 μl yields 1 μM final concentration in assay for non-specific binding) and store in aliquots at −20° C.; (e) Assay Buffer: 20 mM Tris (pH 7.8), 1 mM DTT and 3 mM o-phenanthroline; (f) Assay Buffer with 0.1% BSA (for dilution of label only; 0.01% final in assay): 10 μl 10% BSA (heat-inactivated) and 990 μl Assay Buffer; (g) $^{125}$I-Glucagon (NEN, receptor-grade, 2200 Ci/mmol): dilute to 50,000 cpm/25 μl in assay buffer with BSA (about 50 pM final concentration in assay).

Harvesting of CHO/hGLUR Cells for Assay

1. Remove media from confluent flask then rinse once each with PBS (Ca, Mg-free) and Enzyme-free Dissociation Fluid (Specialty Media, Inc.).

2. Add 10 ml Enzyme-free Dissoc. Fluid and hold for about 4 min. at 37° C.

3. Gently tap cells free, triturate, take aliquot for counting and centrifuge remainder for 5 min. at 1000 rpm.

4. Resuspend pellet in Assay Buffer at 75000 cells per 100 μl.

Membrane preparations of CHO/hGLUR cells can be used in place of whole cells at the same assay volume. Final protein concentration of a membrane preparation is determined on a per batch basis.

Assay

The determination of inhibition of glucagon binding can be carried out by measuring the reduction of $I^{125}$-glucagon binding in the presence of compounds of Formula I. The reagents are combined as follows:

| | Compound/Vehicle | 250 μm Glucagon | $^{125}$I-Glucagon | CHO/hGLUR Cells |
|---|---|---|---|---|
| Total | —/5 μl | — | 25 μl | 100 μl |
| Binding + | 5 μl/— | — | 25 μl | 100 μl |
| Compound Nonspecific Binding | —/5 μl | 1 μl | 25 μl | 100 μl |

The mixture is incubated for 60 min. at 22° C. on a shaker at 275 rpm. The mixture is filtered over pre-soaked (0.5% polyethylimine (PEI)) GF/C filtermat using an Innotech Harvester or Tomtec Harvester with four washes of ice-cold 20 mM Tris buffer (pH 7.8). The radioactivity in the filters is determined by a gamma-scintillation counter.

Thus, compounds of the invention may also be shown to inhibit the binding of glucagon to glucagon receptors.

Cyclooxygenase Enzyme Activity Assay

The human monocytic leukemia cell line, THP-1, differentiated by exposure to phorbol esters expresses only COX-1; the human osteosarcoma cell line 143B expresses predominantly COX-2. THP-1 cells are routinely cultured in RPMI complete media supplemented with 10% FBS and human osteosarcoma cells (HOSC) are cultured in minimal essential media supplemented with 10% fetal bovine serum (MEM-10% FBS); all cell incubations are at 37° C. in a humidified environment containing 5% $CO_2$.

COX-1 Assay

In preparation for the COX-1 assay, THP-1 cells are grown to confluency, split 1:3 into RPMI containing 2% FBS and 10 mM phorbol 12-myristate 13-acetate (TPA), and incubated for 48 hours on a shaker to prevent attachment. Cells are pelleted and resuspended in Hank's Buffered Saline (HBS) at a concentration of 2.5×10$^6$ cells/mL and plated in 96-well culture plates at a density of 5×10$^5$ cells/mL. Test compounds are diluted in HBS and added to the desired final concentration and the cells are incubated for an additional 4 hours. Arachidonic acid is added to a final concentration of 30 mM, the cells incubated for 20 minutes at 37° C., and enzyme activity determined as described below.

COX-2 Assay

For the COX-2 assay, subconfluent HOSC are trypsinized and resuspended at 3×10$^6$ cells/mL in MEM-FBS containing 1 ng human IL-1 b/mL, plated in 96-well tissue culture plates at a density of 3×10$^4$ cells per well, incubated on a shaker for 1 hour to evenly distribute cells, followed by an additional 2 hour static incubation to allow attachment. The media is then replaced with MEM containing 2% FBS (MEM-2% FBS) and 1 ng human IL-1 b/mL, and the cells incubated for 18–22 hours. Following replacement of media with 190 mL MEM, 10 mL of test compound diluted in HBS is added to achieve the desired concentration and the cells incubated for 4 hours. The supernatants are removed and replaced with MEM containing 30 mM arachidonic acid, the cells incubated for 20 minutes at 37° C., and enzyme activity determined as described below.

COX Activity Determined

After incubation with arachidonic acid, the reactions are stopped by the addition of 1 N HCl, followed by neutralization with 1 N NaOH and centrifugation to pellet cell debris. Cyclooxygenase enzyme activity in both HOSC and THP-1 cell supernatants is determined by measuring the concentration of $PGE_2$ using a commercially available ELISA (Neogen #404110). A standard curve of $PGE_2$ is used for calibration, and commercially available COX-1 and COX-2 inhibitors are included as standard controls.

Accordingly, the compounds of the invention or a pharmaceutical composition thereof are useful for prophylaxis and treatment of rheumatoid arthritis; Pagets disease; osteophorosis; multiple myeloma; uveititis; acute and chronic myelogenous leukemia; pancreatic β cell destruction; osteoarthritis; rheumatoid spondylitis; gouty arthritis; inflammatory bowel disease; adult respiratory distress syndrome (ARDS); psoriasis; Crohn's disease; allergic rhinitis; ulcerative colitis; anaphylaxis; contact dermatitis; asthma; muscle degeneration; cachexia; Reiter's syndrome; type I and type II diabetes; bone resorption diseases; graft vs. host reaction; ischemia reperfusion injury; atherosclerosis; brain trauma; Alzheimer's disease; stroke; myocardial infarction; multiple sclerosis; cerebral malaria; sepsis; septic shock; toxic shock syndrome; fever, and myalgias due to infection. HIV-1, HIV-2, HIV-3, cytomegalovirus (CMV), influenza, adenovirus, the herpes viruses (including HSV-1, HSV-2), and herpes zoster, all of which are sensitive to TNF-α and/or IL-1 inhibition or glucagon antagonism, will also be positively effected by the compounds and methods of the invention.

The compounds of the present invention also may possess analgesic properties and may be useful for the treatment of pain disorders, such as hyperalgesia due to excessive IL-1. The compounds of the present invention may also prevent the production of prostaglandins by inhibition of enzymes in the human arachidonic acid/prostaglandin pathway, including cyclooxygenase (WO 96/03387, incorporated herein by reference in its entirety).

Because of their ability to lower TNF-α and IL-1 concentrations or inhibit glucagon binding to its receptor, the compounds of the invention are also useful research tools for studying the physiology associated with blocking these effects.

The methods of the invention comprise administering an effective dose of a compound of the invention, a pharmaceutical salt thereof, or a pharmaceutical composition of either, to a subject (i.e., an animal, preferably a mammal, most preferably a human) in need of a reduction in the level of TNF-α, IL-1, IL-6, and/or IL-8 levels and/or reduction in plasma glucose levels and/or which subject may be suffering from rheumatoid arthritis; Pagets disease; osteophorosis; multiple myeloma; uveititis; acute and chronic myelogenous leukemia; pancreatic β cell destruction; osteoarthritis; rheumatoid spondylitis; gouty arthritis; inflammatory bowel disease; adult respiratory distress syndrome (ARDS); psoriasis; Crohn's disease; allergic rhinitis; ulcerative colitis; anaphylaxis; contact dermatitis; asthma; muscle degeneration; cachexia; Reiter's syndrome; type I and type II diabetes; bone resorption diseases; graft vs. host reaction; Alzheimer's disease; stroke; myocardial infarction; ischemia reperfusion injury; atherosclerosis; brain trauma; multiple sclerosis; cerebral malaria; sepsis; septic shock; toxic shock syndrome; fever, and myalgias due to infection, or which subject is infected by HIV-1, HIV-2, HIV-3, cytomegalovirus (CMV), influenza, adenovirus, the herpes viruses (including HSV-1, HSV-2), or herpes zoster.

In another aspect, this invention comprises the use of a compound of the invention, or pharmaceutically acceptable salts thereof, in the manufacture of a medicament for the treatment either acutely or chronically of a TNF-α, IL-1β, IL-6, and/or IL-8 mediated disease state, including those described previously. Also, the compounds of this invention are useful in the manufacture of a analgesic medicament and a medicament for treating pain disorders, such as hyperalgesia. The compounds of the present invention also are useful in the manufacture of a medicament to prevent the production of prostaglandins by inhibition of enzymes in the human arachidonic acid/prostaglandin pathway.

In still another aspect, this invention provides a pharmaceutical composition comprising an effective TNF-α, IL-1β, IL-6, and/or IL-8 lowering amount and/or effective plasma glucose level lowering amount of a compound of the invention and a pharmaceutically acceptable carrier or diluent, and if desired other active ingredients. The compounds of the invention are administered by any suitable route, preferably in the form of a pharmaceutical composition adapted to such a route, and in a dose effective for the treatment intended. Therapeutically effective doses of the compounds of the present invention required to arrest the progress or prevent tissue damage associated with the disease are readily ascertained by one of ordinary skill in the art using standard methods.

For the treatment of TNF-α, IL-1β, IL-6, and IL-8 mediated diseases and/or hyperglycemia, the compounds of the present invention may be administered orally, parentally, by inhalation spray, rectally, or topically in dosage unit formulations containing conventional pharmaceutically acceptable carriers, adjuvants, and vehicles. The term parenteral as used herein includes, subcutaneous, intravenous, intramuscular, intrasternal, infusion techniques or intraperitoneally.

The dosage regimen for treating a TNF-α, IL-1, IL-6, and IL-8 mediated diseases and/or hyperglycemia with the compounds of this invention and/or compositions of this invention is based on a variety of factors, including the type of disease, the age, weight, sex, medical condition of the patient, the severity of the condition, the route of administration, and the particular compound employed. Thus, the dosage regimen may vary widely, but can be determined routinely using standard methods. Dosage levels of the order from about 0.01 mg to 30 mg per kilogram of body weight per day, preferably from about 0.1 mg to 10 mg/kg, more preferably from about 0.25 mg to 1 mg/kg are useful for all methods of use disclosed herein.

The pharmaceutically active compounds of this invention can be processed in accordance with conventional methods of pharmacy to produce medicinal agents for administration to patients, including humans and other mammals.

For oral administration, the pharmaceutical composition may be in the form of, for example, a capsule, a tablet, a suspension, or liquid. The pharmaceutical composition is preferably made in the form of a dosage unit containing a given amount of the active ingredient. For example, these may contain an amount of active ingredient from about 1 to 2000 mg, preferably from about 1 to 500 mg, more preferably from about 5 to 150 mg. A suitable daily dose for a human or other mammal may vary widely depending on the condition of the patient and other factors, but, once again, can be determined using routine methods.

The active ingredient may also be administered by injection as a composition with suitable carriers including saline, dextrose, or water. The daily parenteral dosage regimen will be from about 0.1 to about 30 mg/kg of total body weight, preferably from about 0.1 to about 10 mg/kg, and more preferably from about 0.25 mg to 1 mg/kg.

Injectable preparations, such as sterile injectable aqueous or oleaginous suspensions, may be formulated according to the known are using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

Suppositories for rectal administration of the drug can be prepared by mixing the drug with a suitable non-irritating excipient such as cocoa butter and polyethylene glycols that are solid at ordinary temperatures but liquid at the rectal temperature and will therefore melt in the rectum and release the drug.

A suitable topical dose of active ingredient of a compound of the invention is 0.1 mg to 150 mg administered one to four, preferably one or two times daily. For topical administration, the active ingredient may comprise from 0.001% to 10% w/w, e.g., from 1% to 2% by weight of the formulation, although it may comprise as much as 10% w/w, but preferably not more than 5% w/w, and more preferably from 0.1% to 1% of the formulation.

Formulations suitable for topical administration include liquid or semi-liquid preparations suitable for penetration through the skin (e.g., liniments, lotions, ointments, creams, or pastes) and drops suitable for administration to the eye, ear, or nose.

For administration, the compounds of this invention are ordinarily combined with one or more adjuvants appropriate for the indicated route of administration. The compounds may be admixed with lactose, sucrose, starch powder, cellulose esters of alkanoic acids, stearic acid, talc, magnesium stearate, magnesium oxide, sodium and calcium salts of phosphoric and sulphuric acids, acacia, gelatin, sodium alginate, polyvinylpyrrolidine, and/or polyvinyl alcohol, and tableted or encapsulated for conventional administration. Alternatively, the compounds of this invention may be dissolved in saline, water, polyethylene glycol, propylene glycol, ethanol, corn oil, peanut oil, cottonseed oil, sesame oil, tragacanth gum, and/or various buffers. Other adjuvants and modes of administration are well known in the pharmaceutical art. The carrier or diluent may include time delay material, such as glyceryl monostearate or glyceryl distearate alone or with a wax, or other materials well known in the art.

The pharmaceutical compositions may be made up in a solid form (including granules, powders or suppositories) or in a liquid form (e.g., solutions, suspensions, or emulsions). The pharmaceutical compositions may be subjected to conventional pharmaceutical operations such as sterilization and/or may contain conventional adjuvants, such as preservatives, stabilizers, wetting agents, emulsifiers, buffers etc.

Solid dosage forms for oral administration may include capsules, tablets, pills, powders, and granules. In such solid dosage forms, the active compound may be admixed with at least one inert diluent such as sucrose, lactose, or starch. Such dosage forms may also comprise, as in normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting, sweetening, flavoring, and perfuming agents.

Compounds of the present invention can possess one or more asymmetric carbon atoms and are thus capable of existing in the form of optical isomers as well as in the form of racemic or non-racemic mixtures thereof. The optical isomers can be obtained by resolution of the racemic mixtures according to conventional processes, e.g., by formation of diastereoisomeric salts, by treatment with an optically active acid or base. Examples of appropriate acids are tartaric, diacetyltartaric, dibenzoyltartaric, ditoluoyltartaric, and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another available method involves synthesis of covalent diastereoisomeric molecules by reacting compounds of the invention with an optically pure acid in an activated form or an optically pure isocyanate. The synthesized diastereoisomers can be separated by conventional means such as chromatography, distillation, crystallization or sublimation, and then hydrolyzed to deliver the enantiomerically pure compound. The optically active compounds of the invention can likewise be obtained by using active starting materials. These isomers may be in the form of a free acid, a free base, an ester or a salt.

The compounds of the present invention can be used in the form of salts derived from inorganic or organic acids. The salts include, but are not limited to, the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hyroxy-ethanesulfonate, lactate, maleate, methansulfonate, nicotinate, 2-naphthalenesulfonate, oxalate, palmoate, pectinate, persulfate, 2-phenylpropionate, picrate, pivalate, propionate, succinate, tartrate, thiocyanate, tosylate, mesylate, and undecanoate. Also, the basic nitrogen-containing groups can be quaternized with such agents as lower alkyl halides, such as methyl, ethyl, propyl, and butyl chloride, bromides and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids that may be employed to from pharmaceutically acceptable acid addition salts include such inorganic acids as hydrochloric acid, sulphuric acid and phosphoric acid and such organic acids as oxalic acid, maleic acid, succinic acid and citric acid. Other examples include salts with alkali metals or alkaline earth metals, such as sodium, potassium, calcium or magnesium or with organic bases.

While the compounds of the invention can be administered as the sole active pharmaceutical agent, they can also be used in combination with one or more compounds of the invention or other agents. When administered as a combination, the therapeutic agents can be formulated as separate compositions that are given at the same time or different times, or the therapeutic agents can be given as a single composition.

The foregoing is merely illustrative of the invention and is not intended to limit the invention to the disclosed compounds. Variations and changes which are obvious to one skilled in the art are intended to be within the scope and nature of the invention which are defined in the appended claims.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A compound of formula

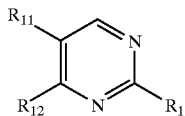

or a pharmaceutically acceptable salt thereof, wherein
wherein $R_1$ is -Z-Y, provided that (1) the total number of aryl, heteroaryl, cycloalkyl and heterocyclyl radicals in each -Z-Y is 0–3; and (2) the combined total number of aryl, heteroaryl, cycloalkyl and heterocyclyl radicals in $R_1$ is 0–4;
wherein each Z is a bond;
each Y is independently a
(1) hydrogen radical;
(2) halo or nitro radical;
(3) —C(O)—$R_{20}$ or —C($NR_5$)—$NR_5R_{21}$ radical;
(4) —$OR_{21}$, —O—C(O)—$R_{21}$, —O—C(O)—$NR_5R_{21}$ or —O—C(O)—$NR_{22}$—S(O)$_2$—$R_{20}$ radical;
(5) —$SR_{21}$, —S(O)—$R_{20}$, —S(O)$_2$—$R_{20}$, —S(O)$_2$—$NR_5R_{21}$, —S(O)$_2$—$NR_{22}$—C(O)—$R_{21}$, —S(O)$_2$—$NR_{22}$—C(O)—$OR_{22}$ or —S(O)$_2$—$NR_{22}$—C(O)—$NR_5R_{21}$ radical; or
(6) —$NR_5R_{21}$, —$NR_{22}$—C(O)—$R_{21}$, —$NR_{22}$—C(O)—$OR_{20}$, —$NR_{22}$—C(O)—$NR_5R_{21}$, —$NR_{22}$—C($NR_5$)—$NR_5R_{21}$, —$NR_{22}$—S(O)$_2$—$R_{20}$ or —$NR_{22}$—S(O)$_2$—$NR_5R_{21}$ radical;
wherein each $R_5$ is independently
(1) hydrogen radicals;
(2) alkyl, alkenyl or alkynyl radicals optionally substituted by 1–3 radicals of amino, alkylamino, dialkylamino, hydroxy, alkoxy, alkylthio, —SO$_3$H or halo; or
(3) aryl, heteroaryl, aralkyl, heteroaralkyl, heterocyclyl, heterocyclylalkyl, cycloalkyl or cycloalkylalkyl radicals optionally substituted by 1–3 radicals of amino, alkylamino, dialkylamino, hydroxy, alkoxy, alkylthio, alkyl or haloalkyl; and
wherein each $R_{20}$ is independently
(1) alkyl, alkenyl or alkynyl radicals optionally substituted by 1–3 radicals of amino, alkylamino, dialkylamino, alkanoylamino, alkoxycarbonylamino, N-(alkoxycarbonyl)-N-(alkyl)amino, aminocarbonylamino, alkylsulfonylamino, hydroxy, alkoxy, alkylthio, alkylsulfinyl, alkylsulfonyl, halo or aralkoxy, aralkylthio, aralkylsulfonyl, cycloalkyl, heterocyclyl, aryl or heteroaryl radicals optionally substituted by 1–3 radicals of amino, alkylamino, dialkylamino, alkanoylamino, alkoxycarbonylamino, alkylsulfonylamino, alkanoyl, hydroxy, alkoxy, alkylthio, alkylsulfinyl, alkylsulfonyl, halo, alkyl or haloalkyl;
(2) heterocyclyl radical optionally substituted by 1–3 radicals of amino, alkylamino, dialkylamino, alkanoylamino, alkoxycarbonylamino, alkylsulfonylamino, hydroxy, alkoxy, alkylthio, alkyl or haloalkyl; or
(3) aryl or heteroaryl radicals optionally substituted by 1–3 radicals of amino, alkylamino, dialkylamino, alkanoylamino, alkoxycarbonylamino, alkylsulfonylamino, alkoxycarbonyl, hydroxy, alkoxy, alkylthio, cyano, halo, azido, alkyl or haloalkyl;
each $R_{21}$ is independently hydrogen radical or $R_{20}$;
each $R_{22}$ is independently
(1) hydrogen radical;
(2) alkyl radical optionally substituted by a radical of heterocyclyl, aryl or heteroaryl optionally substituted by 1–3 radicals of amino, alkylamino, dialkylamino, alkanoylamino, alkoxycarbonylamino, alkylsulfonylamino, hydroxy, alkoxy, alkylthio, alkylsulfinyl, alkylsulfonyl, cyano, halo, alkyl or haloalkyl; or
(3) heterocyclyl, aryl or heteroaryl radicals optionally substituted by 1–3 radicals of amino, alkylamino, dialkylamino, alkanoylamino, alkoxycarbonylamino, alkylsulfonylamino, hydroxy, alkoxy, alkylthio, alkylsulfinyl, alkylsulfonyl, cyano, halo, alkyl or haloalkyl; provided when Y is —$NR_{22}$—C(O)—$NH_2$, then $R_{22}$ is other then an optionally substituted aryl radical; and
$R_{11}$ is an aryl radical, wherein the aryl radical is substituted by 1–2 radicals of
(1) $R_{30}$;
(2) halo or cyano radicals;
(3) —C(O)—$R_{30}$, —C(O)—$OR_{29}$, —C(O)—$NR_{31}R_{32}$ or —C($NR_{31}$)—$NR_{31}R_{32}$ radicals; or
(4) —$OR_{29}$, —$SR_{29}$, —S(O)—$R_{30}$, —S(O)$_2$—$R_{30}$, —S(O)$_2$—$NR_{31}R_{32}$, —$NR_{31}R_{32}$ or —$NR_{33}$—C(O)—$R_{29}$ radicals;
$R_{12}$ is a heteroaryl radical, wherein the heteroaryl radical is optionally substituted by 1–2 radicals of
(1) $R_{30}$;
(2) halo or cyano radicals;
(3) —C(O)—$R_{30}$, —C(O)—$OR_{29}$, —C(O)—$NR_{31}R_{32}$ or —C($NR_{31}$)—$NR_{31}R_{32}$ radicals; or
(4) —$OR_{29}$, —$SR_{29}$, —S(O)—$R_{30}$, —S(O)$_2$—$R_{30}$, —S(O)$_2$—$NR_{31}R_{32}$, —$NR_{31}R_{32}$ or —$NR_{33}$—C(O)—$R_{29}$ radicals;
provided that the total number of aryl, heteroaryl, cycloalkyl and heterocyclyl radicals substituted on each of $R_{11}$ and $R_{12}$ is 0–1;
wherein each $R_{30}$ is independently
(1) alkyl, alkenyl or alkynyl radicals optionally substituted by 1–3 radicals of —$NR_{31}R_{31}$, —$CO_2R_{23}$, hydroxy, alkoxy, alkylthio, alkylsulfinyl, alkylsulfonyl, cyano, halo or aralkoxy, aralkylthio, aralkylsulfonyl, heterocyclyl, aryl or heteroaryl radicals optionally substituted by 1–3 radicals of amino, alkylamino, dialkylamino, alkanoylamino, alkoxycarbonylamino, alkylsulfonylamino, hydroxy, alkoxy, alkylthio, alkylsulfinyl, alkylsulfonyl, cyano, halo, alkyl or haloalkyl;

(2) heterocyclyl radical optionally substituted by 1–3 radicals of amino, alkylamino, dialkylamino, alkanoylamino, alkoxycarbonylamino, alkylsulfonylamino, hydroxy, alkoxy, alkylthio, cyano, alkyl or haloalkyl; or (3) aryl or heteroaryl radicals optionally substituted by 1–3 radicals of amino, alkylamino, dialkylamino, alkanoylamino, alkoxycarbonylamino, alkylsulfonylamino, hydroxy, alkoxy, alkylthio, cyano, halo, alkyl or haloalkyl;

each $R_{29}$ is independently hydrogen radical or $R_{30}$;

each $R_{31}$ and $R_{32}$ are each independently (1) hydrogen radicals;

(2) alkyl radical optionally substituted by an cycloalkyl, aryl, heterocyclyl or heteroaryl radical optionally substituted by 1–3 radicals of amino, alkylamino, dialkylamino, alkanoylamino, alkoxycarbonylamino, alkylsulfonylamino, hydroxy, alkoxy, alkylthio, cyano, alkyl or haloalkyl; or (3) aryl, heteroaryl, heterocyclyl or cycloalkyl radical optionally substituted by 1–3 radicals of amino, alkylamino, dialkylamino, alkanoylamino, alkoxycarbonylamino, alkylsulfonylamino, hydroxy, alkoxy, alkylthio, cyano, alkyl or haloalkyl; and wherein each $R_{33}$ is independently (1) hydrogen radical; or (2) alkyl radical optionally substituted by a radical of heterocyclyl, aryl or heteroaryl optionally substituted by 1–3 radicals of amino, alkylamino, dialkylamino, alkanoylamino, alkoxycarbonylamino, alkylsulfonylamino, hydroxy, alkoxy, alkylthio, cyano, alkyl or haloalkyl; and provided that (1) when $R^{11}$ is phenyl and $R^{12}$ is 4-pyridyl, then $R^1$ is other than H, methyl, or amino; and (2) when $R^{11}$ is 2-methylphenyl and $R^{12}$ is 2-pyridyl, then $R^1$ is other than n-propyl.

2. The compound of claim 1 or a pharmaceutically acceptable salt thereof, wherein wherein $R_1$ is -Z-Y, provided that (1) the total number of aryl, heteroaryl, cycloalkyl and heterocyclyl radicals in each -Z-Y is 0–3; and (2) the combined total number of aryl, heteroaryl, cycloalkyl and heterocyclyl radicals in $R_1$ is 0–4;

each Y is independently a (1) hydrogen radical;

(2) halo or nitro radical;

(3) —C(O)—$R_{20}$ or —C($NR_5$)—$NR_5R_{21}$ radical;

(4) —$OR_{21}$, —O—C(O)—$R_{21}$, —O—C(O)—$NR_5R_{21}$ or —O—C(O)—$NR_{22}$—S(O)$_2$—$R_{20}$ radical;

(5) —$SR_{21}$, —S(O)—$R_{20}$, —S(O)$_2$—$R_{20}$, —S(O)$_2$—$NR_5R_{21}$, —S(O)—$NR_{22}$—C(O)—$R_{21}$, —S(O)$_2$—$NR_{22}$—C(O)—$OR_{20}$ or —S(O)$_2$—$NR_{22}$—C(O)—$NR_5R_{21}$ radical; or (6) —$NR_5R_{21}$, —$NR_{22}$—C(O)—$R_{21}$, —$NR_{22}$—C(O)—$OR_{20}$, —$NR_{22}$—C(O)—$NR_5R_{21}$, —$NR_{22}$—C($NR_5$)—$NR_5R_{21}$, —$NR_{22}$—S(O)$_2$—$R_{20}$ or —$NR_{22}$—S(O)$_2$—$NR_5R_{21}$ radical;

each $R_5$ is independently (1) hydrogen radicals;

(2) $C_1$–$C_8$ alkyl, $C_2$–$C_8$ alkenyl or $C_2$–$C_8$ alkynyl radicals optionally substituted by 1–3 radicals of amino, $C_1$–$C_4$ alkylamino, di-($C_1$–$C_4$-alkyl)amino, hydroxy, $C_1$–$C_4$ alkoxy, $C_1$–$C_4$ alkylthio, —SO$_3$H or halo; or (3) aryl, heteroaryl, aryl-$C_1$–$C_4$-alkyl, heteroaryl-$C_1$–$C_4$-alkyl, heterocyclyl, heterocyclyl-$C_1$–$C_4$-alkyl, $C_3$–$C_8$ cycloalkyl or $C_3$–$C_8$-cycloalkyl-$C_1$–$C_4$-alkyl radicals optionally substituted by 1–3 radicals of amino, $C_1$–$C_4$ alkylamino, di-($C_1$–$C_4$-alkyl)amino, hydroxy, $C_1$–$C_4$ alkoxy, $C_1$–$C_4$ alkylthio, $C_1$–$C_4$ alkyl or $C_1$–$C_4$ haloalkyl of 1–3 halo radicals;

each $R_{20}$ is independently (1) $C_1$–$C_8$ alkyl, $C_2$–$C_8$ alkenyl or $C_2$–$C_8$ alkynyl radicals optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, N-(($C_1$–$C_4$ alkoxy)carbonyl)-N-($C_1$–$C_4$ alkyl)amino, aminocarbonylamino, $C_1$–$C_4$ alkylsulfonylamino, hydroxy, $C_1$–$C_4$ alkoxy, $C_1$–$C_4$ alkylthio, $C_1$–$C_4$ alkylsulfinyl, $C_1$–$C_4$ alkylsulfonyl, halo or aryl-$C_1$–$C_4$-alkoxy, aryl-$C_1$–$C_4$-alkylthio, aryl-$C_1$–$C_4$-alkylsulfonyl, $C_3$–$C_8$ cycloalkyl, heterocyclyl, aryl or heteroaryl radicals optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, $C_1$–$C_5$ alkanoyl, hydroxy, $C_1$–$C_4$ alkoxy, $C_1$–$C_4$ alkylthio, $C_1$–$C_4$ alkylsulfinyl, $C_1$–$C_4$ alkylsulfonyl, halo, $C_1$–$C_4$ alkyl or $C_1$–$C_4$ haloalkyl of 1–3 halo radicals;

(2) heterocyclyl radical optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, $C_1$–$C_4$ alkyl or $C_1$–$C_4$ haloalkyl of 1–3 halo radicals; or (3) aryl or heteroaryl radicals optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, ($C_1$–$C_4$ alkoxy)carbonyl, hydroxy, $C_1$–$C_4$ alkoxy, $C_1$–$C_4$ alkylthio, cyano, halo, azido, $C_1$–$C_4$ alkyl or $C_1$–$C_4$ haloalkyl of 1–3 halo radicals;

each $R_{21}$ is independently hydrogen radical or $R_{20}$;

each $R_{22}$ is independently (1) hydrogen radical;

(2) $C_1$–$C_4$ alkyl radical optionally substituted by a radical of heterocyclyl, aryl or heteroaryl optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, $C_1$–$C_4$ alkylsulfinyl, $C_1$–$C_4$ alkylsulfonyl, cyano, halo, $C_1$–$C_4$ alkyl or $C_1$–$C_4$ haloalkyl of 1–3 halo radicals; or (3) heterocyclyl, aryl or heteroaryl radicals optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, $C_1$–$C_4$ alkylsulfinyl, $C_1$–$C_4$ alkylsulfonyl, cyano, halo, $C_1$–$C_4$ alkyl or $C_1$–$C_4$ haloalkyl of 1–3 halo radicals; provided when Y is —$NR_{22}$—C(O)—$NH_2$, then $R_{22}$ is other then an optionally substituted aryl radical;

$R_{11}$ is a phenyl radical substituted by 1–2 radicals of amino, dimethylamino, acetamido, hydroxy, halo, cyano, methoxy, methylthio, methylsulfinyl, methylsulfonyl, aminocarbonyl, methyl or trifluoromethyl radicals;

each $R_{30}$ is independently
(1) $C_1$–$C_4$ alkyl, $C_2$–$C_4$ alkenyl or $C_2$–$C_4$ alkynyl radicals optionally substituted by 1–3 radicals of —$NR_{31}R_{31}$, —$CO_2R_{23}$, hydroxy, $C_1$–$C_4$ alkoxy, $C_1$–$C_4$ alkylthio, $C_1$–$C_4$ alkylsulfinyl, $C_1$–$C_4$ alkylsulfonyl, cyano, halo or aryl-$C_1$–$C_4$-alkoxy, aryl-$C_1$–$C_4$-alkylthio, aryl-$C_1$–$C_4$-alkylsulfonyl, heterocyclyl, aryl or heteroaryl radicals optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, $C_1$–$C_4$ alkylsulfinyl, $C_1$–$C_4$ alkylsulfonyl, cyano, halo, $C_1$–$C_4$ alkyl or $C_1$–$C_4$ haloalkyl of 1–3 halo radicals;
(2) heterocyclyl radical optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, cyano, $C_1$–$C_4$ alkyl or $C_1$–$C_4$ haloalkyl of 1–3 halo radicals; or
(3) aryl or heteroaryl radicals optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, cyano, halo, $C_1$–$C_4$ alkyl or $C_1$–$C_4$ haloalkyl of 1–3 halo radicals;

each $R_{29}$ is independently hydrogen radical or $R_{30}$;

each $R_{31}$ and $R_{32}$ are each independently
(1) hydrogen radicals;
(2) $C_1$–$C_4$ alkyl radical optionally substituted by an $C_3$–$C_8$ cycloalkyl, aryl, heterocyclyl or heteroaryl radical optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, cyano, $C_1$–$C_4$ alkyl or $C_1$–$C_4$ haloalkyl of 1–3 halo radicals; or
(3) aryl, heteroaryl, heterocyclyl or $C_3$–$C_8$ cycloalkyl radical optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, cyano, $C_1$–$C_4$ alkyl or $C_1$–$C_4$ haloalkyl of 1–3 halo radicals; and each $R_{33}$ is independently
(1) hydrogen radical; or
(2) $C_1$–$C_4$ alkyl radical optionally substituted by a radical of heterocyclyl, aryl or heteroaryl optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, cyano, $C_1$–$C_4$ alkyl or $C_1$–$C_4$ haloalkyl of 1–3 halo radicals; and wherein heterocyclyl is a radical of a monocyclic or bicyclic saturated heterocyclic ring system having 5–8 ring members per ring, wherein 1–3 ring members are oxygen, sulfur or nitrogen heteroatoms, which is optionally partially unsaturated or benzo-fused and optionally substituted by 1–2 oxo or thioxo radicals; aryl is a phenyl or naphthyl radical; and heteroaryl is radical of a monocyclic or bicyclic aromatic heterocyclic ring system having 5–6 ring members per ring, wherein 1–3 ring members are oxygen, sulfur or nitrogen heteroatoms, which is optionally benzo-fused or saturated $C_3$–$C_4$-carbocyclic-fused.

3. The compound of claim 2 or a pharmaceutically acceptable salt thereof, wherein
each $R_5$ is independently
(1) hydrogen radicals;
(2) $C_1$–$C_4$ alkyl, $C_2$–$C_5$ alkenyl or $C_2$–$C_5$ alkynyl radicals optionally substituted by 1–3 radicals of amino, $C_1$–$C_4$ alkylamino, di-($C_1$–$C_4$-alkyl)amino, hydroxy, $C_1$–$C_4$ alkoxy, $C_1$–$C_4$ alkylthio, —$SO_3H$ or halo; or
(3) aryl, heteroaryl, aryl-$C_1$–$C_4$-alkyl, heteroaryl-$C_1$–$C_4$-alkyl, heterocyclyl, heterocyclyl-$C_1$–$C_4$-alkyl, $C_3$–$C_8$ cycloalkyl or $C_3$–$C_8$-cycloalkyl-$C_1$–$C_4$-alkyl radicals optionally substituted by 1–3 radicals of amino, $C_1$–$C_4$ alkylamino, di-($C_1$–$C_4$-alkyl)amino, hydroxy, $C_1$–$C_4$ alkoxy, $C_1$–$C_4$ alkylthio, $C_1$–$C_4$ alkyl or $C_1$–$C_4$ haloalkyl of 1–3 halo radicals;

each $R_{20}$ is independently
(1) $C_1$–$C_8$ alkyl, $C_2$–$C_5$ alkenyl or $C_2$–$C_5$ alkynyl radicals optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, N-(($C_1$–$C_4$ alkoxy)carbonyl)-N-($C_1$–$C_4$ alkyl)amino, aminocarbonylamino, $C_1$–$C_4$ alkylsulfonylamino, hydroxy, $C_1$–$C_4$ alkoxy, $C_1$–$C_4$ alkylthio, $C_1$–$C_4$ alkylsulfinyl, $C_1$–$C_4$ alkylsulfonyl, halo or aryl-$C_1$–$C_4$-alkoxy, aryl-$C_1$–$C_4$-alkylthio, aryl-$C_1$–$C_4$-alkylsulfonyl, $C_3$–$C_8$ cycloalkyl, heterocyclyl, aryl or heteroaryl radicals optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, $C_1$–$C_5$ alkanoyl, hydroxy, $C_1$–$C_4$ alkoxy, $C_1$–$C_4$ alkylthio, $C_1$–$C_4$ alkylsulfinyl, $C_1$–$C_4$ alkylsulfonyl, halo, $C_1$–$C_4$ alkyl or $C_1$–$C_4$ haloalkyl of 1–3 halo radicals;
(2) heterocyclyl radical optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, $C_1$–$C_4$ alkyl or $C_1$–$C_4$ haloalkyl of 1–3 halo radicals; or
(3) aryl or heteroaryl radicals optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, ($C_1$–$C_4$ alkoxy)carbonyl, hydroxy, $C_1$–$C_4$ alkoxy, $C_1$–$C_4$ alkylthio, cyano, halo, azido, $C_1$–$C_4$ alkyl or $C_1$–$C_4$ haloalkyl of 1–3 halo radicals;

each $R_{21}$ is independently hydrogen radical or $R_{20}$;
each $R_{30}$ is independently
(1) $C_1$–$C_4$ alkyl radical optionally substituted by 1–3 radicals of
(a) —$NR_{31}R_{31}$;
(b) $C_1$–$C_4$ alkoxy-carbonyl or phenoxycarbonyl or phenylmethoxycarbonyl optionally substituted by 1–3 radicals of amino, alkylamino, di-($C_1$–$C_4$-alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, cyano, halo, $C_1$–$C_4$ alkyl or trifluoromethyl; or (c) hydroxy, $C_1$–$C_4$ alkoxy, $C_1$–$C_4$ alkylthio, or phenyl-$C_1$–$C_4$-alkoxy, phenyl-$C_1$–$C_4$-alkylthio, heterocyclyl, phenyl or heteroaryl radicals optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, hydroxy, $C_1$–$C_4$ alkoxy, $C_1$–$C_4$ alkylthio, cyano, halo, $C_1$–$C_4$ alkyl or $C_1$–$C_4$ haloalkyl of 1–3 halo radicals;

(2) $C_1$–$C_4$ haloalkyl of 1–3 halo radical; or (3) aryl or heteroaryl radicals optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy) carbonylamino, hydroxy, $C_1$–$C_4$ alkoxy, $C_1$–$C_4$ alkylthio, cyano, halo, $C_1$–$C_4$ alkyl or trifluoromethyl radicals;

each $R_{29}$ is independently hydrogen radical or $R_{30}$;

each $R_{31}$ is independently
(1) hydrogen radicals; or
(2) $C_1$–$C_4$ alkyl radical optionally substituted by an phenyl or heteroaryl radical optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy) carbonylamino, hydroxy, $C_1$–$C_4$ alkoxy, $C_1$–$C_4$ alkylthio, cyano, $C_1$–$C_4$ alkyl or trifluoromethyl radicals; and each $R_{32}$ is independently
(1) hydrogen radicals;
(2) $C_1$–$C_4$ alkyl radical optionally substituted by an $C_3$–$C_6$ cycloalkyl, aryl, heterocyclyl or heteroaryl radical optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy) carbonylamino, $C_1$–$C_4$ alkylsulfonylamino, hydroxy, $C_1$–$C_4$ alkoxy, $C_1$–$C_4$ alkylthio, cyano, $C_1$–$C_4$ alkyl or $C_1$–$C_4$ haloalkyl of 1–3 halo radicals; or
(3) aryl, heteroaryl, heterocyclyl or $C_3$–$C_6$ cycloalkyl radical optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy) carbonylamino, $C_1$–$C_4$ alkylsulfonylamino, hydroxy, $C_1$–$C_4$ alkoxy, $C_1$–$C_4$ alkylthio, cyano, $C_1$–$C_4$ alkyl or $C_1$–$C_4$ haloalkyl of 1–3 halo radicals; and each $R_{33}$ is independently hydrogen or $C_1$–$C_4$ alkyl radical.

4. The compound of claim 3 or a pharmaceutically acceptable salt thereof, wherein wherein $R_1$ is -Z-Y, provided that (1) the total number of aryl, heteroaryl, cycloalkyl and heterocyclyl radicals in $R_1$ is 0–3;

Y is a
(1) hydrogen radical;
(2) halo radical;
(3) —C(O)—$R_{20}$ or —C(N$R_5$)—N$R_5R_{21}$ radical;
(4) —O$R_{21}$, —O—C(O)—$R_{21}$ or —O—C(O)—N$R_5R_{21}$ radical;
(5) —S$R_{21}$, —S(O)—$R_{20}$, —S(O)$_2$—$R_{20}$ or —S(O)$_2$—N$R_5R_{21}$ radical; or
(6) —N$R_5R_{21}$, —N$R_{22}$—C(O)—$R_{21}$, —N$R_{22}$—C(O)—O$R_{20}$, —N$R_{22}$—C(O)—N$R_5R_{21}$, —N$R_{22}$—C(N$R_5$)—N$R_5R_{21}$, —N$R_{22}$—S(O)$_2$—$R_{22}$ or —N$R_{20}$—S(O)$_2$—N$R_5R_{21}$ radical;

each $R_5$ is independently
(1) hydrogen radicals;
(2) $C_1$–$C_4$ alkyl or $C_2$–$C_5$ alkenyl radicals optionally substituted by 1–3 radicals of amino, di-($C_1$–$C_4$-alkyl)amino, hydroxy, $C_1$–$C_4$ alkoxy, $C_1$–$C_4$ alkylthio, —SO$_3$H or halo; or
(3) phenyl-$C_1$–$C_2$-alkyl, heteroaryl-$C_1$–$C_2$-alkyl, heterocyclyl-$C_1$–$C_2$-alkyl or $C_3$–$C_6$-cycloalkyl-$C_1$–$C_2$-alkyl radicals optionally substituted by 1–3 radicals of amino, di-($C_1$–$C_4$-alkyl)amino, hydroxy, $C_1$–$C_4$ alkoxy, $C_1$–$C_4$ alkylthio, $C_1$–$C_4$ alkyl or $C_1$–$C_2$ haloalkyl of 1–3 halo radicals;

each $R_{20}$ is independently
(1) $C_1$–$C_8$ alkyl or $C_2$–$C_5$ alkenyl radicals optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, N-(($C_1$–$C_4$ alkoxy)carbonyl)-N-($C_1$–$C_4$ alkyl)amino, aminocarbonylamino, hydroxy, $C_1$–$C_4$ alkoxy, $C_1$–$C_4$ alkylthio, $C_1$–$C_4$ alkylsulfinyl, $C_1$–$C_4$ alkylsulfonyl, halo or aryl-$C_1$–$C_4$-alkoxy, aryl-$C_1$–$C_4$-alkylthio, aryl-$C_1$–$C_4$-alkylsulfonyl, $C_3$–$C_6$ cycloalkyl, heterocyclyl, aryl or heteroaryl radicals optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, $C_1$–$C_5$ alkanoyl, hydroxy, $C_1$–$C_4$ alkoxy, $C_1$–$C_4$ alkylthio, halo, $C_1$–$C_4$ alkyl or $C_1$–$C_2$ haloalkyl of 1–3 halo radicals;
(2) heterocyclyl radical optionally substituted by 1–2 radicals of amino, $C_1$–$C_4$ alkylamino, di-($C_1$–$C_4$ alkyl)amino, $C_1$–$C_5$ alkanoylamino, ($C_1$–$C_4$ alkoxy) carbonylamino, hydroxy, $C_1$–$C_4$ alkoxy, $C_1$–$C_4$ alkylthio or $C_1$–$C_4$ alkyl; or
(3) aryl or heteroaryl radicals optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy) carbonylamino, $C_1$–$C_4$ alkylsulfonylamino, ($C_1$–$C_4$ alkoxy)carbonyl, hydroxy, $C_1$–$C_4$ alkoxy, $C_1$–$C_4$ alkylthio, cyano, halo, azido, $C_1$–$C_4$ alkyl or $C_1$–$C_2$ haloalkyl of 1–3 halo radicals;

each $R_{21}$ is independently hydrogen radical or $R_{20}$;

each $R_{22}$ is independently
(1) hydrogen radical; or
(2) $C_1$–$C_4$ alkyl radical optionally substituted by a radical of phenyl or heteroaryl optionally substituted by 1–3 radicals of amino, di-($C_1$–$C_2$ alkyl)amino, $C_1$–$C_5$ alkanoylamino, ($C_1$–$C_4$ alkoxy) carbonylamino, hydroxy, $C_1$–$C_4$ alkoxy, $C_1$–$C_4$ alkylthio, cyano, halo, $C_1$–$C_4$ alkyl or $C_1$–$C_2$ haloalkyl of 1–3 halo radicals;

each $R_{30}$ is independently
(1) $C_1$–$C_4$ alkyl radical optionally substituted by
(a) amino, $C_1$–$C_4$ alkylamino or di-($C_1$–$C_4$-alkyl)amino radicals; or
(b) hydroxy, $C_1$–$C_4$ alkoxy, heterocyclyl, phenyl or heteroaryl radicals optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, hydroxy, $C_1$–$C_4$ alkoxy, $C_1$–$C_4$ alkylthio, cyano, halo, $C_1$–$C_4$ alkyl or trifluoromethyl radicals;
(2) $C_1$–$C_2$ haloalkyl of 1–3 halo radical; or
(3) aryl or heteroaryl radicals optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy) carbonylamino, hydroxy, $C_1$–$C_4$ alkoxy, $C_1$–$C_4$ alkylthio, cyano, halo, $C_1$–$C_4$ alkyl or trifluoromethyl radicals;

each $R_{29}$ is independently hydrogen radical or $R_{30}$;

each $R_{31}$ is independently hydrogen or $C_1$–$C_4$ alkyl radicals; and each $R_{32}$ is independently
  (1) hydrogen radicals;
  (2) $C_1$–$C_4$ alkyl radical optionally substituted by phenyl or heteroaryl radical optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, hydroxy, $C_1$–$C_4$ alkoxy, $C_1$–$C_4$ alkyl or trifluoromethyl radicals; or
  (3) phenyl or heteroaryl radical optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, hydroxy, $C_1$–$C_4$ alkoxy, $C_1$–$C_4$ alkyl or trifluoromethyl radicals; and each $R_{33}$ is independently hydrogen or methyl radical; and wherein heterocyclyl is a radical of a monocyclic saturated heterocyclic ring system having 5–6 ring members, wherein 1–3 ring members are oxygen, sulfur or nitrogen heteroatoms, which is optionally benzo-fused and optionally substituted by 1–2 oxo or thioxo radicals; aryl is a phenyl or naphthyl radical; and heteroaryl is radical of a monocyclic aromatic heterocyclic ring system having 5–6 ring members, wherein 1–3 ring members are oxygen, sulfur or nitrogen heteroatoms, which is optionally benzo-fused or saturated $C_3$–$C_4$-carbocyclic-fused.

5. The compound of claim 4 or a pharmaceutically acceptable salt thereof, wherein each $R_5$ is independently
  (1) hydrogen radical;
  (2) $C_1$–$C_4$ alkyl radical optionally substituted by 1–3 radicals of amino, di-($C_1$–$C_2$-alkyl)amino, hydroxy, $C_1$–$C_2$ alkoxy, $C_1$–$C_2$ alkylthio or halo; or
  (3) phenyl-$C_1$–$C_2$-alkyl, heteroaryl-$C_1$–$C_2$-alkyl, heterocyclyl-$C_1$–$C_2$-alkyl or $C_3$–$C_6$-cycloalkyl-$C_1$–$C_2$-alkyl radicals optionally substituted by 1–3 radicals of amino, di-($C_1$–$C_2$-alkyl)amino, hydroxy, $C_1$–$C_2$ alkoxy, $C_1$–$C_2$ alkylthio, methoxy, methylthio, $C_1$–$C_4$ alkyl or trifluoromethyl radicals;

each $R_{22}$ is independently hydrogen or $C_1$–$C_4$ alkyl radical;

each $R_{30}$ is independently
  (1) $C_1$–$C_4$ alkyl radical optionally substituted by a phenyl or heteroaryl radical optionally substituted by 1–3 radicals of amino, di-($C_1$–$C_2$ alkyl)amino, acetamido, hydroxy, $C_1$–$C_2$ alkoxy, halo, $C_1$–$C_4$ alkyl or trifluoromethyl radicals;
  (2) trifluoromethyl radical; or
  (3) aryl or heteroaryl radicals optionally substituted by 1–3 radicals of amino, di-($C_1$–$C_2$ alkyl)amino, acetamido, hydroxy, $C_1$–$C_2$ alkoxy, halo, $C_1$–$C_4$ alkyl or trifluoromethyl radicals;

each $R_{29}$ is independently hydrogen radical or $R_{30}$; and each $R_{32}$ is independently
  (1) hydrogen radicals;
  (2) $C_1$–$C_4$ alkyl radical or $C_1$–$C_2$ alkyl radical substituted by phenyl or heteroaryl radical optionally substituted by 1–3 radicals of amino, di-($C_1$–$C_2$ alkyl) amino, acetamido, hydroxy, $C_1$–$C_2$ alkoxy, $C_1$–$C_4$ alkyl or trifluoromethyl radicals; or
  (3) phenyl or heteroaryl radical optionally substituted by 1–3 radicals of amino, di-($C_1$–$C_2$ alkyl)amino, acetamido, hydroxy, $C_1$–$C_2$ alkoxy, $C_1$–$C_4$ alkyl or trifluoromethyl radicals; and wherein heterocyclyl is a radical of a monocyclic saturated heterocyclic ring system having 5–6 ring members, wherein 1–2 ring members are oxygen, sulfur or nitrogen heteroatoms, which is optionally benzo-fused and optionally substituted by 1–2 oxo or thioxo radicals; aryl is a phenyl or naphthyl radical; and heteroaryl is radical of a monocyclic aromatic heterocyclic ring system having 5–6 ring members, wherein 1–2 ring members are oxygen, sulfur or nitrogen heteroatoms, which is optionally benzo-fused.

6. The compound of claim 5 or a pharmaceutically acceptable salt thereof, wherein wherein $R_1$ is -Z-Y, provided that (1) the total number of aryl, heteroaryl, cycloalkyl and heterocyclyl radicals in $R_1$ is 0–2;

Y is a
  (1) hydrogen radical;
  (2) —C(O)—$R_{20}$ radical;
  (3) —$OR_{21}$, —$SR_{21}$, —S(O)—$R_{20}$, —S(O)$_2$—$R_{20}$ or —S(O)$_2$—$NR_5R_{21}$ radical; or
  (4) —$NR_5R_{21}$, —$NR_{22}$—C(O)—$R_{21}$, —$NR_{22}$—C(O)—$OR_{20}$, —$NR_{22}$—C(O)—$NR_5R_{21}$, —$NR_{22}$—S(O)$_2$—$R_{20}$ or —$NR_{22}$—S(O)$_2$—$NR_5R_{21}$ radical;

each $R_5$ is independently
  (1) hydrogen radical;
  (2) $C_1$–$C_4$ alkyl radical optionally substituted by 1–3 halo radicals; or
  (3) phenyl-$C_1$–$C_2$-alkyl or heteroaryl-$C_1$–$C_2$-alkyl, radicals optionally substituted by 1–3 radicals of amino, dimethylamino, hydroxy, methoxy, methylthio, methyl or trifluoromethyl radicals;

each $R_{20}$ is independently
  (1) $C_1$–$C_8$ alkyl or $C_2$–$C_5$ alkenyl radicals optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, N-(($C_1$–$C_4$ alkoxy)carbonyl)-N-($C_1$–$C_4$ alkyl)amino, aminocarbonylamino, hydroxy, $C_1$–$C_4$ alkoxy, $C_1$–$C_4$ alkylthio, $C_1$–$C_4$ alkylsulfinyl, $C_1$–$C_4$ alkylsulfonyl, halo or aryl-$C_1$–$C_4$-alkoxy, aryl-$C_1$–$C_4$-alkylthio, aryl-$C_1$–$C_4$-alkylsulfonyl, $C_3$–$C_6$ cycloalkyl, heterocyclyl, aryl or heteroaryl radicals optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, $C_1$–$C_5$ alkanoyl, hydroxy, $C_1$–$C_4$ alkoxy, $C_1$–$C_4$ alkylthio, halo, $C_1$–$C_4$ alkyl or $C_1$–$C_2$ haloalkyl of 1–3 halo radicals;
  (2) heterocyclyl radical optionally substituted by 1–2 radicals of amino, di-($C_1$–$C_4$ alkyl)amino, ($C_1$–$C_4$ alkoxy)carbonylamino, hydroxy, $C_1$–$C_4$ alkoxy, $C_1$–$C_4$ alkylthio or $C_1$–$C_4$ alkyl; or
  (3) aryl or heteroaryl radicals optionally substituted by 1–2 radicals of amino, $C_1$–$C_4$ alkylamino, di-($C_1$–$C_4$ alkyl)amino, acetamido, ($C_1$–$C_4$ alkoxy)carbonylamino, $C_1$–$C_4$ alkylsulfonylamino, ($C_1$–$C_4$ alkoxy)carbonyl, hydroxy, $C_1$–$C_4$ alkoxy, $C_1$–$C_4$ alkylthio, cyano, halo, azido, $C_1$–$C_4$ alkyl or trifluoromethyl radicals;

each $R_{21}$ is independently hydrogen radical or $R_{20}$;

each $R_{30}$ is independently
  (1) $C_1$–$C_4$ alkyl radical optionally substituted by a phenyl or heteroaryl radical optionally substituted by 1–3 radicals of amino, dimethylamino, acetamido, hydroxy, halo, methoxy, methyl or trifluoromethyl radicals;

(2) trifluoromethyl radical; or (3) aryl or heteroaryl radicals optionally substituted by 1–3 radicals of amino, dimethylamino, acetamido, hydroxy, halo, methoxy, methyl or trifluoromethyl radicals;

each $R_{29}$ is independently hydrogen radical or $R_{30}$;

each $R_{31}$ is independently hydrogen, methyl or ethyl radicals; and each $R_{32}$ is independently (1) hydrogen radicals;

(2) $C_1$–$C_4$ alkyl radical or $C_1$–$C_2$ alkyl radical substituted by phenyl or heteroaryl radical optionally substituted by 1–3 radicals of amino, dimethylamino, acetamido, hydroxy, methoxy, methyl or trifluoromethyl radicals; or (3) phenyl or heteroaryl radical optionally substituted by 1–3 radicals of amino, dimethylamino, acetamido, hydroxy, methoxy, methyl or trifluoromethyl radicals.

7. The compound of claim 6 or a pharmaceutically acceptable salt thereof, wherein $R_{30}$ is independently (1) $C_1$–$C_4$ alkyl radical optionally substituted by a phenyl or heteroaryl radical optionally substituted by 1–2 radicals of amino, dimethylamino, acetamido, hydroxy, halo, methoxy, methyl or trifluoromethyl radicals;

(2) trifluoromethyl radical; or (3) aryl or heteroaryl radicals optionally substituted by 1–3 radicals of amino, dimethylamino, acetamido, hydroxy, halo, methoxy, methyl or trifluoromethyl radicals;

$R_{29}$ is an aryl or heteroaryl radicals optionally substituted by 1–2 radicals of amino, dimethylamino, acetamido, hydroxy, halo, methoxy, methyl or trifluoromethyl radicals; and $R_{32}$ is independently (1) hydrogen or $C_1$–$C_4$ alkyl radical; or (2) phenyl or heteroaryl radical optionally substituted by 1–2 radicals of amino, dimethylamino, acetamido, hydroxy, methoxy, methyl or trifluoromethyl radicals.

8. The compound of claim 7 or a pharmaceutically acceptable salt thereof, wherein wherein $R_1$ is -Z-Y, provided that (1) the total number of aryl, heteroaryl, cycloalkyl and heterocyclyl radicals in $R_1$ is 0–1;

each $R_5$ is independently hydrogen or $C_1$–$C_4$ alkyl radical;

each $R_{20}$ is independently (1) $C_1$–$C_8$ alkyl radicals optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, N-(($C_1$–$C_4$ alkoxy)carbonyl)-N-($C_1$–$C_4$ alkyl)amino, aminocarbonylamino, hydroxy, $C_1$–$C_4$ alkoxy, $C_1$–$C_4$ alkylthio, $C_1$–$C_4$ alkylsulfinyl, $C_1$–$C_4$ alkylsulfonyl, halo or $C_3$–$C_6$ cycloalkyl, heterocyclyl, aryl or heteroaryl radicals optionally substituted by 1–2 radicals of amino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, halo, $C_1$–$C_4$ alkyl or trifluoromethyl radicals;

(2) heterocyclyl radical optionally substituted by 1–2 radicals of hydroxy, $C_1$–$C_4$ alkoxy, $C_1$–$C_4$ alkylthio or $C_1$–$C_4$ alkyl; or (3) aryl or heteroaryl radicals optionally substituted by 1–2 radicals of ($C_1$–$C_4$ alkoxy)carbonyl, amino, $C_1$–$C_4$ alkylamino, di-($C_1$–$C_4$ alkyl)amino, hydroxy, $C_1$–$C_4$ alkoxy, $C_1$–$C_4$ alkylthio, cyano, halo, azido, $C_1$–$C_4$ alkyl or trifluoromethyl radicals;

each $R_{21}$ is independently hydrogen radical or $R_{20}$; and $R_{12}$ is a heteroaryl radical optionally substituted by 1–2 radicals of amino, dimethylamino, acetamido, hydroxy, halo, cyano, methoxy, methyl or trifluoromethyl radicals.

9. The compound of claim 8 or a pharmaceutically acceptable salt thereof, wherein Y is a (1) hydrogen radical;

(2) —C(O)—$R_{20}$ radical;

(3) —O$R_{21}$, —S$R_{21}$, —S(O)—$R_{20}$, —S(O)$_2$—$R_{20}$ or —S(O)$_2$—NR$_5$R$_{21}$ radical; or (4) —NR$_5$R$_{21}$, —NR$_{22}$—C(O)—$R_{21}$ or —NR$_{22}$—S(O)$_2$—$R_{20}$ radical;

$R_5$ is a hydrogen radical;

each $R_{20}$ is independently (1) $C_1$–$C_6$ alkyl radicals optionally substituted by 1–3 radicals of amino, methylamino, dimethylamino, t-butoxycarbonylamino, N-((t-butoxy)carbonyl)-N-(methyl)amino, aminocarbonylamino, hydroxy, butoxy, methoxy, butylthio, methylthio, methylsulfinyl, methylsulfonyl, halo or $C_5$–$C_6$ cycloalkyl, heterocyclyl, phenyl or heteroaryl radicals optionally substituted by 1–2 radicals of amino, dimethylamino, acetamino, hydroxy, methoxy, methylthio, halo, methyl or trifluoromethyl radicals;

(2) heterocyclyl radical optionally substituted by 1–2 radicals of hydroxy or $C_1$–$C_4$ alkyl; or (3) aryl or heteroaryl radicals optionally substituted by 1–2 radicals of amino, dimethylamino, hydroxy, methoxy, methylthio, halo, methyl or trifluoromethyl radicals;

each $R_{21}$ is independently hydrogen radical or $R_{20}$;

each $R_{22}$ is independently hydrogen or methyl radical; and $R_{12}$ is a 4-pyridyl, 4-quinolinyl, 4-imidazolyl or 4-pyrimidinyl radical optionally substituted by a radical of amino, dimethylamino, acetamido, hydroxy, halo, cyano, methoxy, methyl or trifluoromethyl radicals.

10. The compound of claim 9 or a pharmaceutically acceptable salt thereof, wherein Y is a (1) —C(O)—$R_{20}$ radical;

(2) —O$R_{21}$, —S$R_{21}$, —S(O)—$R_{20}$, —S(O)$_2$—$R_{20}$ or —S(O)$_2$—NR$_5$R$_{21}$ radical; or (3) —NR$_5$R$_{21}$, —NR$_{22}$—C(O)—$R_{21}$ or —NR$_{22}$—S(O)$_2$—$R_{20}$ radical;

each $R_{20}$ is independently (1) $C_1$–$C_6$ alkyl radicals optionally substituted by 1–3 radicals of amino, methylamino, dimethylamino, t-butoxycarbonylamino, N-((t-butoxy)carbonyl)-N-(methyl)amino, aminocarbonylamino, hydroxy, butoxy, methoxy, butylthio, methylthio, methylsulfinyl, methylsulfonyl, halo or $C_5$–$C_6$ cycloalkyl, heterocyclyl, phenyl or heteroaryl radicals optionally substituted by 1–2 radicals of amino, dimethylamino, acetamino, hydroxy, methoxy, methylthio, halo, methyl or trifluoromethyl radicals;
(2) heterocyclyl radical; or
(3) aryl or heteroaryl radicals optionally substituted by 1–2 radicals of amino, dimethylamino, hydroxy, methoxy, methylthio, halo, methyl or trifluoromethyl radicals; and each $R_{21}$ is independently hydrogen radical or $R_{20}$.

11. The compound of claim 10 or a pharmaceutically acceptable salt thereof, wherein Y is a —$OR_{21}$, —$SR_{21}$ or —$NR_5R_{21}$ radical;
each $R_{20}$ is independently
(1) $C_1$–$C_6$ alkyl radicals optionally substituted by 1–3 radicals of amino, methylamino, dimethylamino, hydroxy or phenyl or heteroaryl radicals optionally substituted by 1–2 radicals of amino, dimethylamino, hydroxy, methoxy, methylthio, halo, methyl or trifluoromethyl radicals;
(2) heterocyclyl radical; or
(3) aryl or heteroaryl radicals optionally substituted by 1–2 radicals of amino, dimethylamino, hydroxy, methoxy, methylthio, halo, methyl or trifluoromethyl radicals;

each $R_{21}$ is independently hydrogen radical or $R_{20}$; and $R_{12}$ is a 4-pyridyl radical optionally substituted by a radical of amino, dimethylamino, acetamido, hydroxy, halo, cyano, methoxy, methyl or trifluoromethyl radicals.

12. The compound of claim 1 which is:
5-(4-Fluorophenyl)-2-(4-pyridyl)-4-(4-pyridyl)-pyrimidine,
5-(4-Fluorophenyl)-2-(2-methylthiazol-4-yl)-4-(4-pyridyl)-pyrimidine,
5-(4-Fluorophenyl)-4-(4-pyridyl)-2-(2-thienyl)-pyrimidine,
2-(2-Diethylaminoethylamino)-5-(4-fluorophenyl)-4-(4-pyridyl)-pyrimidine,
2-(4-Aminobutylamino)-5-(4-fluorophenyl)-4-(4-pyridyl)-pyrimidine,
2-(2,6-Dichlorobenzyl)-5-(4-fluorophenyl)-4-(4-pyridyl)-pyrimidine,
2-(2,6-Dichlorophenylamino)-5-(4-fluorophenyl)-4-(4-pyridyl)-pyrimidine,
2-(2,6-Dimethylphenylamino)-5-(4-fluorophenyl)-4-(4-pyridyl)-pyrimidine,
5-(4-Fluorophenyl)-2-(2-methoxyphenylamino)-4-(4-pyridyl)-pyrimidine,
5-(4-Fluorophenyl)-2-(4-fluorophenylamino)-4-(4-pyridyl)-pyrimidine,
5-(4-Fluorophenyl)-2-phenylthiomethyl-4-(4-pyridinyl)-pyrimidine,
2-(2-(4-Aminophenyl)ethyl-amino)-5-(4-fluorophenyl)-4-(4-pyridyl)-pyrimidine,
2-(2-(2-Chlorophenyl)ethyl-amino)-5-(4-fluorophenyl)-4-(4-pyridyl)-pyrimidine,
2-(2-(4-Chlorophenyl)ethyl-amino)-5-(4-fluorophenyl)-4-(4-pyridyl)-pyrimidine,
2-(2-(3-Chlorophenyl)ethyl-amino)-5-(4-fluorophenyl)-4-(4-pyridyl)-pyrimidine,
2-(2-(2,4-Dichlorophenyl)ethyl-amino)-5-(4-fluorophenyl)-4-(4-pyridyl)-pyrimidine,
2-(2-(4-Bromophenyl)ethyl-amino)-5-(4-fluorophenyl)-4-(4-pyridyl)-pyrimidine,
5-(4-Fluorophenyl)-2-(2-(2-methoxyphenyl)ethyl-amino)-4-(4-pyridyl)-pyrimidine,
5-(4-Fluorophenyl)-2-(2-(3-methoxyphenyl)ethyl-amino)-4-(4-pyridyl)-pyrimidine,
5-(4-Fluorophenyl)-2-((1-methyl-3-phenylpropyl)-amino)-4-(4-pyridyl)-pyrimidine,
5-(4-Fluorophenyl)-2-((4-phenyl-butyl)-amino)-4-(4-pyridyl)-pyrimidine,
5-(4-Fluorophenyl)-2-morpholino-4-(4-pyridyl)-pyrimidine,
5-(4-Fluorophenyl)-4-(4-pyridyl)-2-(2-pyrrolidinoethylamino)-pyrimidine,
5-(4-Fluorophenyl)-2-(2-morpholinoethylamino)-4-(4-pyridyl)-pyrimidine,
5-(4-Fluorophenyl)-2-(2-piperidinoethylamino)-4-(4-pyridyl)-pyrimidine,
5-(4-Fluorophenyl)-2-(3-(2-pyrrolidinon-1-yl)propyl-amino)-4-(4-pyridyl)-pyrimidine,
2-(2-Aminoethylamino)-5-(4-fluorophenyl)-4-(4-pyridyl)-pyrimidine,
2-(3-Aminopropylamino)-5-(4-fluorophenyl)-4-(4-pyridyl)-pyrimidine,
2-(Benzylamino)-5-(4-fluorophenyl)-4-(4-pyridyl)-pyrimidine,
5-(4-Fluorophenyl)-2-(2-phenylethylamino)-4-(4-pyridyl)-pyrimidine,
5-(4-Fluorophenyl)-2-(N-methyl-N-(2-phenylethyl)-amino)-4-(4-pyridyl)-pyrimidine,
5-(4-Fluorophenyl)-2-(2-hydroxy-2-phenyl-ethyl)amino-4-(4-pyridyl)-pyrimidine,
5-(4-Fluorophenyl)-2-(2-(4-hydroxyphenyl)ethyl-amino)-4-(4-pyridyl)-pyrimidine,
5-(4-Fluorophenyl)-2-(2-(4-fluorophenyl)ethyl-amino)-4-(4-pyridyl)-pyrimidine,
5-(4-Fluorophenyl)-2-(2-(2-fluorophenyl)ethyl-amino)-4-(4-pyridyl)-pyrimidine,
5-(4-Fluorophenyl)-2-((3-phenylpropyl)-amino)-4-(4-pyridyl)-pyrimidine,
2-((2(S)-Amino-3-phenylpropyl)-amino)-5-(4-fluorophenyl)-4-(4-pyridyl)-pyrimidine,
5-(4-Fluorophenyl)-2-(2-phenylaminoethylamino)-4-(4-pyridyl)-pyrimidine,
5-(4-Fluorophenyl)-2-((3-imidazolylpropyl)-amino)-4-(4-pyridyl)-pyrimidine,
5-(4-Fluorophenyl)-4-(4-pyridyl)-2-pyrrolidino-pyrimidine,
5-(4-Fluorophenyl)-2-(1-piperazinyl)-4-(4-pyridyl)-pyrimidine,
2-((S)-2-Amino-3-phenylpropyl)-amino)-4-(4-pyridyl)-5-(3-trifluoromethylphenyl)-pyrimidine,
2-((S)-2-Amino-3-phenylpropyl)-amino)-5-(3-methylphenyl)-4-(4-pyridyl)-pyrimidine,
2-((S)-2-N,N-Dimethylamino-3-phenylpropyl)-amino)-5-(4-fluorophenyl)-4-(4-pyridyl)-pyrimidine,
2-((S)-2-N,N-Dimethylamino-3-phenylpropyl)-amino)-5-(3-methylphenyl)-4-(4-pyridyl)-pyrimidine,
2-((3-Amino-3-phenylpropyl)-amino)-5-(4-fluorophenyl)-4-(4-pyridyl)-pyrimidine,
2-((3-Amino-3-phenylpropyl)-amino)-4-(4-pyridyl)-5-(3-trifluoromethylphenyl)-pyrimidine,
2-((3-Amino-3-(2-fluorophenyl)propyl)-amino)-4-(4-pyridyl)-5-(3-trifluoromethylphenyl)-pyrimidine,
2-((3-Amino-3-phenylpropyl)-amino)-5-(3-methylphenyl)-4-(4-pyridyl)-pyrimidine,
2-((2-Amino-2-methyl-3-phenylpropyl)-amino)-5-(3-methylphenyl)-4-(4-pyridyl)-pyrimidine,
2-((3-Hydroxy-3-phenylpropyl)-amino)-5-(3-methylphenyl)-4-(4-pyridyl)-pyrimidine,
2-(((2S,3S)-3-Amino-2-methyl-3-phenylpropyl)-amino)-4-(4-pyridyl)-5-(3-trifluoromethylphenyl)-pyrimidine,
2-(((2R,3R)-3-Amino-2-methyl-3-phenylpropyl)-amino)-4-(4-pyridyl)-5-(3-trifluoromethylphenyl)-pyrimidine,
2-((S)-3-Benzylpiperazinyl)-4-(4-pyridyl)-5-(3-trifluoromethylphenyl)-pyrimidine, 4-(4-Pyridyl)-2-(((S)-tetrahydroisoquinol-3-ylmethylen)-5-(3-trifluoromethylphenyl)-pyrimidine,
5-(3-Methylphenyl)-4-(4-pyridyl)-2-(((S)-tetrahydroisoquinol-3-ylmethylen)amino)-pyrimidine,
2-(((S)-2-N-Isopropylamino-3-phenylpropyl)-amino)-4-(4-pyridyl)-5-(3-trifluoromethylphenyl)-pyrimidine,
2-(((S)-2-N-Cyclohexylamino-3-phenylpropyl)-amino)-4-(4-pyridyl)-5-(3-trifluoromethylphenyl)-pyrimidine,
2-(((S)-2-N-Isopropylamino-3-phenylpropyl)-amino)-5-(3-methylphenyl)-4-(4-pyridyl)-pyrimidine,
2-(((S)-2-N-Butylamino-3-phenylpropyl)-amino)-5-(3-methylphenyl)-4-(4-pyridyl)-pyrimidine,
2-(((S)-2-N-Cyclohexylamino-3-phenylpropyl)-amino)-5-(3-methylphenyl)-4-(4-pyridyl)-pyrimidine,
5-(4-Fluorophenyl)-2-(((S)-2-N-isopropylamino-3-phenylpropyl)-amino)-4-(4-pyridyl)-pyrimidine,
5-(4-Fluorophenyl)-2-((3-N-isopropylamino-3-phenylpropyl)-amino)-4-(4-pyridyl)-pyrimidine,
2-(((S)-2-N-Glycylamino-3-phenylpropyl)-amino)-4-(4-pyridyl)-5-(3-trifluoromethylphenyl)-pyrimidine,
2-(((S)-2-N-Glycylamino-3-phenylpropyl)-amino)-5-(3-methylphenyl)-4-(4-pyridyl)-pyrimidine,
2-(((S)-2-Amino-3-phenylpropyl)-amino)-5-(3-chloro-4-fluorophenyl)-4-(4-pyridyl)-pyrimidine,
2-(((S)-2-Amino-3-phenylpropyl)-amino)-5-(3-fluorophenyl)-4-(4-pyridyl)-pyrimidine,
2-(((S)-2-Amino-3-phenylpropyl)-amino)-5-(3-isopropylphenyl)-4-(4-pyridyl)-pyrimidine,
5-(3-Acetamidophenyl)-2-(((S)-2-amino-3-phenylpropyl)-amino)-4-(4-pyridyl)-pyrimidine,
2-(((S)-2-Amino-3-phenylpropyl)-amino)-5-(4-chlorophenyl)-4-(4-pyridyl)-pyrimidine,
2-(((S)-2-Amino-3-phenylpropyl)-amino)-5-(benzothienyl)-4-(4-pyridyl)-pyrimidine, or
2-(((S)-2-Amino-3-phenylpropyl)-amino)-5-(2-naphthyl)-4-(4-pyridyl)-pyrimidine, or a pharmaceutically acceptable salt thereof.

13. A pharmaceutical composition comprising a compound of claim 1 and a pharmaceutically acceptable carrier.

* * * * *